United States Patent
Keller et al.

(10) Patent No.: US 10,064,607 B2
(45) Date of Patent: Sep. 4, 2018

(54) TISSUE COLLECTION ASSEMBLY FOR BIOPSY DEVICE

(71) Applicant: Devicor Medical Products, Inc., Cincinnati, OH (US)

(72) Inventors: Bryan R. Keller, Loveland, OH (US); Emmanuel V. Tanghal, Mason, OH (US); Robert M. Householder, Loveland, OH (US); Morgan R. Hunter, Cincinnati, OH (US); Trevor W. V. Speeg, Williamsburg, OH (US); Melody L. Mitro, Cincinnati, OH (US); Andrew P. Nock, Dayton, OH (US); Marcus D. Muffet, Cincinnati, OH (US); Kevin M. Fiebig, Cincinnati, OH (US); Edward A. Rhad, Fairfield, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 143 days.

(21) Appl. No.: 14/469,761

(22) Filed: Aug. 27, 2014

(65) Prior Publication Data

US 2015/0065913 A1 Mar. 5, 2015

Related U.S. Application Data

(60) Provisional application No. 61/993,660, filed on May 15, 2014, provisional application No. 61/986,952, (Continued)

(51) Int. Cl.
*A61B 10/02* (2006.01)
*A61B 10/00* (2006.01)

(52) U.S. Cl.
CPC ...... *A61B 10/0266* (2013.01); *A61B 10/0275* (2013.01); *A61B 10/0283* (2013.01); (Continued)

(58) Field of Classification Search
CPC . A61B 10/02; A61B 10/0266; A61B 10/0275; A61B 10/0283; A61B 2010/0225
See application file for complete search history.

(56) References Cited

U.S. PATENT DOCUMENTS

| 5,526,822 A | 6/1996 | Burbank et al. |
| 5,775,333 A * | 7/1998 | Burbank ............ A61B 10/0266 |
| | | 600/567 |

(Continued)

FOREIGN PATENT DOCUMENTS

| EP | 1642534 A2 | 4/2006 |
| WO | WO 1998/033436 | 8/1998 |

(Continued)

OTHER PUBLICATIONS

International Search Report and Written Opinion dated Dec. 16, 2014 for Application No. PCT/US2014/052952, 15 pages.

(Continued)

*Primary Examiner* — Adam J Eiseman
(74) *Attorney, Agent, or Firm* — Frost Brown Todd LLC

(57) ABSTRACT

A biopsy device comprises a probe body, a needle portion, a hollow cutter, and a tissue sample holder. The needle portion extends distally from the probe body and comprises a transverse tissue receiving aperture. The hollow cutter is translatable relative to the needle portion to sever a tissue sample from tissue protruding though the aperture. The hollow cutter defines a cutter lumen. The tissue sample holder comprises a body and a tissue sample tray. The tissue sample tray is removably engaged with the body and comprises a downwardly extending lumen. The downwardly extending lumen includes a pair of lower openings which are in communication with a chamber defined by the tissue sample tray.

15 Claims, 117 Drawing Sheets

Related U.S. Application Data filed on May 1, 2014, provisional application No. 61/871,005, filed on Aug. 28, 2013.

(52) U.S. Cl.
CPC ... *A61B 10/0096* (2013.01); *A61B 2010/0208* (2013.01); *A61B 2010/0225* (2013.01); *A61B 2217/005* (2013.01)

(56) References Cited

U.S. PATENT DOCUMENTS

| | | | |
|---|---|---|---|
| 5,928,164 A | 7/1999 | Burbank et al. | |
| 6,017,316 A | 1/2000 | Ritchart et al. | |
| 6,086,544 A | 4/2000 | Hibner et al. | |
| 6,162,187 A | 12/2000 | Buzzard et al. | |
| 6,228,055 B1 | 5/2001 | Foerster et al. | |
| 6,371,904 B1 | 4/2002 | Sirimanne et al. | |
| 6,432,065 B1 | 8/2002 | Burdorff et al. | |
| 6,485,436 B1 | 11/2002 | Truckai et al. | |
| 6,626,849 B2 | 9/2003 | Huitema et al. | |
| 6,752,768 B2 | 6/2004 | Burdorff et al. | |
| 6,832,990 B2 | 12/2004 | Kortenbach et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,229,417 B2 | 6/2007 | Foerster et al. | |
| 7,442,171 B2 | 10/2008 | Stephens et al. | |
| 7,465,279 B2 | 12/2008 | Beckman et al. | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,918,803 B2 | 4/2011 | Ritchart et al. | |
| 7,918,804 B2 | 4/2011 | Monson et al. | |
| 7,938,786 B2 | 5/2011 | Ritchie et al. | |
| 7,981,051 B2 | 7/2011 | Quick et al. | |
| 8,083,687 B2 | 12/2011 | Parihar | |
| 8,088,079 B2 | 1/2012 | Kaye et al. | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,371,443 B2 | 2/2013 | Nock et al. | |
| 8,376,957 B2 | 2/2013 | Hibner et al. | |
| 8,454,531 B2 | 6/2013 | Speeg et al. | |
| 8,480,595 B2 | 7/2013 | Speeg et al. | |
| 8,532,747 B2 | 9/2013 | Nock et al. | |
| 8,532,748 B2 | 9/2013 | Leimbach et al. | |
| 8,702,623 B2 | 4/2014 | Parihar et al. | |
| 8,764,680 B2 | 7/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 9,095,326 B2 | 8/2015 | Ritchie et al. | |
| 9,345,457 B2* | 5/2016 | Speeg | A61B 10/0275 |
| 2004/0068291 A1* | 4/2004 | Suzuki | A61B 10/0096 606/205 |
| 2006/0074345 A1 | 4/2006 | Hibner | |
| 2006/0258955 A1* | 11/2006 | Hoffman | A61B 10/06 600/564 |
| 2008/0082021 A1* | 4/2008 | Ichikawa | A61B 1/015 600/563 |
| 2008/0214955 A1 | 9/2008 | Speeg et al. | |
| 2009/0131821 A1 | 5/2009 | Speeg et al. | |
| 2009/0209854 A1 | 8/2009 | Parihar et al. | |
| 2010/0152610 A1 | 6/2010 | Parihar et al. | |
| 2010/0160819 A1 | 6/2010 | Parihar et al. | |
| 2010/0160824 A1* | 6/2010 | Parihar | A61B 10/0096 600/567 |
| 2011/0071391 A1 | 3/2011 | Speeg | |
| 2011/0071423 A1 | 3/2011 | Speeg et al. | |
| 2012/0065542 A1 | 3/2012 | Hibner et al. | |
| 2013/0053724 A1 | 2/2013 | Fiebig et al. | |
| 2013/0150751 A1 | 6/2013 | Fiebig et al. | |
| 2013/0218047 A1 | 8/2013 | Fiebig et al. | |
| 2013/0324882 A1 | 12/2013 | Mescher | |
| 2014/0039343 A1 | 2/2014 | Mescher et al. | |

FOREIGN PATENT DOCUMENTS

| | | |
|---|---|---|
| WO | WO 2000/030531 | 6/2000 |
| WO | WO 2007/019445 | 2/2007 |

OTHER PUBLICATIONS

U.S. Appl. No. 61/566,793, filed Dec. 5, 2011.
U.S. Appl. No. 61/871,005, filed Aug. 28, 2013.
U.S. Appl. No. 61/986,952, filed May 1, 2014.
U.S. Appl. No. 61/993,660, filed May 15, 2014.
Supplementary European Search Report dated Mar. 14, 2017 for Application No. 14839960.3, 6 pages.

* cited by examiner

TISSUE COLLECTION ASSEMBLY FOR BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices and biopsy system components are disclosed in U.S. Pub. No. 2014/0039343, entitled "Biopsy System," published Feb. 6, 2014; U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; and U.S. Pat. No. 8,118,755, entitled "Biopsy Sample Storage," issued Feb. 21, 2012. The disclosure of each of the above-cited U.S. Patents and Publication is incorporated by reference herein.

Additional exemplary biopsy devices and biopsy system components are disclosed in U.S. Pat. Pub. No. 2006/0074345, entitled "Biopsy Apparatus and Method," published Apr. 6, 2006; U.S. Pat. Pub. No. 2008/0146962, entitled "Biopsy System with Vacuum Control Module," published Jun. 19, 2008; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008; U.S. Pat. Pub. No. 2009/0131821, entitled "Graphical User Interface For Biopsy System Control Module," published May 21, 2009; U.S. Pat. Pub. No. 2009/0131820, entitled "Icon-Based User Interface on Biopsy System Control Module," published May 21, 2009; U.S. Pat. Pub. No. 2010/0113973, entitled "Biopsy Device with Rotatable Tissue Sample Holder," published May 6, 2010; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0160824, entitled "Biopsy Device with Discrete Tissue Chambers," published Jun. 24, 2010; U.S. Pat. Pub. No. 2010/0317997, entitled "Tetherless Biopsy Device with Reusable Portion," published Dec. 16, 2010; U.S. Pat. Pub. No. 2012/0109007, entitled "Handheld Biopsy Device with Needle Firing," published May 3, 2012; U.S. Non-Provisional patent application Ser. No. 13/086,567, entitled "Biopsy Device with Motorized Needle Firing," filed Apr. 14, 2011; U.S. Non-Provisional patent application Ser. No. 13/150,950, entitled "Needle Assembly and Blade Assembly for Biopsy Device," filed Jun. 1, 2011; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; U.S. Provisional Patent App. No. 61/566,793, entitled "Biopsy Device With Slide-In Probe," filed Dec. 5, 2011; and U.S. Non-Provisional patent application Ser. No. 13/483,235, entitled "Control for Biopsy Device," filed May 30, 2012. The disclosure of each of the above-cited U.S. Patent Application Publications, U.S. Non-Provisional Patent Applications, and U.S. Provisional Patent Applications is incorporated by reference herein.

In some settings, it may be desirable to mark the location of a biopsy site for future reference. For instance, one or more markers may be deposited at a biopsy site before, during, or after a tissue sample is taken from the biopsy site. Exemplary marker deployment tools include the MAMMOMARK™, MICROMARK®, and CORMARK™ brand devices from Devicor Medical Products, Inc. of Cincinnati, Ohio. Further exemplary devices and methods for marking a biopsy site are disclosed in U.S. Pub. No. 2009/0209854, entitled "Biopsy Method," published Aug. 20, 2009; U.S. Pub. No. 2009/0270725, entitled "Devices Useful in Imaging," published Oct. 29, 2009; U.S. Pub. No. 2010/0049084, entitled "Biopsy Marker Delivery Device," published Feb. 25, 2010; U.S. Pub. No. 2011/0071423, entitled "Flexible Biopsy Marker Delivery Device," published Mar. 24, 2011; U.S. Pub. No. 2011/0071424, entitled "Biopsy Marker Delivery Device," published Mar. 24, 2011; U.S. Pub. No. 2011/0071391, entitled "Biopsy Marker Delivery Device with Positioning Component," published Mar. 24, 2011; U.S. Pat. No. 6,228,055, entitled "Devices for Marking and Defining Particular Locations in Body Tissue," issued May 8, 2001; U.S. Pat. No. 6,371,904, entitled "Subcutaneous Cavity Marking Device and Method," issued Apr. 16, 2002; U.S. Pat. No. 6,993,375, entitled "Tissue Site Markers for In Vivo Imaging," issued Jan. 31, 2006; U.S. Pat. No. 6,996,433, entitled "Imageable Biopsy Site Marker," issued Feb. 7, 2006; U.S. Pat. No. 7,044,957, entitled "Devices for Defining and Marking Tissue," issued May 16, 2006; U.S. Pat. No. 7,047,063, entitled "Tissue Site Markers for In Vivo Imaging," issued May 16, 2006; U.S. Pat. No. 7,229,417, entitled "Methods for Marking a Biopsy Site," issued Jun. 12, 2007; and U.S. Pat. No. 7,465,279, entitled "Marker Device and Method of Deploying a Cavity Marker Using a Surgical Biopsy Device," issued Dec. 16, 2008. The disclosure of each of the above-cited U.S. Patents and U.S. Patent Application Publications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 119 depicts an exploded perspective view of the tissue sample holder assembly of FIG. 115;

FIG. 120 depicts a perspective view of a tissue sample tray of the tissue sample holder assembly of FIG. 115;

FIG. 121 depicts another perspective view of the tissue sample tray of FIG. 120;

FIG. 122 depicts a side elevational view of the tissue sample tray of FIG. 120;

FIG. 123 depicts a top plan view of the tissue sample tray of FIG. 120;

FIG. 124 depicts a perspective view of another exemplary tissue sample tray that may be incorporated into the tissue sample holder assembly of FIG. 115;

FIG. 125 depicts another perspective view of the tissue sample tray of FIG. 124;

FIG. 126 depicts a top plan view of the tissue sample tray of FIG. 124;

FIG. 127 depicts a bottom plan view of the tissue sample tray of FIG. 124;

FIG. 128 depicts a perspective view of an exemplary alternative cover that may be incorporated into the tissue sample holder assembly of FIG. 115;

FIG. 129 depicts a cross-sectional side view of the cover of FIG. 128, taken along line 129-129 of FIG. 128;

FIG. 130 depicts a perspective view of another exemplary alternative tissue sample holder assembly that may be incorporated into the probe of FIG. 4;

Figure 1:
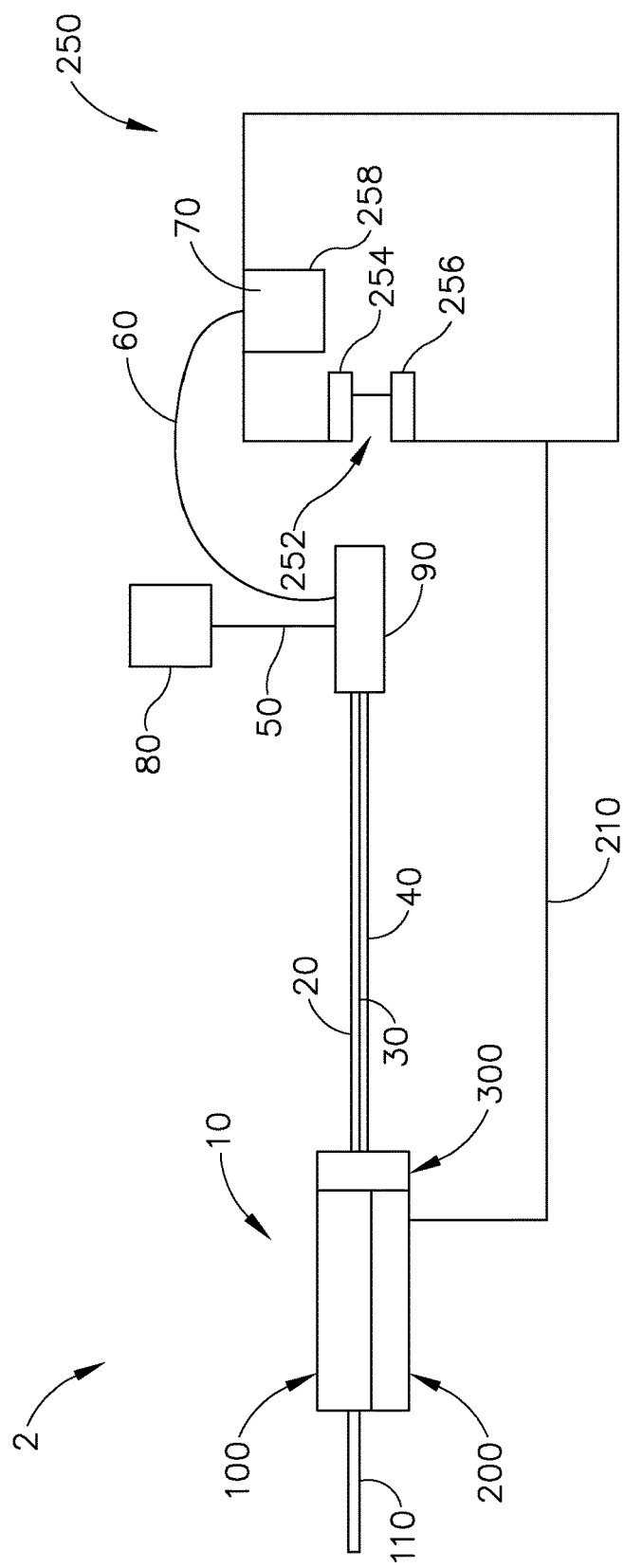
FIG. 1 depicts a schematic view of an exemplary biopsy system.
Figure 2:
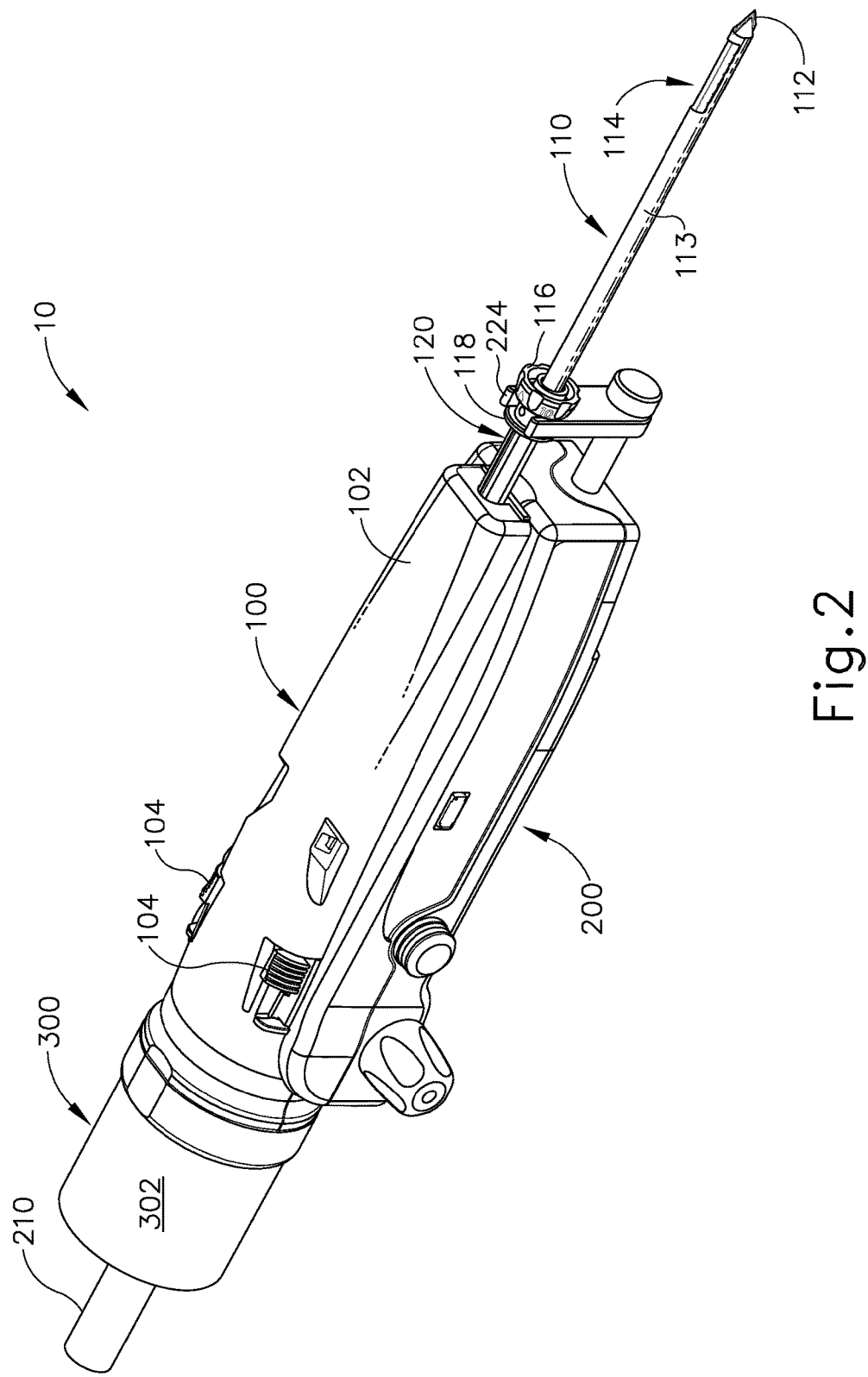
FIG. 2 depicts a perspective view of an exemplary biopsy device of the biopsy system of FIG. 1, including an exemplary probe coupled with an exemplary holster.
Figure 4:
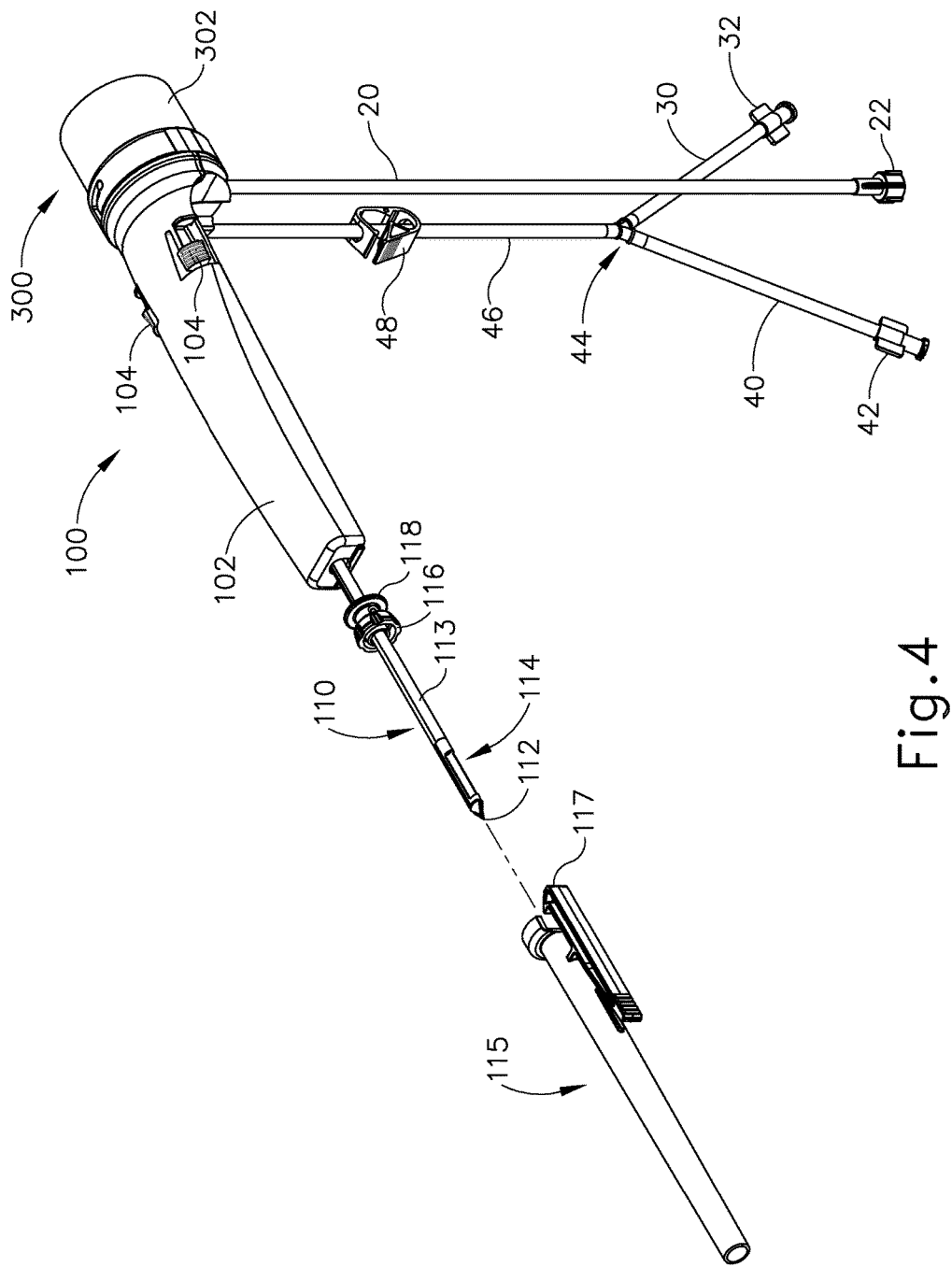
FIG. 4 depicts a perspective view of the probe of the biopsy device of FIG. 2.
Figure 130:
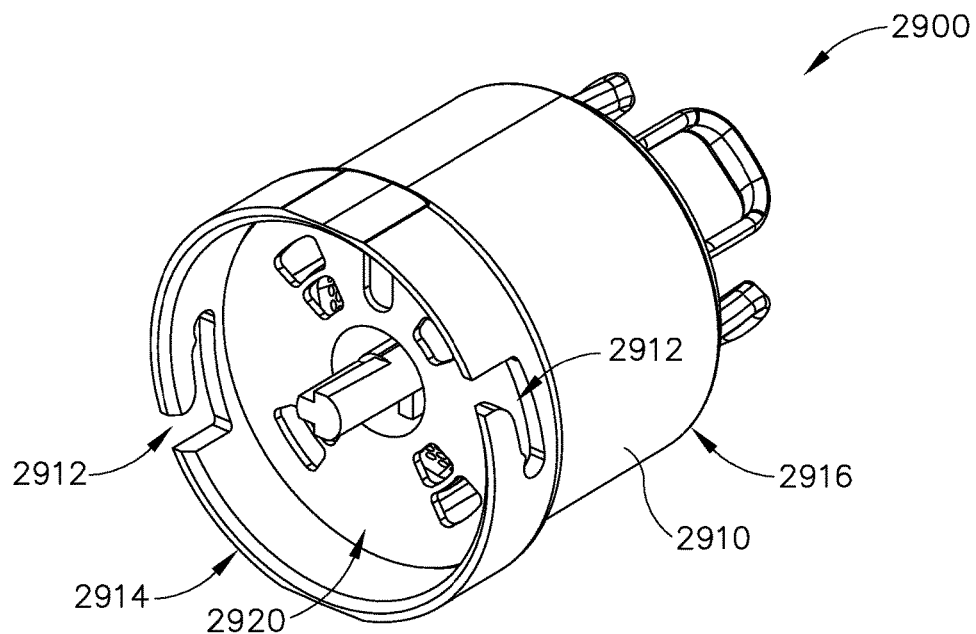
Figure 131:
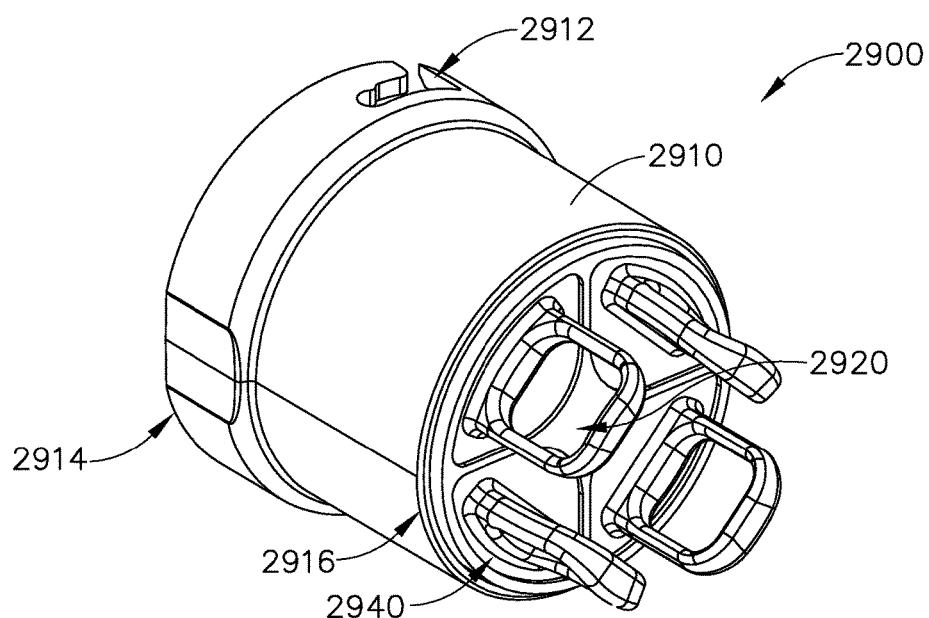
Figure 132:
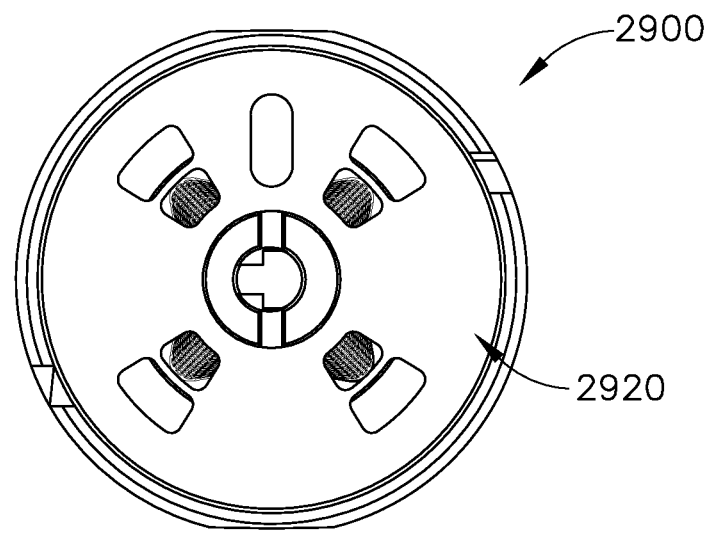
Figure 133:
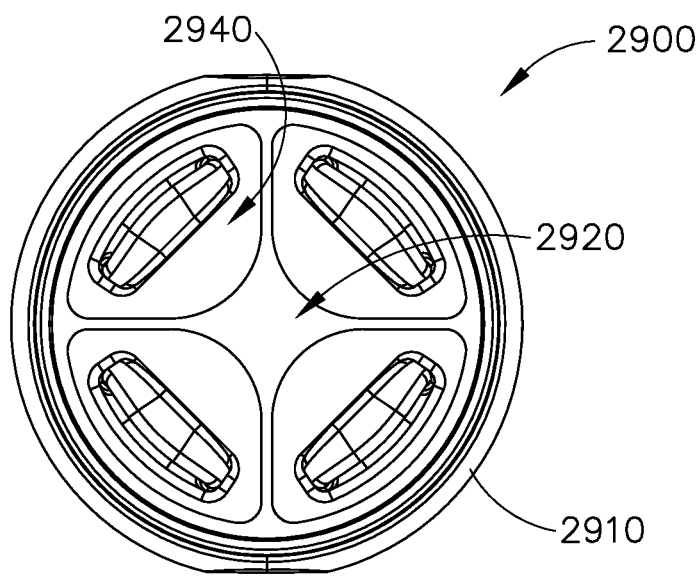
Figure 134:
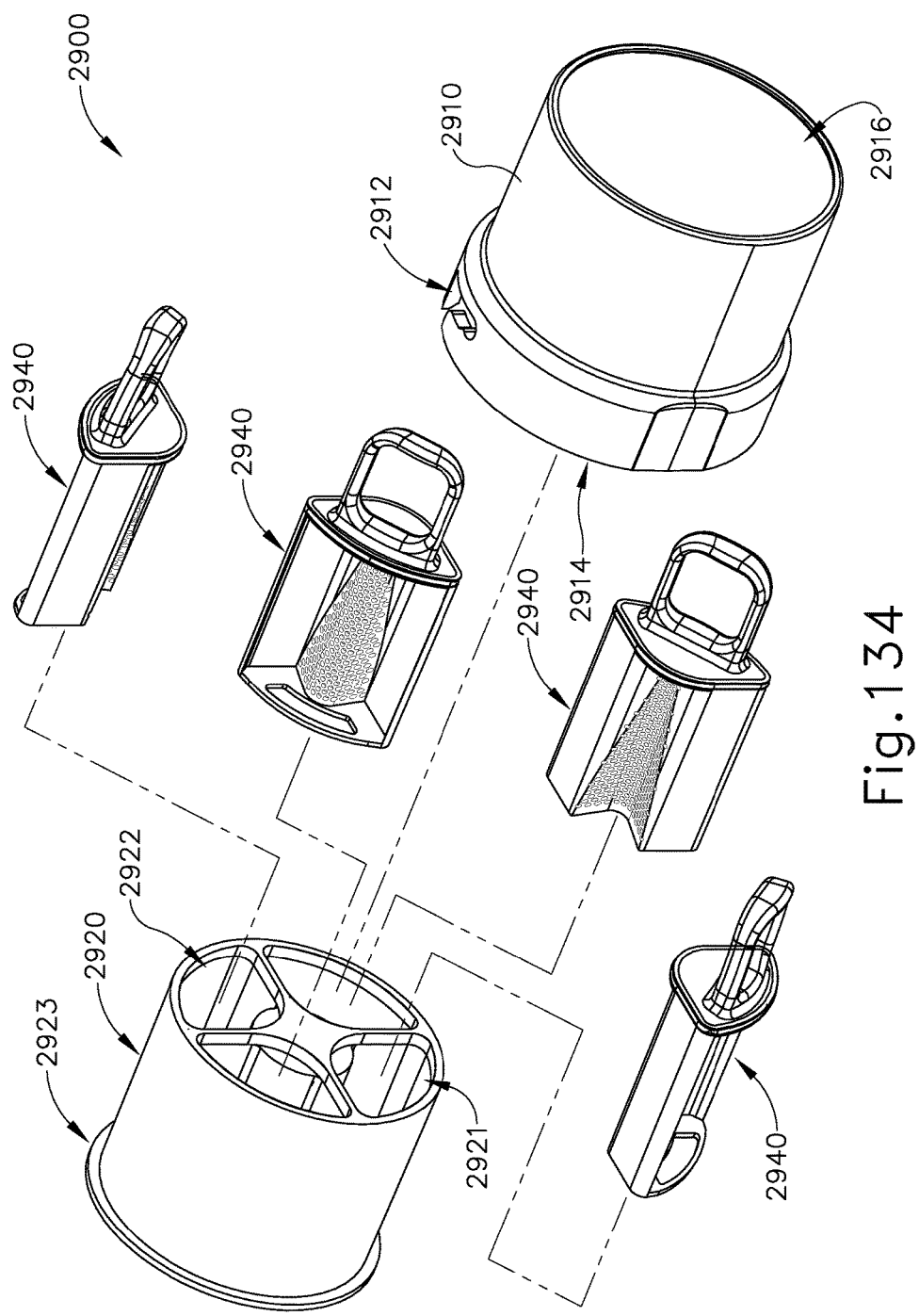
Figure 135:
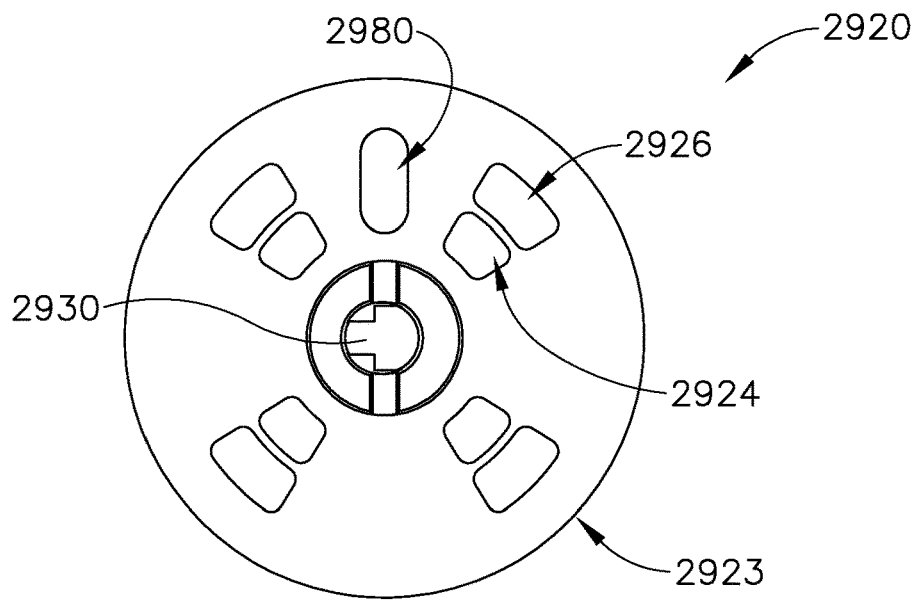
Figure 136:
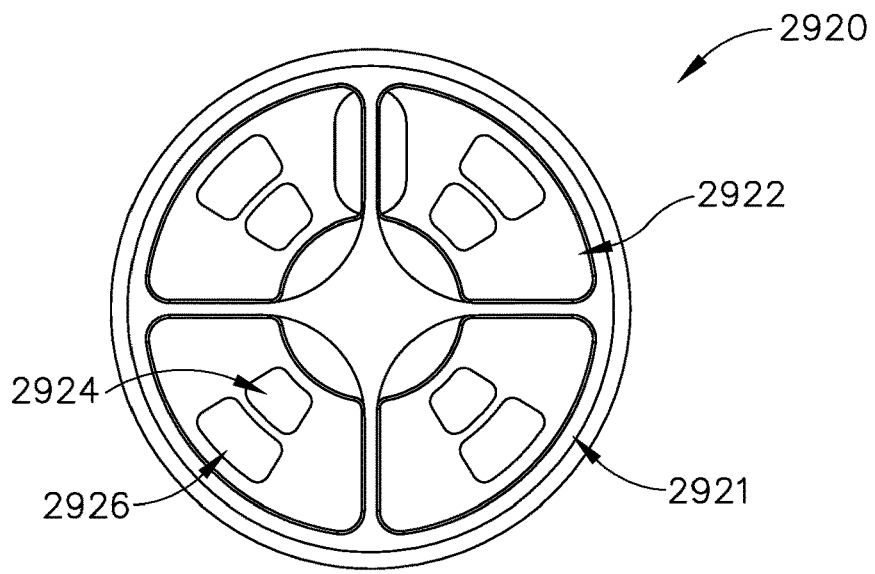
Figure 137:
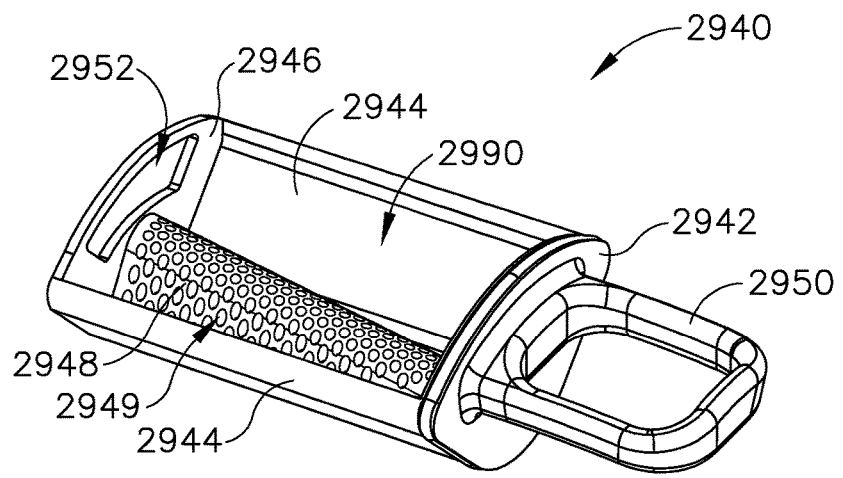
Figure 138:
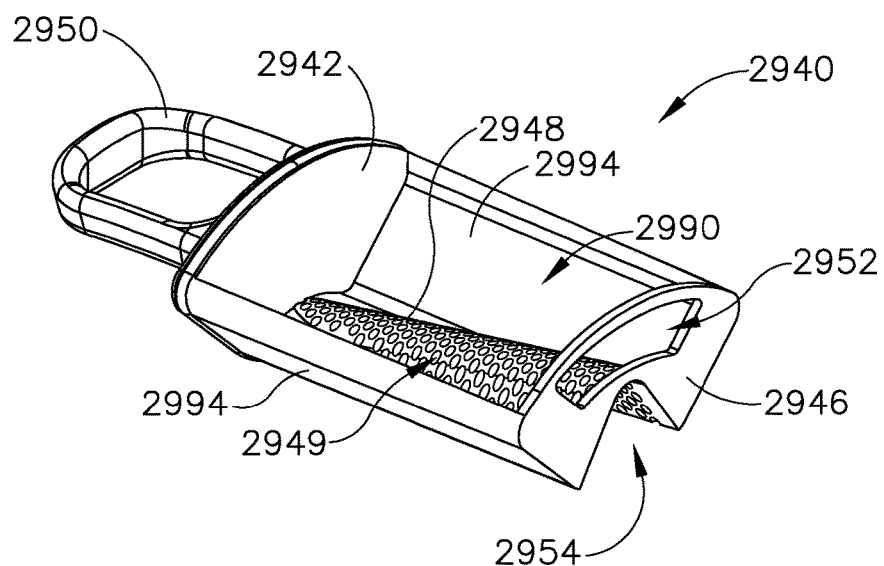
Figure 139:
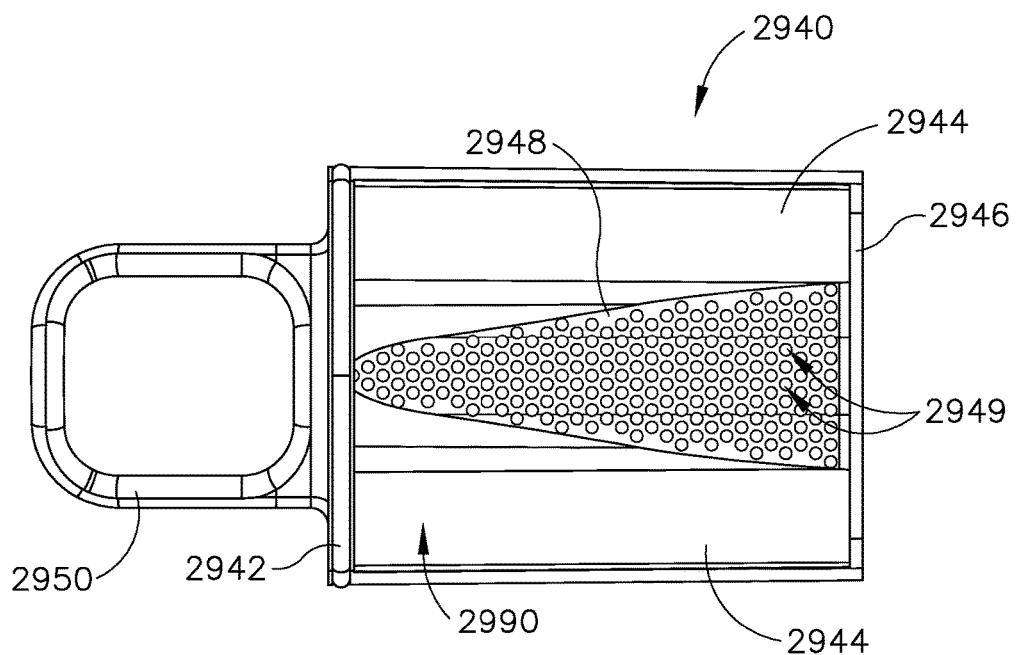
Figure 140:
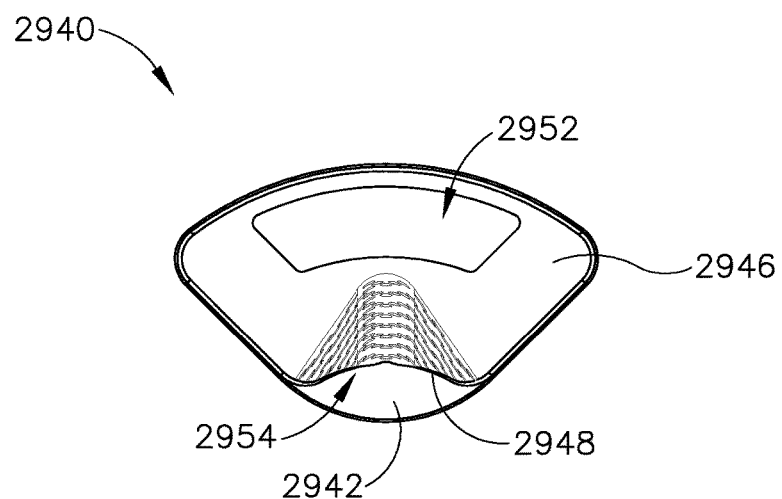
Figure 141:
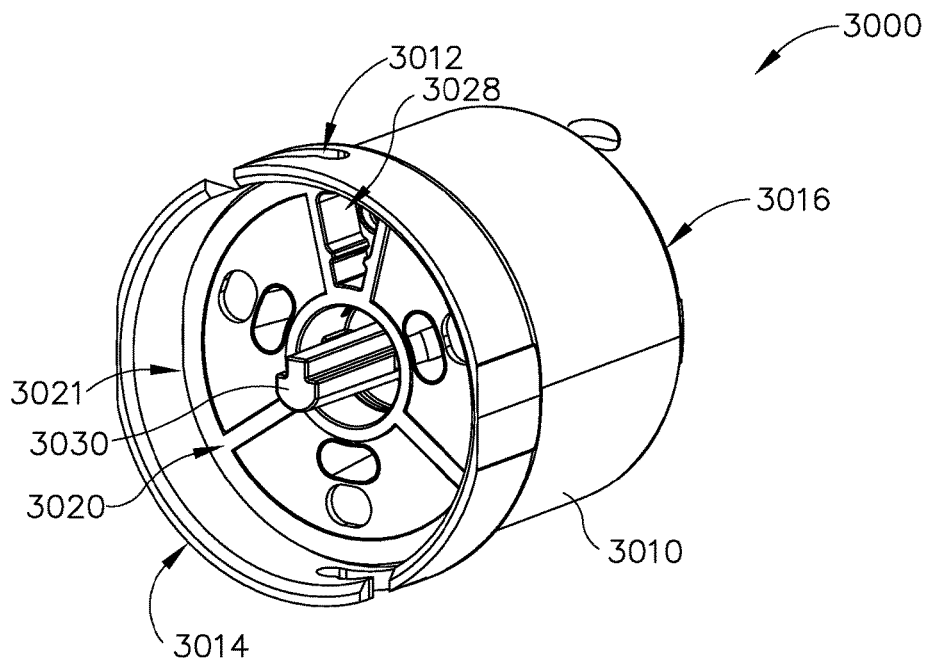
Figure 142:
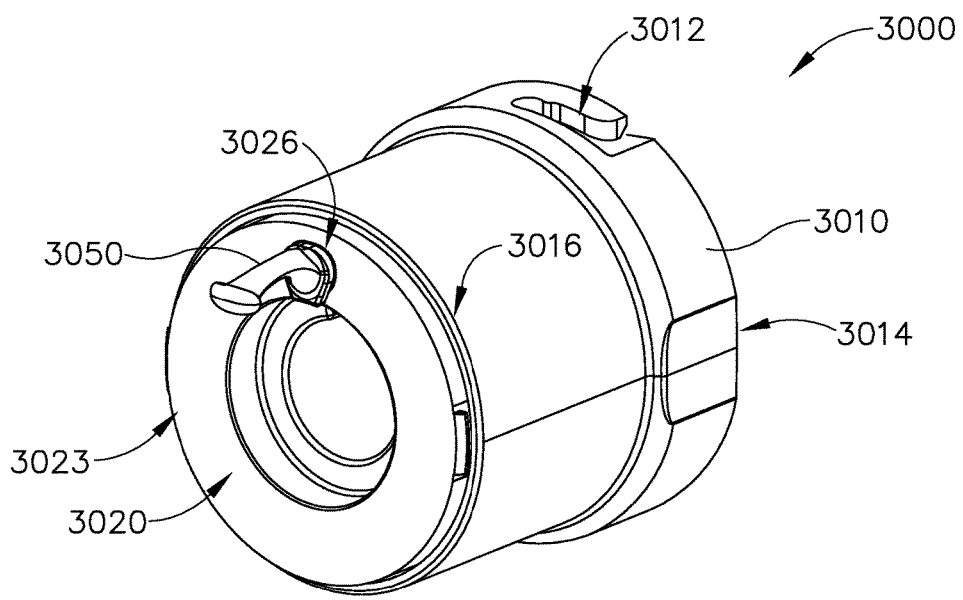
Figure 143:
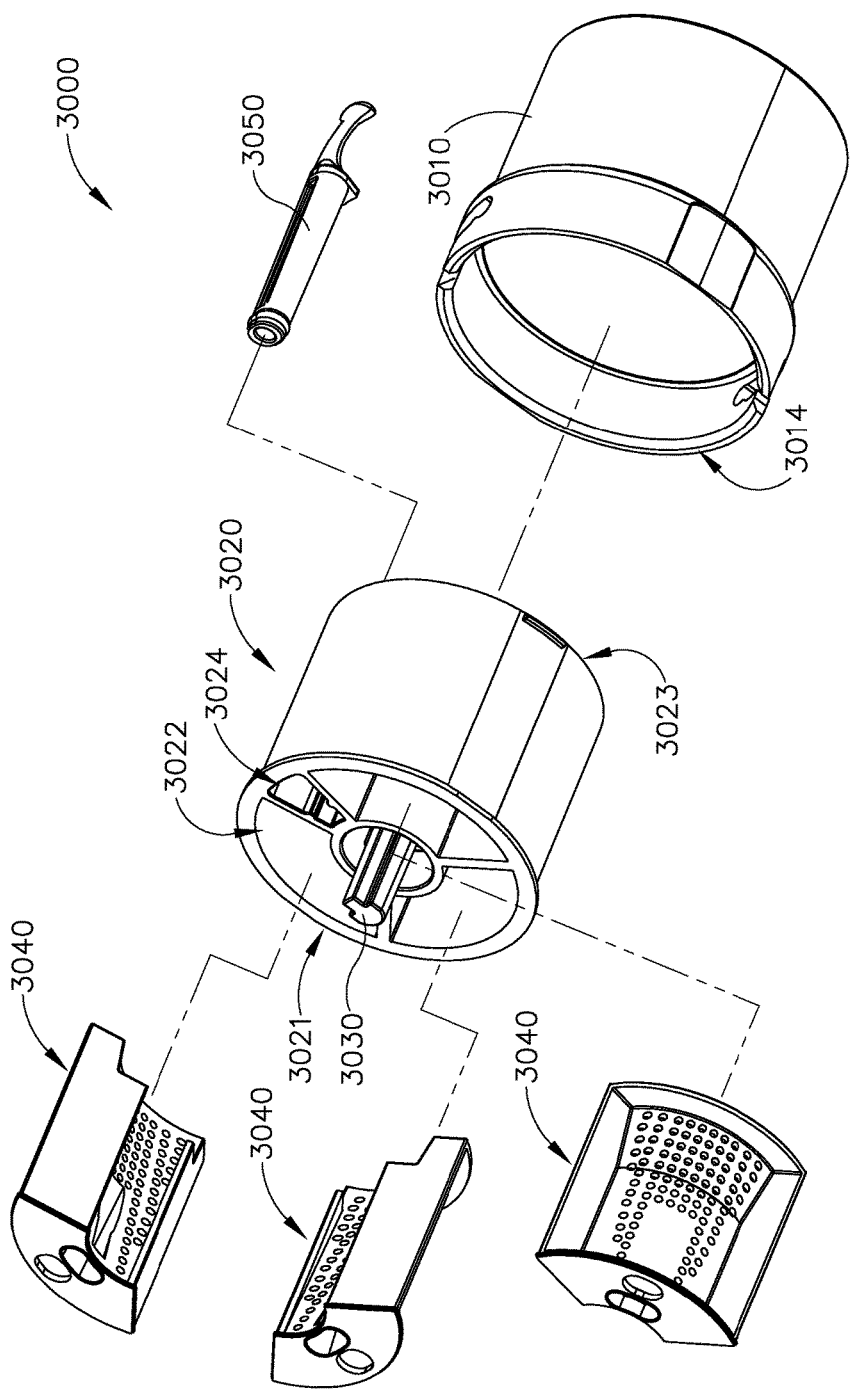
Figure 144:
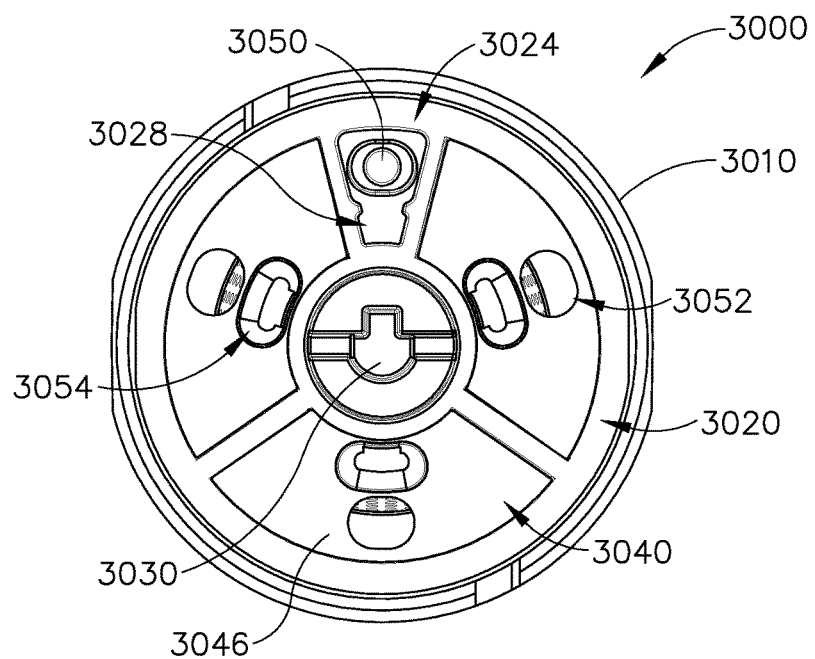
Figure 145:
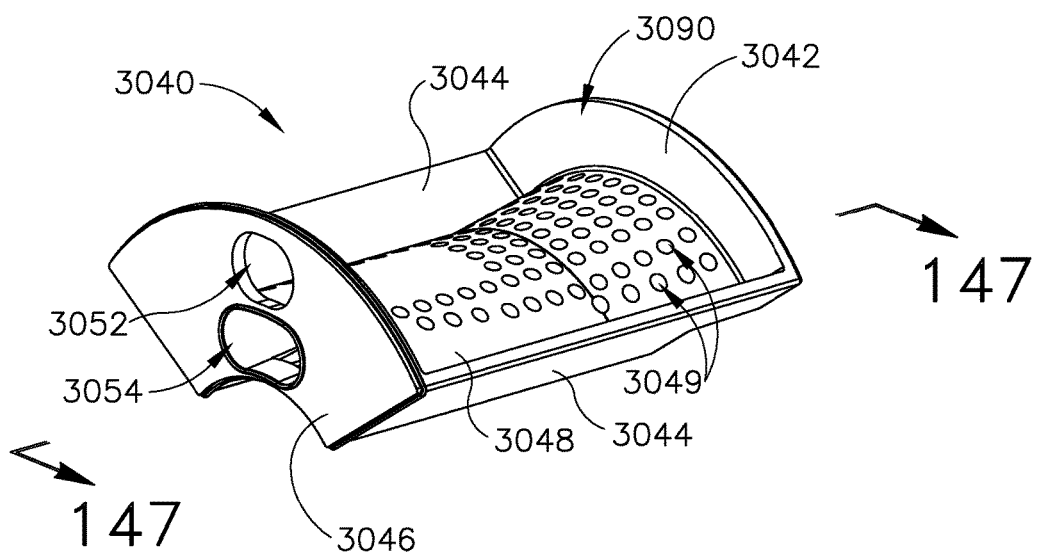
Figure 146:
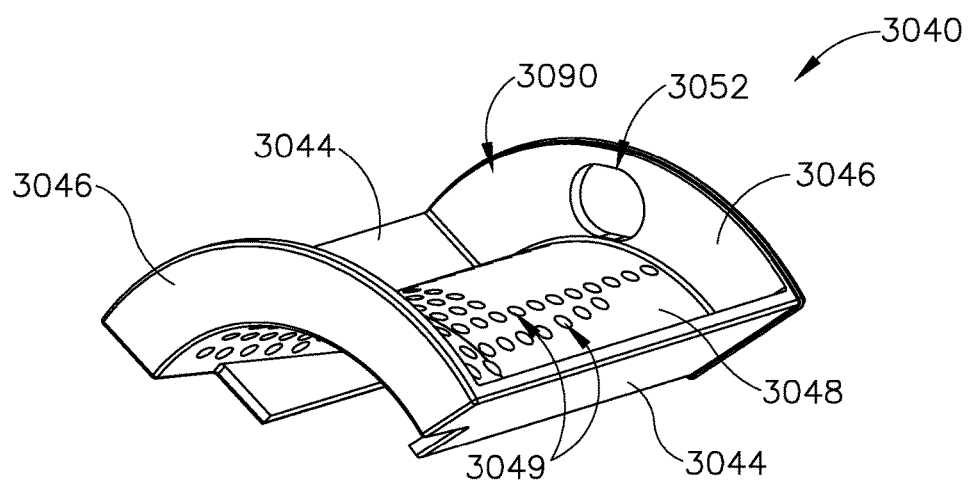
Figure 147:
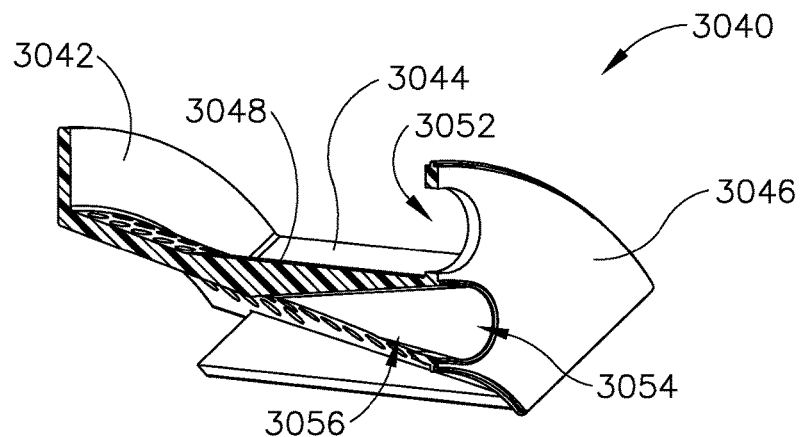
Figure 148:
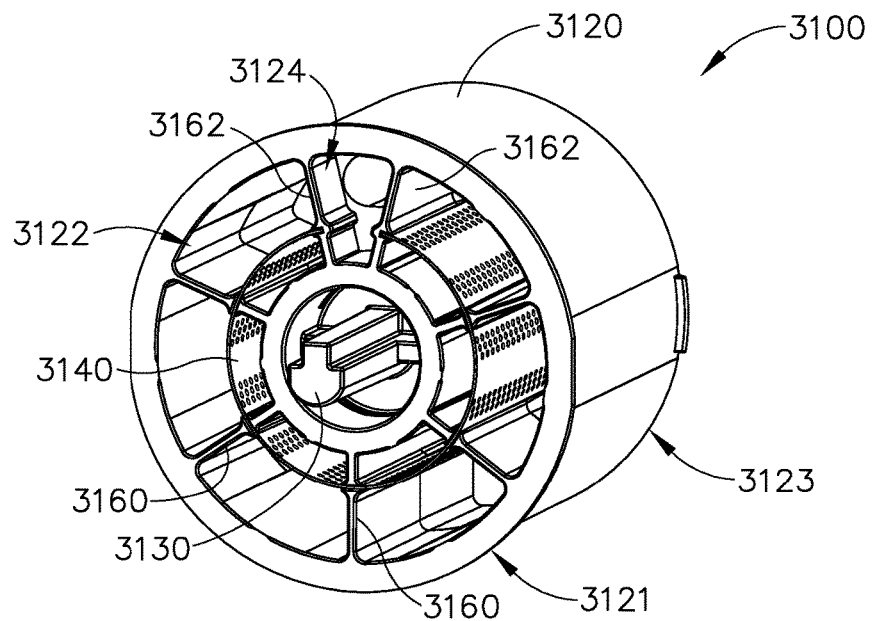
Figure 149:
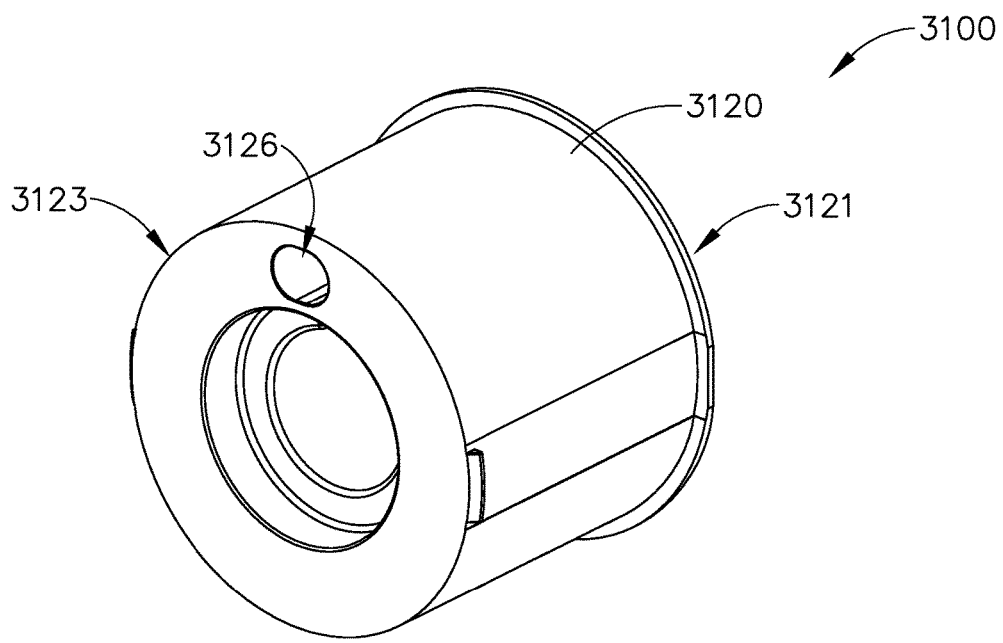
Figure 150:
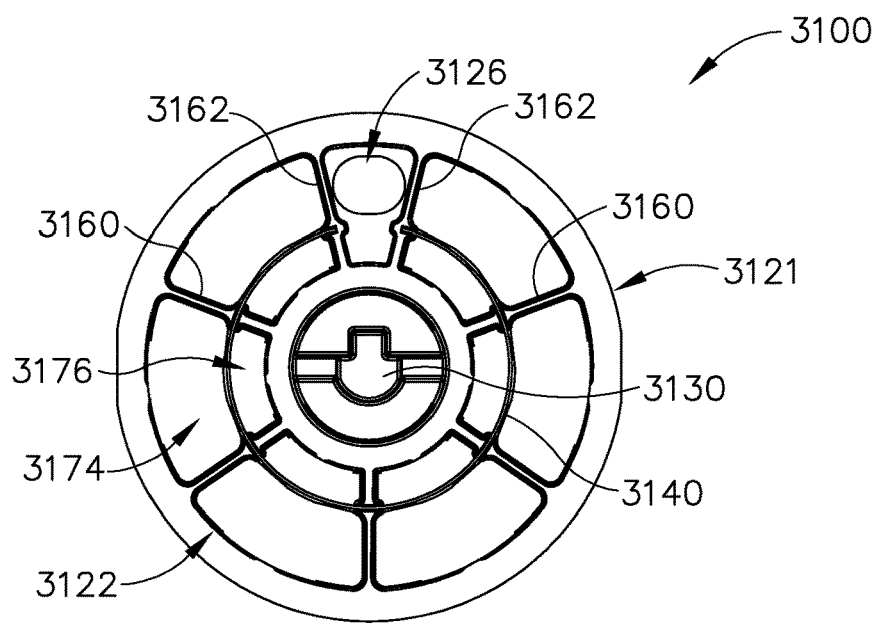
Figure 151:
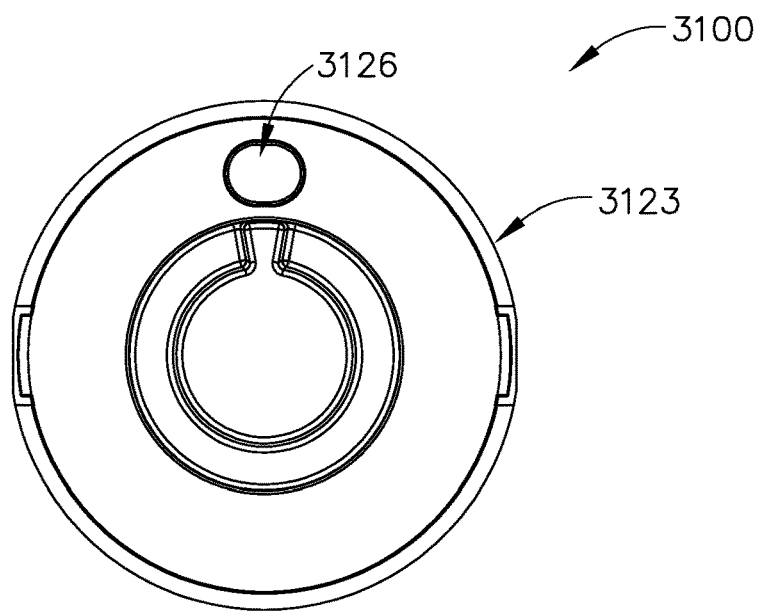
Figure 152:
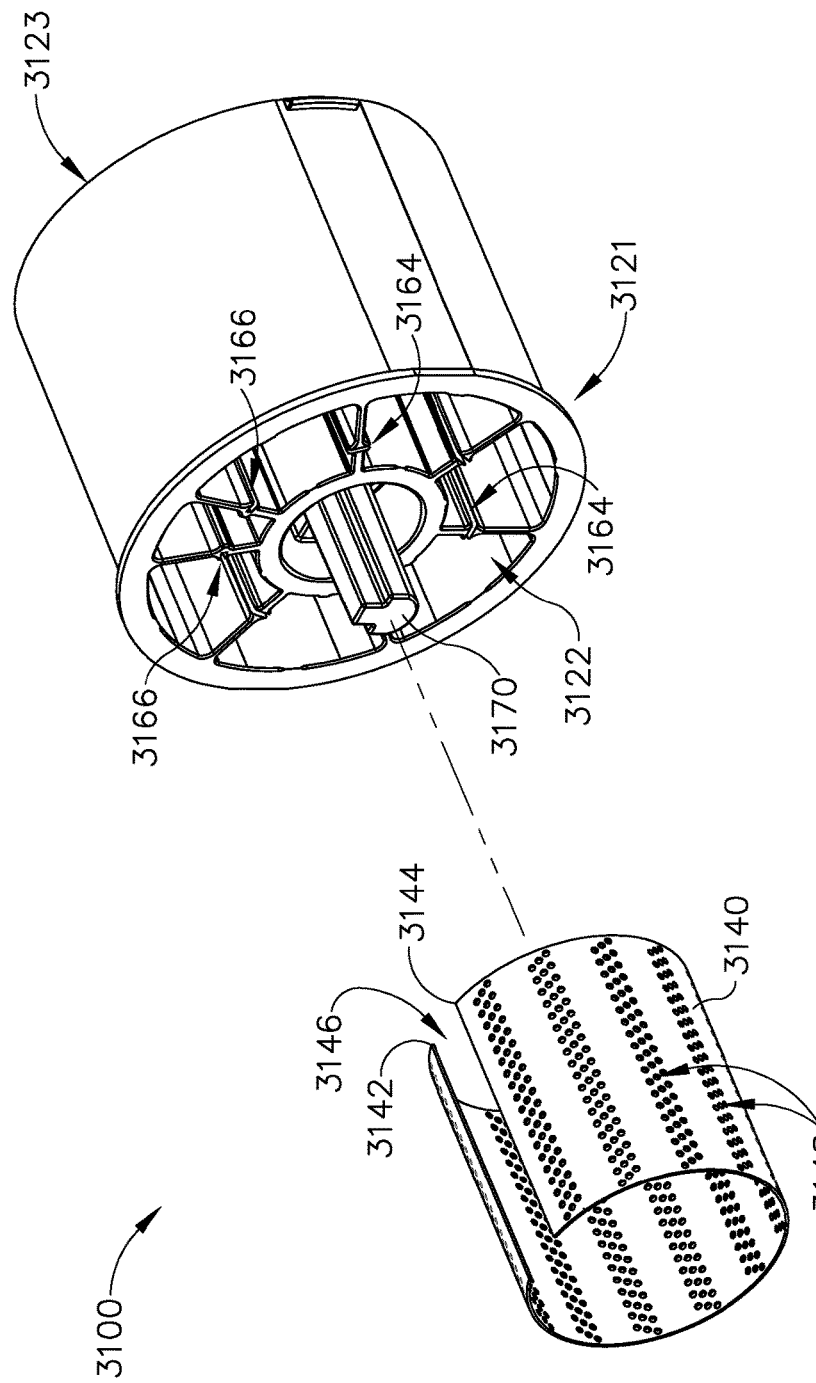
Figure 153:
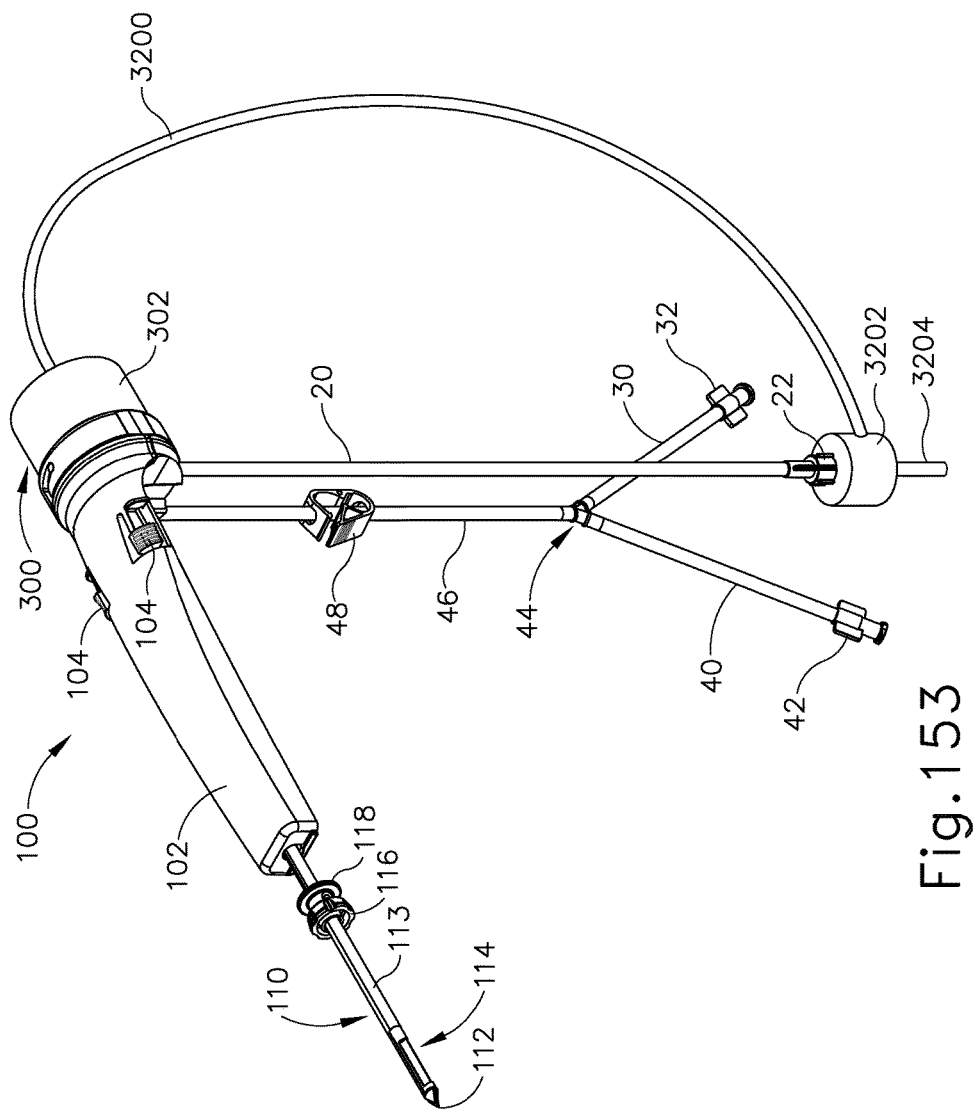
Figure 154:
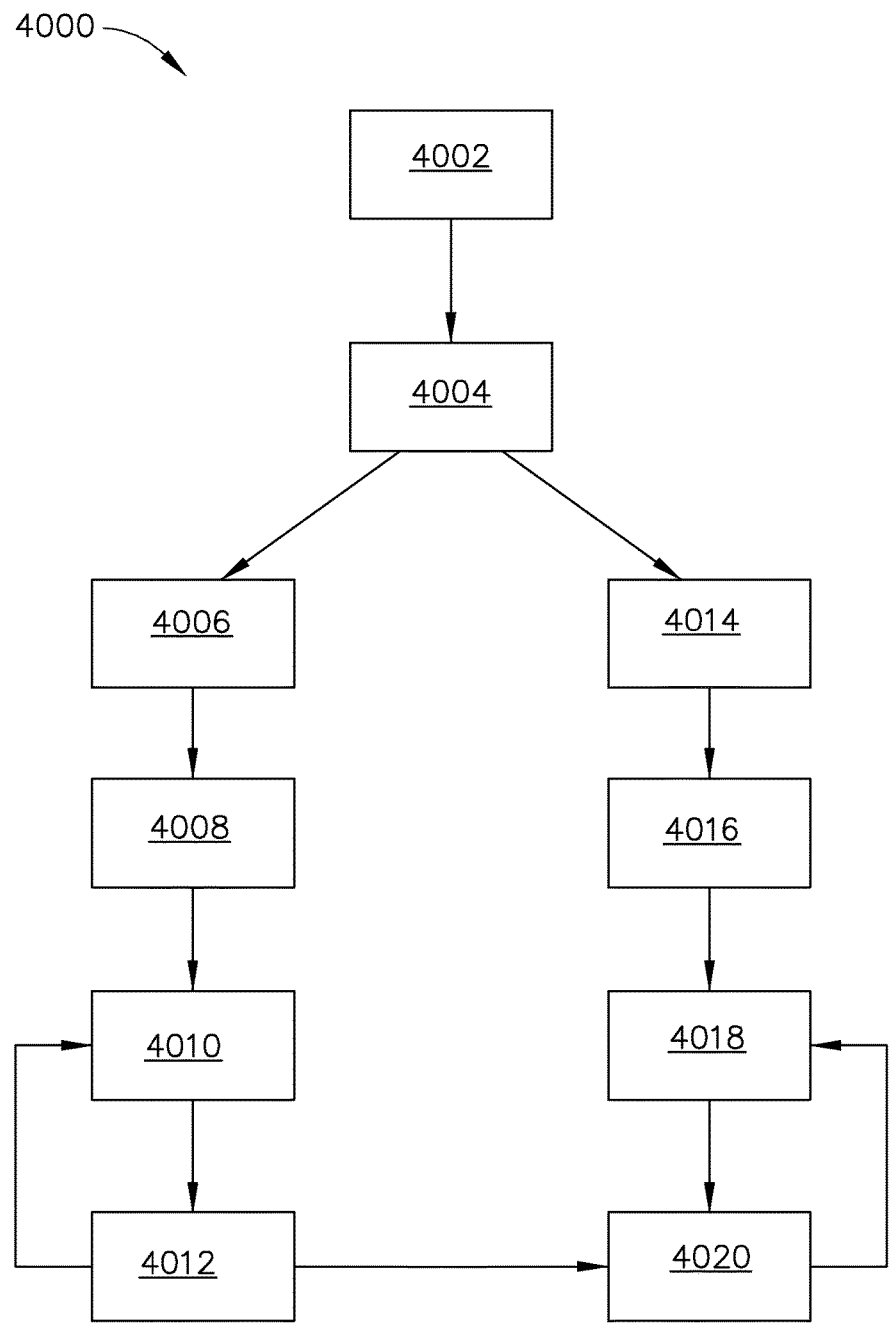
Figure 155:
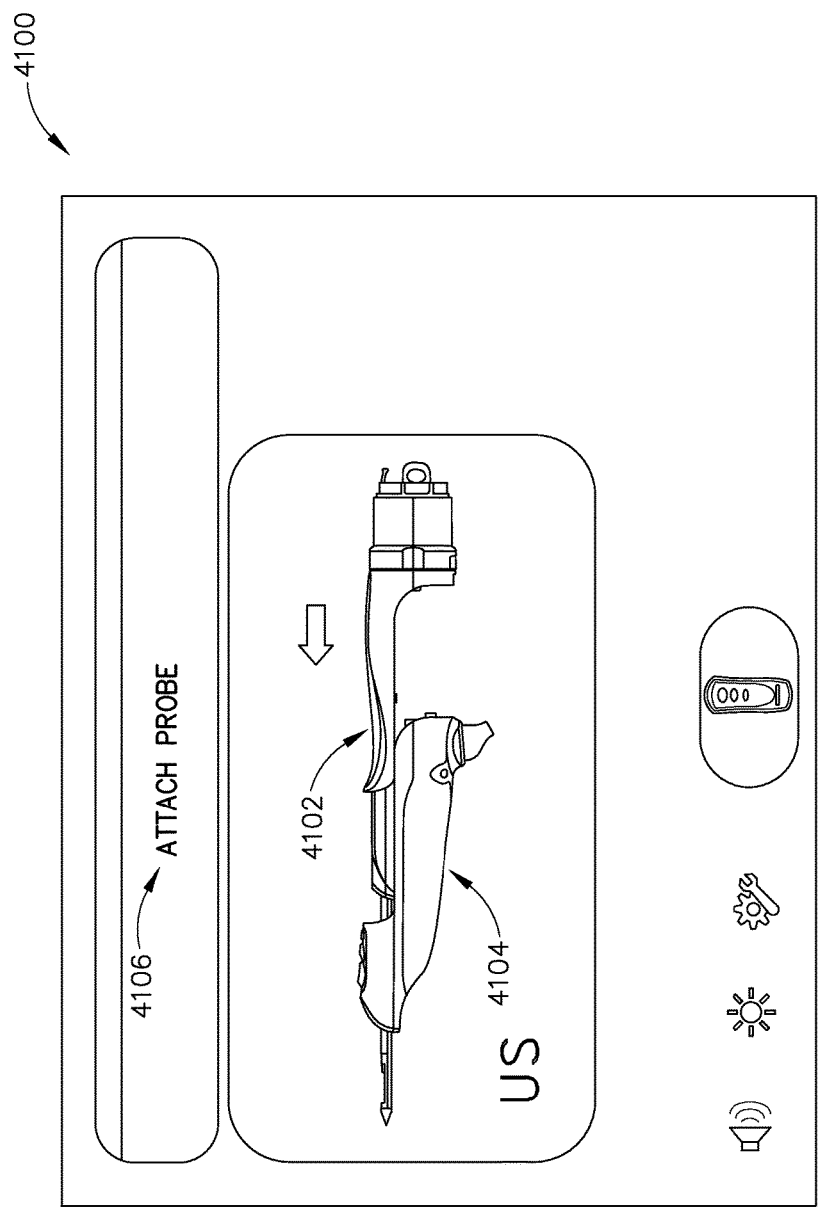
Figure 156:
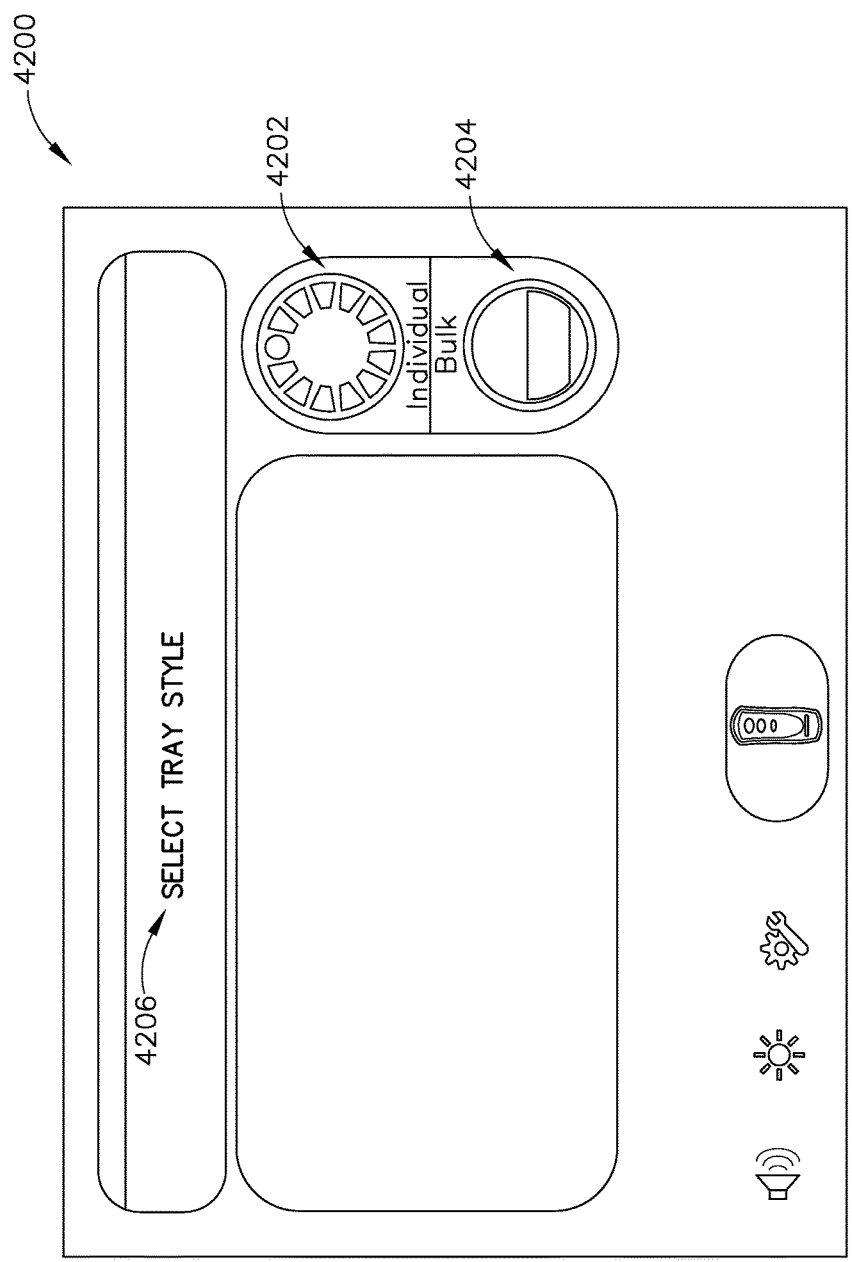
Figure 157:
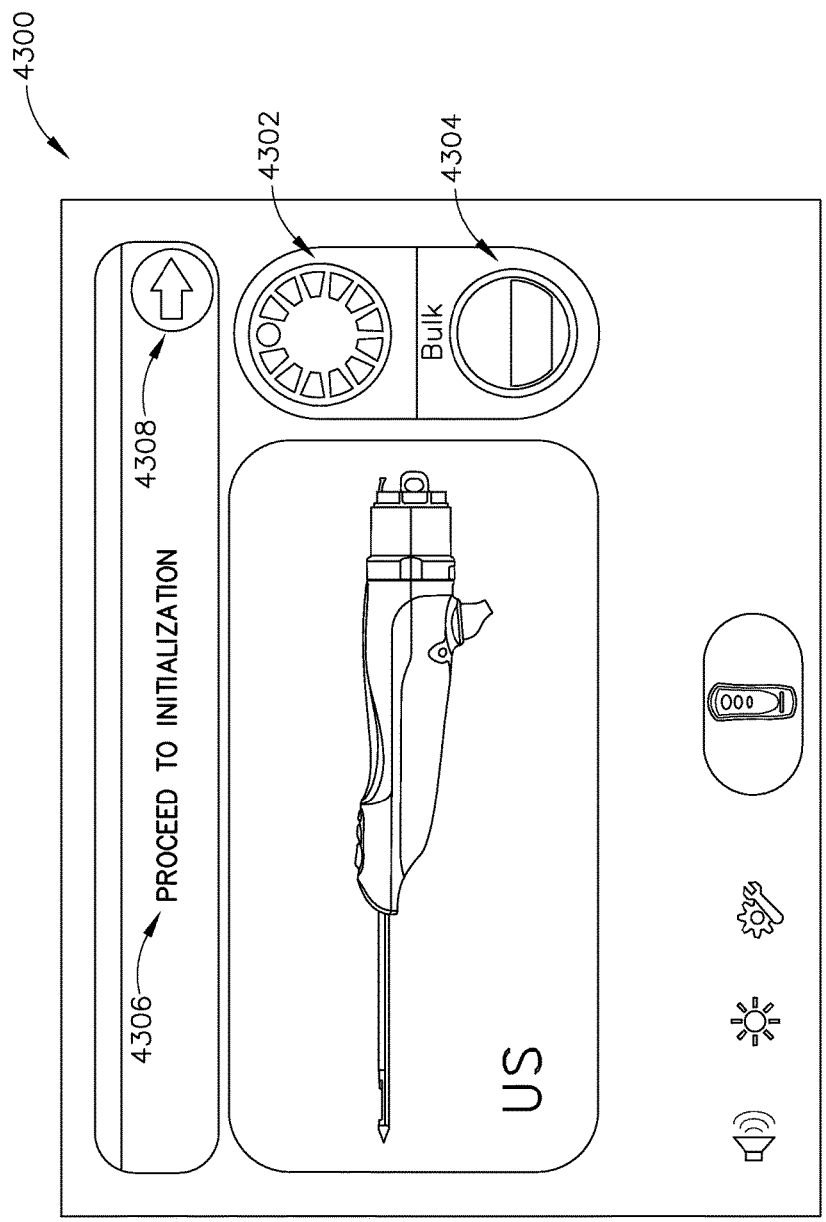
Figure 158:
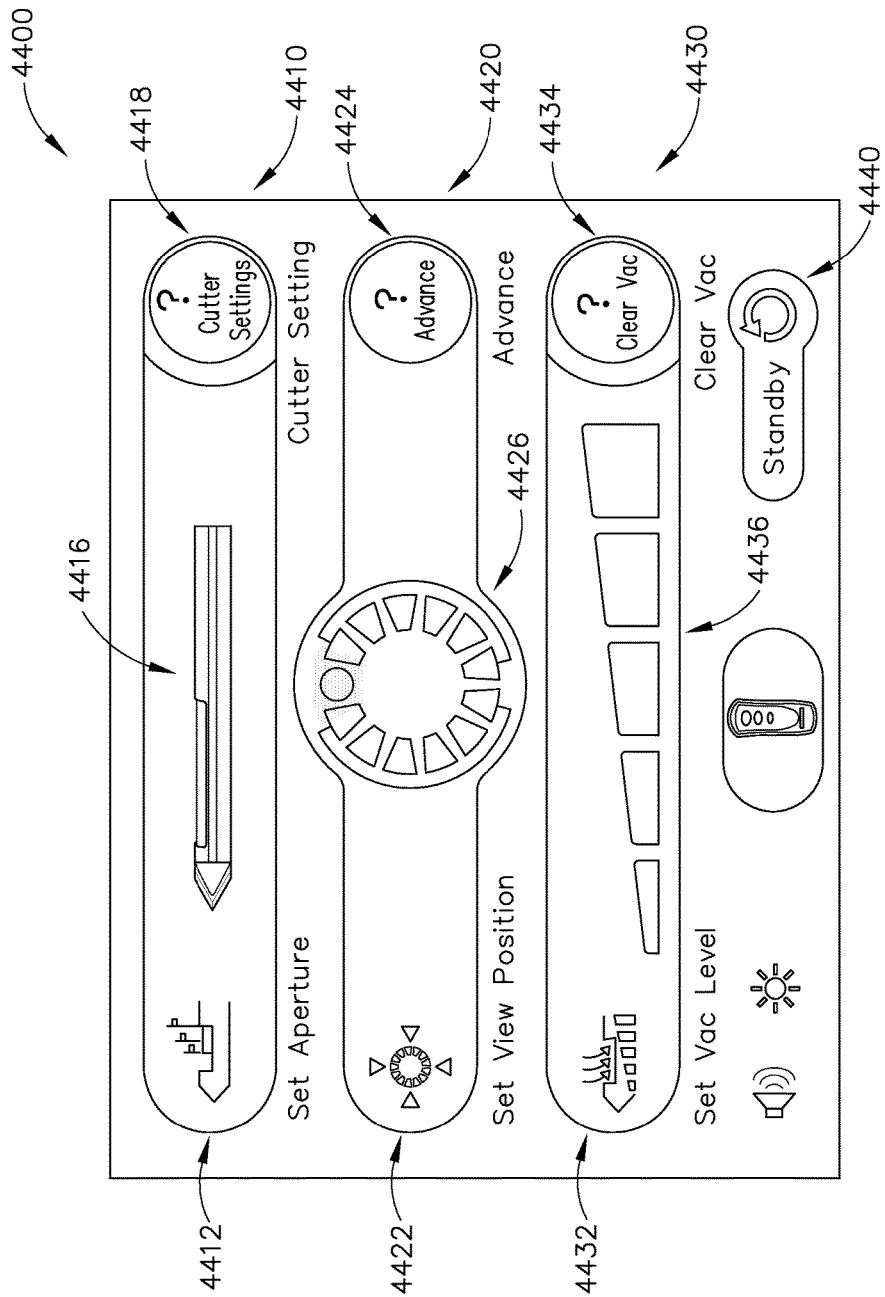
Figure 159:
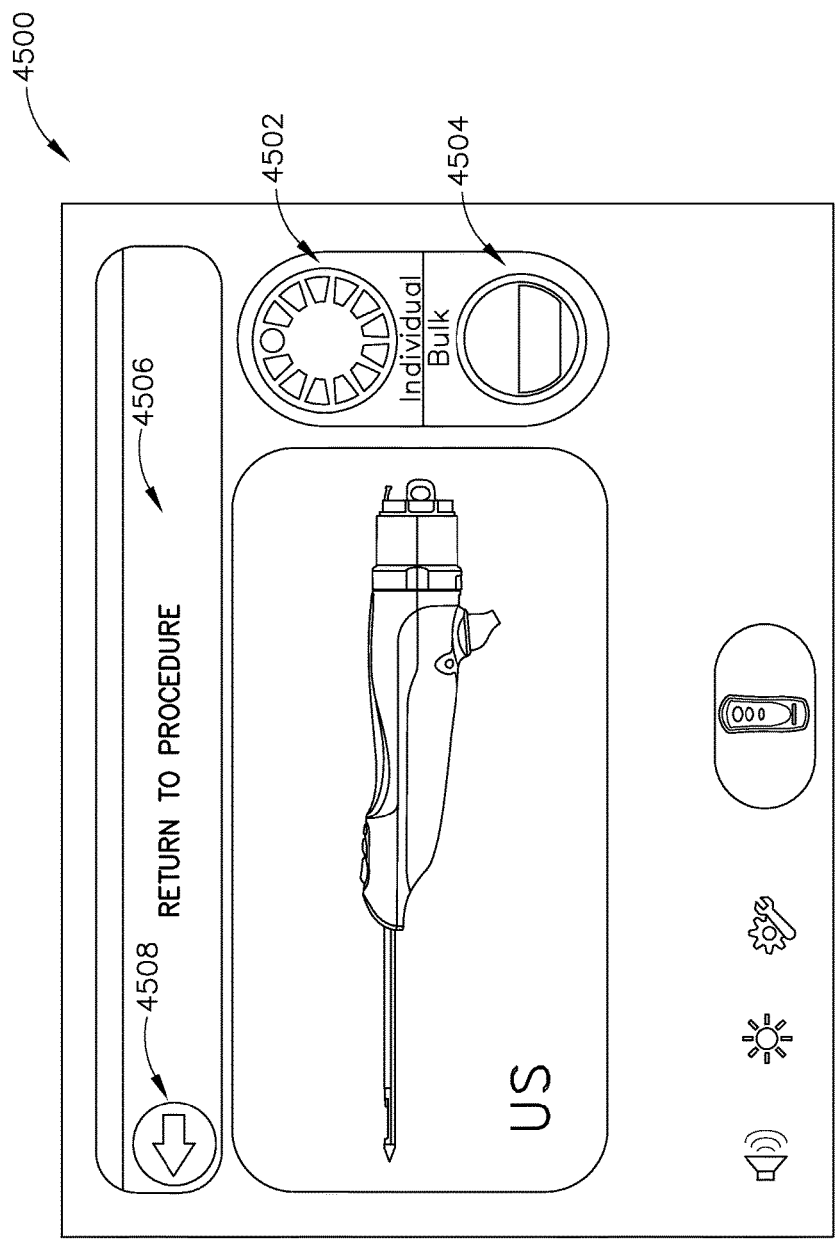
Figure 160:
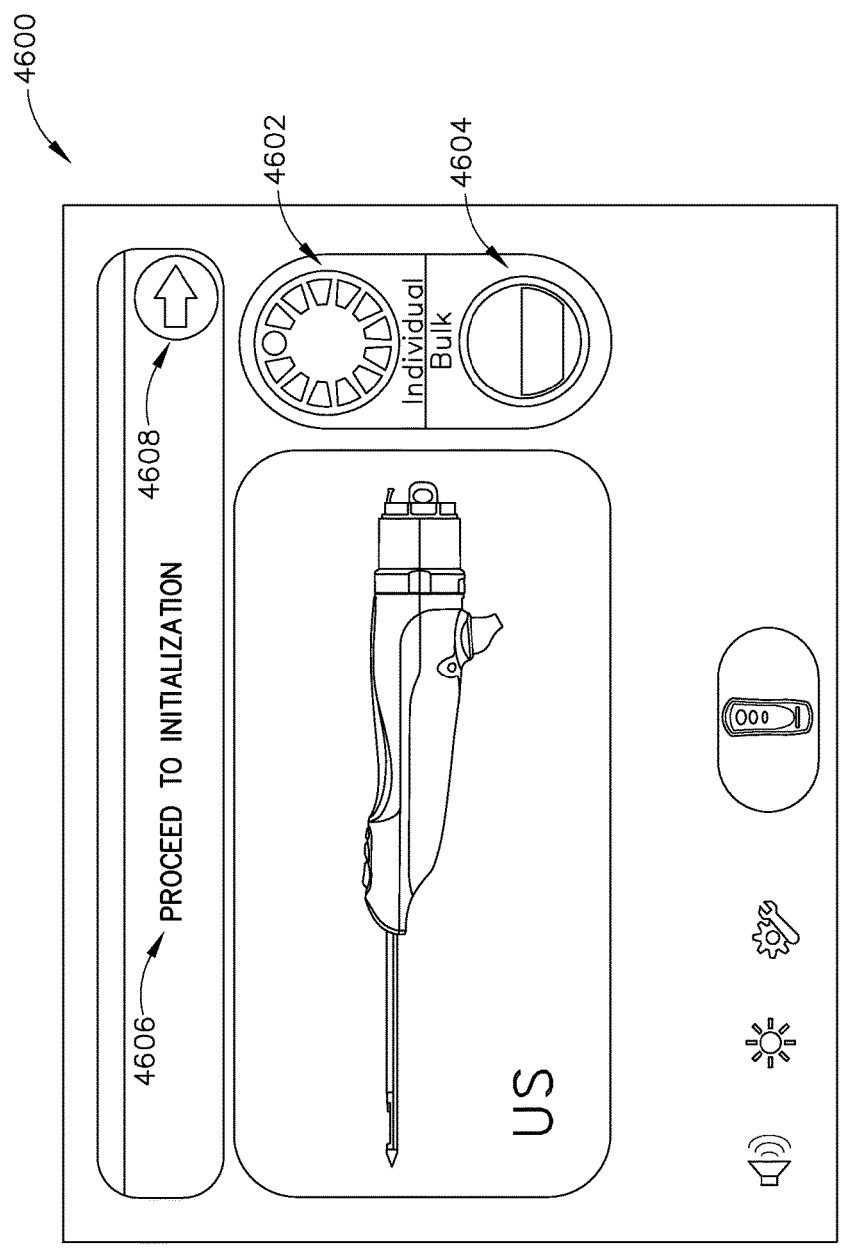
Figure 161:
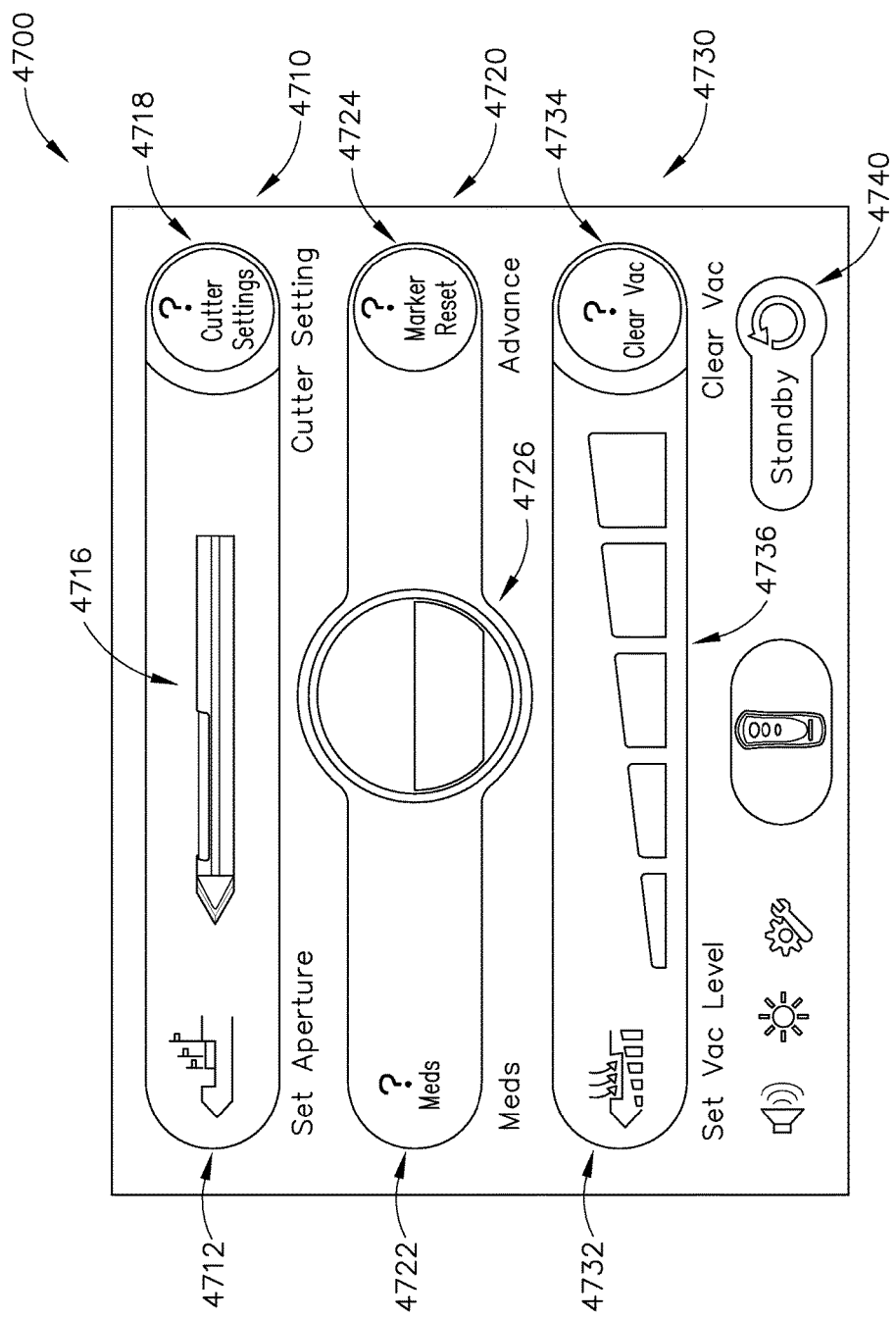
Figure 162:
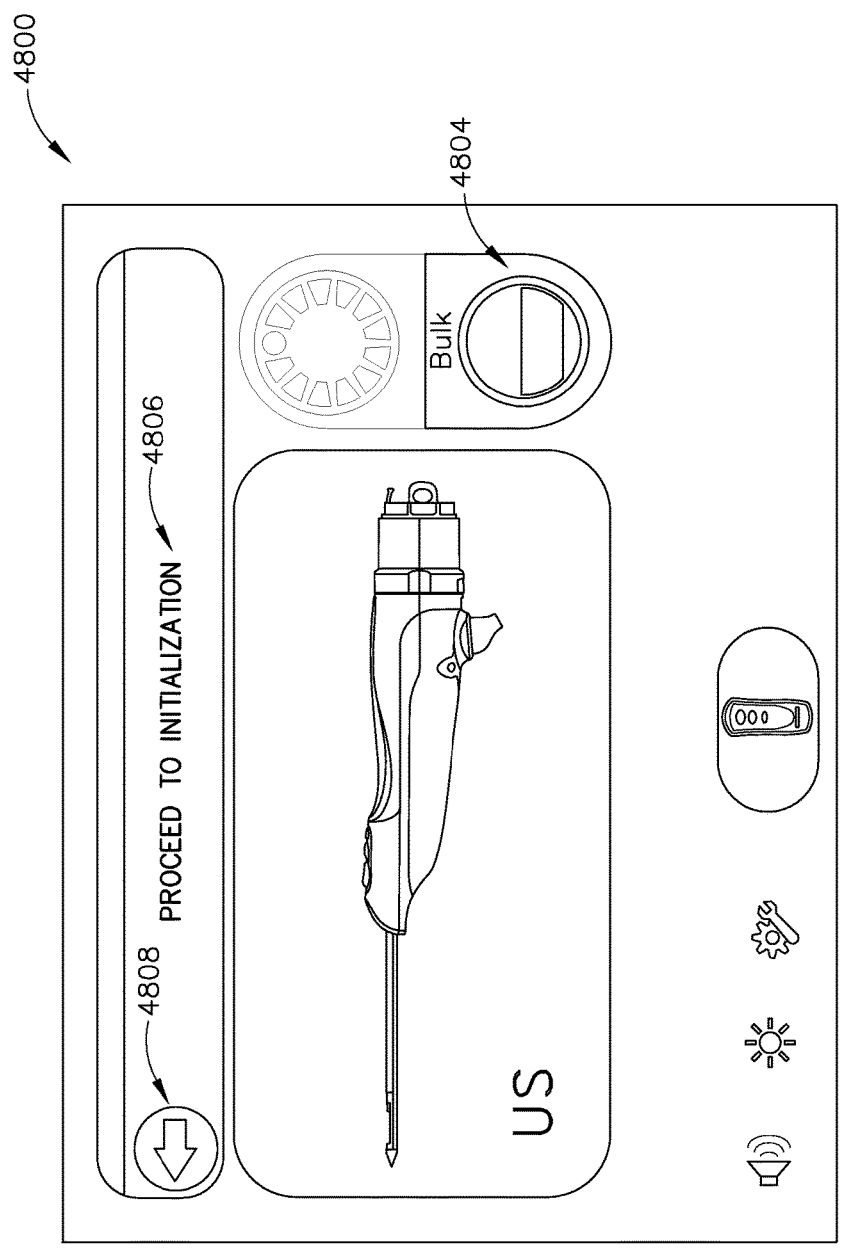
Figure 163:
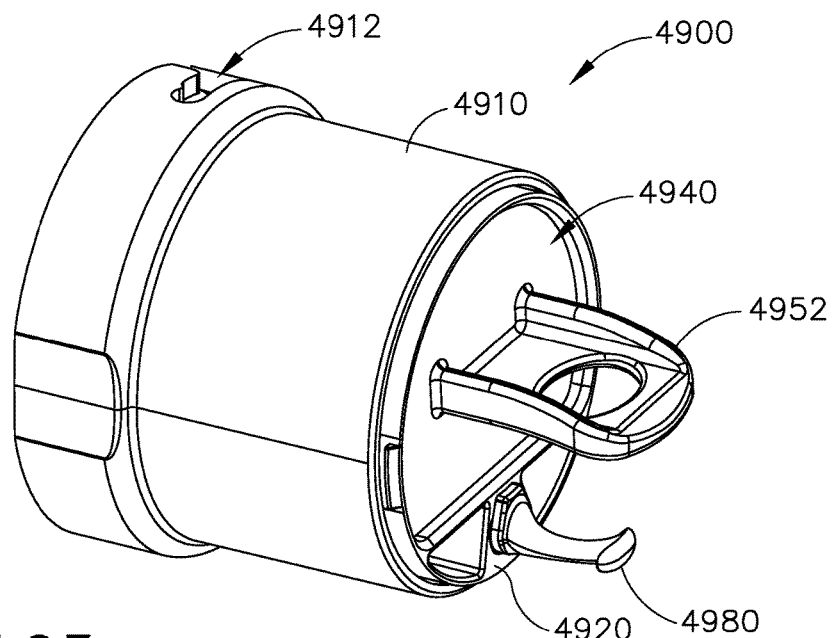
Figure 164:
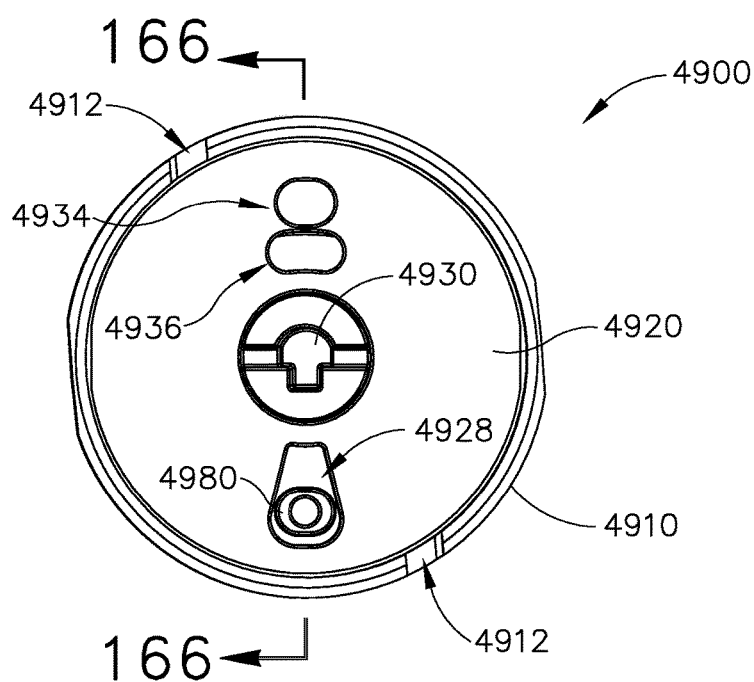
Figure 165:
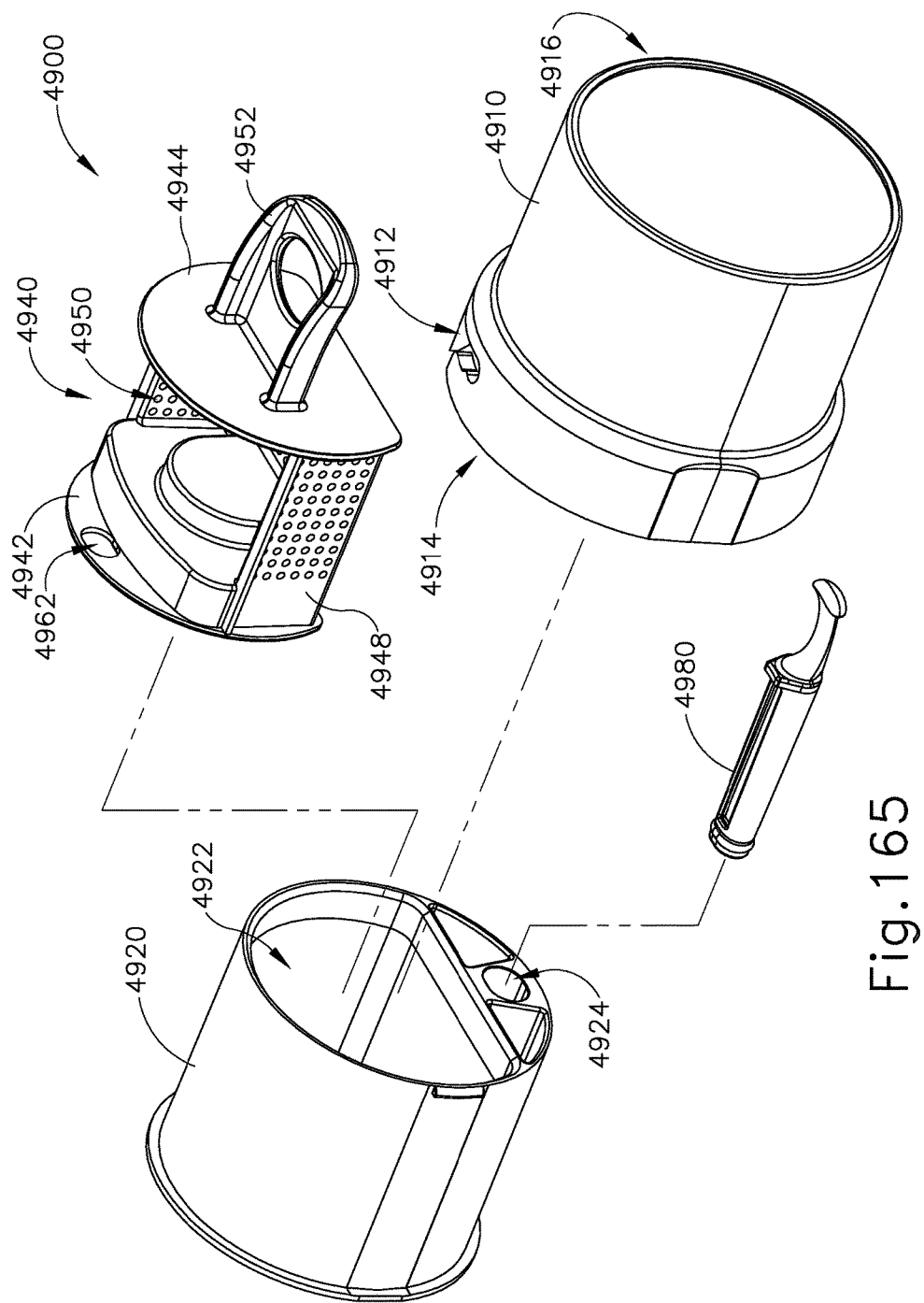
Figure 166:
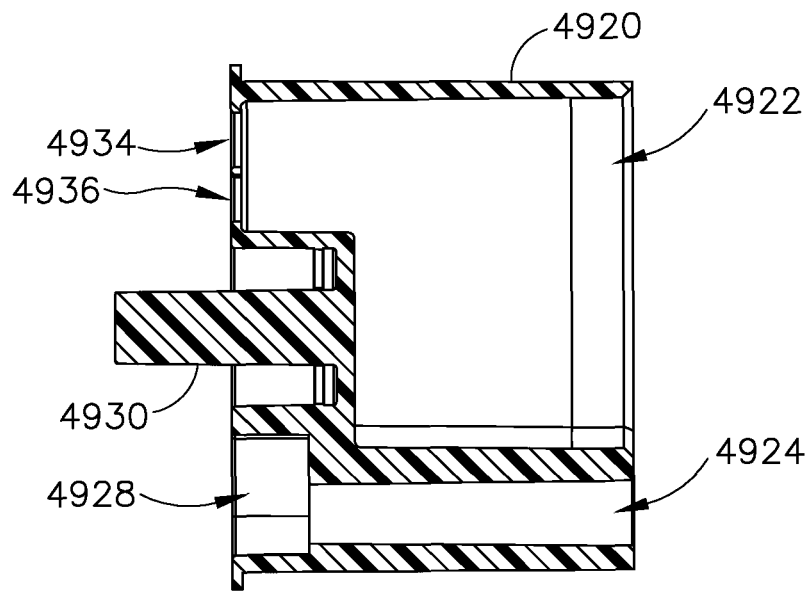
Figure 167:
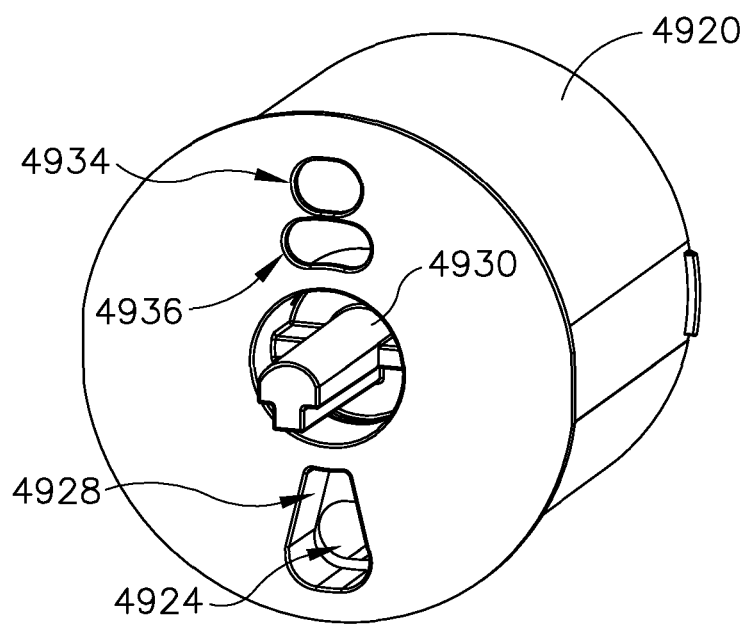
Figure 168:
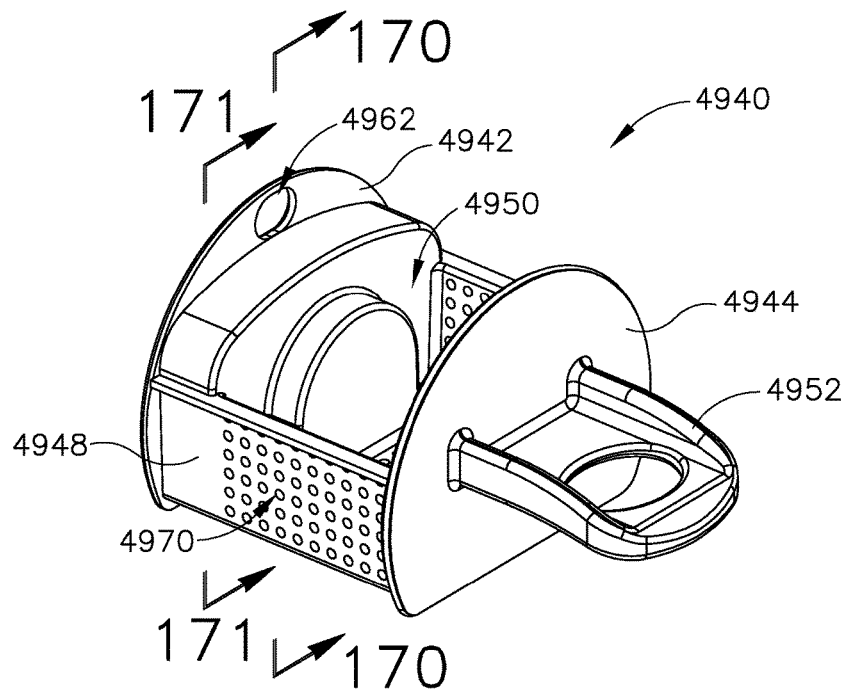
Figure 169:
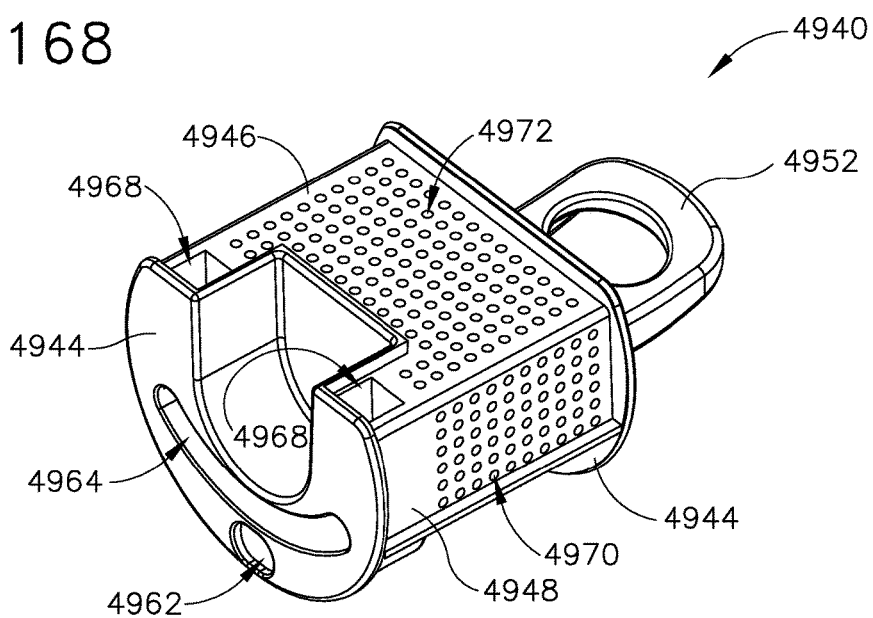
Figure 170:
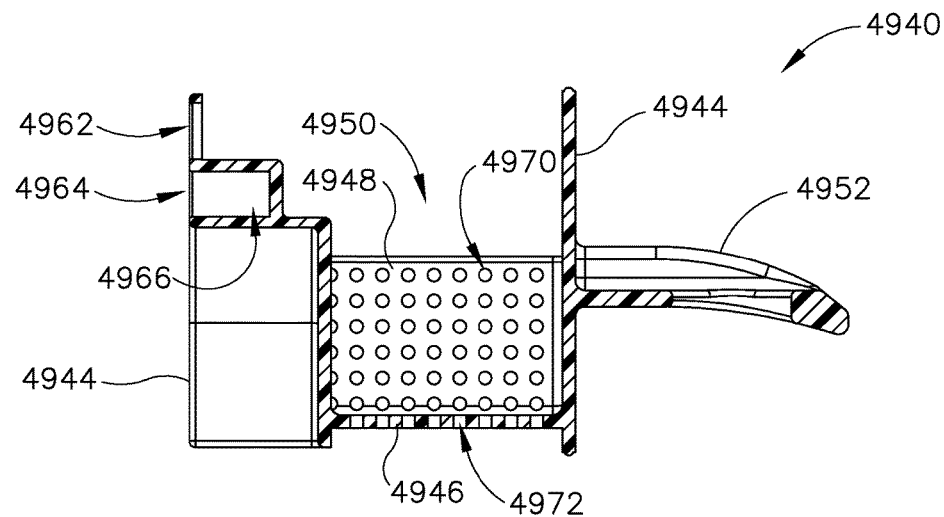
Figure 171:
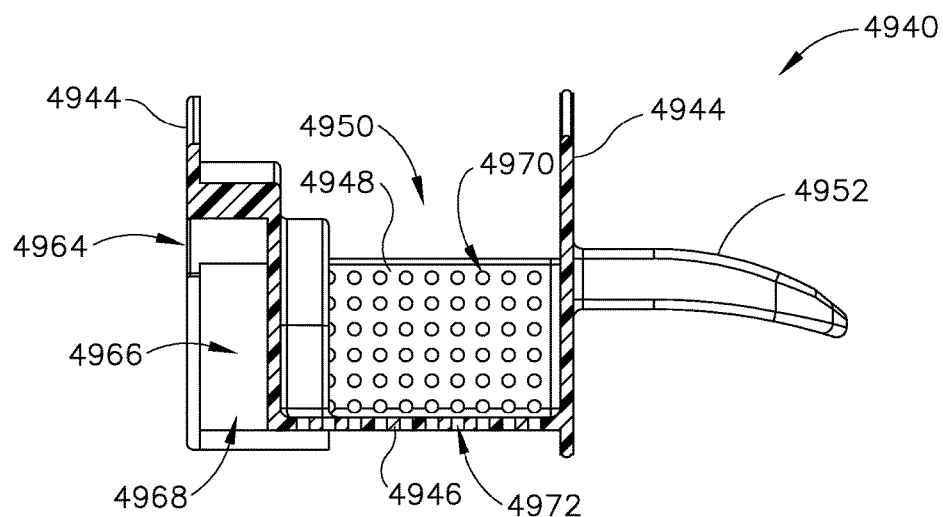
Figure 172:
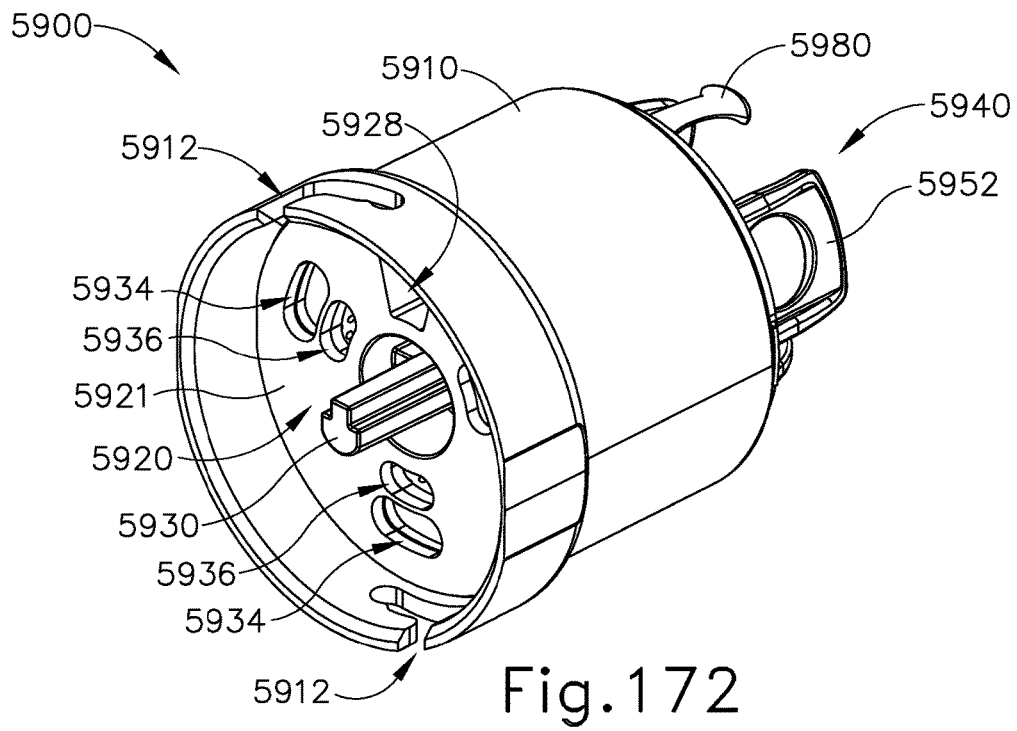
Figure 173:
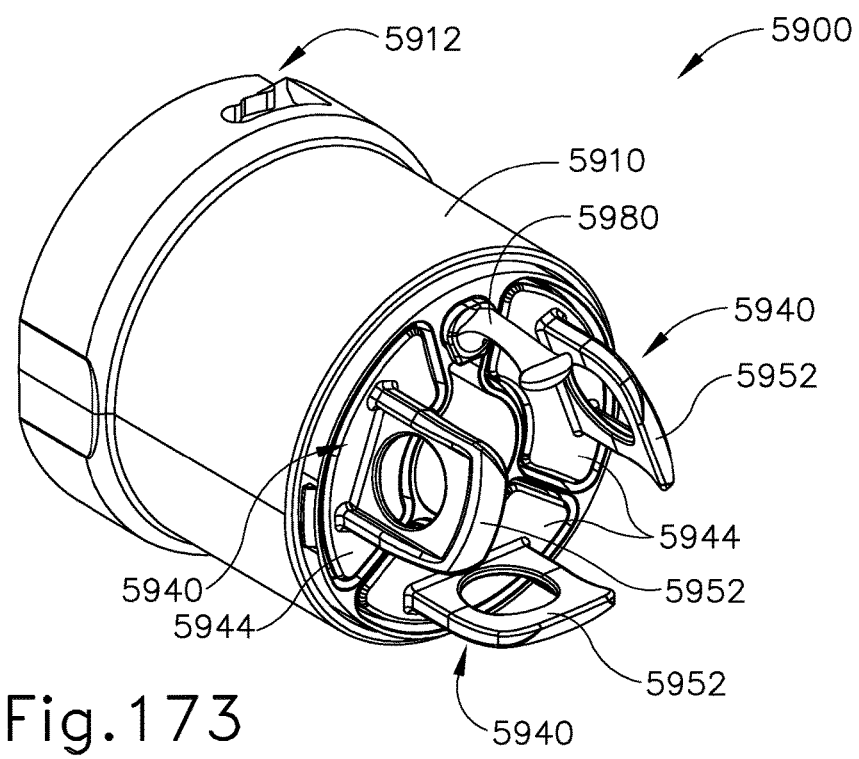
Figure 174:
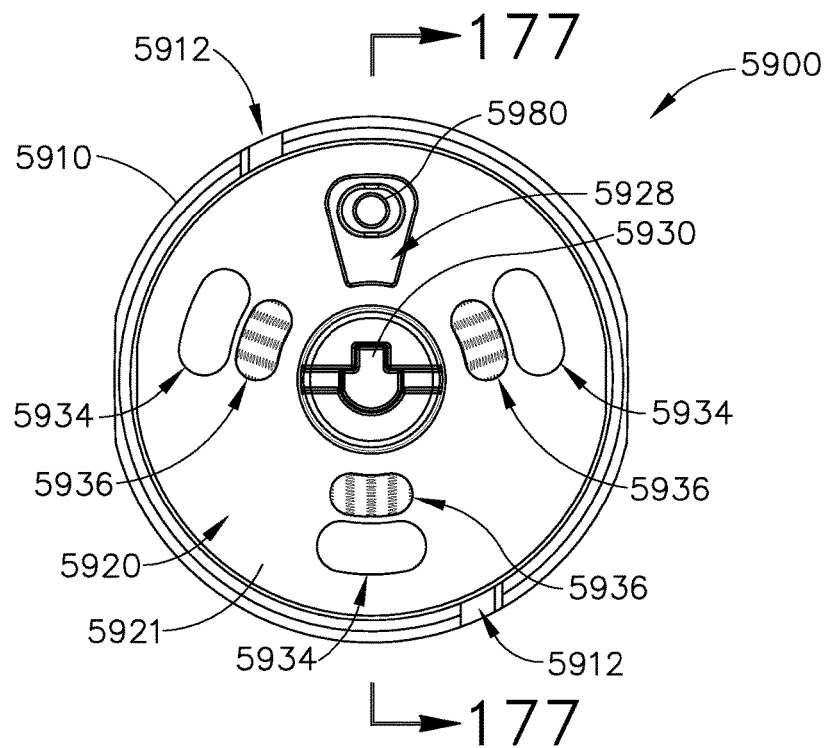
Figure 175:
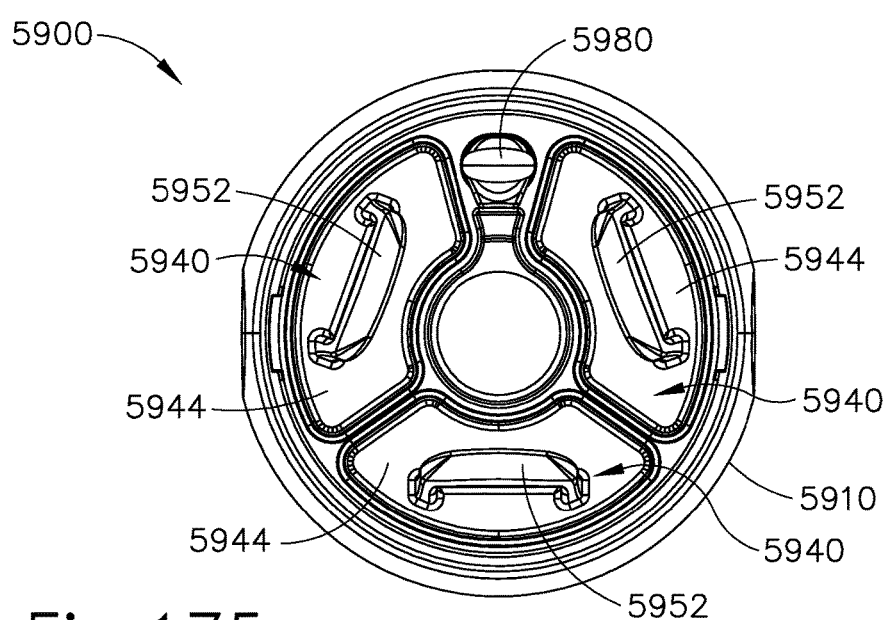
Figure 176:
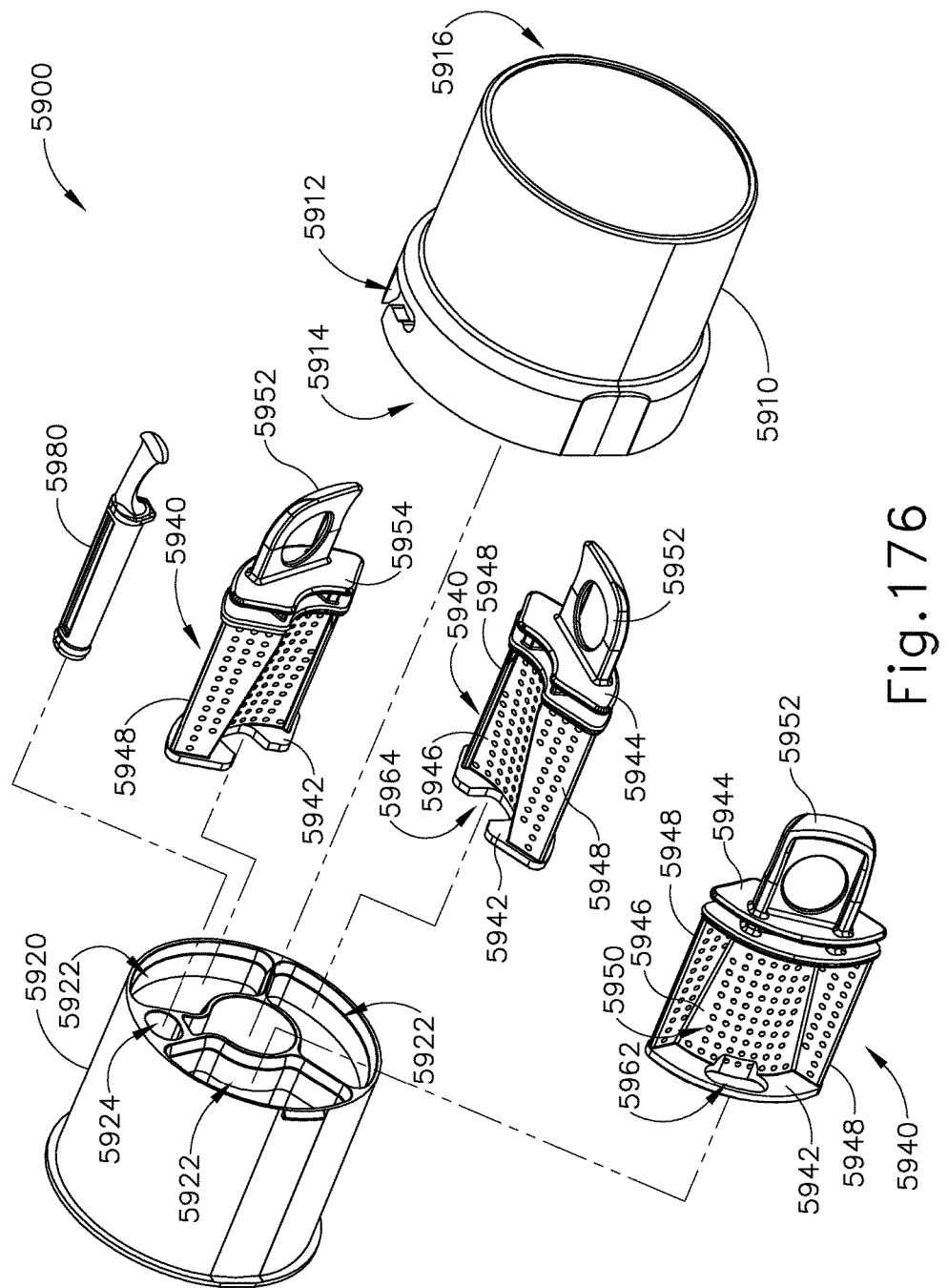
Figure 177:
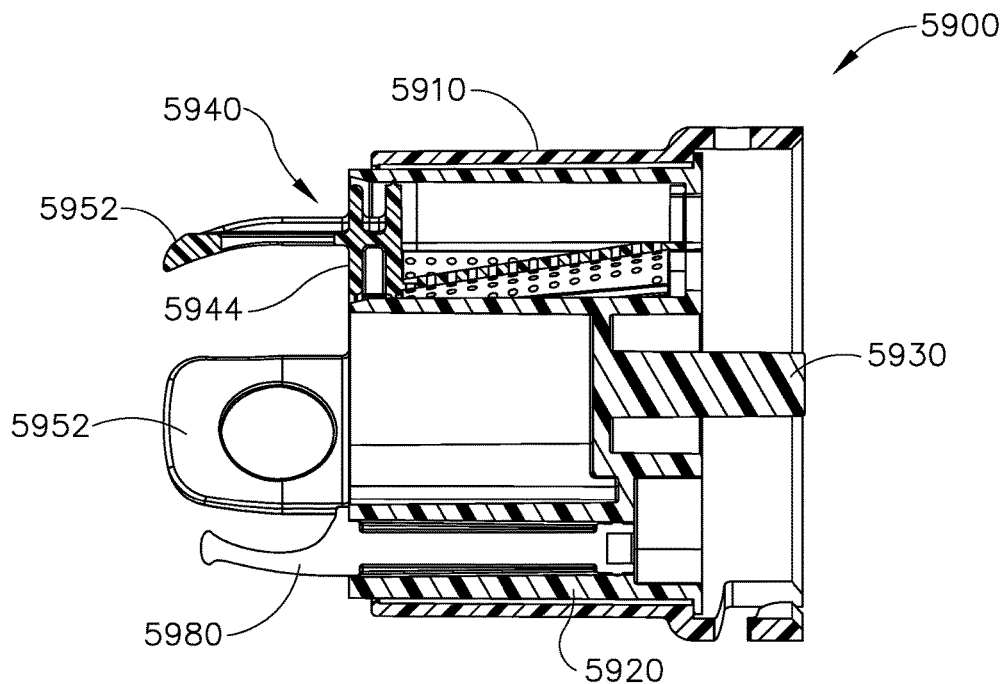
Figure 178:
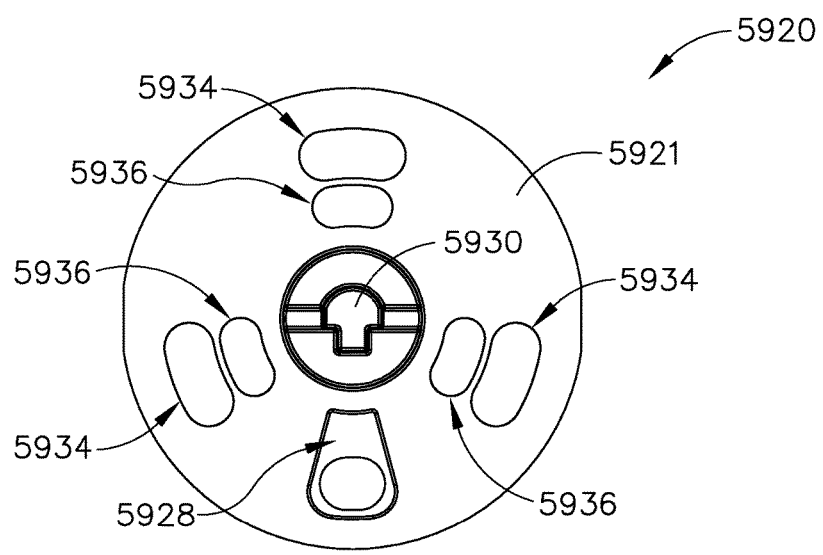
Figure 179:
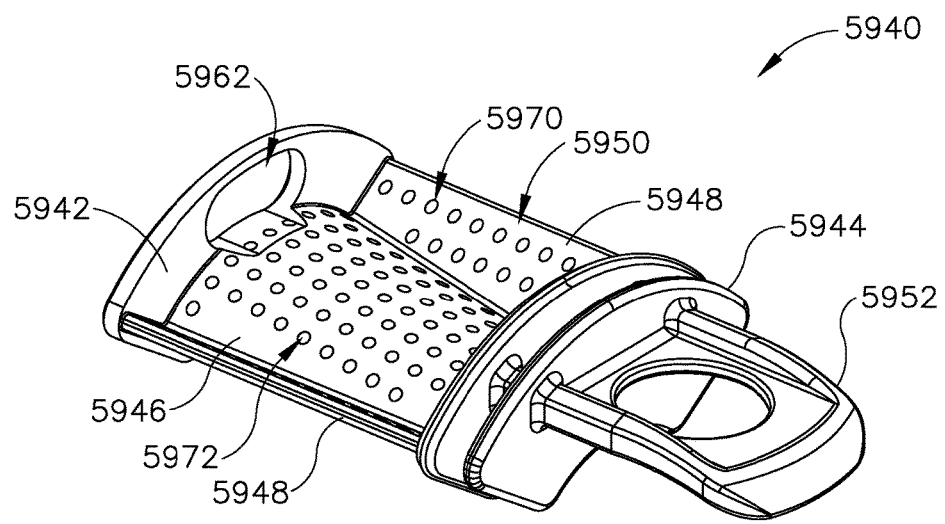
Figure 180:
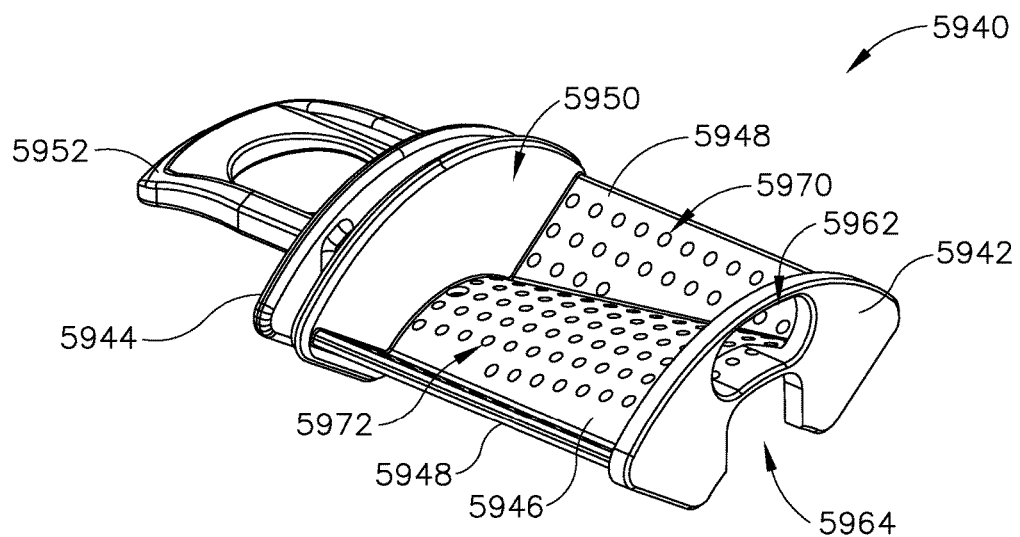
Figure 181:
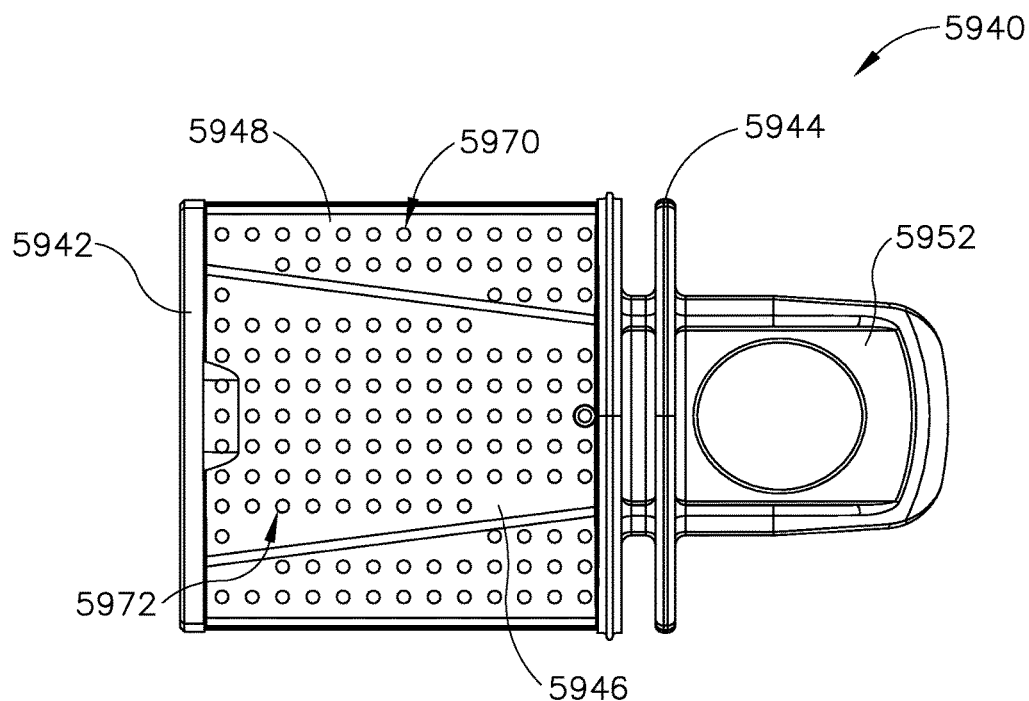

FIG. 131 depicts another perspective view of the tissue sample holder assembly of FIG. 130;

FIG. 132 depicts an end elevational view of the tissue sample holder assembly of FIG. 130;

FIG. 133 depicts another end elevational view of the tissue sample holder assembly of FIG. 130;

FIG. 134 depicts an exploded perspective view of the tissue sample holder assembly of FIG. 130;

FIG. 135 depicts an end elevational view of a rotatable body of the tissue sample holder assembly of FIG. 130;

FIG. 136 depicts another end elevational view of a rotatable body of the tissue sample holder assembly of FIG. 130;

FIG. 137 depicts a perspective view of a tissue sample tray of the tissue sample holder assembly of FIG. 130;

FIG. 138 depicts another perspective view of the tissue sample tray of FIG. 137;

FIG. 139 depicts a top plan view of the tissue sample tray of FIG. 137;

FIG. 140 depicts an end elevational view of the tissue sample tray of FIG. 137;

FIG. 141 depicts a perspective view of another exemplary alternative tissue sample holder assembly that may be incorporated into the probe of FIG. 4;

FIG. 142 depicts another perspective view of the tissue sample holder assembly of FIG. 141;

FIG. 143 depicts an exploded perspective view of the tissue sample holder assembly of FIG. 141;

FIG. 144 depicts an end elevational view of the tissue sample holder assembly of FIG. 141;

FIG. 145 depicts a perspective view of a tissue sample tray of the tissue sample holder assembly of FIG. 141;

FIG. 146 depicts another perspective view of the tissue sample tray of FIG. 145;

FIG. 147 depicts a cross-sectional perspective view of the tissue sample tray of FIG. 145, taken along line 147-147 of FIG. 145;

FIG. 148 depicts a perspective view of another exemplary alternative tissue sample holder assembly that may be incorporated into the probe of FIG. 4;

FIG. 149 depicts another perspective view of the tissue sample holder assembly of FIG. 148;

FIG. 150 depicts an end elevational view of the tissue sample holder assembly of FIG. 148;

FIG. 151 depicts another end elevational view of the tissue sample holder assembly of FIG. 148;

FIG. 152 depicts an exploded perspective view of the tissue sample holder assembly of FIG. 148;

FIG. 153 depicts an exemplary alternative probe assembly including an additional vacuum conduit;

FIG. 154 depicts a flow chart showing an exemplary process that may be carried out using the biopsy system of FIG. 1;

FIG. 155 depicts a screenshot of a graphical user interface that may be provided through the biopsy system of FIG. 1 during performance of the process of FIG. 154;

FIG. 156 depicts another screenshot of a graphical user interface that may be provided through the biopsy system of FIG. 1 during performance of the process of FIG. 154;

FIG. 157 depicts another screenshot of a graphical user interface that may be provided through the biopsy system of FIG. 1 during performance of the process of FIG. 154;

FIG. 158 depicts another screenshot of a graphical user interface that may be provided through the biopsy system of FIG. 1 during performance of the process of FIG. 154;

FIG. 159 depicts another screenshot of a graphical user interface that may be provided through the biopsy system of FIG. 1 during performance of the process of FIG. 154;

FIG. 160 depicts another screenshot of a graphical user interface that may be provided through the biopsy system of FIG. 1 during performance of the process of FIG. 154;

FIG. 161 depicts another screenshot of a graphical user interface that may be provided through the biopsy system of FIG. 1 during performance of the process of FIG. 154;

FIG. 162 depicts another screenshot of a graphical user interface that may be provided through the biopsy system of FIG. 1 during performance of the process of FIG. 154;

FIG. 163 depicts a perspective view of another exemplary alternative tissue sample holder assembly that may be incorporated into the probe of FIG. 4;

FIG. 164 depicts an end elevational view of the tissue sample holder assembly of FIG. 163;

FIG. 165 depicts an exploded perspective view of the tissue sample holder assembly of FIG. 163;

FIG. 166 depicts a cross-sectional side view of a rotatable body of the tissue sample holder assembly of FIG. 163, taken along line 166-166 of FIG. 164;

FIG. 167 depicts a perspective view of the rotatable body of FIG. 166;

FIG. 168 depicts a perspective view of a tissue sample tray of the tissue sample holder assembly of FIG. 163;

FIG. 169 depicts another perspective view of the tissue sample tray of FIG. 168;

FIG. 170 depicts a cross-sectional view of the tissue sample tray of FIG. 168, taken along line 170-170 of FIG. 168; and FIG. 171 depicts another cross-sectional view of the tissue sample tray of FIG. 168, taken along line 171-171 of FIG. 168;

FIG. 172 depicts a perspective view of another exemplary alternative tissue sample holder assembly that may be incorporated into the probe of FIG. 4;

FIG. 173 depicts another perspective view of the tissue sample holder assembly of FIG. 172;

FIG. 174 depicts an end elevational view of the tissue sample holder assembly of FIG. 172;

FIG. 175 depicts another end elevational view of the tissue sample holder assembly of FIG. 172;

FIG. 176 depicts an exploded perspective view of the tissue sample holder assembly of FIG. 172;

FIG. 177 depicts a cross-sectional side view of the tissue sample holder assembly of FIG. 172, taken along line 177-177 of FIG. 174;

FIG. 178 depicts an end elevational view of a rotatable body of the tissue sample holder assembly of FIG. 172;

FIG. 179 depicts a perspective view of a tissue sample tray of the tissue sample holder assembly of FIG. 172;

FIG. 180 depicts another perspective view of the tissue sample tray of FIG. 179;

FIG. 181 depicts a top plan view of the tissue sample tray of FIG. 179; and

Figure 182:
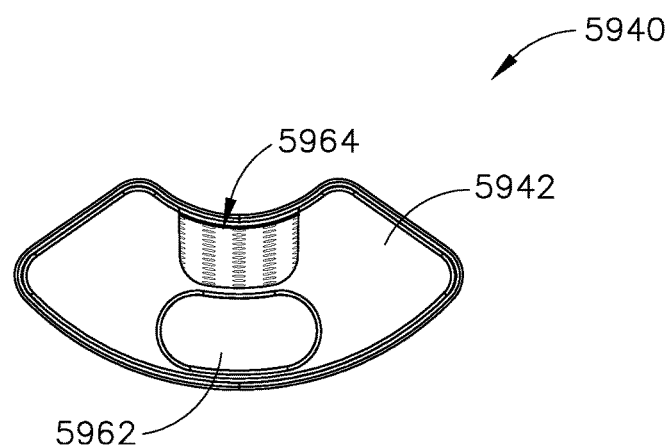

FIG. 182 depicts an end elevational view of the tissue sample tray of FIG. 179.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Biopsy System

FIG. 1 depicts an exemplary biopsy system (2) comprising a biopsy device (10) and a vacuum control module (250). By way of example only, at least some components of biopsy system (2) may be configured and/or operable in accordance with at least some of the teachings of U.S. Pub. No. 2014/0039343, entitled "Biopsy System," published Feb. 6, 2014, the disclosure of which is incorporated by reference herein. Biopsy device (10) of this example comprises a probe (100) and a holster (200). A needle (110) extends distally from probe (100), and is inserted into a patient's tissue to obtain tissue samples as will be described in greater detail below. These tissue samples are deposited in a tissue sample holder (300) at the proximal end of probe (100), as will also be described in greater detail below. It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

As will be described in greater detail below, a vacuum control module (250) is coupled with probe (100) via a valve assembly (90). In particular, vacuum control module (250) includes a tube set interface socket (252), which is configured to couple with valve assembly (90). Tube set interface socket (252) includes a pair of exposed spindles that are rotatably driven by motors (254, 256) to selectively actuate valve assembly (90). Valve assembly (90) is further coupled with a saline bag (80) via a tube (50); and with a vacuum canister (70) via a tube (60). Vacuum canister (70) is disposed in a vacuum canister receiving receptacle (258) of vacuum control module (250). Valve assembly (90) is coupled with probe (100) via a set of tubes (20, 30, 40). As shown in FIG. 4, each tube (20, 30, 40) includes a respective luer fitting (22, 32, 42) that is configured to provide a removable coupling with valve assembly (90). In the present example, vacuum control module (250) cooperates with valve assembly (90) to selectively provide vacuum, saline, atmospheric air, and fluid sealing to probe (100). By way of example only, such communication may be provided in accordance with at least some of the teachings of U.S. Pub. No. 2013/0218047, entitled "Biopsy Device Valve Assembly," published Aug. 22, 2013, the disclosure of which is incorporated by reference herein; and/or at least some of the teachings of U.S. Pub. No. 2014/0039343, entitled "Biopsy System," published Feb. 6, 2014, the disclosure of which is incorporated by reference herein.

Vacuum control module (250) is further coupled with holster (200) via a cable (210), which is operable to communicate electrical power to holster (200) and is further operable to communicate signals such as data and commands, etc., in a bi-directional fashion between holster (200) and vacuum control module (250). These components all cooperate to enable biopsy device (10) to acquire numerous tissue samples from a patient, such as from the patient's breast or other part of the patient's anatomy. By way of example only, such operability may be provided in accordance with at least some of the teachings of U.S. Pub. No. 2014/0039343, entitled "Biopsy System," published Feb. 6, 2014, the disclosure of which is incorporated by reference herein. In addition or in the alternative, such operability may be provided in accordance with any of the other references cited herein.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be pneumatically deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

II. Exemplary Probe

Figure 3:
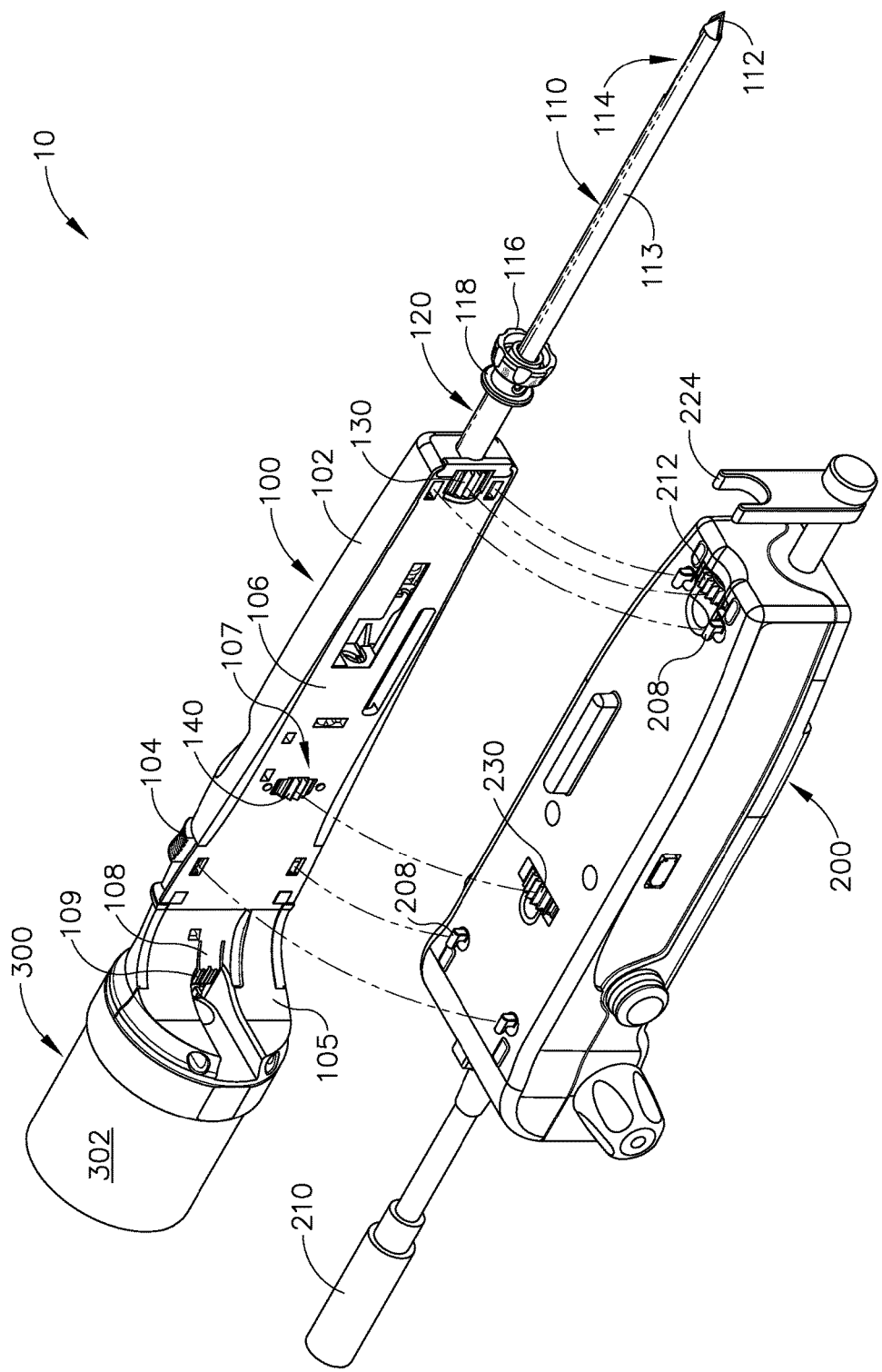
FIG. 3 depicts a perspective view of the biopsy device of FIG. 2, with the probe decoupled from the holster.

As shown in FIGS. 1-6, probe (100) of the present example includes a distally extending needle (110). Probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together. Similarly, gear (130) of probe (100) meshes with exposed gear (212) of holster (200) when probe (100) and holster (200) are coupled together. It should be understood that holster (200) may be constructed and operable in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

A. Exemplary Needle Assembly

Needle (110) of the present example comprises a cannula (113) having a piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pub. No. 2012/0310110, entitled "Needle Assembly and Blade Assembly for Biopsy Device," published Dec. 6, 2012, the disclosure of which is incorporated by reference herein. As another merely illustrative example, tip (112) may be configured in accordance with at least some of the teachings in U.S. Pub. No. 2013/0150751, entitled "Biopsy Device with Slide-In Probe," published Jun. 13, 2013, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). The interior of cutter (150) defines a lumen (151). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
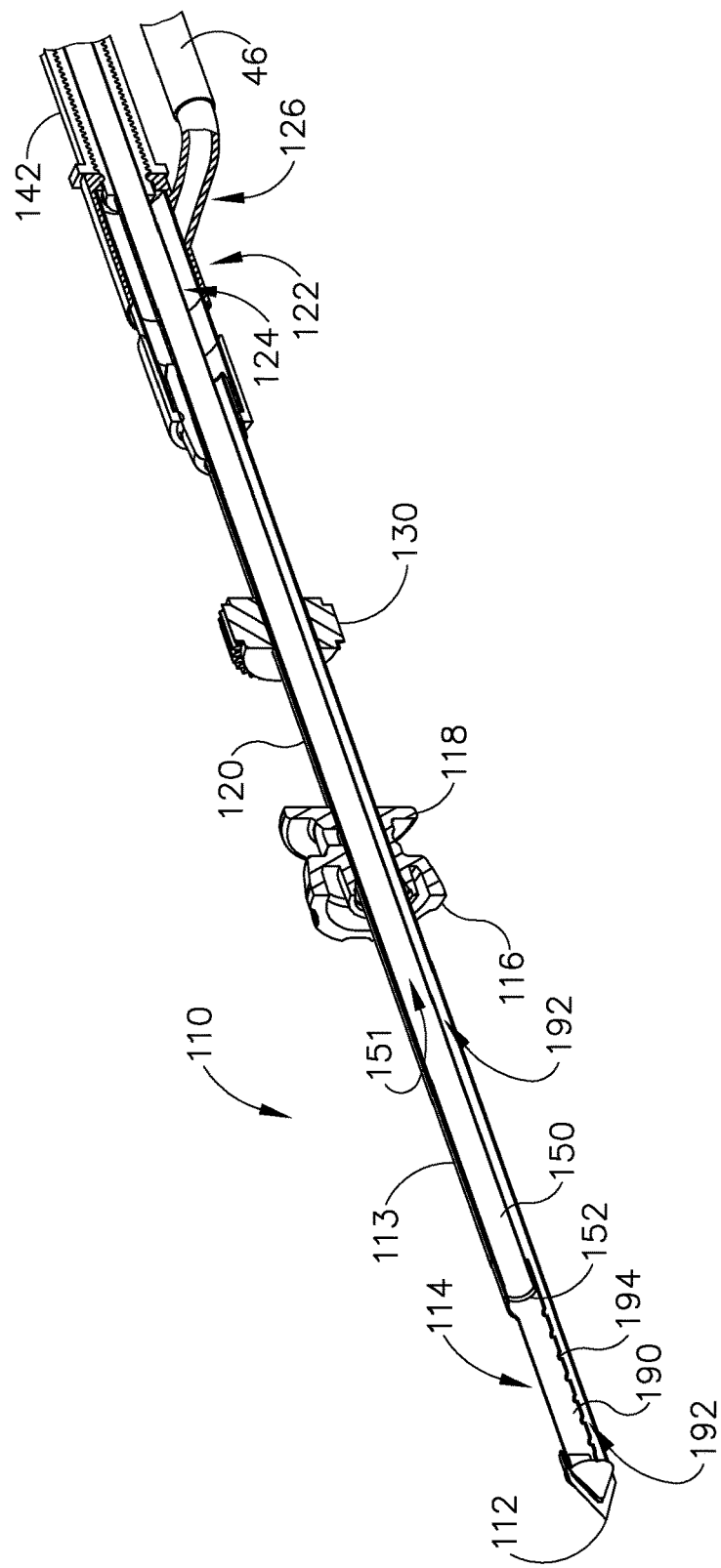
FIG. 6 depicts a cross-sectional view of a needle assembly of the probe of FIG. 4.

As best seen in FIG. 6, needle (110) also includes a sidewall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

A plurality of external openings (not shown) may also be formed in needle (110), and may be in fluid communication with second lumen (192). For instance, such external openings may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings in needle (110) are merely optional.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion of hub member (120) and is keyed to hub member (120), such that rotation of gear (130) will rotate hub member (120) and needle (110); yet hub member (120) and needle (110) may translate relative to gear (130). Gear (130) is rotatably driven by gear (212), as will be described in greater detail below. Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein. By way of example only, needle (110) may be translated longitudinally relative to chassis (106) and top housing (102), by a needle firing mechanism (224) in accordance with at least some of the teachings of U.S. Pub. No. 2012/0265095, entitled "Biopsy Device with Motorized Needle Firing, the disclosure of which is incorporated by reference herein.

As shown in FIGS. 4-7, a manifold (122) is provided at the proximal end of needle (110). Manifold (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that manifold (122) provides fluid communication between second lumen (192) and tube (46). Manifold (122) also seals against the exterior of needle (110) such that manifold (122) provides a fluid tight coupling between second lumen (192) and tube (46) even if needle (110) is translated and/or rotated relative to manifold (122), such as during firing of needle (110) or re-orientation of needle (110), respectively. As shown in FIG. 4, tube (46) is coupled with tubes (30, 40) via a Y-fitting (44), such that tube (46) may receive vacuum, atmospheric air, or saline from tubes (30, 40) based on actuation of valve assembly (90). It should therefore be understood that tube (46) and manifold (122) may provide vacuum, atmospheric air, or saline to second lumen (192). A clip (48) is operable to selectively close tube (46).

As shown in FIG. 4, needle (110) may be provided with a removable cover (115). Cover (115) of this example includes a resiliently biased latch (117) that is configured to engage thumbwheel (116), to thereby removably secure cover (115) to needle (110). Cover (115) is configured to cover tip (112) when latch (117) is engaged with thumbwheel (116), such that cover (115) protects the user of biopsy device (10) from inadvertent contact with tip (112). Cover (115) may also include one or more wiper seals near the proximal end and/or distal end of cover (115), to seal against cannula (113). By way of example only, cover (115) may be configured in accordance with at least some of the teachings in U.S. Provisional Pat. App. No. 61/566,793, the disclosure of which is incorporated by reference herein. Various other suitable configurations for cover (115) will be apparent to those of ordinary skill in the art in view of the teachings herein. Of course, cover (115) may simply be omitted if desired. It should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pub. No. 2008/0214955, the disclosure of which is incorporated by reference herein, and/or in accordance with the teachings of any other reference cited herein.

B. Exemplary Cutter Assembly

Figure 5:
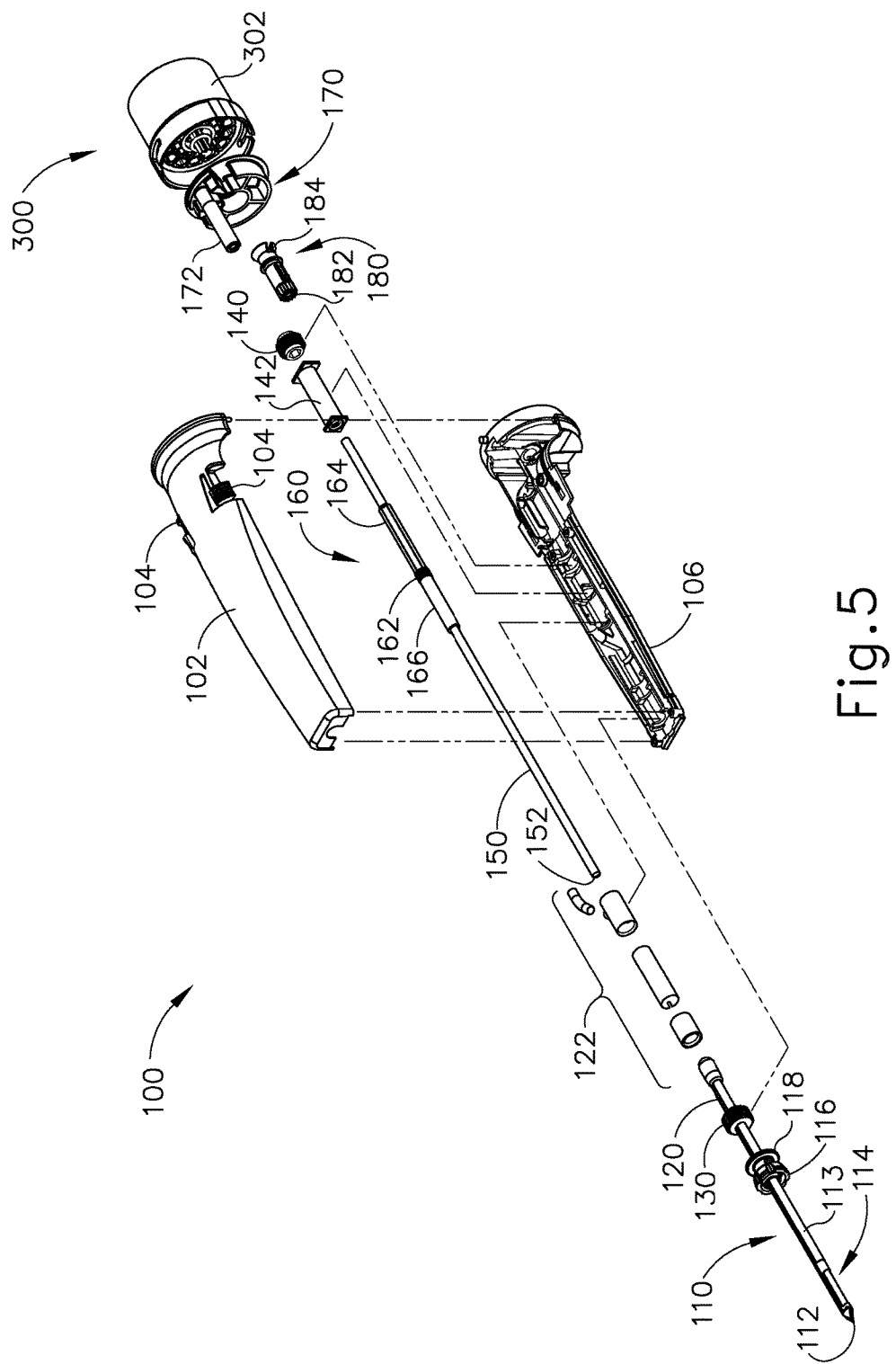
FIG. 5 depicts an exploded view of the probe of FIG. 4.
Figure 7:
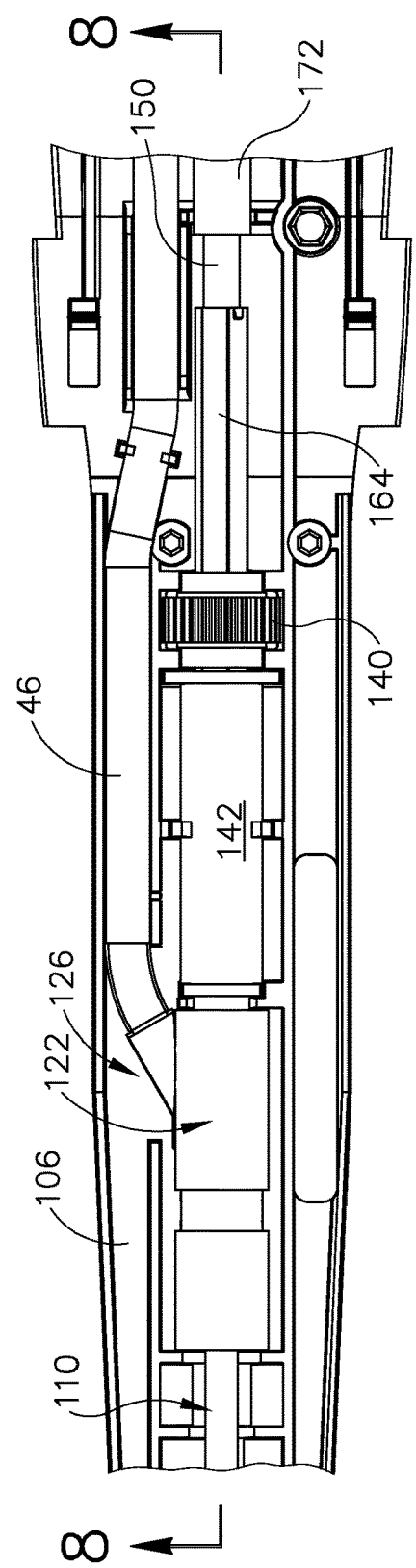
FIG. 7 depicts a partial top plan view of components of the probe of FIG. 4, with a top housing piece removed.
Figure 8:
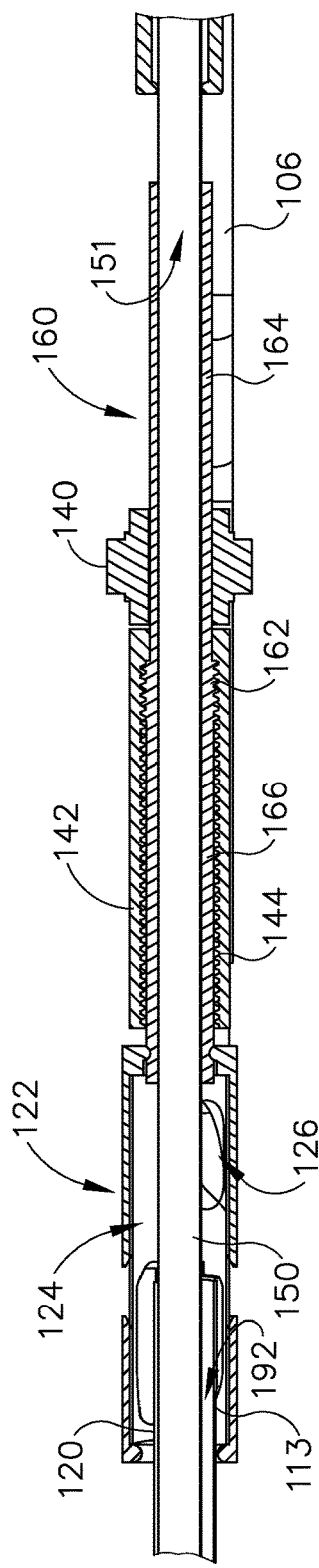
FIG. 8 depicts a cross-sectional view of the components of FIG. 7, taken along line 8-8 of FIG. 7.

As noted above, cutter (150) is operable to simultaneously translate and rotate relative to needle (110) to sever a tissue sample from tissue protruding through lateral aperture (114). As best seen in FIGS. 5 and 7-8 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into manifold (122). Manifold (122) seals against distal portion (166) such that manifold (122) such that manifold (122) maintains the fluid tight coupling between second lumen (192) and tube (46) even when cutter (150) is translated and rotated relative to manifold (122).

A gear (140) is positioned on flats (164) and includes a set of internal flats (not shown) that complement flats (164). Thus, gear (140) rotates overmold (160) and cutter (150) when gear (140) is rotated. However, overmold (160) is slidable relative to gear (140), such that cutter (150) may translate relative to chassis (160) despite gear (140) being longitudinally fixed relative to chassis (160). As noted above and as will be described in greater detail below, gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (160). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pat. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

C. Exemplary Tissue Sample Holder Interface

Figure 10:
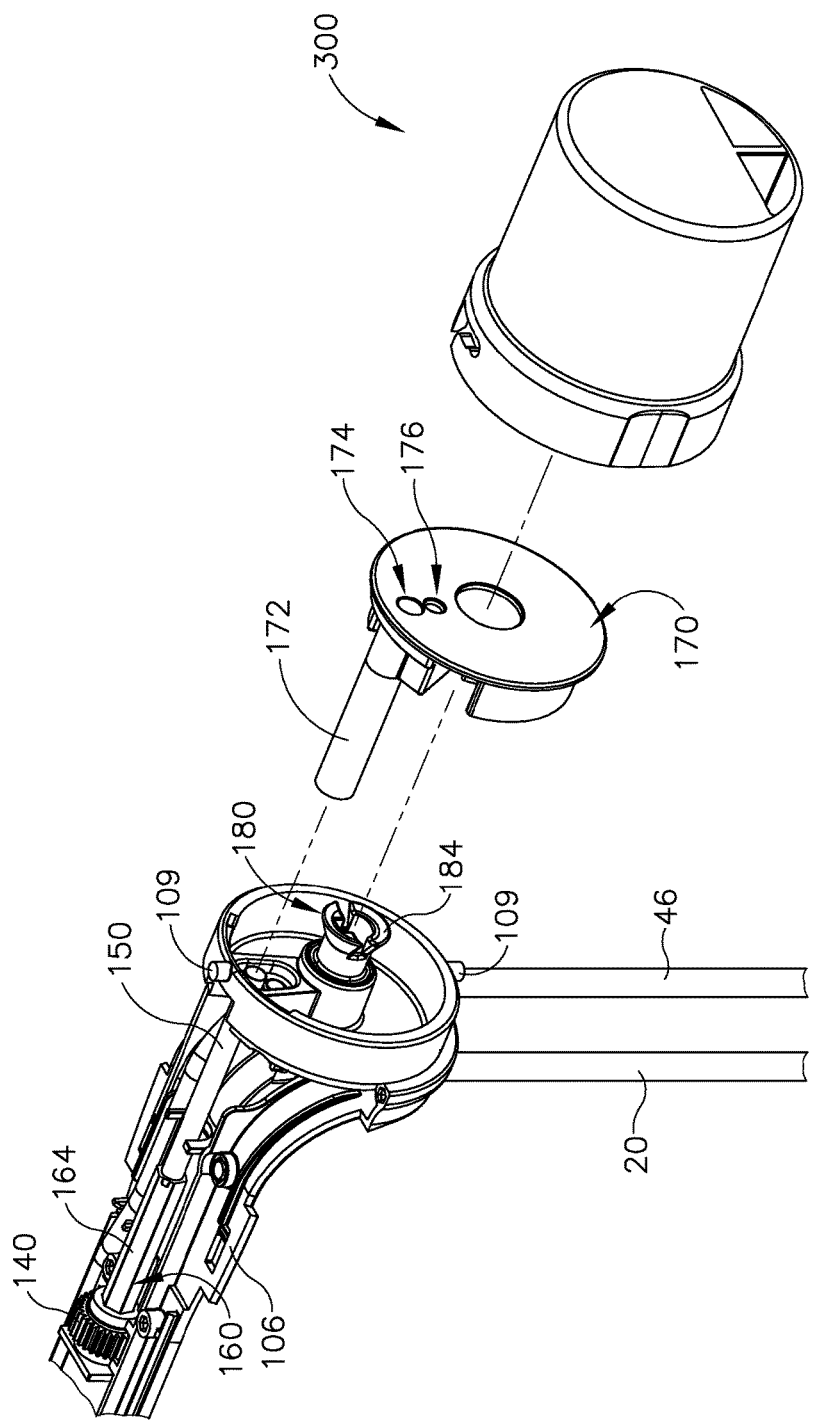
FIG. 10 depicts an exploded view of the tissue sample holder assembly of FIG. 9.
Figure 11:
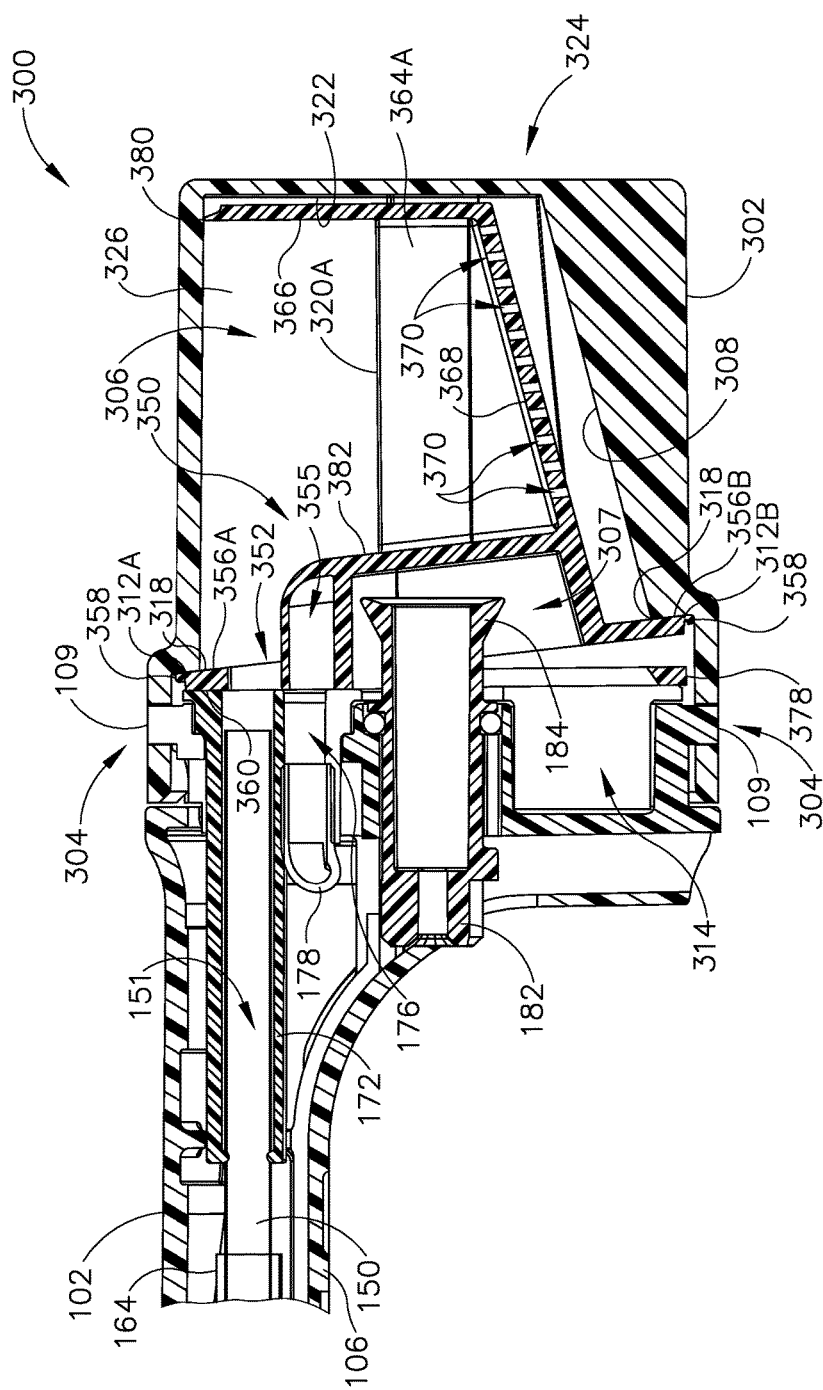
FIG. 11 depicts a cross-sectional side view of the tissue sample holder assembly of FIG. 9, with a tissue chamber aligned with the cutter.

As best seen in FIGS. 10-11, a sealing member (170) is provided at the proximal end of chassis (106) and interfaces with the distal face of circular member (354) of tissue sample tray (350). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of sealing member (170). It should be understood that opening (174) is in fluid communication with lumen (151) of cutter (150). It should also be understood that opening (174) is coaxially aligned with lumen (151) of cutter (150). Thus, severed tissue samples that are drawn proximally through lumen (151) of cutter (150) will ultimately exit proximally through opening (174) and into tissue sample holder (300) as will be described in greater detail below.

Figure 9:
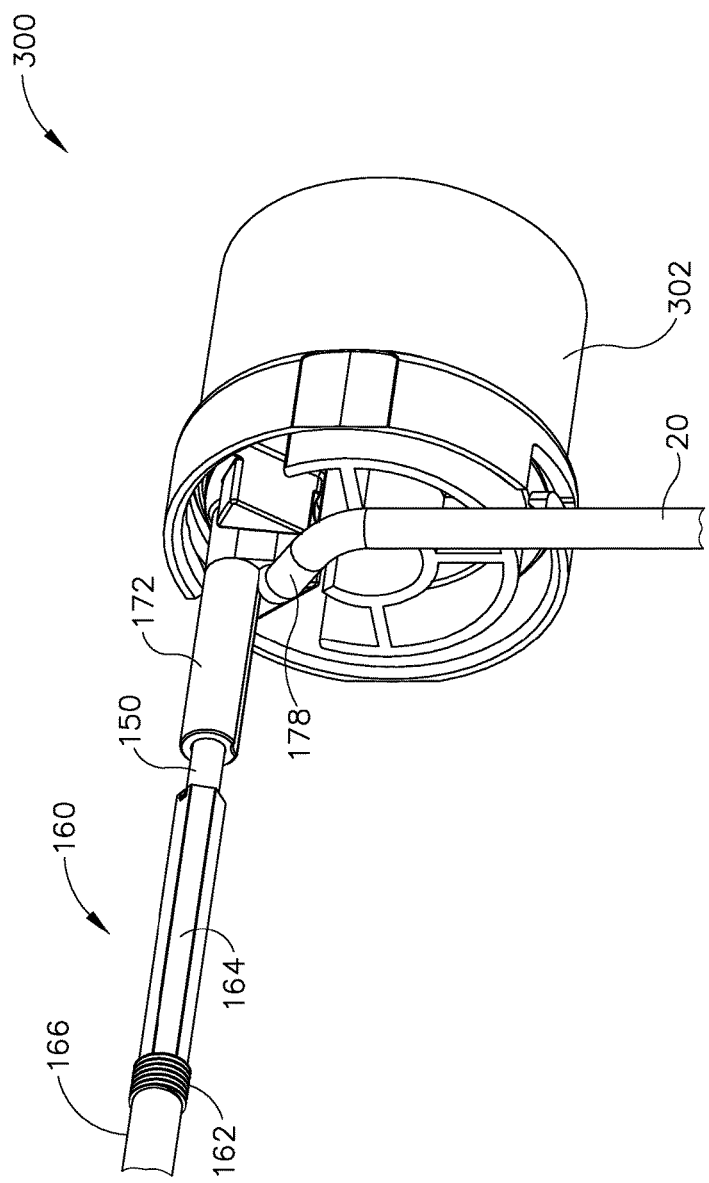
FIG. 9 depicts a perspective view of a tissue sample holder assembly of the probe of FIG. 4.

Sealing member (170) also includes another opening (176), which is positioned below opening (174). As best seen in FIGS. 9 and 11, opening (176) is in fluid communication with a port (178), which is coupled with tube (20). Thus, sealing member (170) provides fluid communication between tube (20) and opening (176) via port (178). Tube (20) is in fluid communication with a vacuum source at vacuum control module (250) as noted above, such that vacuum may be applied to opening (176). Such vacuum may further be communicated to tissue sample holder (300), and ultimately to lumen (151) of cutter (150), as will be described in greater detail below.

As also seen in FIG. 10, chassis (106) includes a pair of outwardly extending bayonet pins (109), which are configured to secure tissue sample holder (300) to probe (100) as will be described in greater detail below.

III. Exemplary Tissue Sample Holder Assemblies with Pull-Out Handle

Tissue sample holder (300) of the present example comprises a tissue sample tray (350) disposed within a cup-shaped cover (302). Tissue sample holder (300) configured to receive tissue samples that are severed by cutter (150) and communicated proximally through lumen (151) of cutter (150). Some versions of probe (100) present a rotation member (180) at a proximal portion of probe (100). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Rotation gear comprises a grasping feature (184) operable to engage a rotatable component of some versions of a tissue sample holder. For instance, U.S. Pub. No. 2014/0039343, entitled "Biopsy System," published Feb. 6, 2014, the disclosure of which is incorporated by reference herein, discloses such a rotatable tissue sample holder. Tissue sample tray (350) of tissue sample holder (300) presents a recess (307) to accommodate grasping feature (184) of rotation member (180) such that any rotation of grasping feature (184) occurs within recess (307) and has no effect on tissue sample holder (300). It should be appreciated that tissue sample holder (300) may come in a kit alone, or along with a multi-chamber tissue sample holder as taught in U.S. Pub. No. 2014/0039343, such that an operator may select which tissue sample holder to couple with probe (100).

Figure 12:
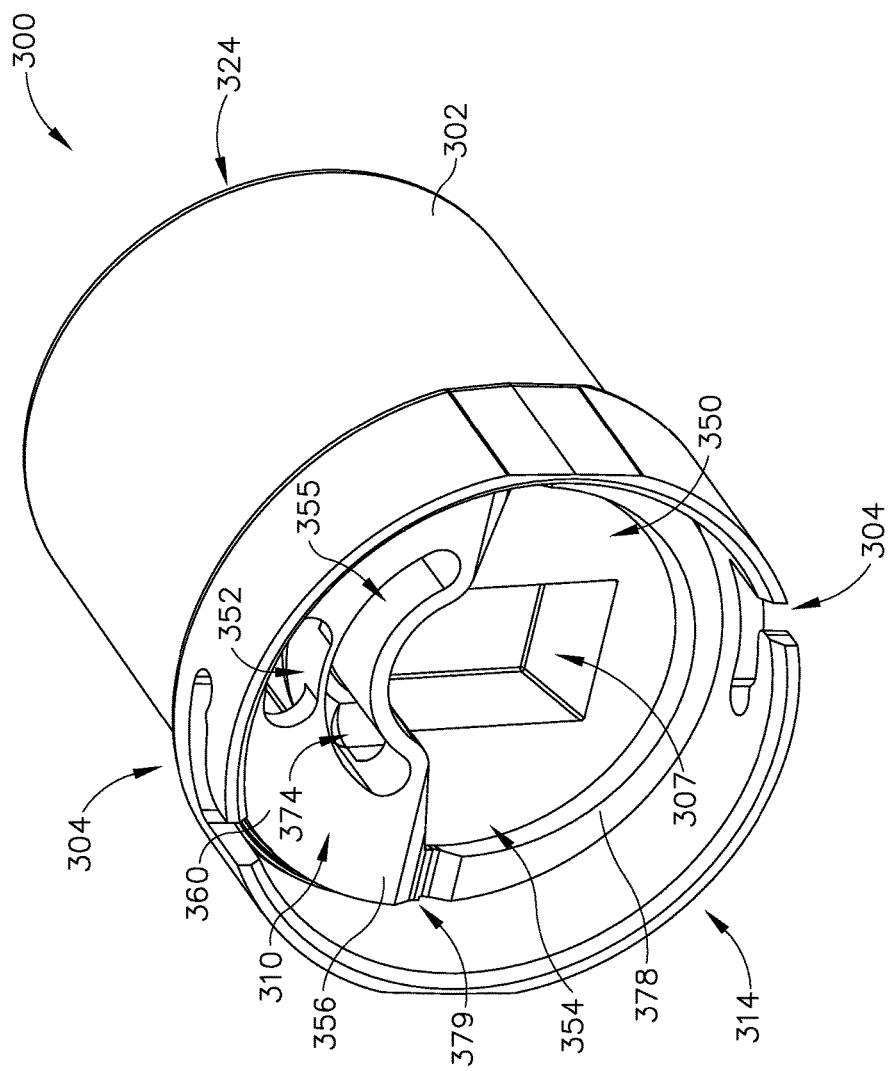
FIG. 12 depicts a perspective view of the tissue sample holder assembly of FIG. 9.
Figure 13:
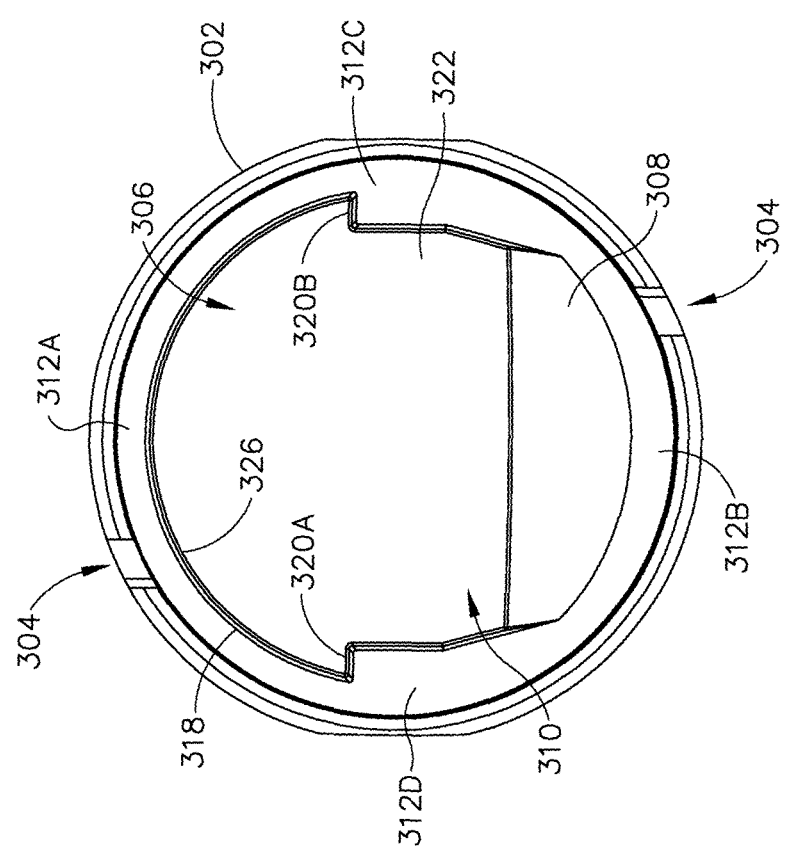
FIG. 13 depicts a front elevational view of a cover of the tissue sample holder assembly of FIG. 9.
Figure 14:
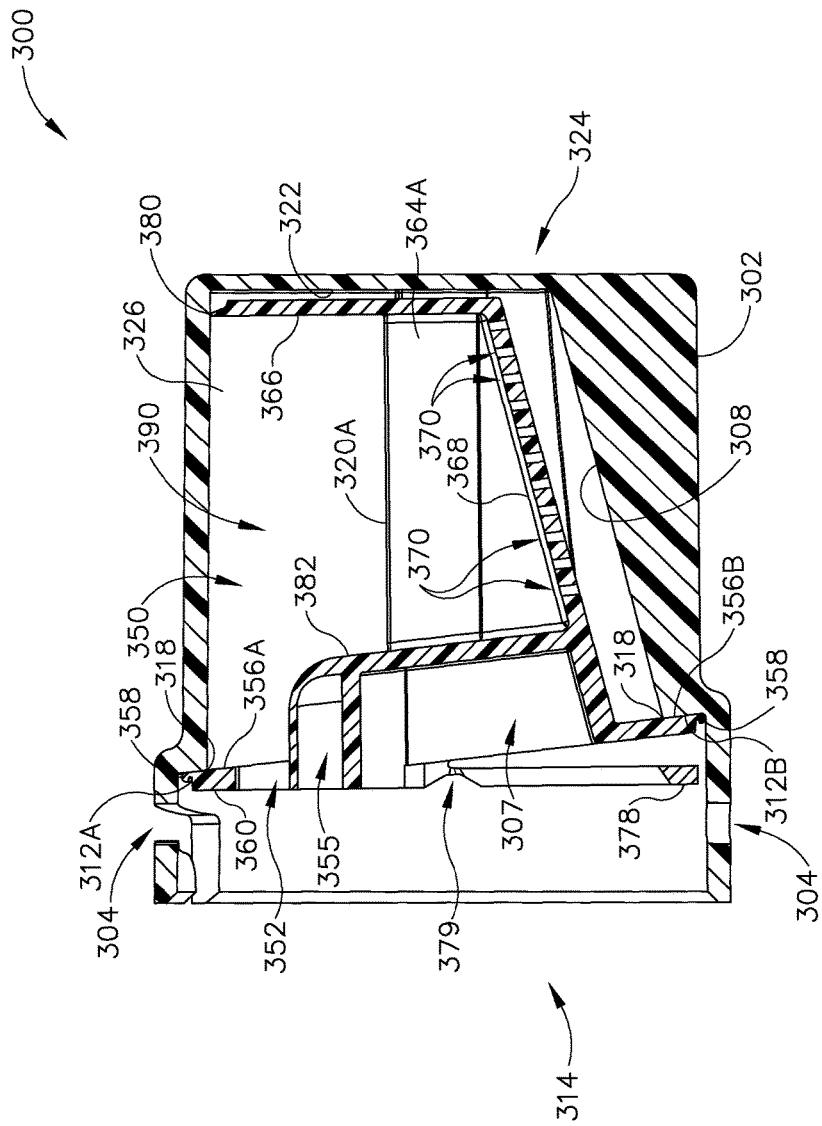
FIG. 14 depicts a cross-sectional side view of the tissue sample holder assembly of FIG. 9.

As best seen in FIGS. 12-16, cover (302) of the present example comprises an interior chamber (306) configured to receive tissue sample tray (350) through a distal opening (310) of cover (302). As best seen in FIG. 13, a distal portion (314) of interior chamber (306) presents a shoulder or lip (312). Lip (312) extends inwardly from a circular interior surface of interior chamber (306) to an interior edge (318) defined by a plurality of features of a proximal portion (324) of interior chamber (306) of cover (302) discussed in further detail below. As best seen in FIG. 14, lip (312) presents a sloped annular distal face. The sloped distal face of lip (312) comprises a distal portion (312A) and a proximal portion (312B). Distal portion (312A) and proximal portion (312B) are disposed on radially opposite sides of lip (312). Distal portion (312A) presents a portion of lip (312) having a longitudinal position more distal than that of proximal portion (312B). The sloped distal face of lip (312) further comprises intermediate portions (312C, 312D) disposed between distal portion (312A) and proximal portion (312B). Intermediate portions (312C, 312D) are flat and angled to provide a substantially smooth transition between distal portion (312A) and proximal portion (312B) along opposite sides of lip (312).

As best seen in FIG. 14, proximal portion (324) of interior chamber (306) defines an arcuate-sloped interior surface (308) slanting downwardly from a proximal surface (322) of interior chamber (306) toward edge (318) of lip (312). As will be discussed in more detail below, arcuate-sloped interior surface (308) is configured to guide fluids to an operative location within interior chamber (306) such that the fluids may be drawn from interior chamber (306). Referring back to FIG. 13, proximal portion (324) of interior chamber (306) further presents a pair of longitudinal lips (320A, 320B) extending from proximal surface (322) of interior chamber (306) to edge (318) of lip (312). As will be discussed in more detail below, tissue sample tray (350) is operable to slide along lips (320A, 320B) in and out of cover (302). The remainder of proximal portion (324) presents an arcuate surface (326) extending from proximal surface (322) of interior chamber (306) to edge (318) of lip (312).

As best seen in FIG. 12, cover (302) comprises a pair of bayonet slots (304) that are configured to couple with a mating pair of bayonet pins (109) of chassis (106) to thereby provide coupling between cover (302) and chassis (106). As best seen in FIG. 10, bayonet pins (109) are disposed at 12 o'clock and 6 o'clock positions at the proximal end of chassis (106), complementing the spacing of bayonet slots (304) of cover (302). Alternatively, any other suitable number of bayonet pins (109) may be provided at any suitable locations. It should also be understood that, while bayonet features (109, 304) provide coupling between cover (302) and chassis (106) in the present example, any other suitable type of coupling may be used (e.g., threaded coupling, snap fit coupling, etc.).

A. Exemplary Tissue Sample Tray with Sloped Distal Face

FIGS. 14 and 16-22 show tissue sample tray (350) of the present example. Tissue sample tray (350) comprises a circular member (354). Recess (307) is formed in circular member (354). As will be discussed in more detail below, a portion (382) of circular member (354) projects proximally into a tissue receiving compartment (390) of tray (350) to accommodate recess (307). As best seen in FIG. 14, circular member (354) extends along a plane that is perpendicular to the longitudinal axis of tissue sample holder (300). Circular member (354) thus presents a sloped annular proximal face (356) that is configured to engage the sloped distal face of lip (312) when tissue sample tray (350) is positioned within interior chamber (306) of cover (302). Sloped proximal face (356) comprises a distal portion (356A) and a proximal portion (356B). Distal portion (356A) and proximal portion (356B) are disposed on radially opposite sides of circular member (354). Distal portion (356A) presents a portion of sloped proximal face (356) having a longitudinal position more distal than that of proximal portion (356B). Sloped proximal face (356) further comprises intermediate portions (356C, 356D) disposed between distal portion (356A) and proximal portion (356B). Intermediate portions (356C, 356D) are flat and angled to provide a substantially smooth transition between distal portion (356A) and proximal portion (356B) along opposite sides of circular member (354). Sloped proximal face (356) of circular member (354) is configured such that sloped proximal face (356) fully apposes the sloped distal face of lip (312) when tissue sample tray (350) is fully inserted in cover (302). It should be understood that, in some versions of tissue sample holder (300), sloped proximal face (356) of circular member (354) may be configured such that sloped proximal face (356) mates with the sloped distal face of lip (312) to thereby form a fluid seal.

An exterior circumference of circular member (354) presents an o-ring-like circular seal (358). Seal (358) is configured to engage the circular interior surface of distal portion (314) of cover (302) to thereby form a fluid seal. Thus, it should be understood that seal (358) fluidly seals an outer perimeter of circular member (354) against an interior surface of cover (302) between proximal portion (324) of interior chamber (306) of cover (302) and distal portion (314) of interior chamber (306) of cover (302). In other words, circular seal (358) provides a fluid tight fit with cover (302).

Tissue sample tray (350) further comprises a sloped floor (368), a pair of sidewalls (364A, 364B), and a proximal wall (366) which, as will be discussed in more detail below, together form tissue receiving compartment (390). Sloped floor (368) extends distally from proximal wall (366) to proximal portion (356A) of sloped proximal face (356) of circular member (354). Sloped floor (368) slants downwardly from proximal wall (366) to sloped proximal face (356) of circular member (354) at an angle similar to that of arcuate-sloped interior surface (308). As shown in FIG. 14, a gap is defined between the underside of sloped floor (368) of tissue sample tray (350) and arcuate-sloped interior surface (308) of cover (302). It should be understood that fluid drawn into tissue sample holder (300) during a biopsy procedure (e.g., blood, saline, etc.) may flow within this gap. Sloped floor (368) comprises a plurality of apertures (370) that pass completely through sloped floor (368). Apertures (370) are configured to allow fluid to pass through from tissue receiving compartment (390) into the gap between sloped floor (368) and arcuate-sloped interior surface (308) of cover (302).

Figure 15:
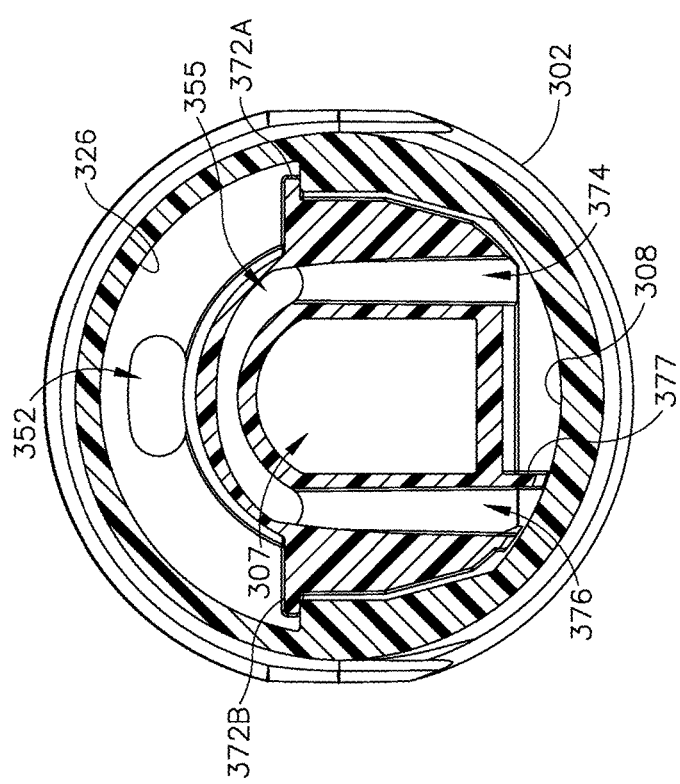
FIG. 15 depicts a cross-sectional end view of the tissue sample holder assembly of FIG. 9.
Figure 16:
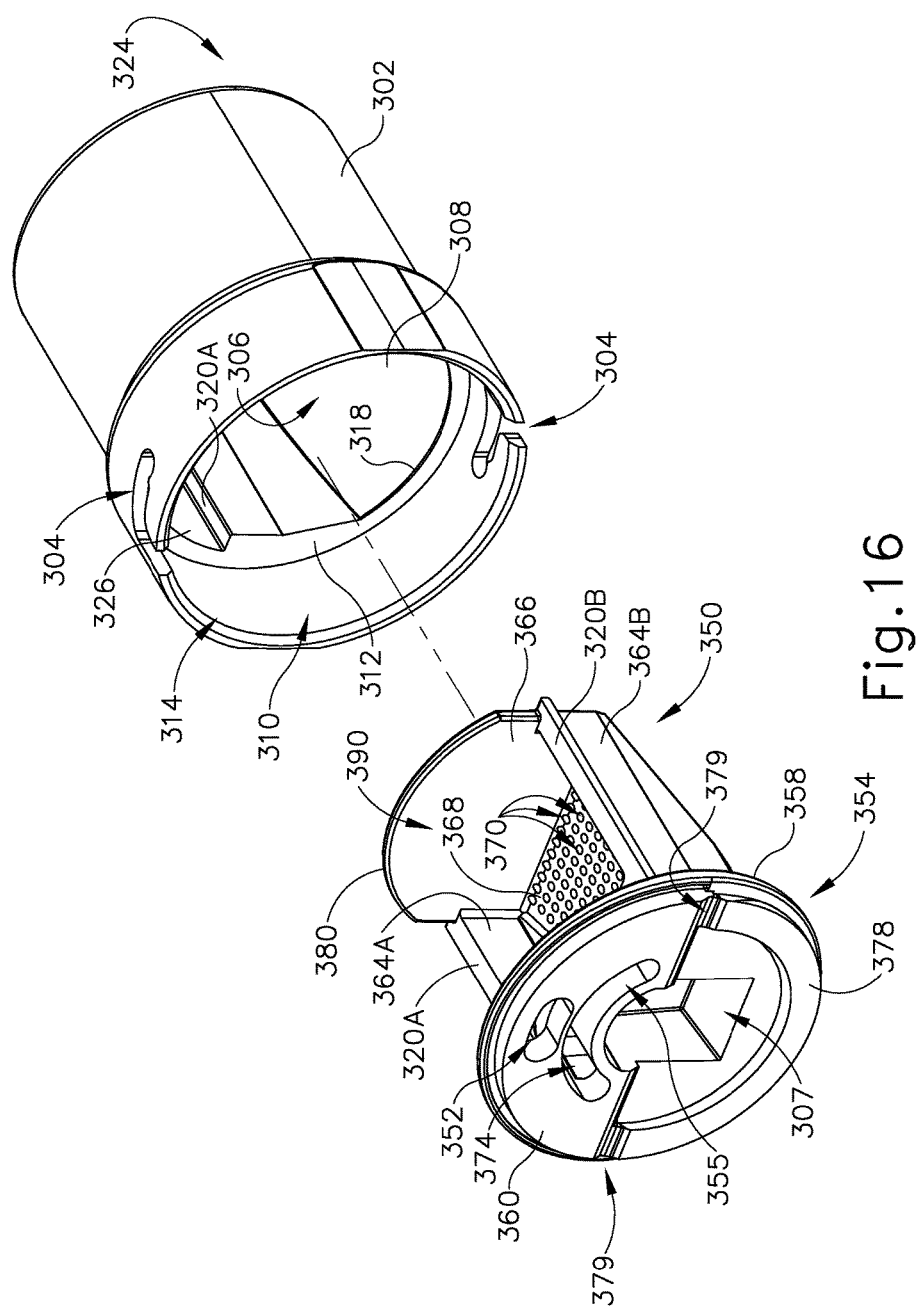
FIG. 16 depicts an exploded perspective view of the tissue sample holder assembly of FIG. 9.
Figure 19:
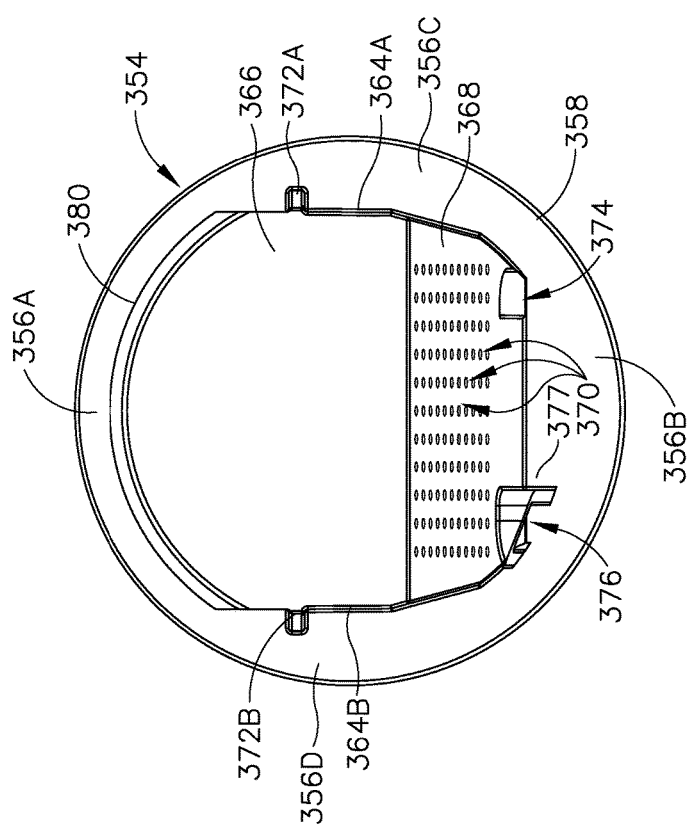
FIG. 19 depicts a back elevational view of the tissue sample tray of FIG. 17.

Sidewalls (364A, 364B) extend distally from proximal wall (366) to sloped proximal face (356) of circular member (354). A bottom portion of each wall (364A, 364B) connects with sloped floor (368). Thus, it should be understood that circular member (354), sloped floor (368), sidewalls (364A, 364B), and proximal wall (366) together form tissue receiving compartment (390). As will be discussed in more detail below, this tissue receiving compartment (390) is oriented to receive tissue samples drawn into interior chamber (306) through lumen (151) of cutter (150). As best seen in FIGS. 15 and 19, each wall (364A, 364B) presents a longitudinally extending flange (372A, 372B) protruding outwardly from an upper portion of walls (364A, 364B). Flanges (372A, 372B) are configured to rest on longitudinal lips (320A, 320B) of interior chamber (306) of cover (302) when tissue sample tray (350) is positioned within interior chamber (306).

Figure 17:
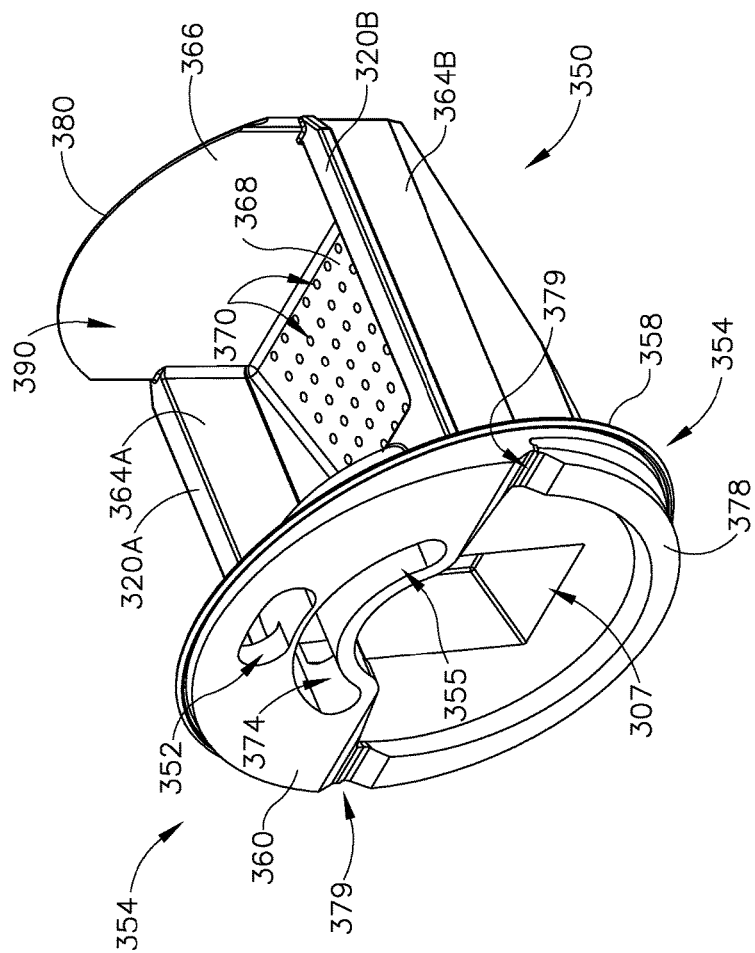
FIG. 17 depicts a perspective view of a tissue sample tray of the tissue sample holder assembly of FIG. 9.
Figure 18:
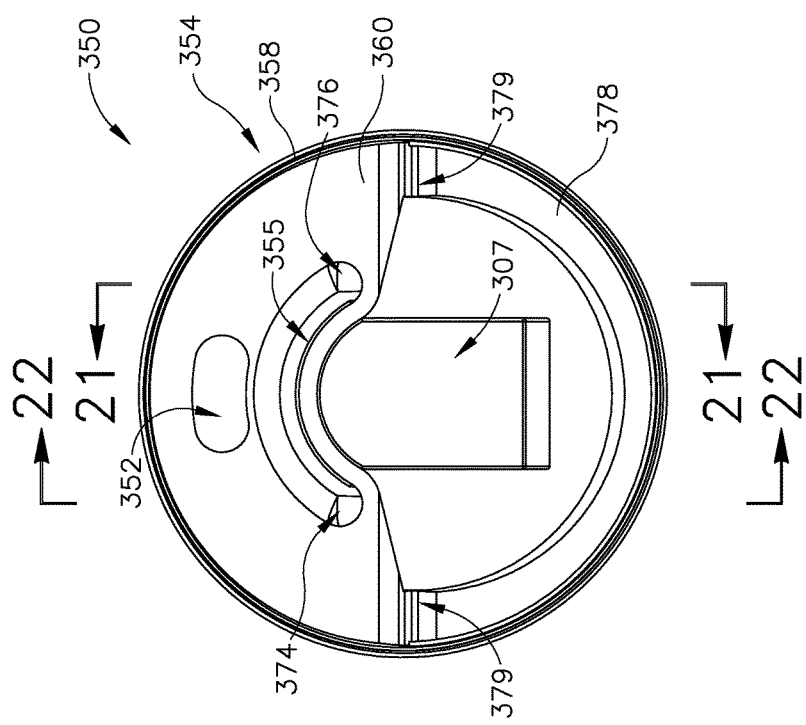
FIG. 18 depicts a front elevational view of the tissue sample tray of FIG. 17.
Figure 21:
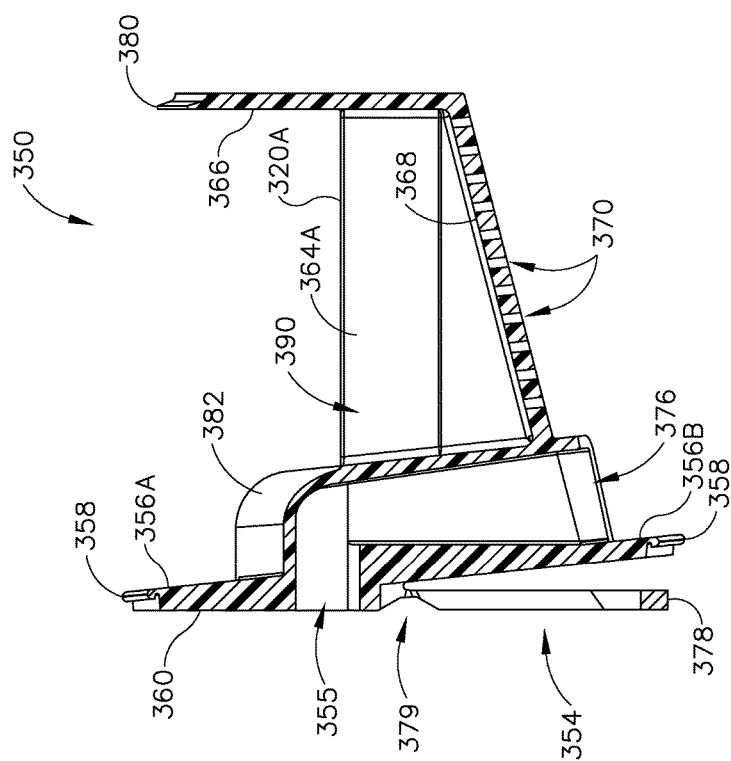
FIG. 21 depicts a cross-sectional view of the tissue sample tray of FIG. 17, taken along line 21-21 of FIG. 18.
Figure 22:
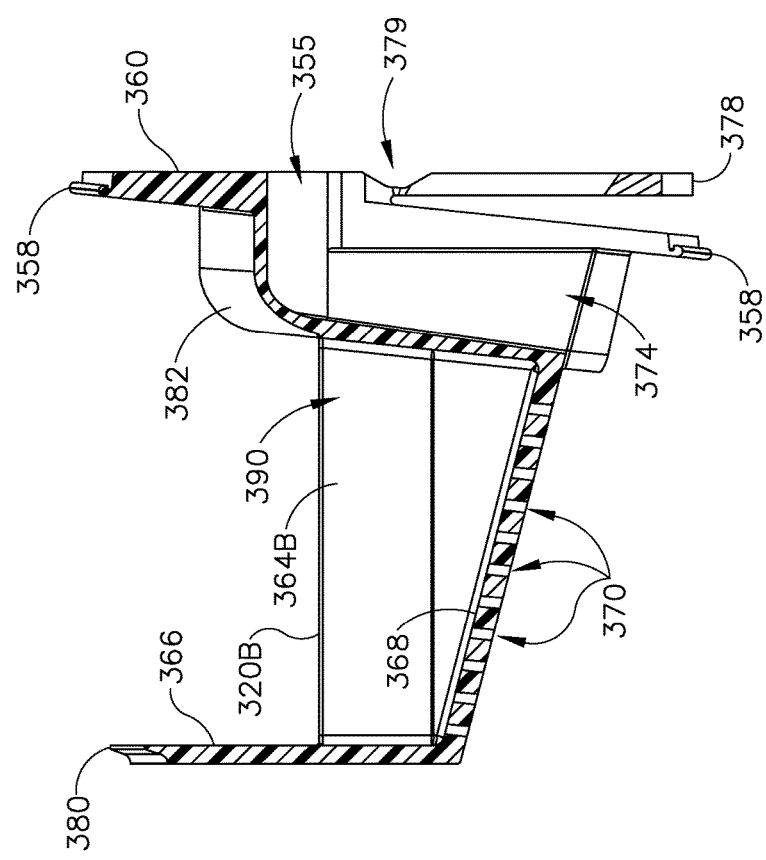
FIG. 22 depicts another cross-sectional view of the tissue sample tray of FIG. 17, taken along line 22-22 of FIG. 18.

As best seen in FIGS. 17 and 18, circular member (354) presents a distal face (360). Distal face (360) includes an oblong opening (352) that passes completely through circular member (354), such that opening (352) is in fluid communication with tissue receiving compartment (390). Distal face (360) further includes an oblong-arcuate opening (355), which extends from distal face (360) and into a sump portion (382) of circular member (354). As best seen in FIGS. 21 and 22, sump portion (382) defines a pair of downwardly extending vacuum lumens (374, 376) that are in fluid communication with opening (355). As will be described in greater detail below, vacuum lumens (374, 376) and opening (355) are configured to cooperate to provide vacuum to interior chamber (306). As best seen in FIG. 15, vacuum lumens (374, 376) pass through sump portion (382) of circular member (354) on opposite sides of recess (307). First vacuum lumen (374) is in fluid communication with a first lateral portion of interior chamber (306) while second vacuum lumen (376) is in fluid communication with a second lateral portion of interior chamber (306).

Figure 20:
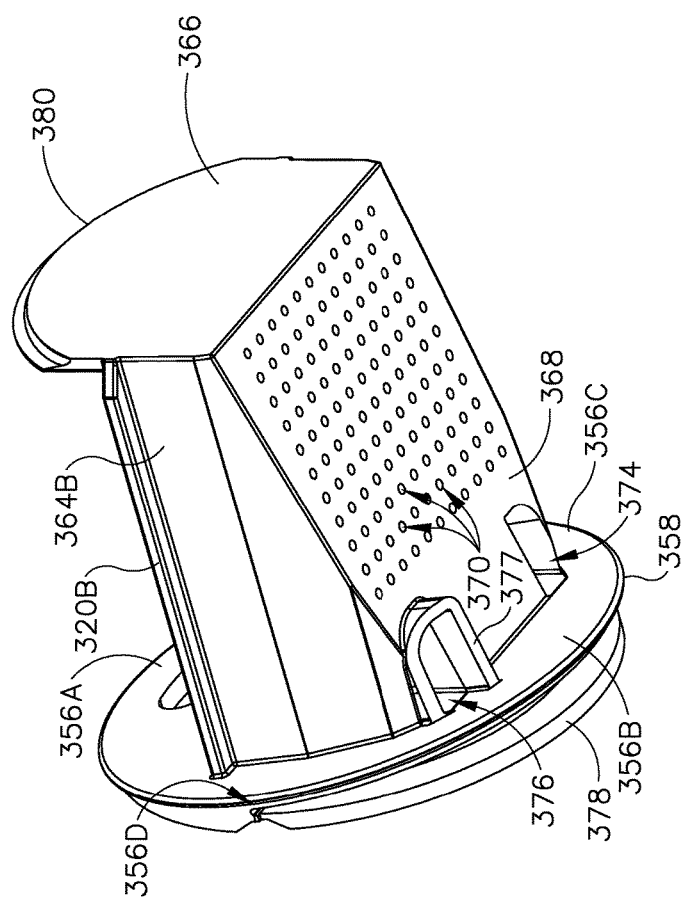
FIG. 20 depicts a another perspective view of the tissue sample tray of FIG. 17.

As shown in FIGS. 15, 19, and 20, tissue sample tray (350) of the present example further includes a downwardly extending lip (377) associated with second vacuum lumen (376), such that second vacuum-lumen (376) extends downwardly toward arcuate-sloped interior surface (308) further than first vacuum-lumen (374). In the present example, lip (377) does not contact interior surface (308). It should be understood that second vacuum-lumen (376) may be more likely to draw fluid because of the proximity of lip (377) interior surface (308). In other words, lip (377) may provide increased suction at second vacuum lumen (376) as soon as the level of fluid in tissue sample holder (300) reaches lip (377).

Referring back to FIGS. 10-11, a sealing member (170) interfaces with the distal face of circular member (354) of tissue sample tray (350) when tissue sample holder (300) is secured to probe (100). Opening (174) of sealing member (170) is configured to align with oblong opening (352). When tissue sample holder (300) is secured to probe (100), sealing member (170) seals against the distal face of circular member (354) such that openings (174, 352) are in fluid tight fluid communication. As noted above, opening (174) is also in fluid communication with lumen (151) of cutter (150); and opening (174) is coaxially aligned with lumen (151) of cutter (150). Thus, severed tissue samples that are drawn proximally through lumen (151) of cutter (150) will ultimately exit proximally through opening (174) and into opening (352).

Opening (176) of sealing member (170) is configured to align with oblong-arcuate opening (355). When tissue sample holder (300) is secured to probe (100), sealing member (170) seals against the distal face of circular member (354) such that openings (176, 355) are in fluid tight fluid communication. As noted above, opening (176) is in fluid communication with port (178), which is coupled with tube (20). Thus, sealing member (170) provides fluid communication between tube (20) and second oblong-arcuate opening (356) via port (178) and opening (176). As further noted above, tube (20) is in fluid communication with a vacuum source at vacuum control module (250), such that vacuum may be applied to tissue sample holder (300) via openings (176 356). Tissue sample holder (300) may further communicate this vacuum to lumen (151) of cutter (150) via opening (174) and cutter seal (172). Thus, vacuum applied from tube (20) may ultimately reach lumen (151) of cutter (150) and provide proximal communication of tissue samples through lumen (151) to tissue sample holder (300).

It should be understood from the foregoing that cover (302), tissue sample tray (350), and sealing member (170) cooperate to form a sealed system whereby vacuum is communicated through tube (20), oblong-arcuate opening (355), vacuum-lumens (374, 376), interior chamber (306), plurality of apertures (370), oblong opening (352), and into lumen (151) of cutter (150). This vacuum communicated to lumen (151) of cutter (150) is operable to draw severed tissue samples through oblong opening (352) and into tissue receiving compartment (390). Fluid that is drawn into tissue receiving compartment (390) may pass through apertures (370), into the gap defined between sloped floor (368) of tissue sample tray (350) and arcuate-sloped interior surface (308) of cover (302). This fluid may be drawn from the gap and into second vacuum lumen (376). The fluid may be further communicated to tube (20) via openings (355, 176). In other words, tube (20) may be used to suction fluid from tissue sample holder (300), in addition to providing suction through lumen (151) of cutter (150).

After each tissue sample is drawn proximally into tissue sample holder (300) and captured within tissue receiving compartment (390), a user may remove tissue sample holder (300) from probe (100); then remove tissue sample tray (350) from cover (302) and thereby access the tissue samples. To assist a user in removing tissue sample tray (350) from cover (302), tissue sample tray (350) of the present example comprises an arcuate handle (378). Handle (378) is connected to circular member (354) via a pair of living hinges (379). Living hinges (379) permit handle (378) to be deflected to a point where it does not interfere with a fluid seal between circular member (354) and sealing member (170) when tissue sample holder (300) is coupled with probe (100). Living hinges (379) further permit handle (378) to be deflected away from circular member (354) to facilitate grasping of handle (378) by the user.

As best seen in FIG. 14, proximal wall (366) comprises an outwardly extending arcuate edge (380) that is configured to engage arcuate surface (326) of interior chamber (306). Edge (380) bears against arcuate surface (326) such that edge (380) acts as a wiper to remove any fluid or tissue debris from arcuate surface (326) as tissue sample tray (350) is removed from cover (302). It should be understood that seal (358) may also act as a wiper to remove any fluid or tissue debris within distal portion (314) of cover (302) as tissue sample tray (350) is removed from cover (302).

B. Exemplary Tissue Sample Tray with Straight Distal Face

Figure 23:
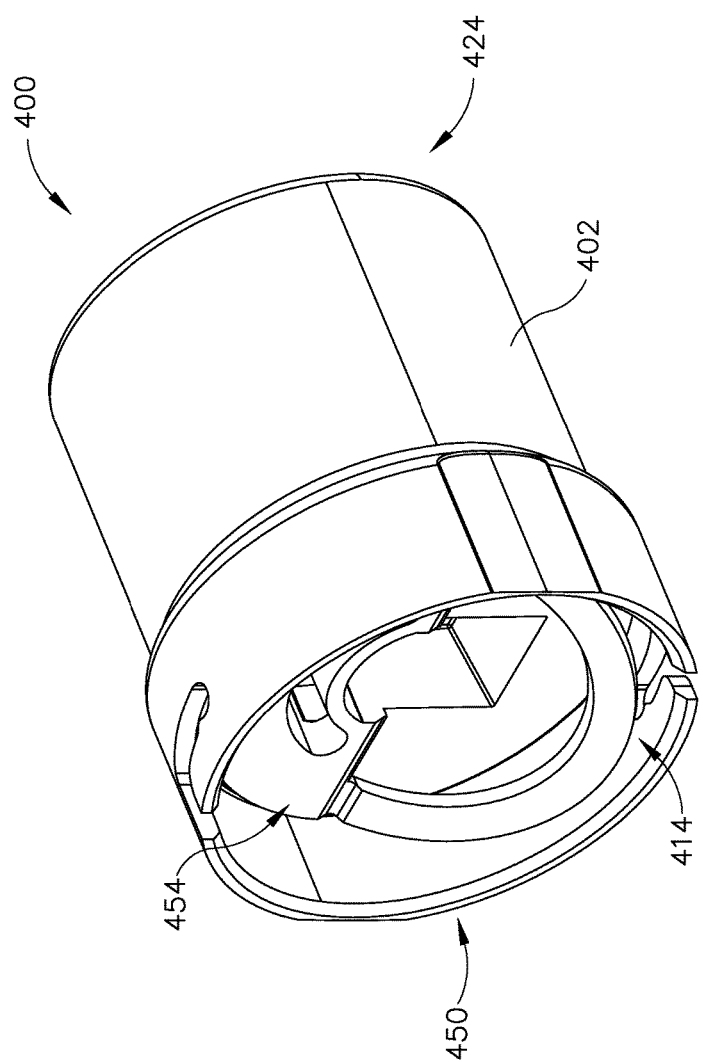
FIG. 23 depicts a perspective view of an exemplary alternative tissue sample holder assembly.
Figure 24:
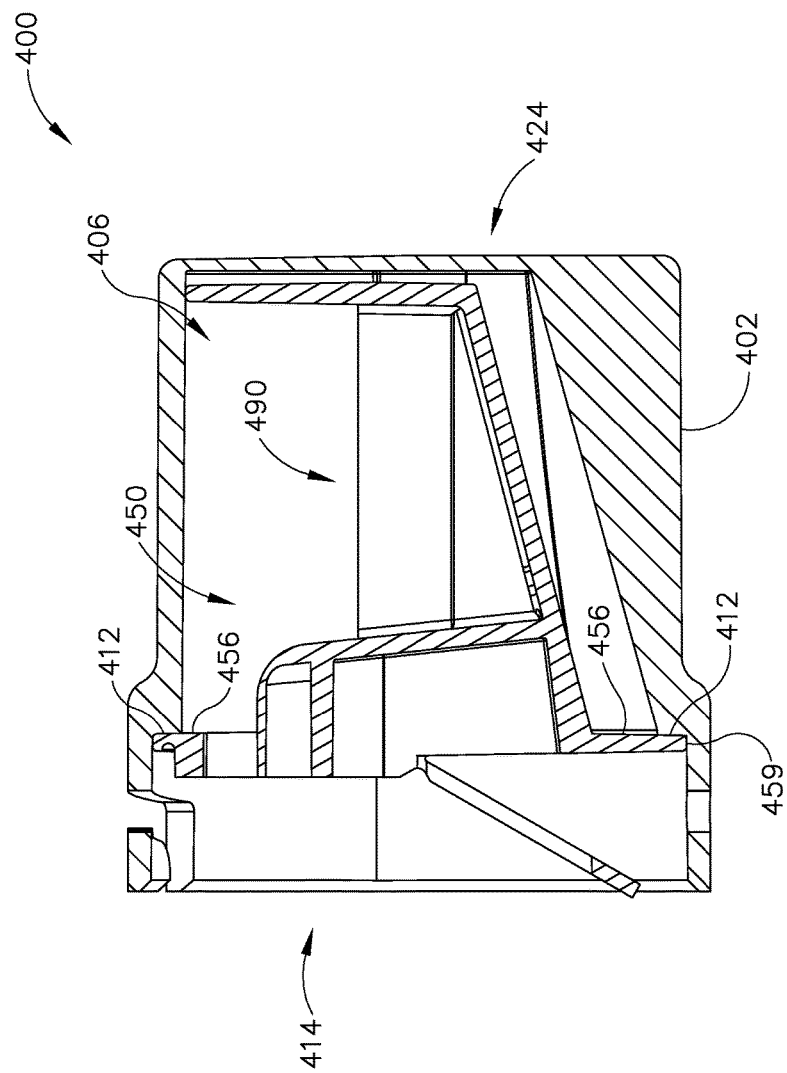
FIG. 24 depicts a cross-sectional view of the tissue sample holder assembly of FIG. 23.

FIGS. 23-24 show an exemplary alternative tissue sample holder (400). Tissue sample holder (400) is configured to operate substantially similar to tissue sample holder (300) discussed above except for the differences discussed below. In particular, tissue sample holder (400) of the present example is configured to facilitate the passage of vacuum from tube (20) and into lumen (151) of cutter (150) to thereby draw tissue samples from lumen (151) of cutter (150) an into a tissue receiving compartment (490).

Tissue sample holder (400) of the present example comprises a cup or cover (402) and a tissue sample tray (450). Tissue sample tray (450) comprises a circular member (454). As best seen in FIG. 24, circular member (454) presents an annular proximal face (456) that is configured to engage a lip (412) of cover (402) when tissue sample tray (450) is positioned within an interior chamber (406) of cover (402). Annular proximal face (456) is not sloped in this example. In particular, annular proximal face (456) extends along a plane that is perpendicular to the longitudinal axis of tissue sample holder (400). It should be understood that, in some versions of tissue sample holder (400), proximal face (456) of circular member (454) may be configured such that proximal face (456) mates with lip (412) to thereby form a fluid seal.

Figure 25:
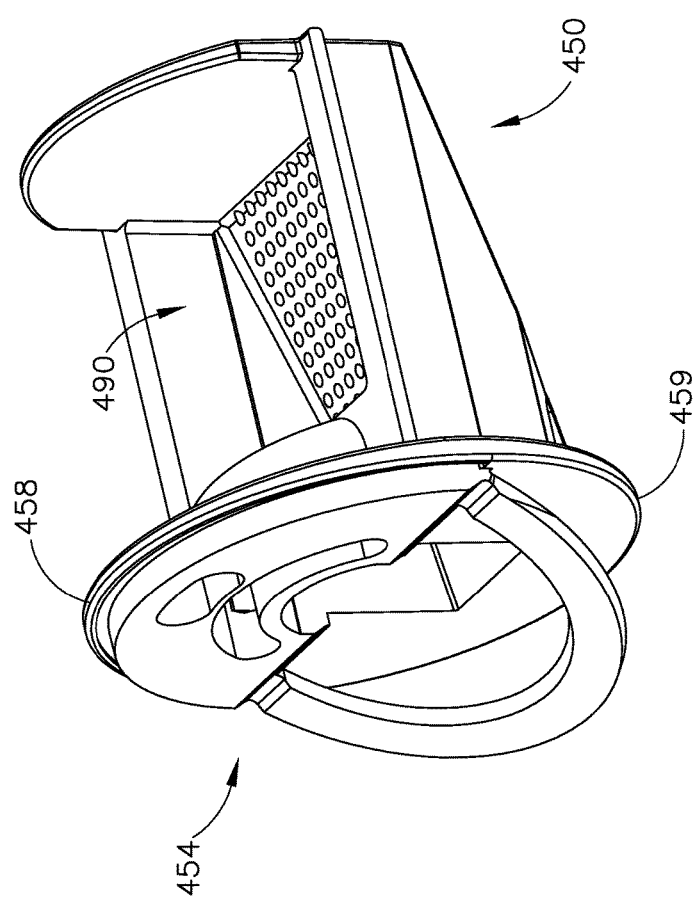
FIG. 25 depicts a perspective view of a tissue sample tray of the tissue sample holder assembly of FIG. 23.
Figure 26:
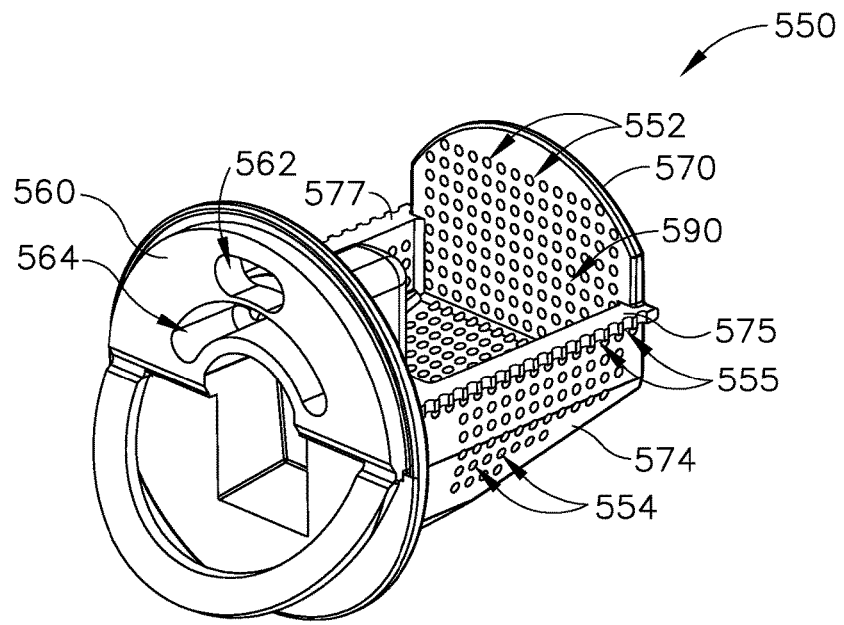
FIG. 26 depicts a perspective view of an exemplary alternative tissue sample tray that may be incorporated into the tissue sample holder assembly of FIG. 23.
Figure 27:
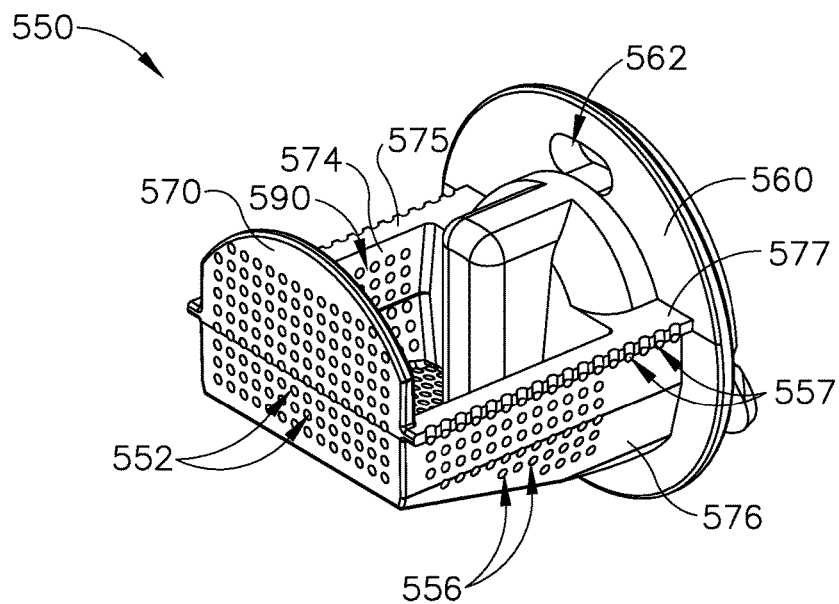
FIG. 27 depicts another perspective view of the tissue sample tray of FIG. 26.
Figure 28:
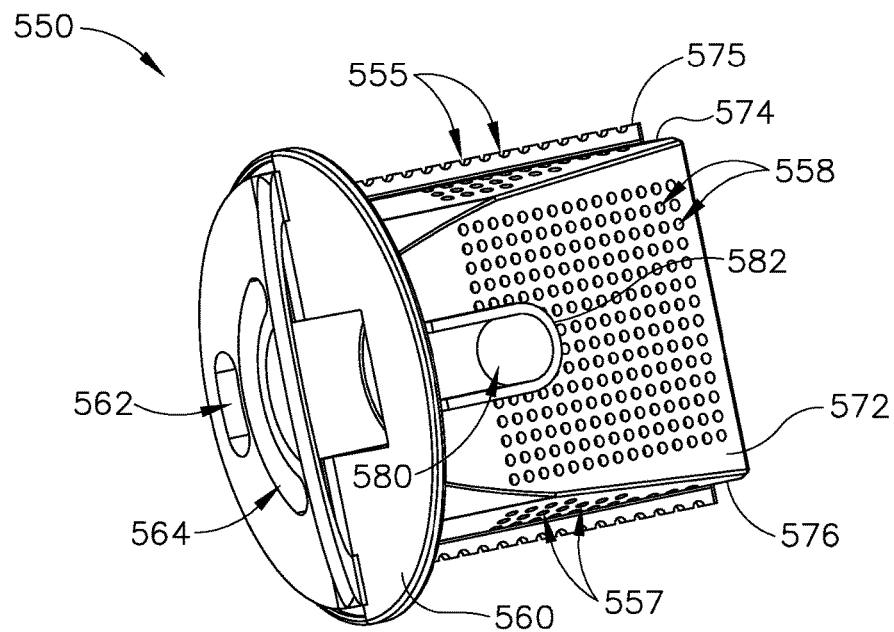
FIG. 28 depicts another perspective view of the tissue sample tray of FIG. 26.

As shown in FIGS. 24-25, a first portion of an exterior circumference of circular member (454) presents an o-ring-like arcuate seal (458). Seal (458) only extends along an upper portion of the exterior circumference of circular member (454) in this example. Seal (458) is configured to engage a first portion of a circular interior surface of a distal portion (414) of cover (402) to thereby form a fluid seal. A second portion of an exterior circumference of circular member (454) presents an arcuate wiper seal (459). Seal (459) only extends along a lower portion of the exterior circumference of circular member (454) in this example. Seal (459) is configured to engage a second portion of the circular interior surface of distal portion (414) of cover (402) to thereby form a fluid seal. Thus, it should be understood that seals (458, 459) together fluidly seal an outer perimeter of circular member (454) against an interior surface of cover (402) between a proximal portion (424) of interior chamber (406) of cover (402) and distal portion (414) of interior chamber (406) of cover (402).

Aside from the differences noted above, tissue sample holder (400) is constructed and operable identically to tissue sample holder (300). Tissue sample holders (300, 400) are thus interchangeable with respect to probe (100).

C. Exemplary Tissue Sample Tray with Perforated Walls and Single Central Sump

FIGS. 26-31 show an exemplary alternative tissue sample tray (550) that may be readily incorporated into tissue sample holder (400) in lieu of tissue sample tray (450). Tissue sample tray (550) is substantially identical to tissue sample tray (450) except for the differences noted below. Tissue sample tray (550) of the present example comprises a circular member (560), a proximal wall (570), a floor (572), and a pair of sidewalls (574, 576) extending between proximal wall (570) and circular member (560). Circular member (560), walls (570, 574, 576), and floor (572) cooperate to define a tissue receiving compartment (590). Sidewalls (574, 576) each include an outwardly and longitudinally extending flange (575, 577) that is configured to engage cover (402) when tissue sample tray (550) is inserted in cover (402).

Figure 29:
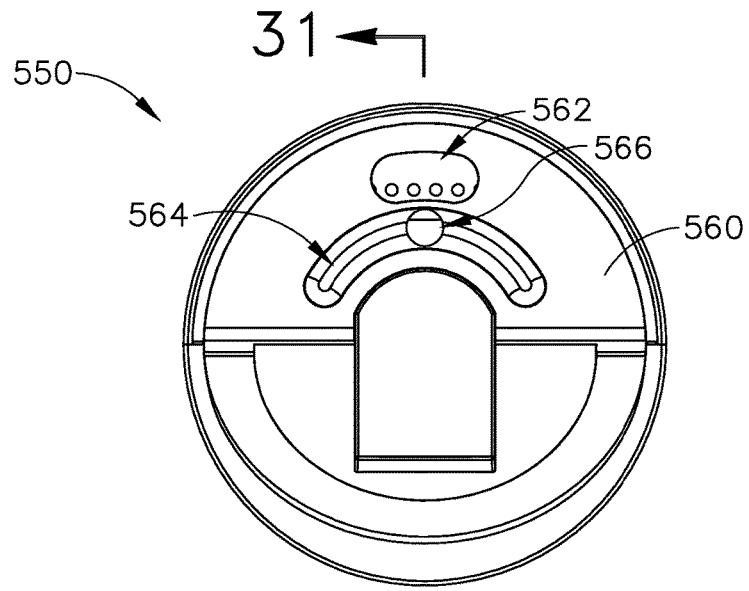
FIG. 29 depicts an end elevational view of the tissue sample tray of FIG. 26.
Figure 30:
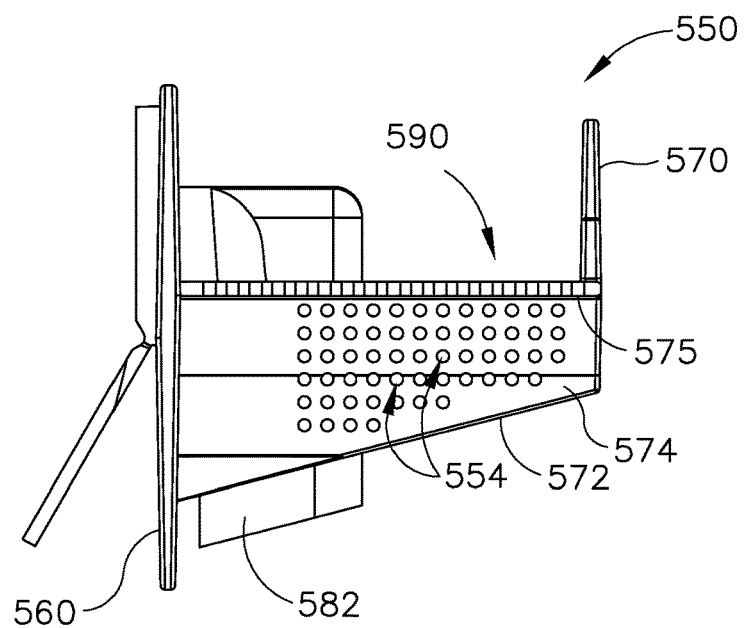
FIG. 30 depicts a side elevational view of the tissue sample tray of FIG. 26.
Figure 31:
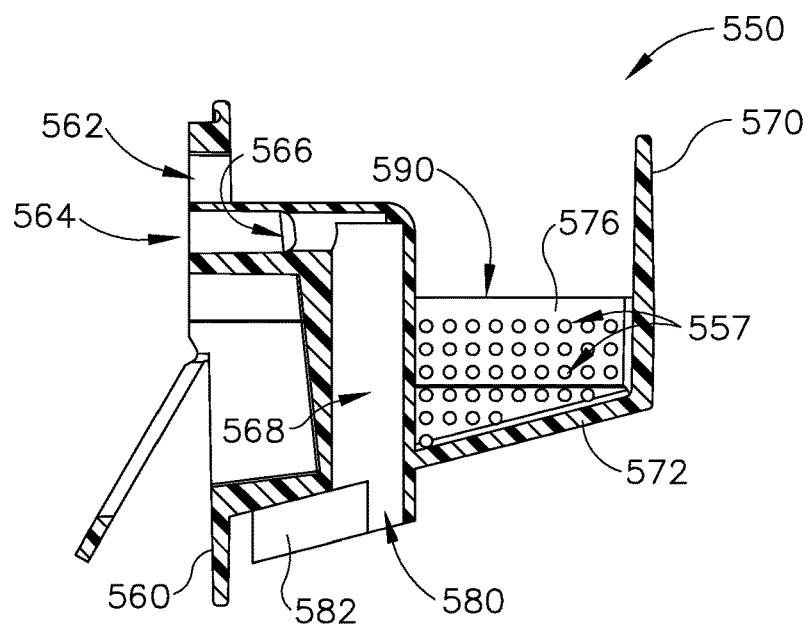
FIG. 31 depicts a cross-sectional side view of the tissue sample tray of FIG. 26, taken along line 31-31 of FIG. 29.
Figure 32:
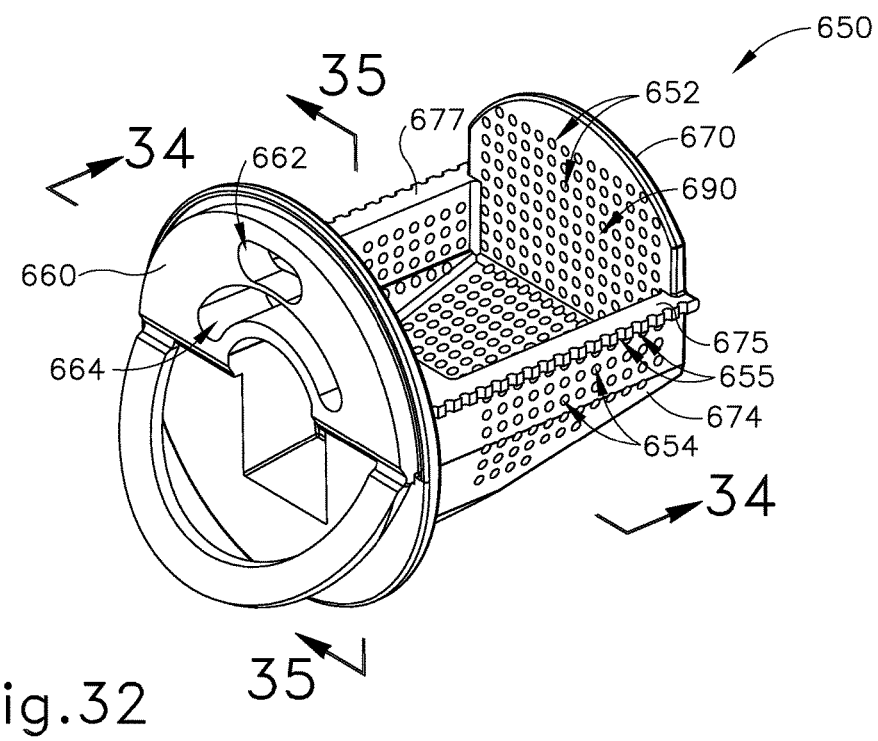
FIG. 32 depicts a perspective view of another exemplary alternative tissue sample tray that may be incorporated into the tissue sample holder assembly of FIG. 23.
Figure 33:
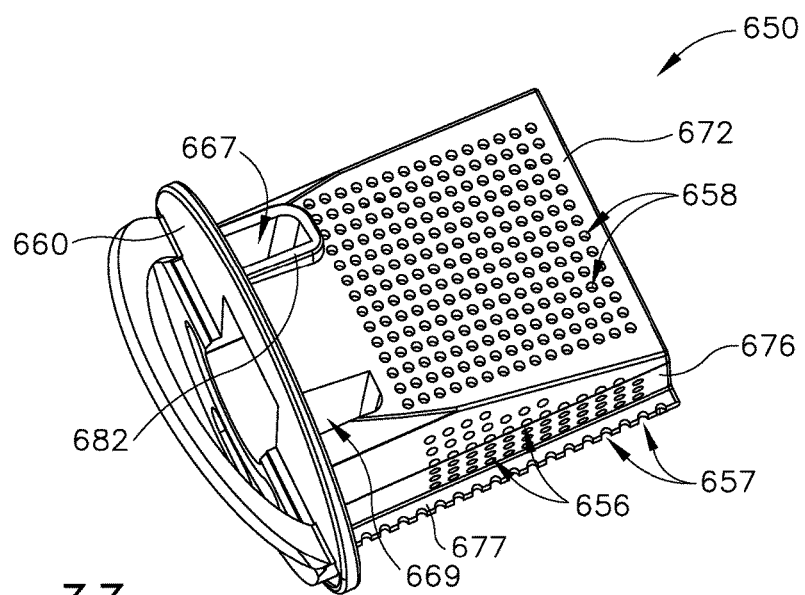
FIG. 33 depicts another perspective view of the tissue sample tray of FIG. 32.

As best seen in FIG. 29, circular member (560) defines an upper opening (562) and a lower recess (564) with a lower opening (566). Opening (562) and recess (564) are configured to align with corresponding openings (174, 176) of sealing member (170) when a tissue sample holder incorporating tissue sample tray (550) is coupled with probe (100). Upper opening (562) is in direct fluid communication with tissue receiving compartment (590). As best seen in FIG. 31, lower recess (564) provides a fluid pathway to a lower opening (566), which is in fluid communication with a sump lumen (568). Sump lumen (568) terminates in a lower opening (580) at the distal end of floor (572). A lip (582) extends downwardly from floor (572) and surrounds lower opening (580). Lip (582) is configured to come close to but not contact the interior surface of cover (402) when tissue sample tray (550) is inserted in cover (402). Lip (582) is thus configured and operable similarly to lip (377) described above.

In the present example, a plurality of drainage apertures (552, 554, 556, 558) are formed through walls (570, 574, 576) and floor (572), respectively. Flanges (575, 577) of sidewalls (574, 576) also include a plurality of drainage recesses (555, 557). It should be understood that, when vacuum from tube (20) is applied through openings (176, 566), such vacuum will be communicated via sump lumen (568) and lower opening (580) to the space defined between the outer surface of floor (572) and the inner surface of cover (402); and to the space defined between the outer surfaces of sidewalls (574, 576) and the inner surface of cover (402). It should be understood that drainage apertures drainage apertures (552, 554, 556, 558) and drainage recesses (555, 557) may all provide pathways for such vacuum to reach tissue receiving compartment (590) and lumen (151) of cutter (150). It should also be understood that drainage apertures drainage apertures (552, 554, 556, 558) and drainage recesses (555, 557) may all provide pathways for fluid to drain from tissue receiving compartment (590) and thereby be drawn out via lower opening (580), sump lumen (568), and openings (176, 566).

D. Exemplary Tissue Sample Tray with Perforated Walls and Dual Sumps

FIGS. 32-35 show another exemplary alternative tissue sample tray (650) that may be readily incorporated into tissue sample holder (400) in lieu of tissue sample tray (450). Tissue sample tray (650) is substantially identical to tissue sample tray (450) except for the differences noted below. Tissue sample tray (650) of the present example comprises a circular member (660), a proximal wall (670), a floor (672), and a pair of sidewalls (674, 676) extending between proximal wall (670) and circular member (660). Circular member (660), walls (670, 674, 676), and floor (672) cooperate to define a tissue receiving compartment (690). Sidewalls (674, 676) each include an outwardly and longitudinally extending flange (675, 677) that is configured to engage cover (402) when tissue sample tray (650) is inserted in cover (402).

Figure 34:
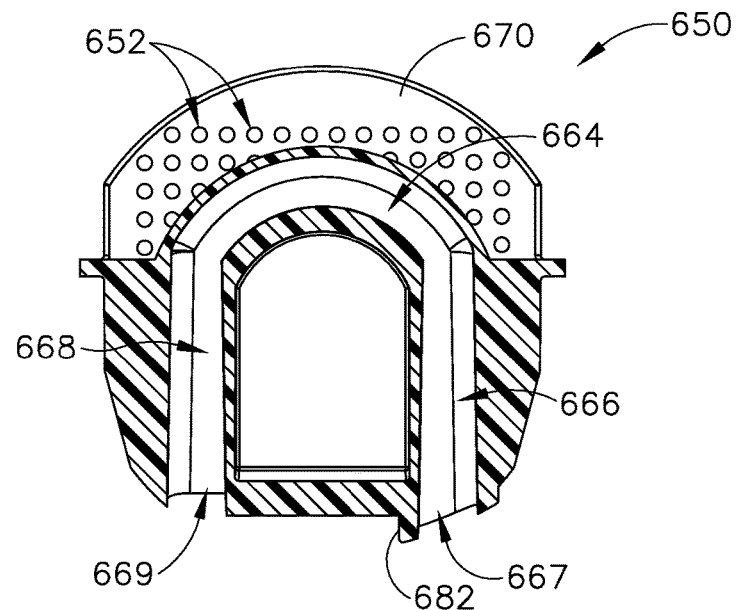
FIG. 34 depicts a cross-sectional end view of the tissue sample tray of FIG. 32, taken along line 34-34 of FIG. 32.
Figure 35:
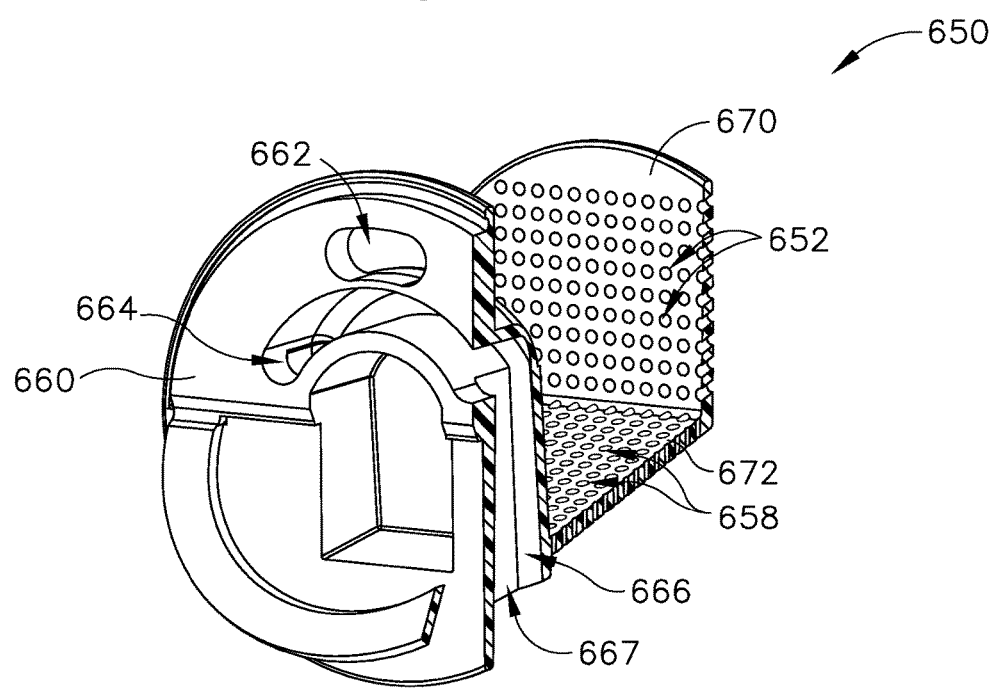
FIG. 35 depicts a cross-sectional perspective view of the tissue sample tray of FIG. 32, taken along line 35-35 of FIG. 32.

As best seen in FIG. 35, circular member (660) defines an upper opening (662) and a lower recess (664). Opening (662) and recess (664) are configured to align with corresponding openings (174, 176) of sealing member (170) when a tissue sample holder incorporating tissue sample tray (650) is coupled with probe (100). Upper opening (662) is in direct fluid communication with tissue receiving compartment (690). As best seen in FIG. 34, lower recess (664) is in fluid communication with a pair of sump lumens (666, 668). Sump lumen (666) terminates in a lower opening (667) at the distal end of floor (672). Sump lumen (668) terminates in a lower opening (669) at the distal end of floor (672). Lumens (666, 668) and their corresponding openings (667, 669) are laterally offset from each other. A lip (682) extends downwardly from floor (672) and surrounds lower opening (667). Lip (682) is configured to come close to but not contact the interior surface of cover (402) when tissue sample tray (650) is inserted in cover (402). Lip (682) is thus configured and operable similarly to lip (377) described above.

In the present example, a plurality of drainage apertures (652, 654, 656, 658) are formed through walls (670, 674, 676) and floor (672), respectively. Flanges (675, 677) of sidewalls (674, 676) also include a plurality of drainage recesses (655, 657). Drainage apertures (652, 654, 656, 658) and drainage recesses (655, 657) are configured and operable substantially identically to drainage apertures (552, 554, 556, 558) and drainage recesses (555, 557) described above. It should be understood that, when vacuum from tube (20) is applied through opening (176) and recess (664), such vacuum will be communicated via sump lumens (666, 668) and lower openings (667, 669) to the space defined between the outer surface of floor (672) and the inner surface of cover (402); and to the space defined between the outer surfaces of sidewalls (674, 676) and the inner surface of cover (402). It should further be understood that fluid drained from tissue receiving compartment (690) may be drawn out via lower openings (667, 669), sump lumens (666, 668), recess (664), and opening (176). In some instances, the presence of lip (682) may provide greater suction of fluid through opening (667) than through opening (669).

Figure 36:
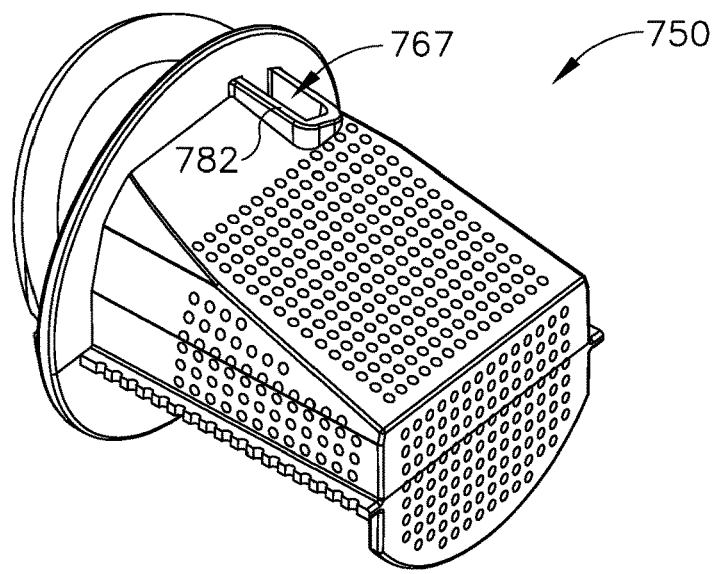
FIG. 36 depicts a perspective view of another exemplary alternative tissue sample tray that may be incorporated into the tissue sample holder assembly of FIG. 23.

FIG. 36 shows another exemplary alternative tissue sample tray (750) that may be readily incorporated into tissue sample holder (400) in lieu of tissue sample tray (450). Tissue sample tray (750) is substantially identical to tissue sample tray (650) described above, except that tissue sample tray (750) of this example has just one lower opening (767) with a lip (782). Tissue sample tray (750) of this example thus lacks an equivalent of lower opening (669). Tissue sample tray (750) is otherwise identical to tissue sample tray (650)

Figure 37:
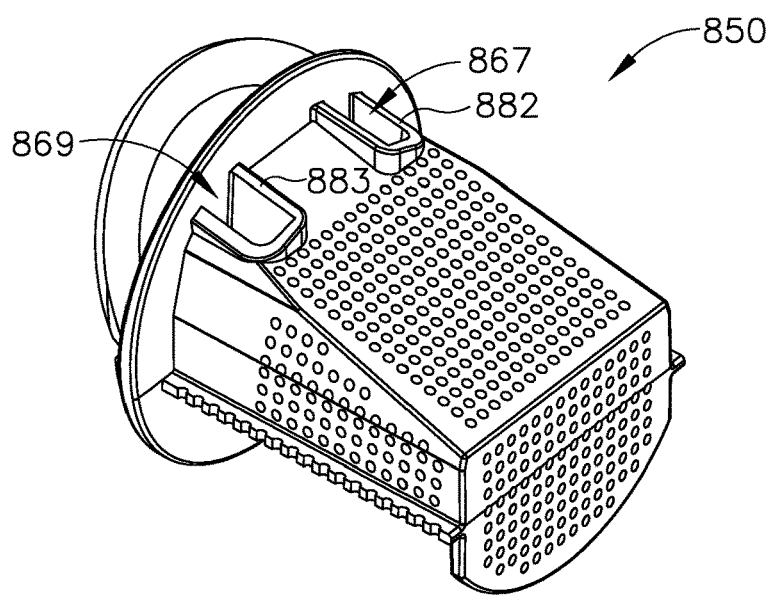
FIG. 37 depicts a perspective view of another exemplary alternative tissue sample tray that may be incorporated into the tissue sample holder assembly of FIG. 23.

FIG. 37 shows another exemplary alternative tissue sample tray (850) that may be readily incorporated into tissue sample holder (400) in lieu of tissue sample tray (450). Tissue sample tray (850) is substantially identical to tissue sample tray (650) described above, except that both lower openings (867, 869) of tissue sample tray (850) in this example have respective lips (882, 883). Tissue sample tray (850) is otherwise identical to tissue sample tray (650).

Figure 38:
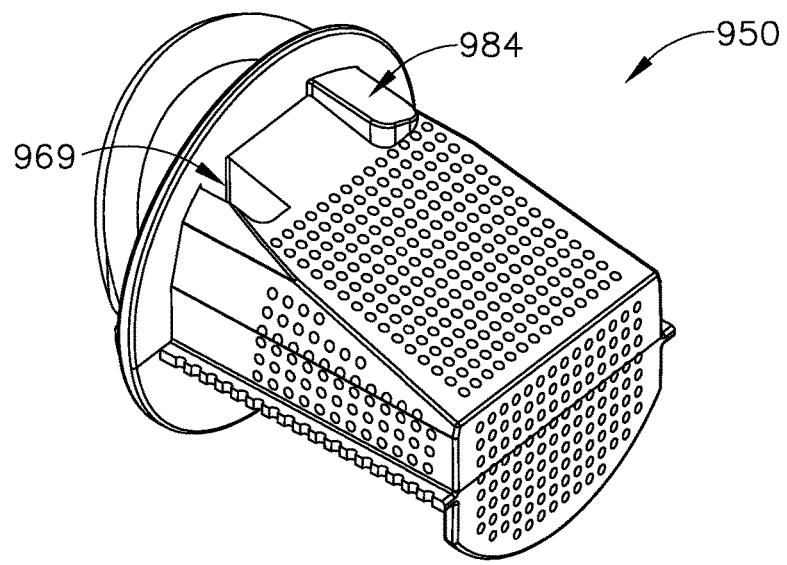
FIG. 38 depicts a perspective view of another exemplary alternative tissue sample tray that may be incorporated into the tissue sample holder assembly of FIG. 23.

FIG. 38 shows another exemplary alternative tissue sample tray (950) that may be readily incorporated into tissue sample holder (400) in lieu of tissue sample tray (450). Tissue sample tray (950) is substantially identical to tissue sample tray (650) described above, except that tissue sample tray (650) of this example has just one lower opening (696). Lower opening (696) does not have a lip in this example. Tissue sample tray (950) of this example thus lacks an equivalent of lower opening (967). Instead, tissue sample tray (950) of this example includes a sealed, downwardly extending protrusion in the same location where lower opening (667) and lip (682) are in tissue sample tray (650). Tissue sample tray (950) is otherwise identical to tissue sample tray (650).

E. Exemplary Tissue Sample Tray with Dual Floors

Figure 39:
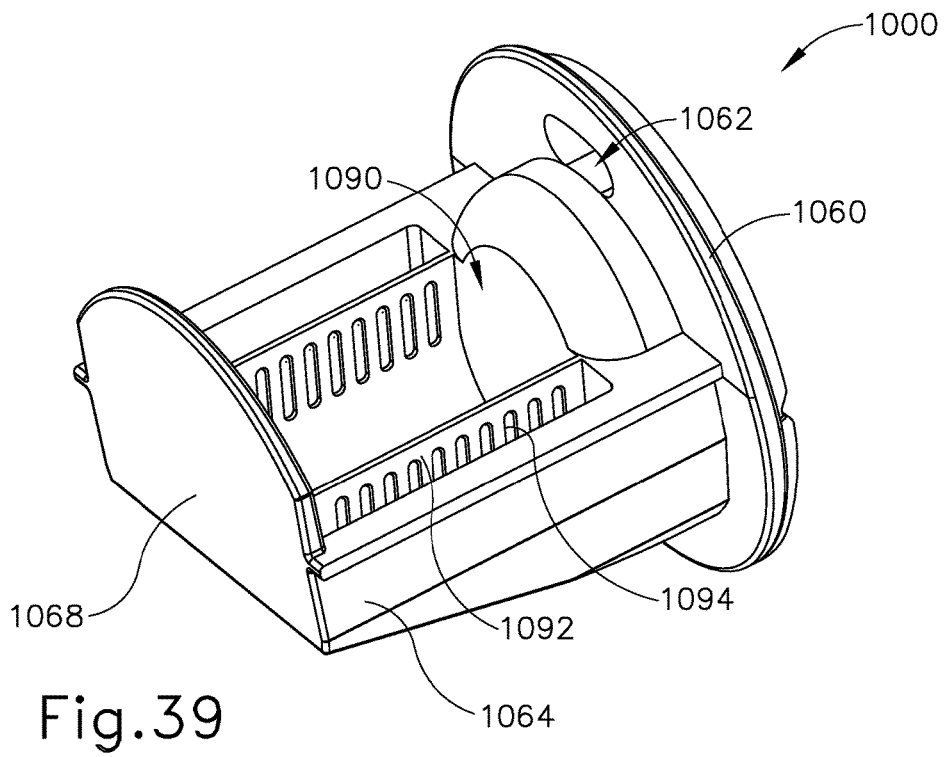
FIG. 39 depicts a perspective view of another exemplary alternative tissue sample tray that may be incorporated into the tissue sample holder assembly of FIG. 23.
Figure 40:
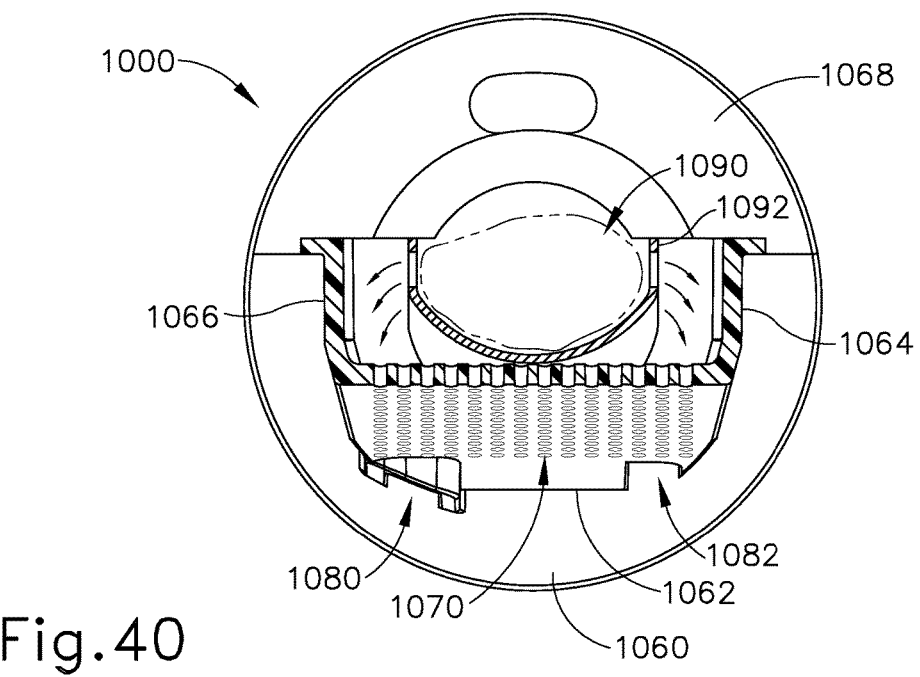
FIG. 40 depicts an end elevational view of the tissue sample tray of FIG. 39.

FIGS. 39-40 show another exemplary alternative tissue sample tray (1000) that may be readily incorporated into tissue sample holder (300) in lieu of tissue sample tray (350). Tissue sample tray (1000) is substantially identical to tissue sample tray (350) except for the differences noted below. Tissue sample tray (1000) of this example comprises a circular member (1060) that is includes an opening (1062) disposed over a tissue receiving compartment (1090). Tissue receiving compartment (1090) is defined by a U-shaped floor (1092). Floor (1092) includes a plurality of drainage slots (1094). U-shaped floor (1092) is positioned within a space that is defined by circular member (1060), a floor (1062), sidewalls (1064, 1066), and a proximal wall (1068). Floor (1062) includes a plurality of drainage openings (1070). Tissue sample tray (1000) also includes a pair of lower openings (1080, 1082) that are configured to provide vacuum from tube (20). It should be understood that vacuum from tube (20) may be communicated to lumen (151) of cutter (150) via openings (1080, 1082, 1070), slots (1094), and opening (1062). It should also be understood that severed tissue samples that are drawn proximally through lumen (151) of cutter (150) may be deposited onto floor (1092). Fluids drawn through lumen (151) of cutter (150) may drain through slots (1094) and openings (1080, 1082, 1070); and may eventually be drawn out through tube (20) via lower openings (1080, 1082).

The inclusion of floor (1092) may prevent severed tissue samples from covering drainage openings (1070), such that floor (1092) may maintain a substantially clear fluid path to all drainage openings (1070), even when a plurality of severed tissue samples have gathered within tissue receiving compartment (1090). In other words, floor (1092) may assist in promoting communication of vacuum from tube (20) to lumen (151) of cutter (150); and drainage of fluid via drainage openings (1071). Tissue sample tray (1000) is otherwise identical to tissue sample tray (350).

F. Exemplary Tissue Sample Tray with Drainage Slots

Figure 41:
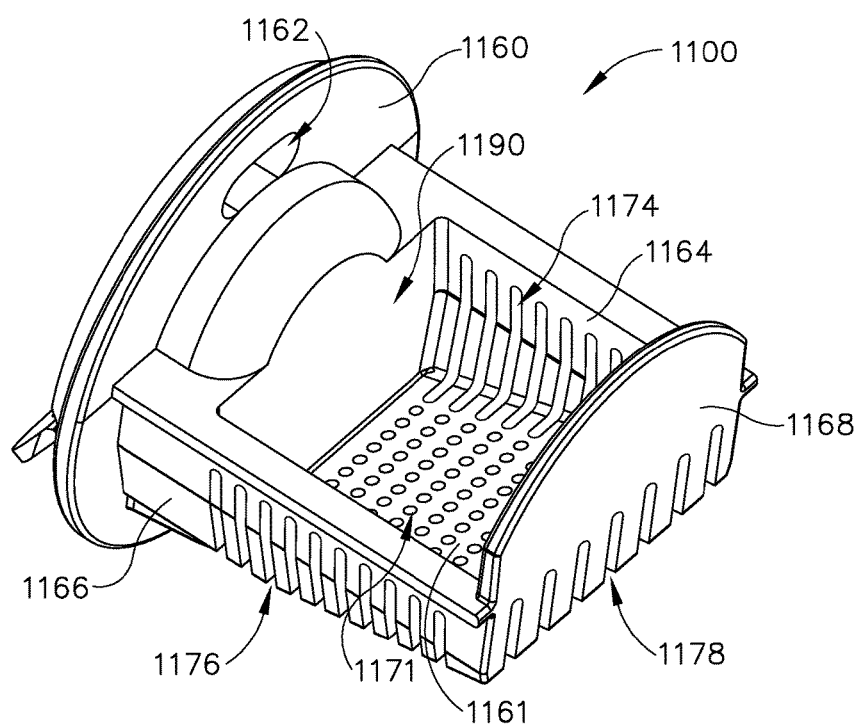
FIG. 41 depicts a perspective view of another exemplary alternative tissue sample tray that may be incorporated into the tissue sample holder assembly of FIG. 23.

FIG. 41 shows another exemplary alternative tissue sample tray (1100) that may be readily incorporated into tissue sample holder (300) in lieu of tissue sample tray (350). Tissue sample tray (1100) is substantially identical to tissue sample tray (350) except for the differences noted below. Tissue sample tray (1100) of this example comprises a circular member (1160) that is includes an opening (1162) disposed over a tissue receiving compartment (1190). Tissue receiving compartment (1190) is defined by circular member (1160), a floor (1161), sidewalls (1164, 1166), and a proximal wall (1168). Floor (1161) includes a plurality of drainage openings (1171). Sidewalls (1164, 1166) and proximal wall (1168) further comprise respective drainage slots (1174, 1176, 1178). Drainage slots (1174, 1176, 1178) cooperate with drainage openings (1171) to provide pathways for vacuum to lumen (151) of cutter via tissue receiving compartment (1190) and opening (1162). Drainage slots (1174, 1176, 1178) also cooperate with drainage openings (1171) to provide pathways for drainage of fluids from tissue receiving compartment (1190). Tissue sample tray (1100) is otherwise identical to tissue sample tray (350).

G. Exemplary Tissue Sample Tray with Tissue Stand-Offs

Figure 42:
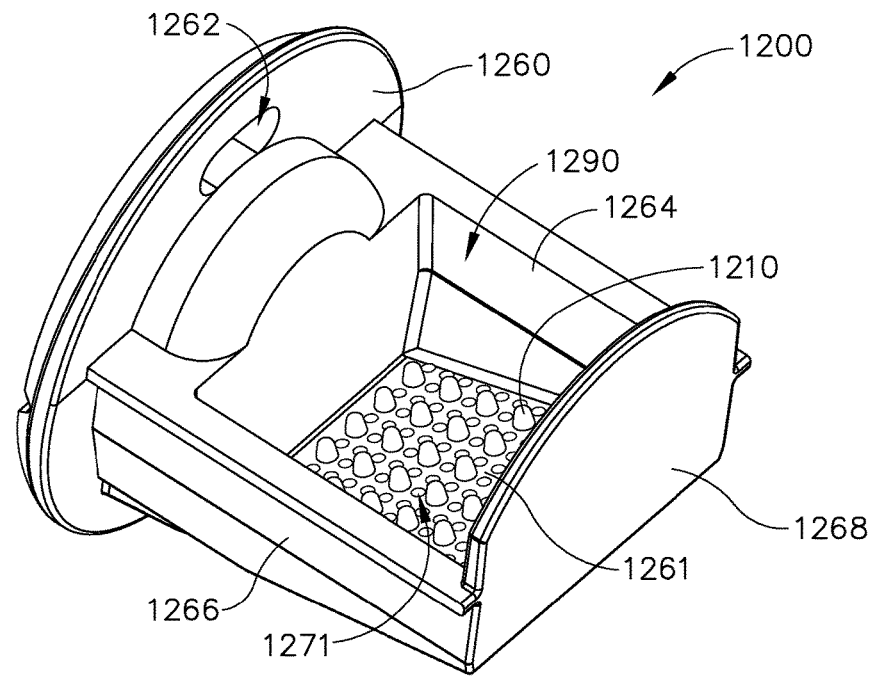
FIG. 42 depicts a perspective view of another exemplary alternative tissue sample tray that may be incorporated into the tissue sample holder assembly of FIG. 23.
Figure 43:
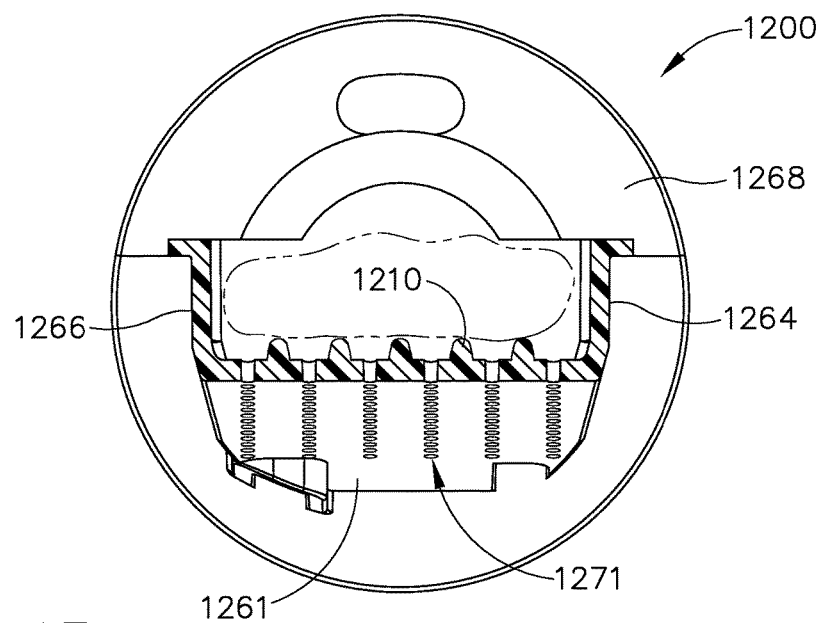
FIG. 43 depicts an end elevational view of the tissue sample tray of FIG. 42.

FIGS. 42-43 show another exemplary alternative tissue sample tray (1200) that may be readily incorporated into tissue sample holder (300) in lieu of tissue sample tray (350). Tissue sample tray (1200) is substantially identical to tissue sample tray (350) except for the differences noted below. Tissue sample tray (1200) of this example comprises a circular member (1260) that is includes an opening (1262) disposed over a tissue receiving compartment (1290). Tissue receiving compartment (1290) is defined by circular member (1260), a floor (1261), sidewalls (1264, 1266), and a proximal wall (1268). Floor (1261) includes a plurality of drainage openings (1271). Drainage openings (1271) provide pathways for vacuum to lumen (151) of cutter (150) via tissue receiving compartment (1290) and opening (1262). Drainage openings (1271) also provide pathways for drainage of fluids from tissue receiving compartment (1290).

Tissue sample tray (1200) of the present example further includes a plurality of protrusions (1210) extending upwardly from floor (1261), in spaces between drainage openings (1271). In the present example, protrusions (1210) are rounded like domes or hemispheres, though it should be understood that protrusions (1210) may have any other suitable configurations. Protrusions (1210) are configured to act as standoffs for tissue samples that collect in tissue receiving compartment (1290), such that protrusions (1210) keep the tissue samples from gathering directly on floor (1261) and blocking drainage openings (1271). Protrusions (1210) thus maintain a substantially clear fluid path to all drainage openings (1271), even when a plurality of severed tissue samples have gathered within tissue receiving compartment (1290). In other words, protrusions (1210) assist in promoting communication of vacuum from tube (20) to lumen (151) of cutter (150); and drainage of fluid from tissue receiving compartment (1290) via drainage openings (1271). Tissue sample tray (1200) is otherwise identical to tissue sample tray (350).

H. Exemplary Tissue Sample Tray with Divider

Figure 44:
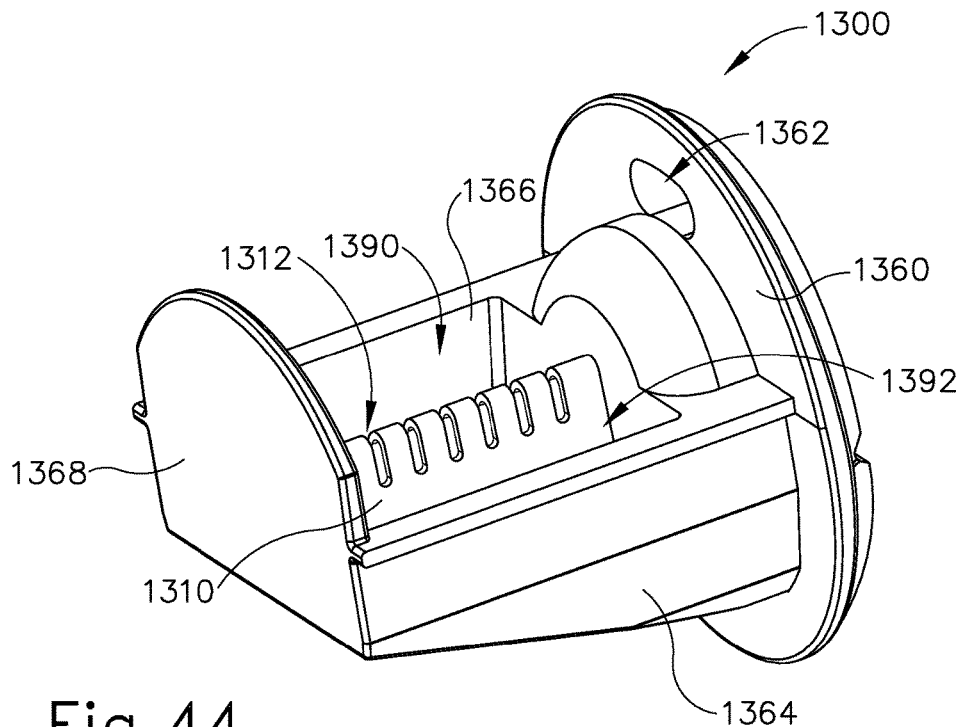
FIG. 44 depicts a perspective view of another exemplary alternative tissue sample tray that may be incorporated into the tissue sample holder assembly of FIG. 23.
Figure 45:
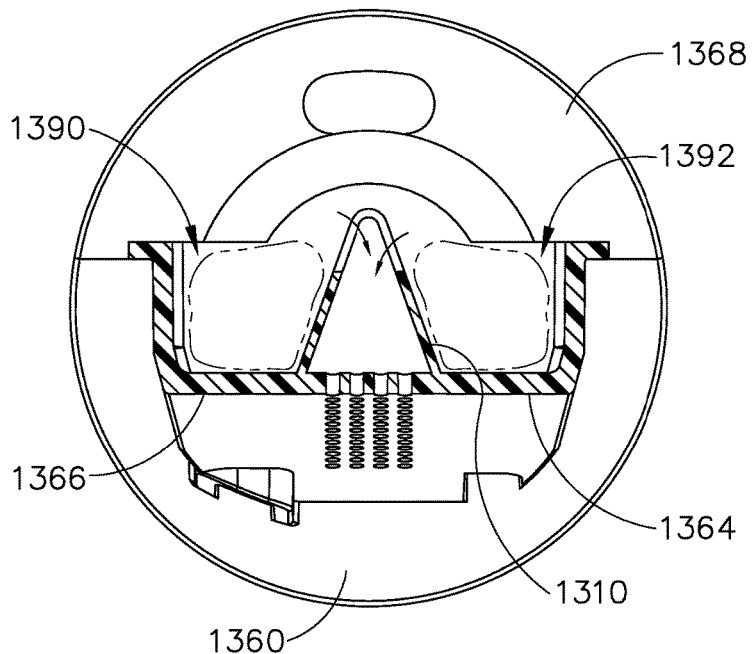
FIG. 45 depicts an end elevational view of the tissue sample tray of FIG. 44.
Figure 46:
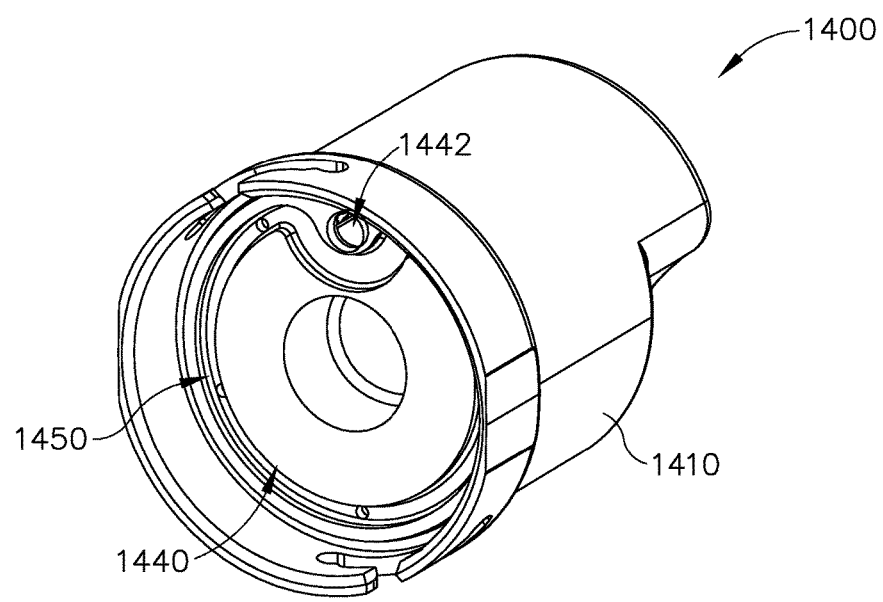
FIG. 46 depicts a perspective view of an exemplary alternative tissue sample holder assembly that may be incorporated into the probe of FIG. 4.

FIGS. 44-45 show another exemplary alternative tissue sample tray (1300) that may be readily incorporated into tissue sample holder (300) in lieu of tissue sample tray (350). Tissue sample tray (1300) is substantially identical to tissue sample tray (350) except for the differences noted below. Tissue sample tray (1300) of this example comprises a circular member (1360) that is includes an opening (1362) disposed over a hump wall (1310) and a pair of tissue receiving compartments (1390, 1392). Tissue receiving compartment (1390) is defined by circular member (1360), a sidewall (1366), hump wall (1310), and a proximal wall (1368). Tissue receiving compartment (1392) is defined by circular member (1360), a sidewall (1364), hump wall (1310), and proximal wall (1368). Hump wall (1310) thus separates tissue receiving compartments (1390, 1392).

Hump wall (1310) includes a plurality of transversely extending drainage slots (1312). Drainage slots (1312) are in fluid communication with tube (20) in accordance with the teachings above. Drainage slots (1312) thus provide pathways for vacuum to lumen (151) of cutter (150) via opening (1262). Drainage slots (1312) also provide pathways for drainage of fluids from tissue receiving compartments (1390, 1392). For instance, fluid may gather in each tissue receiving compartments (1390, 1392) until the fluid reaches the level of drainage slots (1312), at which point the fluid is drawn out via slots (1312) under the influence of vacuum from tube (20). In addition or in the alternative, as severed tissue samples gather in each tissue receiving compartments (1390, 1392), the tissue samples may displace the fluid, further driving the fluid toward slots (1312). As tissue samples are communicated proximally through opening (1362) hump wall (1310) may deflect the tissue samples into either tissue receiving compartment (1390) or tissue receiving compartment (1392). In some versions, hump wall (1310), sidewalls (1364, 1366), and/or proximal wall (1368) include additional drainage openings to further promote communication of vacuum and drainage of fluid.

IV. Exemplary Alternative Tissue Sample Holder Assemblies with Lobed Cup Cover

In some instances, it may be desirable to provide a version of a tissue sample holder where the outer cover does not have a circular cross-sectional profile. Changing the cross-sectional profile of the outer cover may improve the ability of the tissue sample holder to communicate vacuum from tube (20) to lumen (151) of cutter (150). In addition or in the alternative, changing the cross-sectional profile of the outer cover may improve the ability of the tissue sample holder to provide drainage of fluids that are drawn proximally through lumen (151) of cutter (150). Various examples of tissue sample holders with covers having non-circular cross-sectional profiles will be described in greater detail below, while other examples will be apparent to those of ordinary skill in the art in view of the teachings herein.

A. Exemplary Tissue Sample Holder with Shelf and Continuous Drainage Trough

Figure 47:
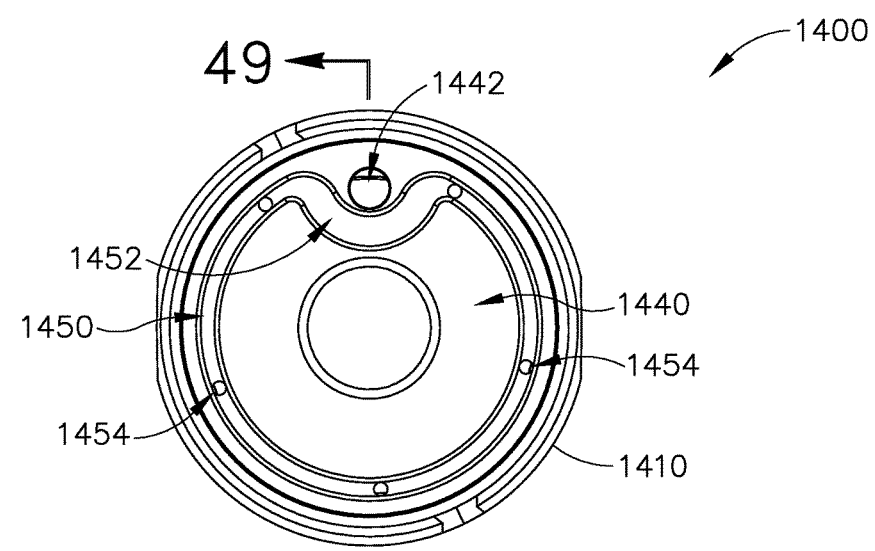
FIG. 47 depicts an end elevational view of the tissue sample holder assembly of FIG. 46.
Figure 48:
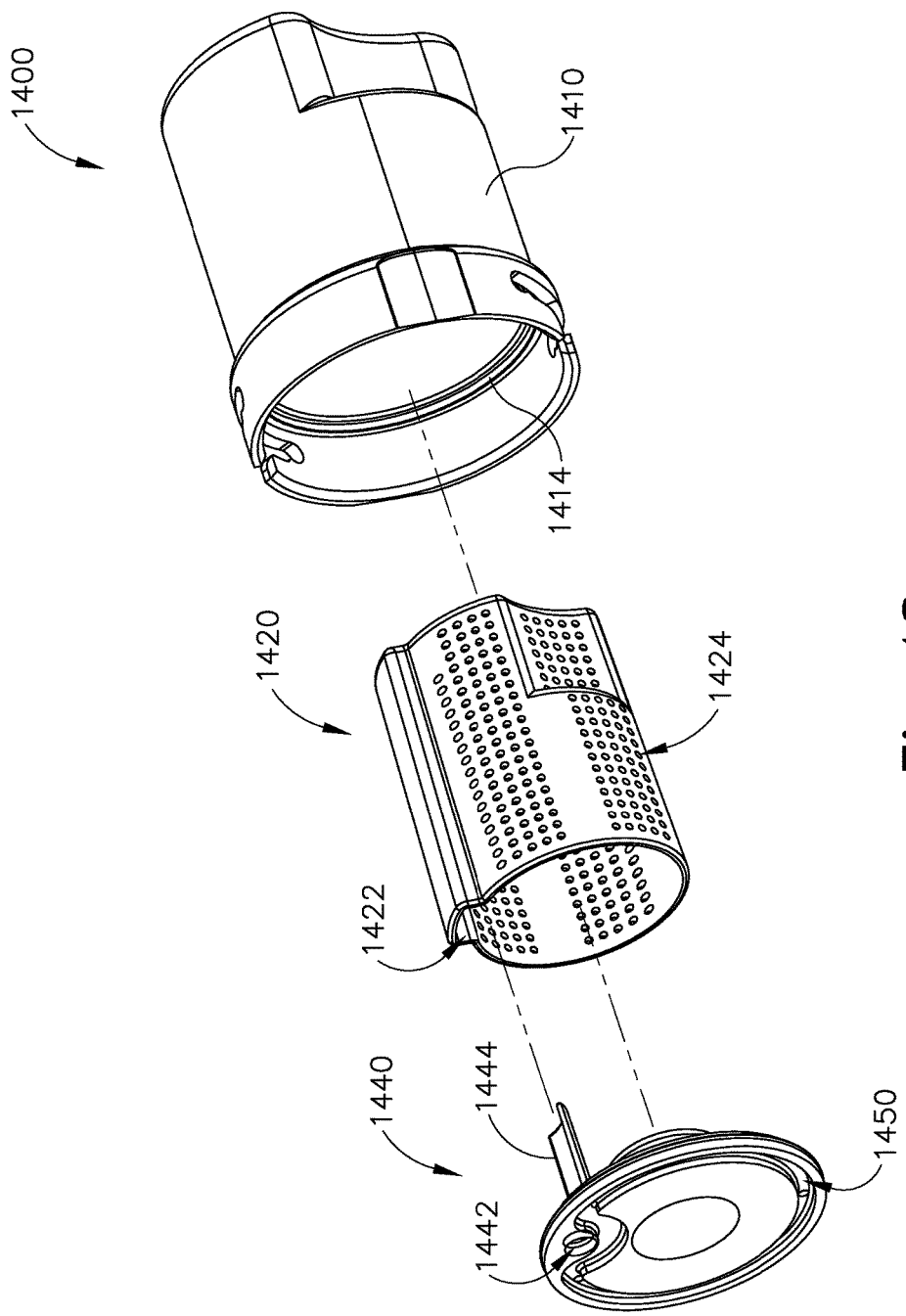
FIG. 48 depicts an exploded perspective view of the tissue sample holder assembly of FIG. 46.
Figure 49:
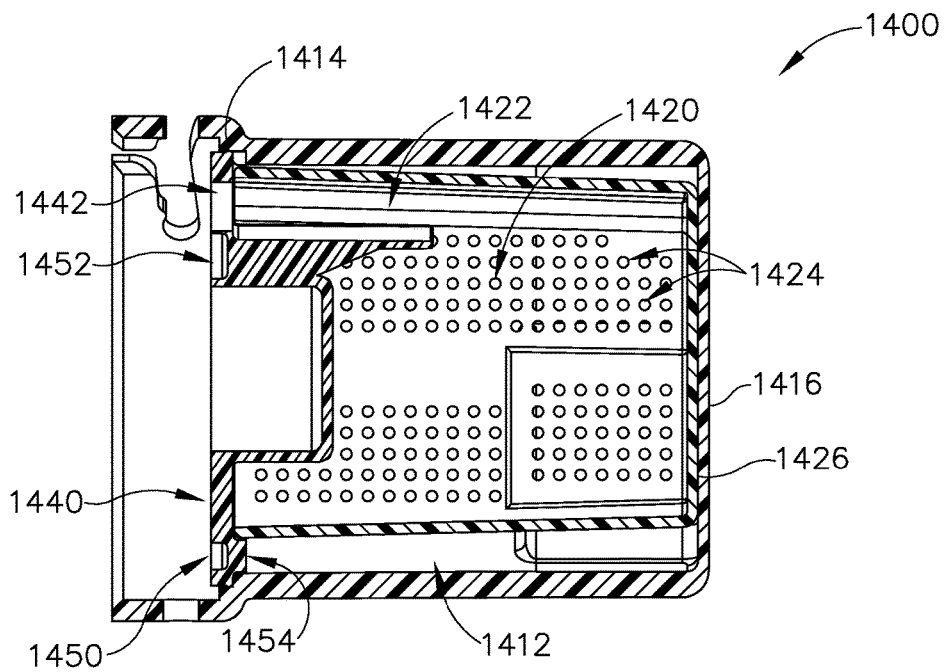
FIG. 49 depicts a cross-sectional side view of the tissue sample holder assembly of FIG. 46, taken along line 49-49 of FIG. 47.
Figure 50:
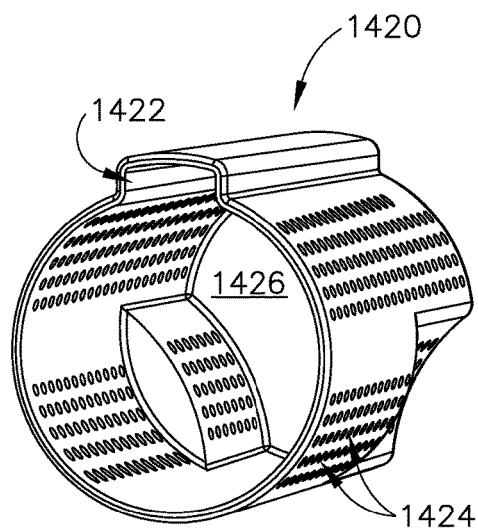
FIG. 50 depicts a perspective view of a basket of the tissue sample holder assembly of FIG. 46.

FIGS. 46-52 show an exemplary alternative tissue sample holder (1400) that may be coupled with probe (100) in place of tissue sample holder (300). Tissue sample holder (1400) of this example comprises a cup-like outer cover (1410), a basket (1420), and an end cap (1440). Outer cover (1410) of the present example comprises a proximal portion that has three lobes, such that the proximal portion of outer cover (1410) does not have a circular cross-sectional profile. Basket (1420) is configured to complement the configuration of outer cover (1410). Basket (1420) defines an upper channel (1422) and a plurality of drainage openings (1424). As best seen in FIG. 49, when basket (1420) is disposed in outer cover (1410), a gap (1412) is defined between basket (1420) and outer cover (1410). Gap (1412) extends about the lateral perimeter of basket (1420), terminating at channel (1422), end cap (1440), and proximal wall (1416) of outer cover (1416)

Figure 51:
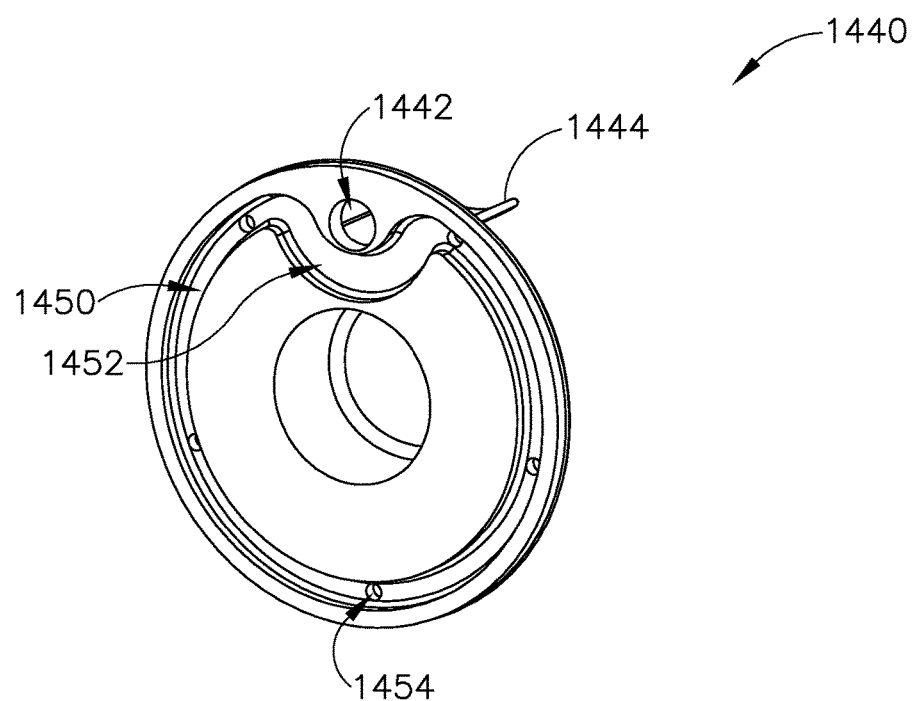
FIG. 51 depicts a perspective view of an end cap of the tissue sample holder assembly of FIG. 46.
Figure 52:
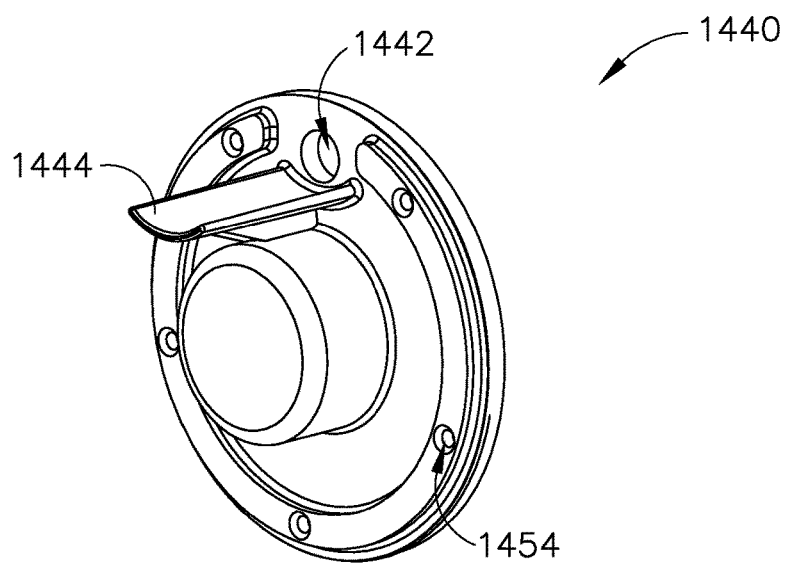
FIG. 52 depicts another perspective view of the end cap of FIG. 51.

As best seen in FIGS. 48-49, end cap (1440) of the present example is configured to fit at the distal end of basket (1420) and engage an annular shoulder (1414) of outer cover (1410). In particular, end cap (1440) seals against annular shoulder (1414) and holds the proximal wall (1426) of basket (1420) in engagement with proximal wall (1416) of outer cover (1416). As best seen in FIGS. 47 and 51, the distal face of end cap (1440) includes an upper opening (1442) and a trough (1450). Trough (1450) includes a dip section (1452) and a plurality of openings (1454). Trough (1450) forms a continuous fluid path at the distal face of end cap (1440). As best seen in FIGS. 49 and 52, a shelf (1444) extends proximally from end cap (1440). Shelf (1444) is positioned just beneath upper opening (1442). When tissue sample holder (1400) is assembled, shelf (1444) extends into upper channel (1422) of basket (1420).

When tissue sample holder (1400) is secured to probe (100), upper opening (1442) is positioned to align with opening (174); while dip section (1452) is positioned to align with opening (176). End cap (1440) will seal against sealing member (170) when tissue sample holder (1400) is secured to probe (100), thereby providing a sealed path for fluid communication between openings (1442, 174); and between opening (176) and trough (1450) (via dip section (1452). Thus, severed tissue samples that are drawn proximally through lumen (151) of cutter (150) will ultimately exit proximally through openings (174, 1442) and onto shelf (1444). In some versions, tissue sample holder (1400) is configured such that shelf (1444) and channel (1422) define a gap that is at least as large as the inner diameter of lumen (151) of cutter (150). This may prevent tissue samples from getting jammed in the space between shelf (1444) and channel (1422).

Vacuum applied through tube (20) will be communicated to trough (1450) via port (178), opening (176) and dip section (152). This vacuum in trough (1450) will be further communicated to gap (1412) via openings (1454). While five openings (1454) are shown, it should be understood that trough (1450) may have any other suitable number of openings (1454) at any suitable positions. The vacuum in gap (1412) will reach the interior of basket (1420) via openings (1424), ultimately reaching lumen (151) of cutter (150) via openings (1442, 174). In addition to providing a path for vacuum to reach lumen (151) of cutter (150) from tube (20), openings (1442, 174, 1424), gap (1412), openings (1454), trough (1450), and opening (176) also provide a path for suctioning fluid from tissue sample holder (1400) via tube (20).

It should be understood from the foregoing that tissue samples that are severed by cutter (150) may be communicated to shelf (1444) in tissue sample holder (1400). When cover (1400) and at least channel (1422) of basket (1420) are transparent, this may provide the operator with an opportunity to easily visually inspect each severed tissue sample. The severed tissue sample may then be dumped from shelf (1440) into the interior of basket (1420). Alternatively, the next tissue sample communicated to shelf (1444) may push the previous sample off of shelf (1444) into the interior of basket (1420). Once a suitable number of tissue samples have been gathered in basket (1420), tissue sample holder (1400) may be removed from probe (100). End cap (1440) may then be removed to reveal the tissue samples in basket (1420). In some instances, the tissue samples may simply be dumped from basket (1420) or pulled from basket (1420) (e.g., using forceps, etc.). In some other instances, basket (1420) may be removed from cover (1410) and basket (1420) may be transported with tissue samples therein. Other suitable ways in which tissue samples may be handled will be apparent to those of ordinary skill in the art in view of the teachings herein.

Figure 53:
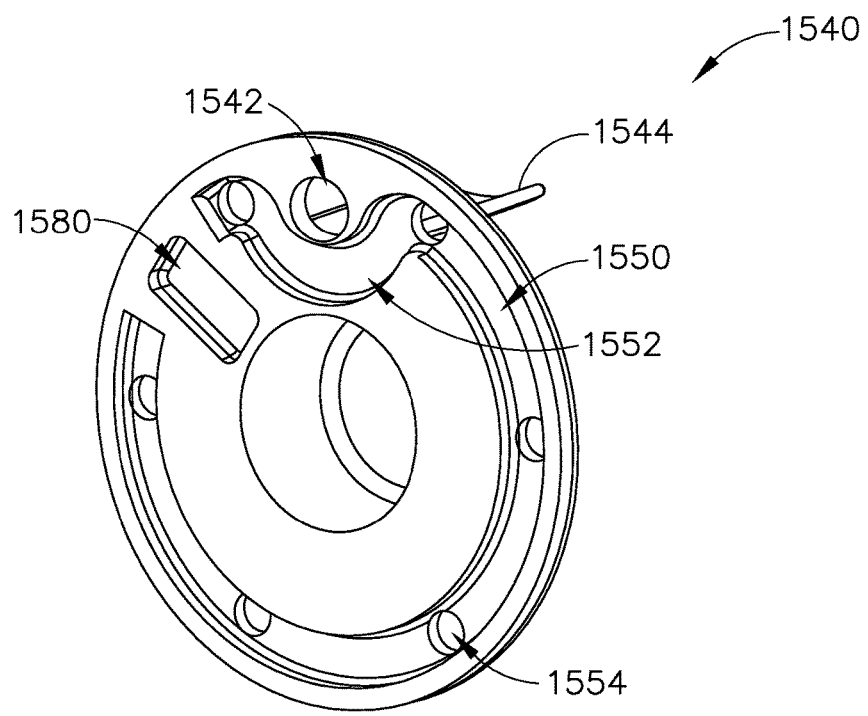
FIG. 53 depicts a perspective view of an exemplary alternative end cap that may be incorporated into the tissue sample holder assembly of FIG. 46.
Figure 54:
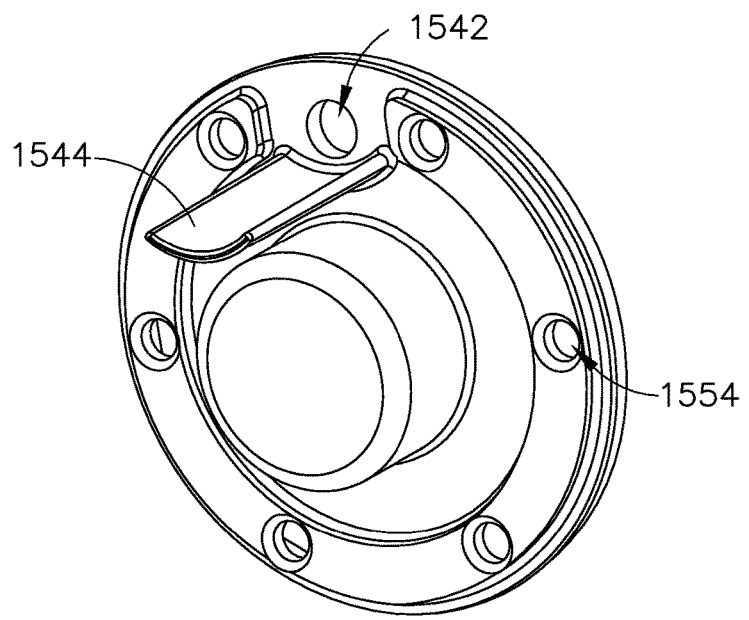
FIG. 54 depicts another perspective view of the end cap of FIG. 53.
Figure 55:
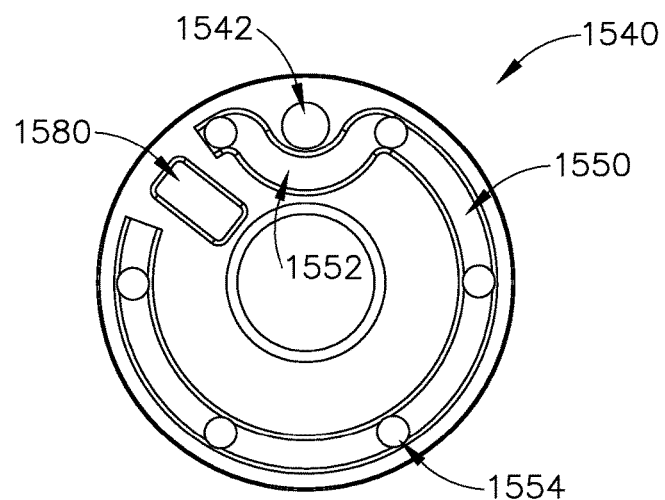
FIG. 55 depicts an end elevational view of the end cap of FIG. 53.
Figure 56:
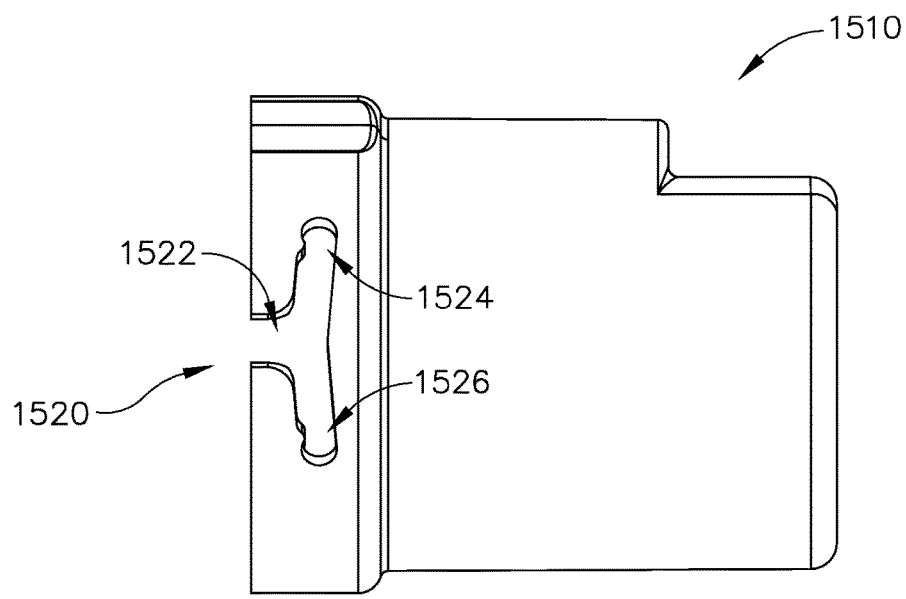
FIG. 56 depicts a side elevational view of a cover that may be incorporated into the tissue sample holder assembly of FIG. 46.
Figure 57:
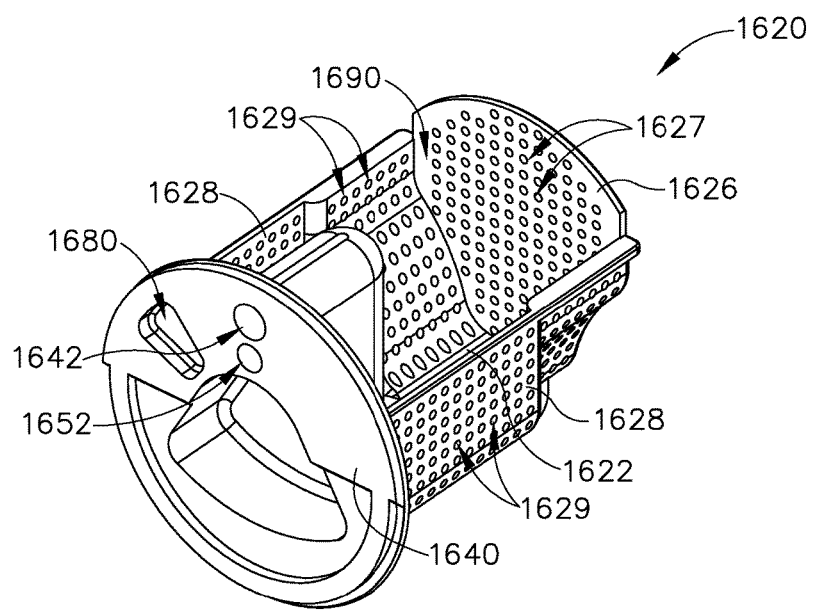
FIG. 57 depicts a perspective view of an exemplary alternative tissue sample tray that may be combined with the cover of FIG. 56 to form a tissue sample holder assembly.

B. Exemplary Tissue Sample Holder with Shelf, Drainage Trough, and Short Circuit Trough FIGS. 53-56 show exemplary components that may be used to modify tissue sample holder (1400) to selectively provide a short circuit that bypasses basket (1420). In particular, FIGS. 53-55 show an exemplary end cap (1540) that may be used to replace end cap (1440); while FIG. 56 shows an exemplary outer cover (1510) that may be used to replace outer cover (1410). End cap (1540) is substantially identical to end cap (1440) in that end cap (1540) includes an upper opening (1542), a trough (1550) with a dip section (1552) and a plurality of openings (1554), and a proximally extending shelf (1544). Unlike end cap (1440), end cap (1540) of this example comprises a second trough (1580), which is fluidly isolated from trough (1550). In the present example, trough (1580) interrupts trough (1550), such that trough (1550) does not extend about a full perimeter of the distal face of end cap (1540). In some other versions, troughs (1550, 1580) are configured and arranged such that trough (1550) extends about a full perimeter of the distal face of end cap (1540), forming a continuous path.

Outer cover (1510) of the present example includes a pair of diametrically opposed, two-pronged bayonet slots (1520). Each bayonet slot (1520) is configured to receive a corresponding bayonet pin (109) of chassis (106). Each bayonet slot (1520) of this example includes a longitudinally extending pin entry channel (1522), a first circumferentially extending channel (1524), and a second circumferentially extending channel (1526). When securing outer cover (1510) to probe (100), the operator aligns pins (109) with corresponding entry channels (1522) and pushes outer cover (1510) distally toward probe (100). The operator then rotates outer cover (1510) relative to probe (100) to position pins (109) in either corresponding first circumferentially extending channels (1524) or corresponding second circumferentially extending channels (1526). In other words, a tissue sample holder (1400) incorporating outer cover (1510) and end cap (1540) may be selectively positioned between a first angular orientation relative to probe (100) or a second angular orientation relative to probe (100). In the first angular orientation, pins (109) are disposed in corresponding first circumferentially extending channels (1524). In the second angular orientation, pins (109) are disposed in corresponding second circumferentially extending channels (1526). In some versions, the second angular orientation is offset approximately 53° from the first angular orientation. Alternatively, any other suitable offset may be used.

When a tissue sample holder (1400) incorporating outer cover (1510) and end cap (1540) is disposed in the first angular orientation, opening (1542) of end cap (1540) aligns with opening (174) of sealing member (170); while dip section (1552) aligns with opening (176) of sealing member (170). This modified tissue sample holder (1400) in the first angular orientation thus operates substantially identically to tissue sample holder (1400) described above (with end cap (1440) and cover (1510)). In other words, in the first angular orientation, tissue samples are communicated proximally through lumen (151) of cutter (150) onto shelf (1544), eventually being deposited in basket (1420). Fluids communicated through lumen (151) of cutter (150) are suctioned through tube (20) via openings (1424, 1454) and trough (1550). When a tissue sample holder (1400) incorporating outer cover (1510) and end cap (1540) is disposed in the second angular orientation, second trough (1580) is in fluid communication with both openings (174, 176) of sealing member (170); and opening (1542) and trough (1550) are both fluidly isolated from corresponding openings (174, 176). Trough (1580) thus effectively provides a short circuit coupling openings (174, 176) together; bypassing basket (1420) and other interior components/regions of tissue sample holder (1400).

In some instances, it may be desirable to operate biopsy device (10) with a tissue sample holder (1400) incorporating outer cover (1510) and end cap (1540) in the second angular orientation in order to administer one or more fluids (e.g., medication(s) and/or other kinds of fluids) to a biopsy site. For instance, with needle (110) disposed in the patient's tissue, cutter (150) may be retracted to a proximal position to effectively open lateral aperture (114). A source of medical fluid (or other kind of fluid) may be coupled with either luer fitting (32, 42) in order to place tube (46) in fluid communication with the source of medical fluid (or other kind of fluid). As described above, tube (46) is in fluid communication with second lumen (192) via manifold (122). As also described above, second lumen (192) is in fluid communication with lateral aperture (114) via openings (194). Medical fluid (or any other kind of fluid) may thereby be delivered to the tissue via lateral aperture (114). It should also be understood that vacuum may be applied through tube (20) to assist in drawing the medical fluid (or other kind of fluid) through tube (46). By providing a direct fluid path between openings (174, 176), trough (1580) allows this vacuum to bypass basket (1420) and other interior components/regions of tissue sample holder (1400).

It should be understood from the foregoing that a biopsy device (10) having a tissue sample holder (1400) incorporating outer cover (1510) and end cap (1540) may be operated to alternate between the first and second angular orientations during a single biopsy procedure. For instance, biopsy device (10) may be operated with the modified tissue sample holder (1400) in the first angular orientation for a first portion of the procedure, where one or more tissue samples are collected in basket (1420). The operator may then rotate outer cover (1510) (which will also rotate basket (1420) and end cap (1540)) to place the modified tissue sample holder (1400) in the second angular orientation. In the second angular orientation, the operator may administer one or more fluids (e.g., medication(s) and/or other kinds of fluids) to the biopsy site. The operator may then transition the modified tissue sample holder (1400) back to the first angular orientation to collect one or more additional tissue samples. This alternation between the first and second angular orientations may be done as many times as desired.

C. Exemplary Tissue Sample Holder Tray with Sump and Short Circuit Trough

FIGS. 57-62 show an exemplary alternative basket (1620) that may be combined with cover (1510) to form another variation of tissue sample holder (1400). Basket (1620) of this example includes a distal wall (1640), a proximal wall (1626), a set of sidewalls (1628), and a floor (1622). Walls (1626, 1628, 1640) and floor (1622) together define a tissue receiving compartment (1690). Walls (1626, 1628) include drainage openings (1627, 1629). As with all other drainage openings described herein, drainage openings (1627, 1629) of this example are large enough to permit fluids to pass therethrough; yet are small enough to prevent tissue samples from passing therethrough.

Figure 58:
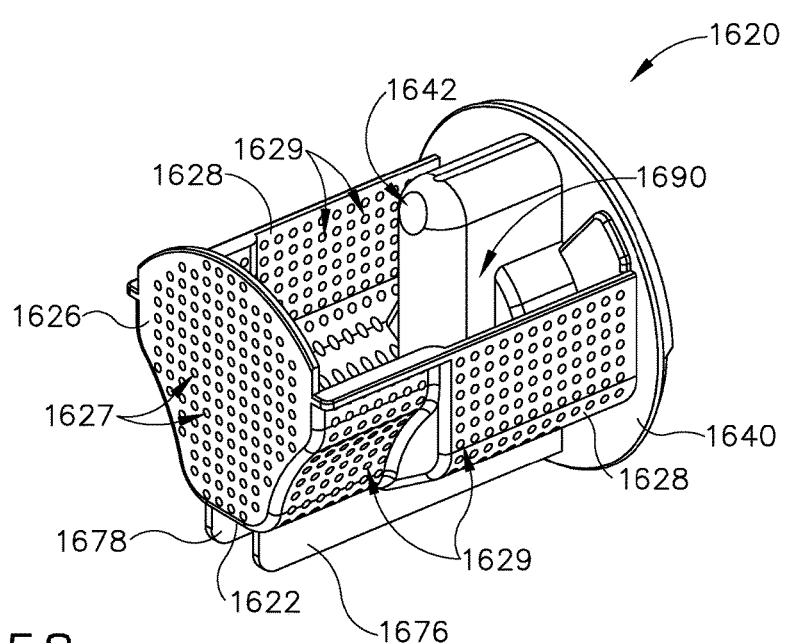
FIG. 58 depicts another perspective view of the tissue sample tray of FIG. 57.
Figure 59:
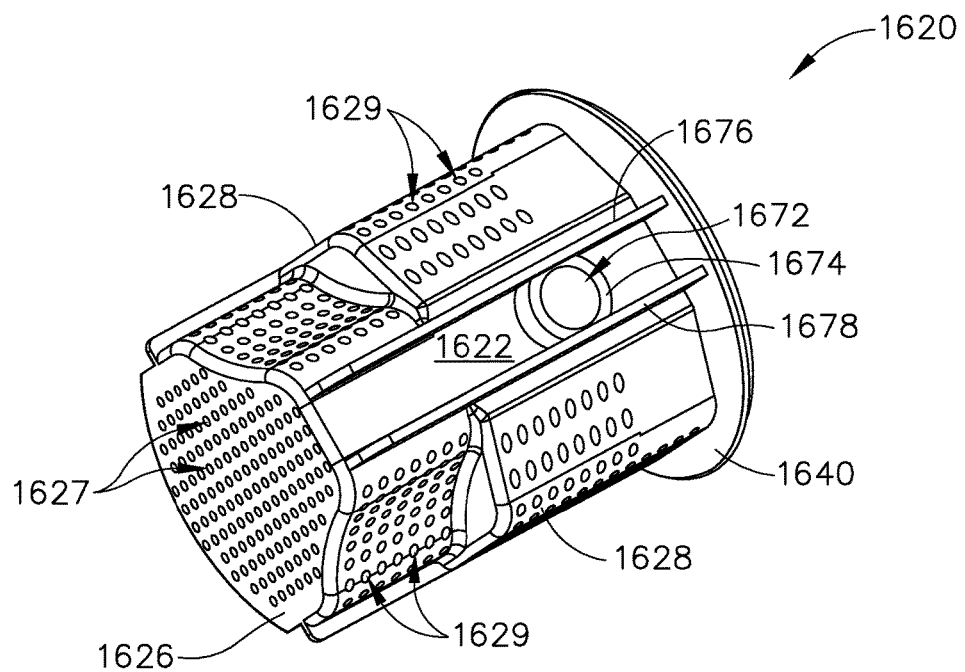
FIG. 59 depicts another perspective view of the tissue sample tray of FIG. 57.
Figure 60:
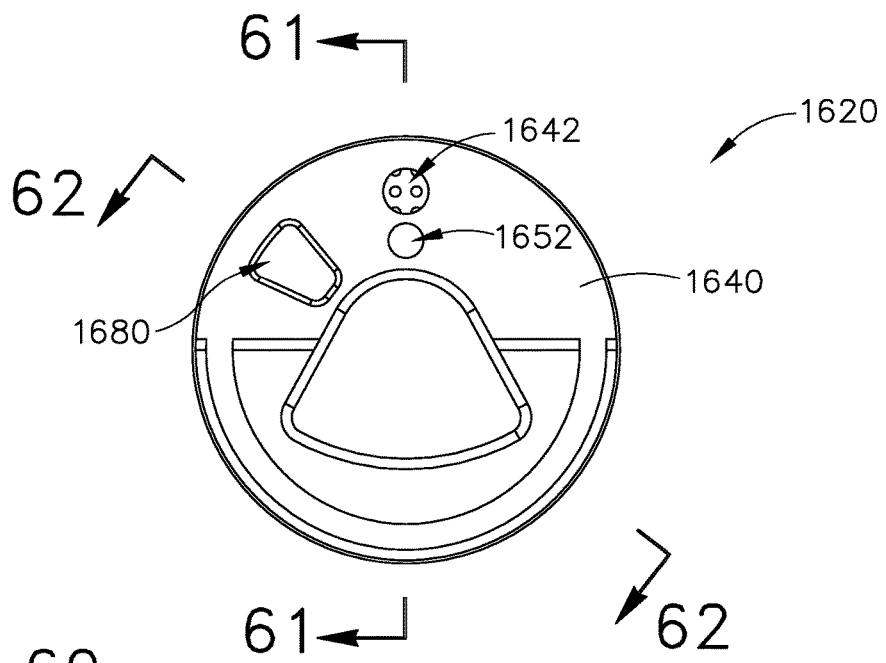
FIG. 60 depicts an end elevational view of the tissue sample tray of FIG. 57.
Figure 61:
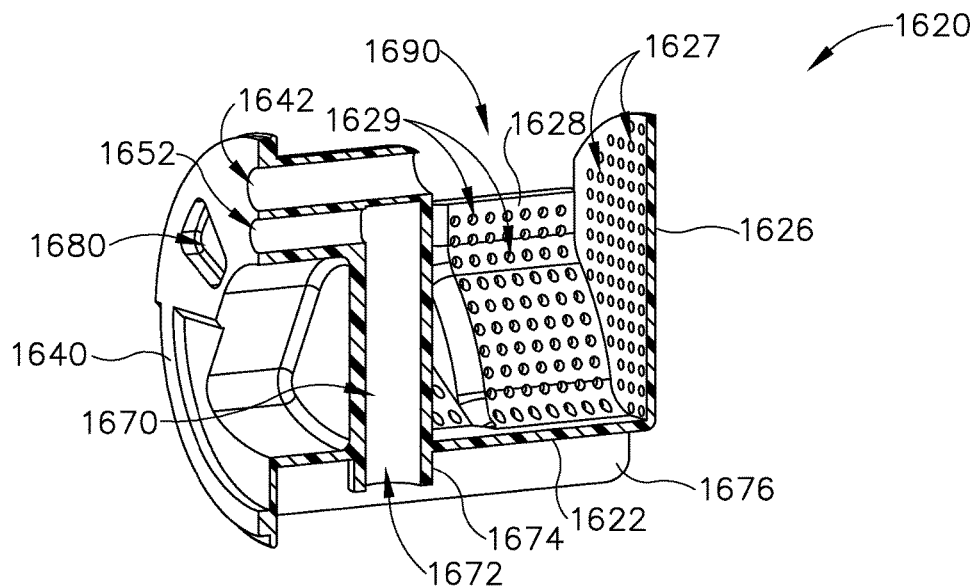
FIG. 61 depicts a cross-sectional perspective view of the tissue sample tray of FIG. 57, taken along line 61-61 of FIG. 60.
Figure 62:
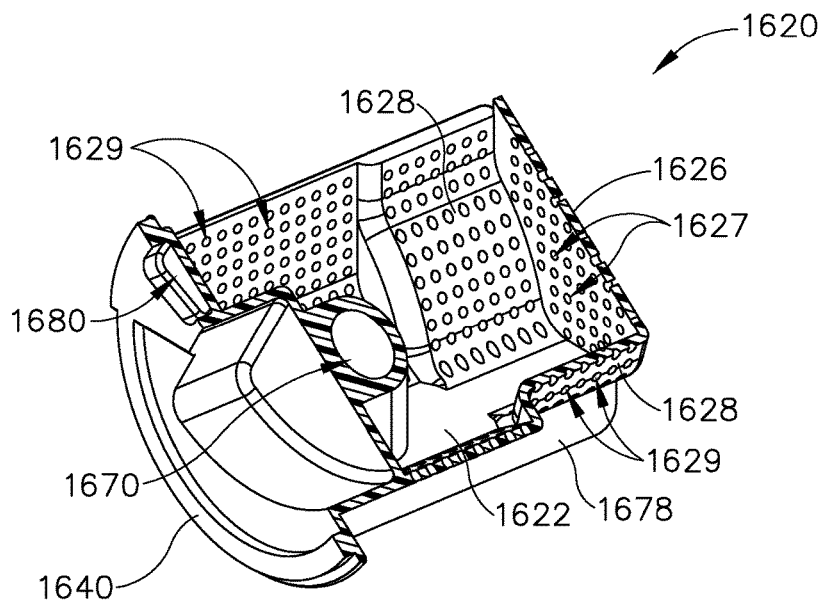
FIG. 62 depicts a cross-sectional perspective view of the tissue sample tray of FIG. 57, taken along line 62-62 of FIG. 60.
Figure 63:
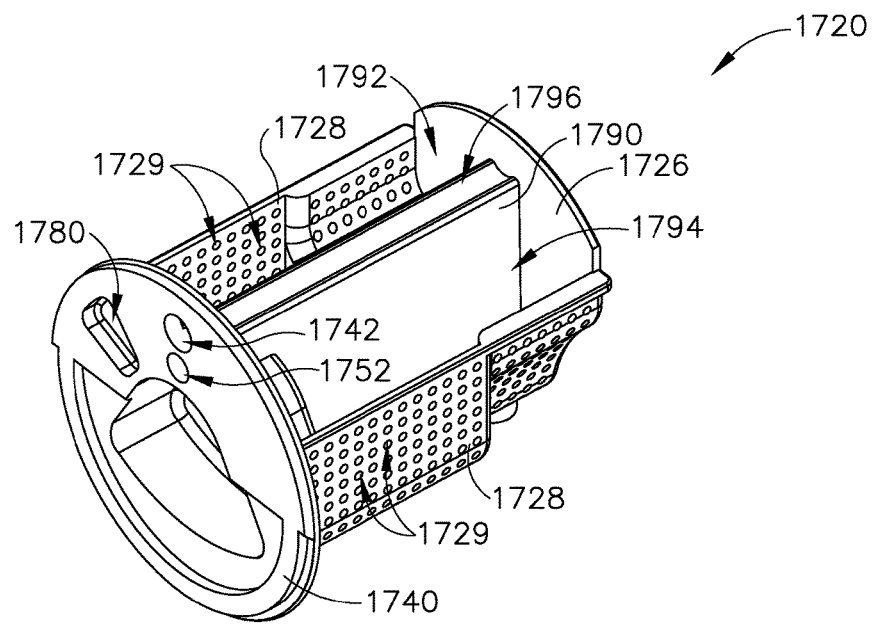
FIG. 63 depicts a perspective view of another exemplary alternative tissue sample tray that may be combined with the cover of FIG. 56 to form a tissue sample holder assembly.

Distal wall (1640) defines an upper opening (1642) and a lower opening (1652). As best seen in FIGS. 58 and 61, upper opening (1642) is in direct communication with tissue receiving compartment (1690). As best seen in FIG. 61, lower opening (1652) is in communication with a sump lumen (1670), which terminates in a sump opening (1672) on the underside of basket (1620). Sump opening (1672) is surrounded by an annular lip (1674). As best seen in FIGS. 58-59, a pair of lips (1676, 1678) extend longitudinally along the full length of the underside of basket (1620), on each lateral side of sump opening (1672). Lips (1676, 1678) are configured to define a small gap between lips (1676, 1678) and the inner surface of cover (1510) when basket (1620) is inserted in cover (1510). Lip (1674) is also configured to define a small gap between lip (1674) and the inner surface of cover (1510) when basket (1620) is inserted in cover (1510), though this gap at lip (1674) is slightly larger than the gap at lips (1676, 1678).

The distal face of distal wall (1640) also includes a trough (1680), which is configured and operable substantially similarly to trough (1580). As with basket (1420) and end cap (1540) described above, basket (1620) of this example may be combined with cover (1510) and coupled with probe (100) at two different angular orientations. In a first angular orientation, upper opening (1642) aligns with opening (174) of sealing member (170); while lower opening (1652) aligns with opening (176) of sealing member (170). Thus, when vacuum is applied via tube (20) and opening (176), this vacuum is communicated through lower opening (1652), sump lumen (1670), and sump opening (1672) to the gap between basket (1620) and the inner surface of cover (1510). This vacuum is further communicated through drainage openings (1627, 1629) to tissue receiving compartment (1690); and further to openings (1642, 174) to reach lumen (151) of cutter (150). It should therefore be understood that vacuum from tube (20) may draw severed tissue samples proximally through lumen (151) to reach tissue receiving compartment (1690). It should also be understood that fluids drawn proximally through lumen (151) may be further drawn into tube (20) via openings (174, 1642), tissue receiving compartment (1690), drainage openings (1627, 1629), sump opening (1672), sump lumen (1670), and openings (1652, 176). Thus, when basket (1620) and cover (1510) are coupled with probe (100) in the first angular orientation, biopsy device (10) may be operated to capture tissue samples in tissue receiving compartment (1690) and drain fluids.

As noted above, basket (1620) and cover (1510) may be rotated relative to probe (100) from the first angular orientation to a second angular orientation. In the second angular orientation, trough (1680) is in fluid communication with both openings (174, 176) of sealing member (170); and openings (1642, 1652) are both fluidly isolated from corresponding openings (174, 176). Trough (1680) thus effectively provides a short circuit coupling openings (174, 176) together; bypassing tissue receiving compartment (1690) and other interior regions of cover (1510). As also described above, this second angular orientation may be used when one or more fluids (e.g., medication(s) and/or other kinds of fluids) is/are being delivered to the biopsy site via needle (110). Alternatively, this second angular orientation may be used for any other suitable purposes.

D. Exemplary Tissue Sample Holder Tray with Shelf, Sump, and Short Circuit Trough FIGS. 63-68 show another exemplary alternative basket (1720) that may be combined with cover (1510) to form another variation of tissue sample holder (1400). Basket (1720) of this example includes a distal wall (1740), a proximal wall (1726), a set of sidewalls (1728), a floor (1722), and a central wall (1790). Walls (1726, 1728, 1740, 1790) and floor (1722) together define a first tissue receiving compartment (1792) and a second tissue receiving compartment (1794). Walls (1728) include drainage openings (1729). Wall (1790) defines an upper shelf (1796).

Figure 64:
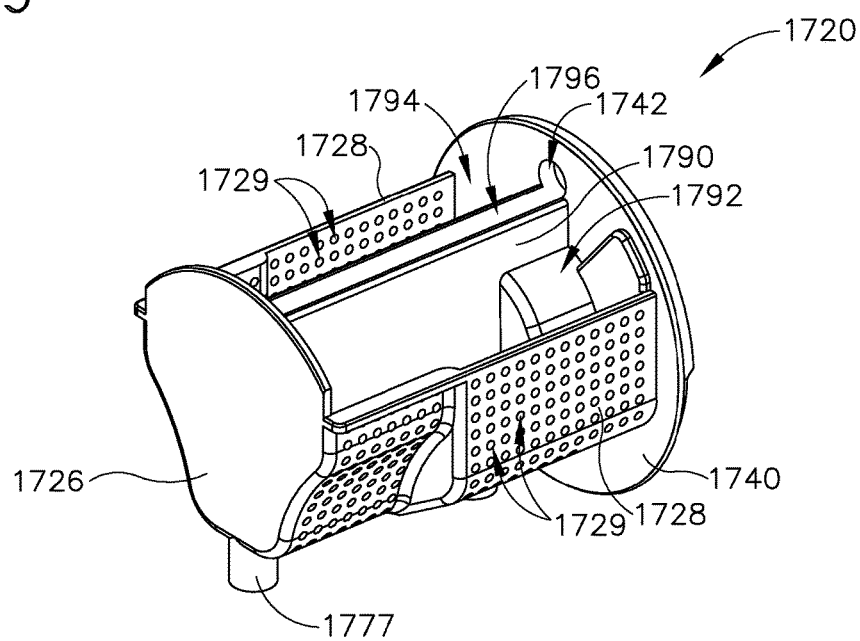
FIG. 64 depicts another perspective view of the tissue sample tray of FIG. 63.
Figure 65:
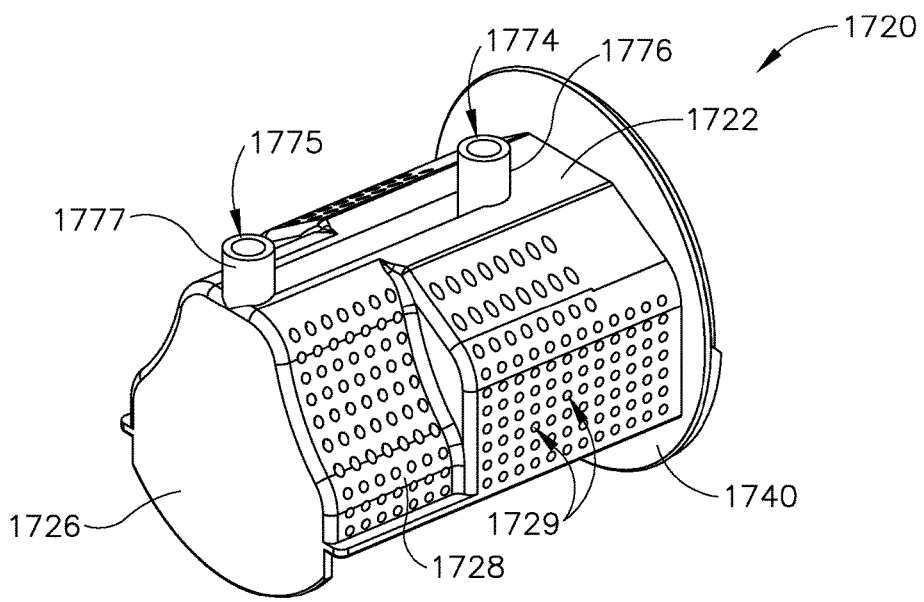
FIG. 65 depicts another perspective view of the tissue sample tray of FIG. 63.
Figure 66:
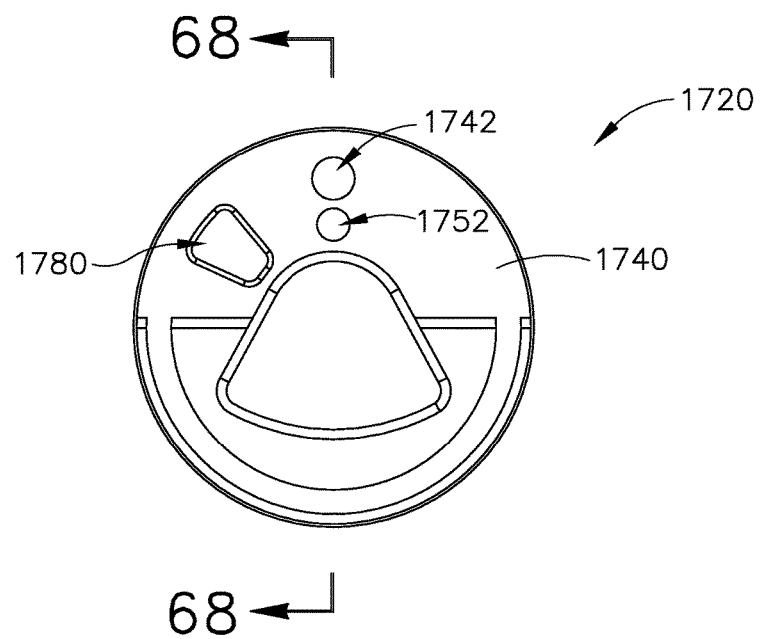
FIG. 66 depicts an end elevational view of the tissue sample tray of FIG. 63.
Figure 67:
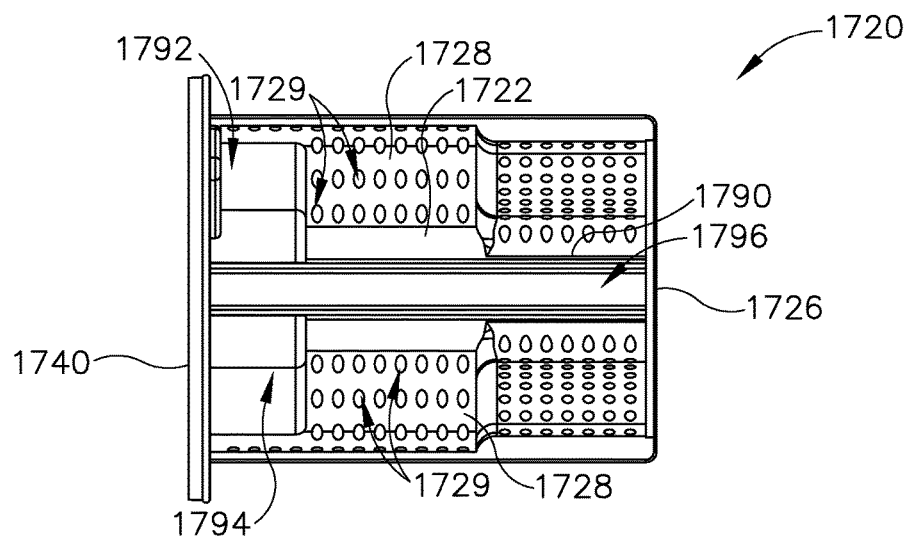
FIG. 67 depicts a top plan view of the tissue sample tray of FIG. 63.
Figure 68:
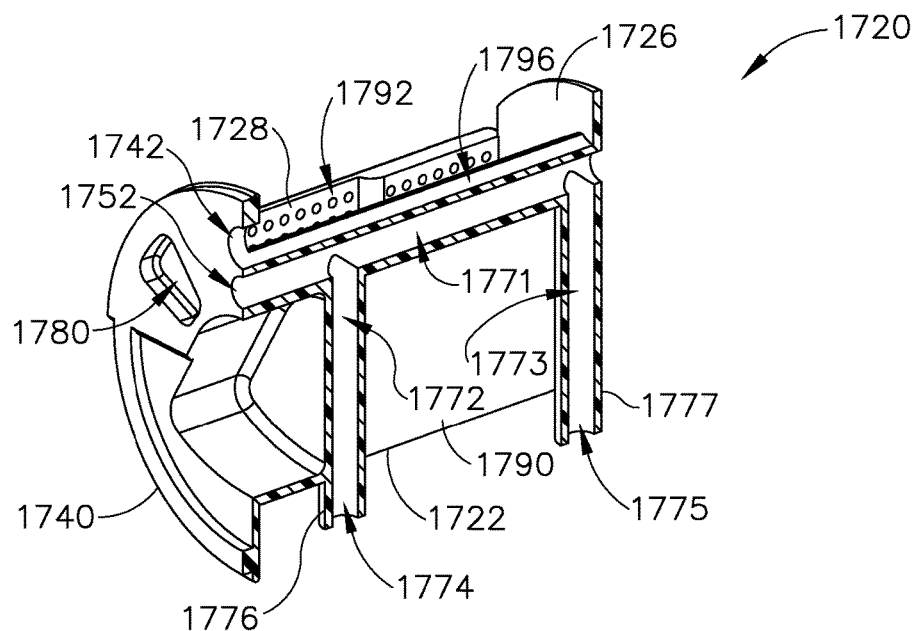
FIG. 68 depicts a cross-sectional side view of the tissue sample tray of FIG. 63, taken along line 68-68 of FIG. 66.
Figure 69:
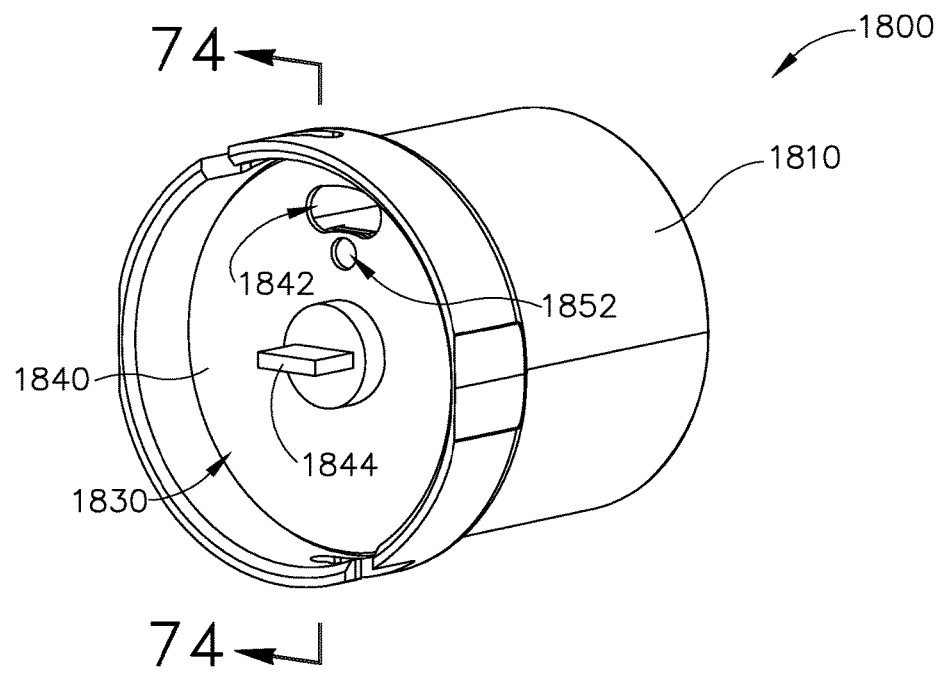
FIG. 69 depicts a perspective view of another exemplary alternative tissue sample holder assembly that may be incorporated into the probe of FIG. 4.

Distal wall (1740) defines an upper opening (1742) and a lower opening (1752). As best seen in FIGS. 64 and 68, upper opening (1742) is in direct communication with shelf (1796). As best seen in FIG. 68, lower opening (1752) is in communication with a first sump lumen (1771), is in further communication with a second sump lumen (1772) and a third sump lumen (1773). Sump lumens (1771, 1772, 1773) extend through central wall (1728). Second sump lumen (1772) terminates in a sump opening (1774) at the underside of basket (1720); while third sump lumen (1773) terminates in a sump opening (1775) at the underside of basket (1720). Each sump opening (1774, 1775) is surrounded by a corresponding annular lip (1776, 1777). Lips (1776, 1777) are configured to define a small gap between lips (1776, 1777) and the inner surface of cover (1510) when basket (1720) is inserted in cover (1510).

The distal face of distal wall (1740) also includes a trough (1780), which is configured and operable substantially similarly to trough (1580). As with basket (1420) and end cap (1540) described above, basket (1720) of this example may be combined with cover (1510) and coupled with probe (100) at two different angular orientations. In a first angular orientation, upper opening (1742) aligns with opening (174) of sealing member (170); while lower opening (1752) aligns with opening (176) of sealing member (170). Thus, when vacuum is applied via tube (20) and opening (176), this vacuum is communicated through lower opening (1752), sump lumens (1771, 1772, 1773), and sump openings (1774, 1775) to the gap between basket (1720) and the inner surface of cover (1510). This vacuum is further communicated through drainage openings (1729) to tissue receiving compartments (1792, 1794); and further to openings (1742, 174) to reach lumen (151) of cutter (150). It should therefore be understood that vacuum from tube (20) may draw severed tissue samples proximally through lumen (151) to reach shelf (1796). Each severed tissue sample may be dumped from shelf (1796) into either tissue receiving compartment (1792, 1794). It should also be understood that fluids drawn proximally through lumen (151) may be further drawn into tube (20) via openings (174, 1742), tissue receiving compartments (1792, 1794), drainage openings (1729), sump openings (1774, 1775), sump lumens (1771, 1772, 1773), and openings (1752, 176). Thus, when basket (1720) and cover (1510) are coupled with probe (100) in the first angular orientation, biopsy device (10) may be operated to capture tissue samples in tissue receiving compartments (1792, 1794) and drain fluids.

As noted above, basket (1720) and cover (1510) may be rotated relative to probe (100) from the first angular orientation to a second angular orientation. In the second angular orientation, trough (1780) is in fluid communication with both openings (174, 176) of sealing member (170); and openings (1742, 1752) are both fluidly isolated from corresponding openings (174, 176). Trough (1780) thus effectively provides a short circuit coupling openings (174, 176) together; bypassing tissue receiving compartments (1792, 1794) and other interior regions of cover (1510). As also described above, this second angular orientation may be used when one or more fluids (e.g., medication(s) and/or other kinds of fluids) is/are being delivered to the biopsy site via needle (110). Alternatively, this second angular orientation may be used for any other suitable purposes.

V. Exemplary Alternative Tissue Sample Holder Assemblies with Pull Tab

As noted above, it may be desirable to facilitate removal of a tissue sample tray or basket from an outer cover of a tissue sample holder assembly. Such removability of a tissue sample tray or basket may further enable removal of tissue samples from the tray/basket and/or enable other processing of tissue samples. Some examples described above (e.g., tissue sample holder (300), etc.) include a pivotable handle that may be used to grasp a tissue sample tray or basket, facilitating removal of the tray or basket from an outer cover. In some other examples, a pull tab is provided for grasping a tissue sample tray or basket, facilitating removal of the tray or basket from an outer cover. Various examples of tissue sample holders that include such pull tabs will be described in greater detail below. Other examples will be apparent to those of ordinary skill in the art in view of the teachings herein.

Unlike the examples described above, the tissue sample trays described below lack a distally presented recess that would accommodate grasping feature (184) of rotation member (180) of probe (100) when the tissue sample holder assembly is coupled with probe (100). It should therefore be understood that the below described tissue sample holders may be used with modified versions of probe (100) that lack rotation member (180). Alternatively, the below described tissue sample holders may be modified to include a recess or other feature that accommodates grasping feature (184) of rotation member (180) of probe (100) when the tissue sample holder assembly is coupled with probe (100).

Figure 70:
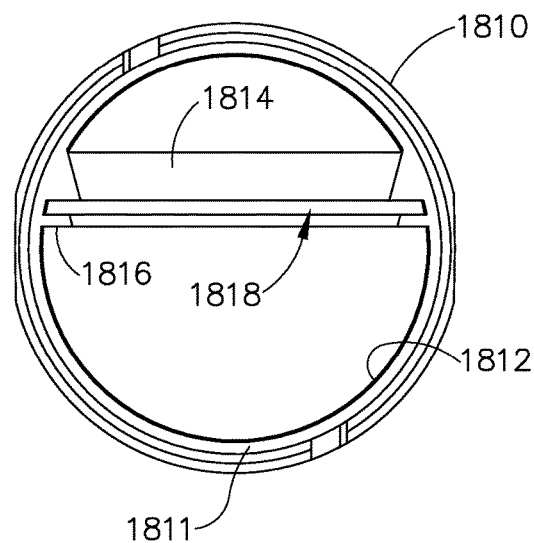
FIG. 70 depicts an end elevational view of a cover of the tissue sample holder assembly of FIG. 69.
Figure 71:
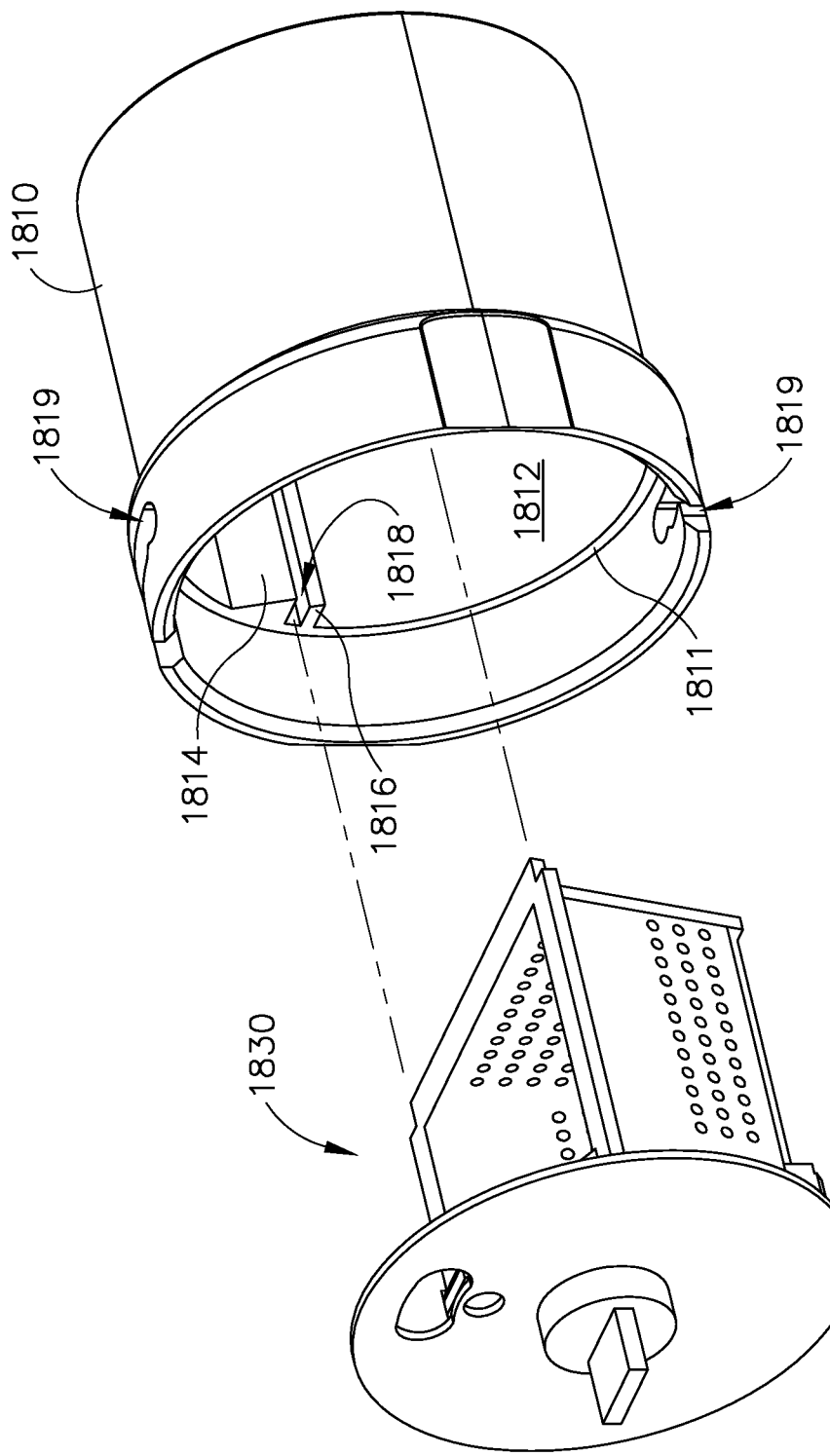
FIG. 71 depicts an exploded perspective view of the tissue sample holder assembly of FIG. 69.

A. Exemplary Tissue Sample Tray with Pull Tab, Flat Floor, and Dual Sump Openings FIGS. 69-75 show another exemplary tissue sample holder assembly (1800) that may be coupled with probe (100). Tissue sample holder assembly (1800) of this example comprises a cover (1810) and a tissue sample tray (1830), which is removably inserted in cover (1810). As best seen in FIGS. 70-71, cover (1810) includes an annular shoulder (1811), an inner surface (1812), an upper interior flange (1814), and a lower interior flange (1816). Flanges (1814, 1816) together define a channel (1818). Flange (1814) includes an upper surface that is obliquely angled relative to flange (1816) and channel (1818). Cover (1810) also includes a pair of bayonet slots (1819) that are configured to receive bayonet pins (109) of chassis (106) to thereby provide coupling between cover (1810) and chassis (106).

Figure 72:
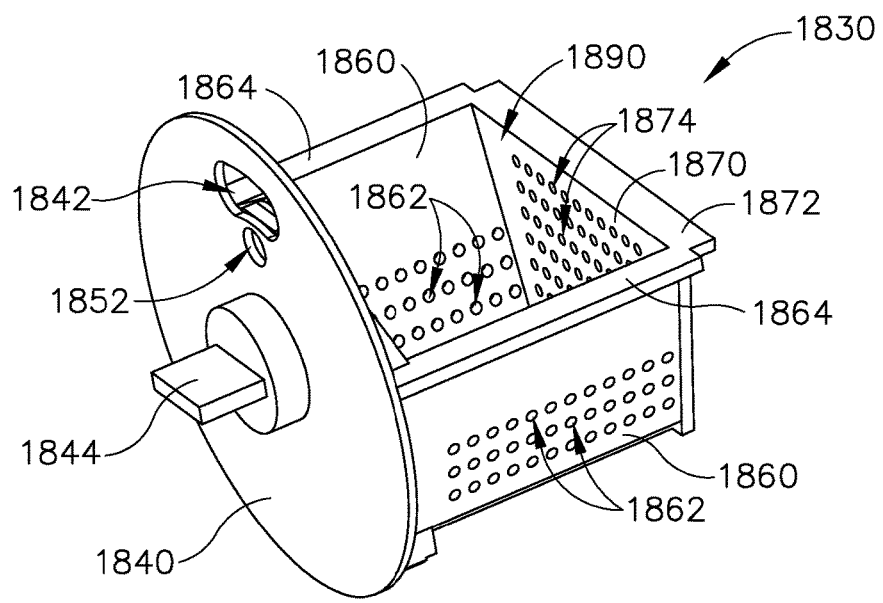
FIG. 72 depicts a perspective view of a tissue sample tray of the tissue sample holder assembly of FIG. 69.
Figure 73:
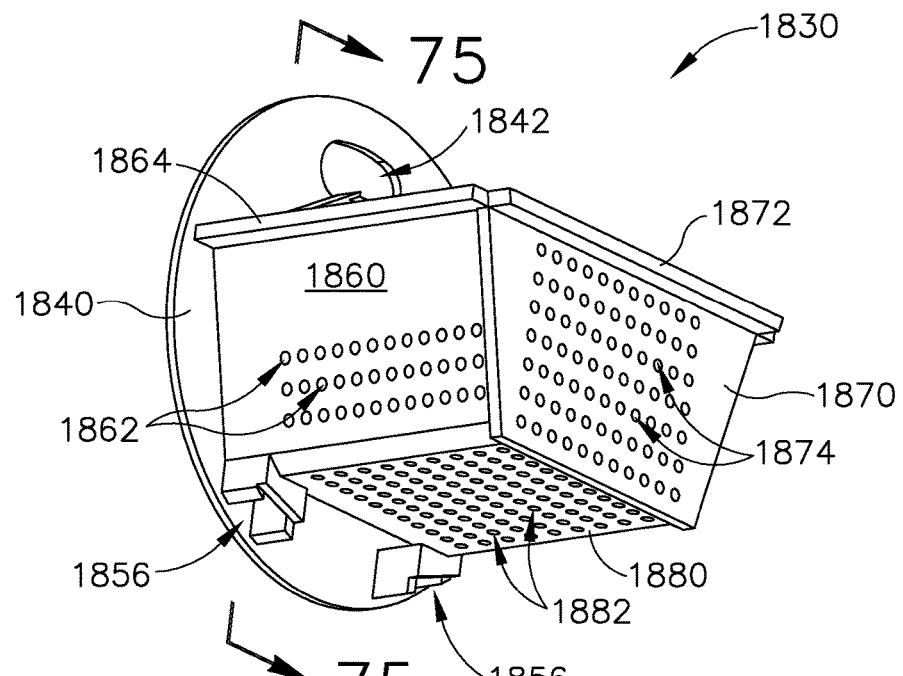
FIG. 73 depicts another perspective view of the tissue sample tray of FIG. 72.
Figure 74:
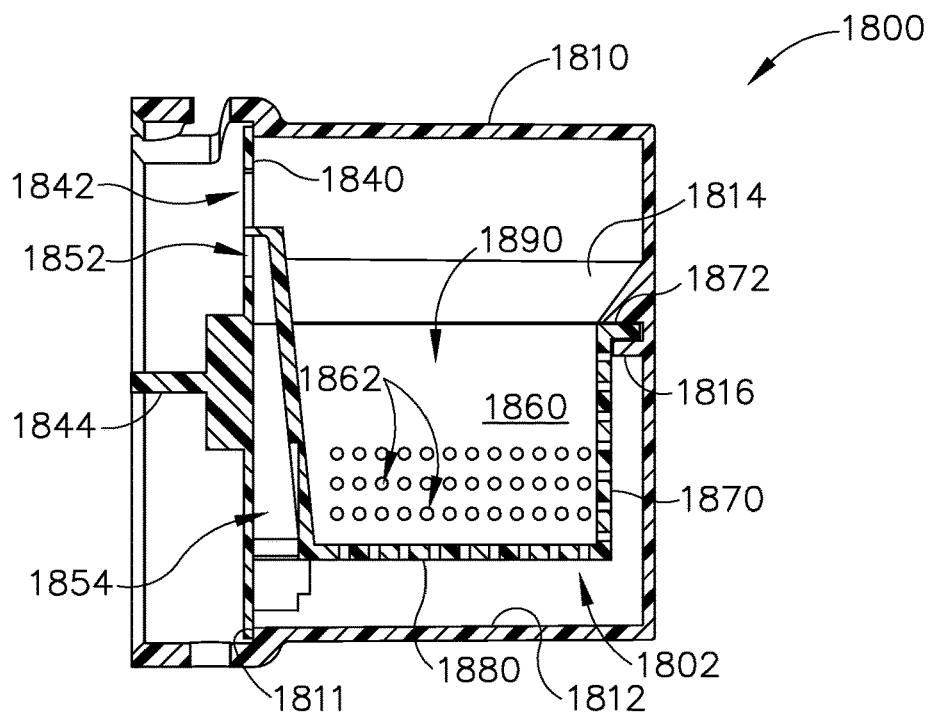
FIG. 74 depicts a cross-sectional side view of the tissue sample holder assembly of FIG. 69, taken along line 74-74 of FIG. 69.

As best seen in FIGS. 72-73, tissue sample tray (1830) of the present example comprises a distal wall (1840), a pair of sidewalls (1860), a proximal wall (1870), and a floor (1880). Walls (1840, 1860, 1870) and floor (1880) together define a tissue receiving compartment (1890). Distal wall (1840) defines an upper opening (1842) and a lower opening (1852). Distal wall (1840) further includes a distally projecting pull tab (1844). As best seen in FIG. 74, distal wall (1840) is configured to seal against annular shoulder (1811) of cover (1810) when tissue sample tray (1830) is inserted in cover (1810). Pull tab (1844) may be used to grasp tissue sample tray (1830) to facilitate removal of tissue sample tray (1830) from cover (1810).

Upper opening (1842) is in direct fluid communication with tissue receiving compartment (1890). Walls (1860, 1870) and floor (1880) include corresponding drainage openings (1862, 1874, 1882) that are also in fluid communication with tissue receiving compartment (1890) to provide drainage of fluids from tissue receiving compartment (1890). Drainage openings (1862, 1874, 1882) also provide pathways for communication of vacuum to tissue receiving compartment (1890) as will be described in greater detail below. Each wall (1860, 1870) also includes a corresponding outwardly extending flange (1864, 1872). As shown in FIGS. 71 and 74, flanges (1864, 1872) are configured to fit in channel (1818) of cover (1810), such that flanges (1814, 1816, 1864, 1872) all cooperate to maintain support and positioning of tissue sample tray (1830) in cover (1810).

Figure 75:
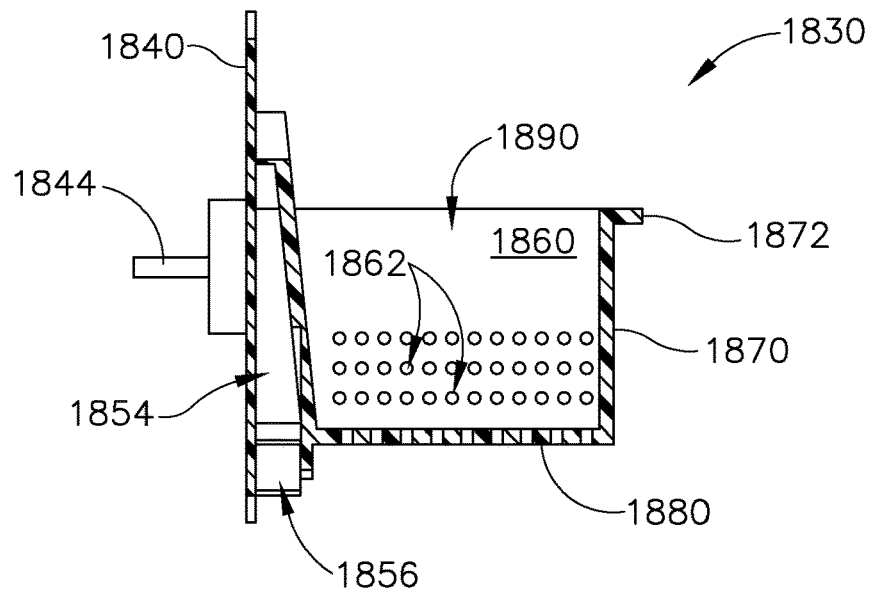
FIG. 75 depicts a cross-sectional side view of the tissue sample tray of FIG. 72, taken along line 75-75 of FIG. 73.

As best seen in FIGS. 74-75, lower opening (1852) is in communication with a sump lumen (1854), which terminates at each end in corresponding sump openings (1856) that are located on the underside of tissue sample tray (1830). As can be seen in FIG. 74, a gap (1802) is defined between the underside of tissue sample tray (1830) and inner surface (1812) of cover (1810). Sump openings (1856) are positioned do draw fluids from this gap (1802).

When tissue sample holder (1800) is coupled with probe (100), upper opening (1842) aligns with opening (174) of sealing member (170); while lower opening (1852) aligns with opening (176) of sealing member (170). Thus, when vacuum is applied via tube (20) and opening (176), this vacuum is communicated through lower opening (1852), sump lumen (1854), and sump openings (1856) to gap (1802). This vacuum is further communicated through drainage openings (1862, 1874, 1882) to tissue receiving compartment (1890); and further to openings (1842, 174) to reach lumen (151) of cutter (150). It should therefore be understood that vacuum from tube (20) may draw severed tissue samples proximally through lumen (151) to reach tissue receiving compartment (1890). It should also be understood that fluids drawn proximally through lumen (151) may be further drawn into tube (20) via openings (174, 1842), tissue receiving compartment (1890), drainage openings (1862, 1874, 1882), sump openings (1856), sump lumen (1854), and openings (1852, 176). Thus, when tissue sample holder (1830) is coupled with probe (100), biopsy device (10) may be operated to capture tissue samples in tissue receiving compartment (1890) and drain fluids. The angled configuration of flange (1814) may assist in guiding fluids into tissue receiving compartment (1890) during operation.

Figure 76:
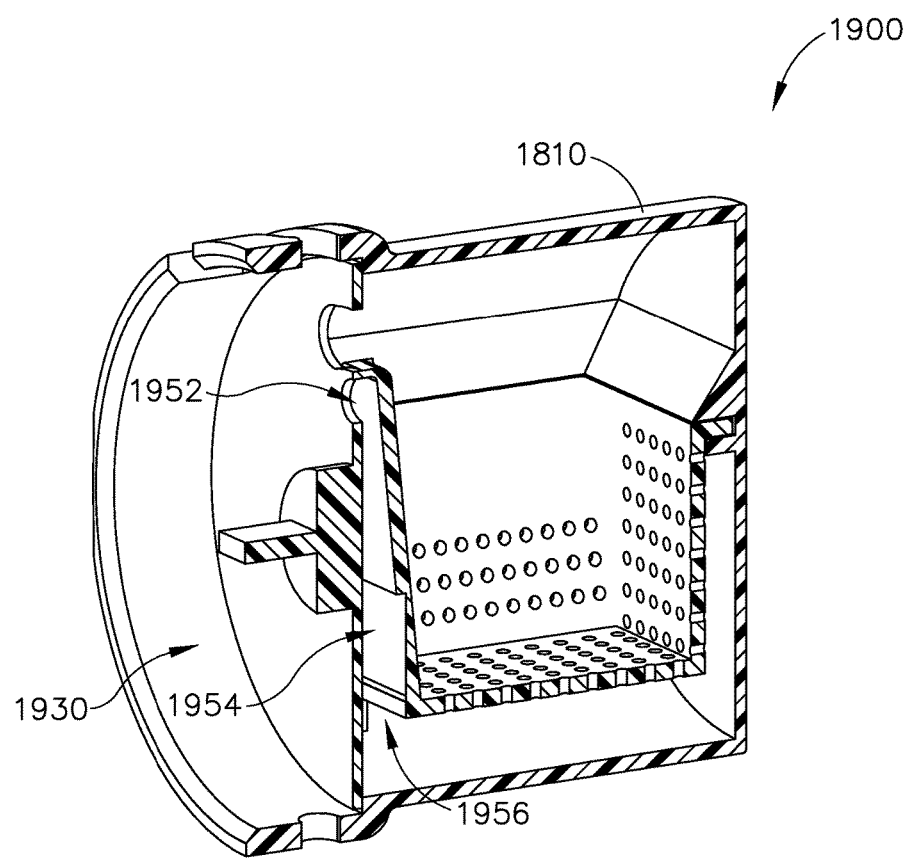
FIG. 76 depicts a cross-sectional perspective view of another exemplary alternative tissue sample holder assembly that may be incorporated into the probe of FIG. 4.
Figure 77:
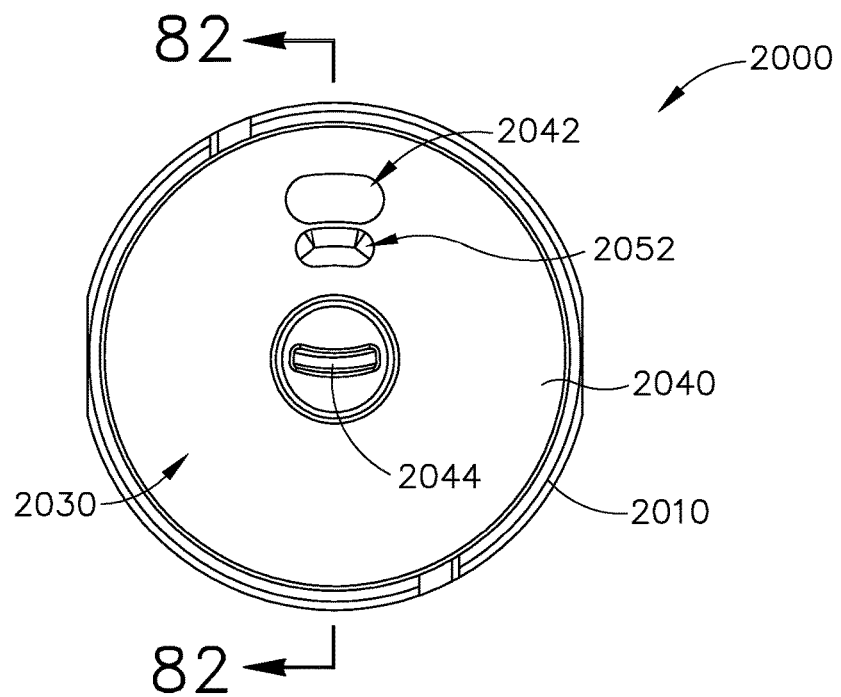
FIG. 77 depicts an end elevational view of another exemplary alternative tissue sample holder assembly that may be incorporated into the probe of FIG. 4.

FIG. 76 shows a tissue sample holder assembly (1900) that incorporates a merely illustrative variation of tissue sample tray (1830). In particular, FIG. 76 shows a tissue sample tray (1930) that includes a single sump opening (1956) that is in communication with a lower opening (1952) in a distal wall (1940) of tissue sample tray (1930) via a sump lumen (1954). Tissue sample tray (1930) of this example is otherwise identical to tissue sample tray (1930), including its fit with cover (1810).

Figure 78:
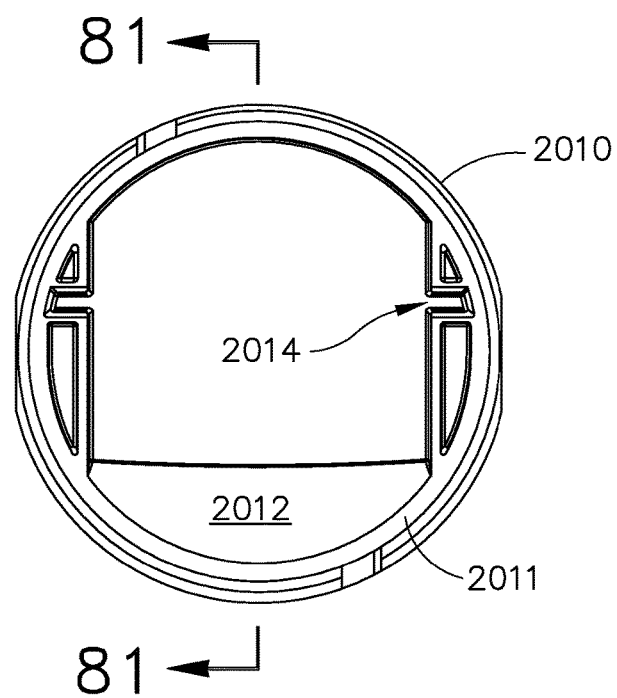
FIG. 78 depicts an end elevational view of a cover of the tissue sample holder assembly of FIG. 77.
Figure 81:
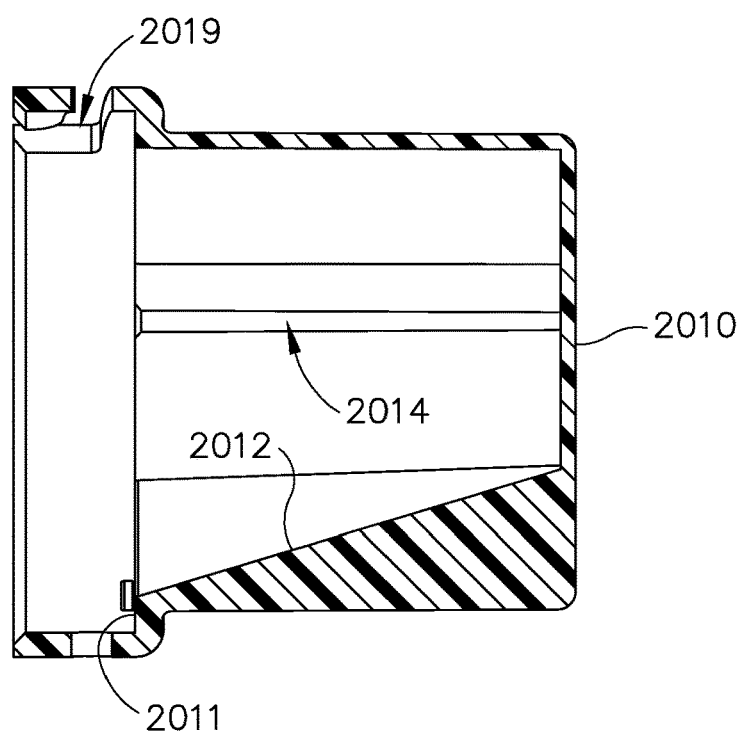
FIG. 81 depicts a cross-sectional side view of the cover of FIG. 78, taken along line 81-81 of FIG. 78.

B. Exemplary Tissue Sample Tray with Pull Tab, Angled Floor, and Single Sump Opening FIGS. 77-86 show another exemplary tissue sample holder assembly (2000) that may be coupled with probe (100). Tissue sample holder assembly (2000) of this example comprises a cover (2010) and a tissue sample tray (2030), which is removably inserted in cover (2010). As best seen in FIGS. 78 and 81, cover (2010) includes an annular shoulder (2011), an obliquely angled inner floor (2012), and a flange receiving channel (2014). Cover (2010) also includes a pair of bayonet slots (2019) that are configured to receive bayonet pins (109) of chassis (106) to thereby provide coupling between cover (2010) and chassis (106).

Figure 82:
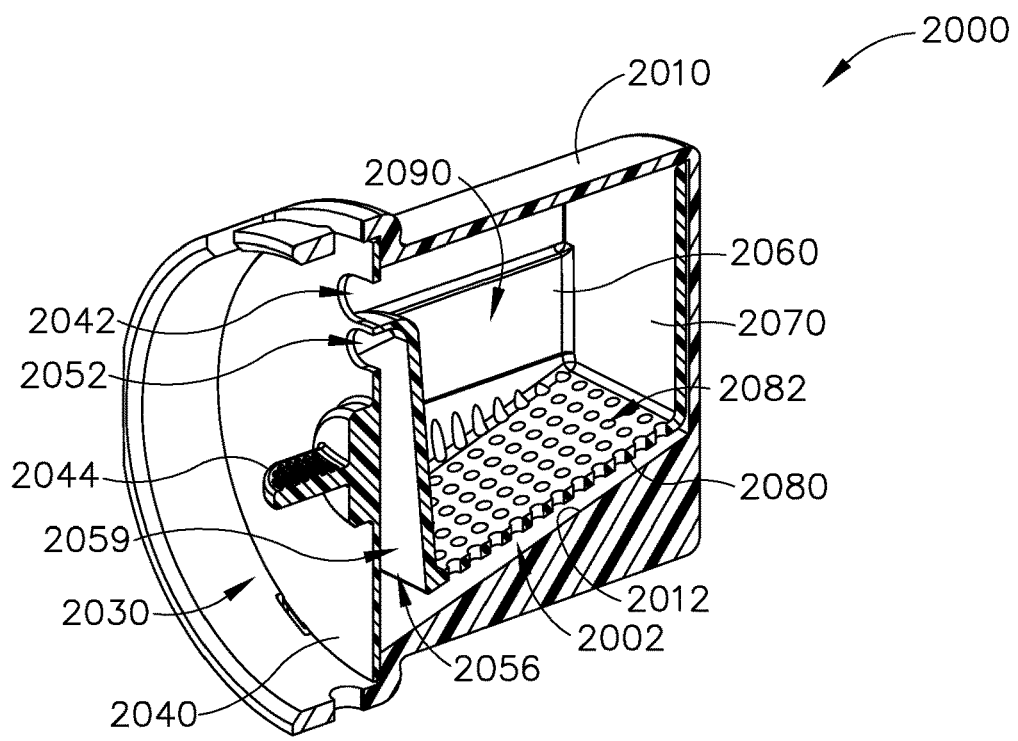
FIG. 82 depicts a cross-sectional perspective view of the tissue sample holder assembly of FIG. 77, taken along line 82-82 of FIG. 77.
Figure 83:
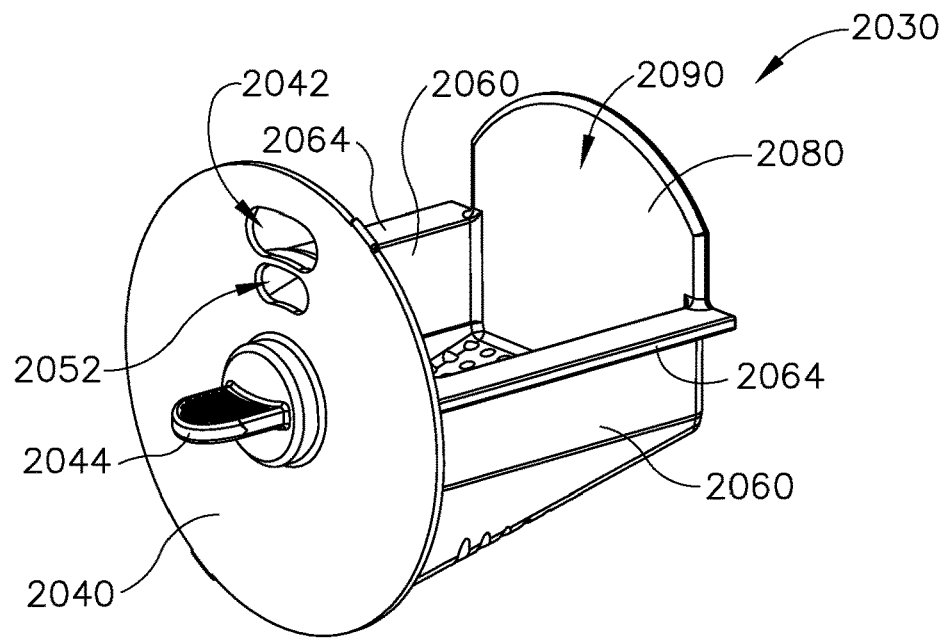
FIG. 83 depicts a perspective view of a tissue sample tray of the tissue sample holder assembly of FIG. 77.
Figure 84:
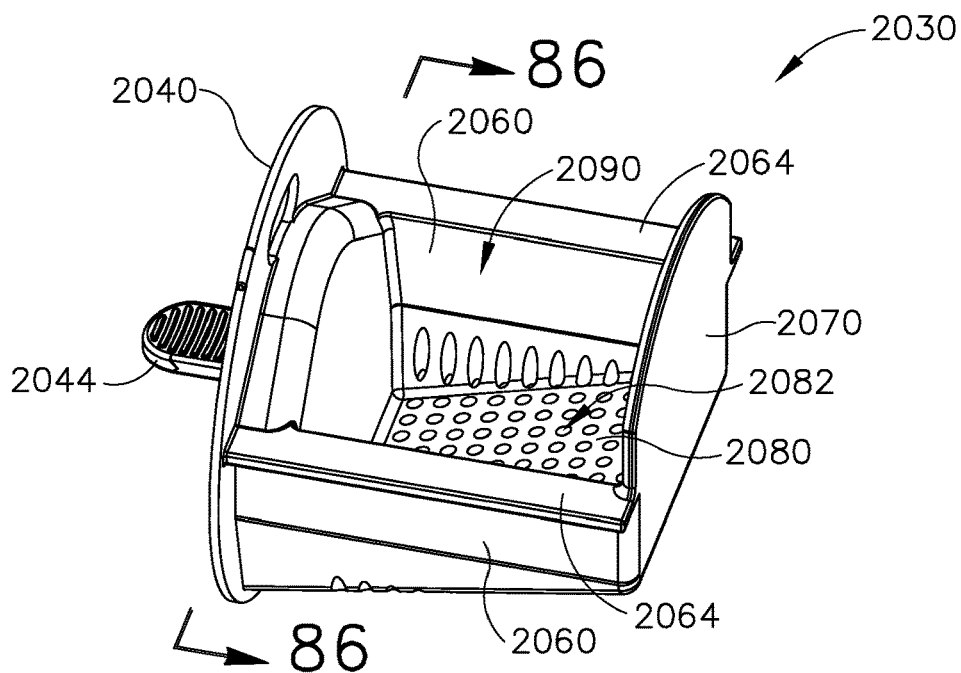
FIG. 84 depicts another perspective view of the tissue sample tray of FIG. 83.
Figure 85:
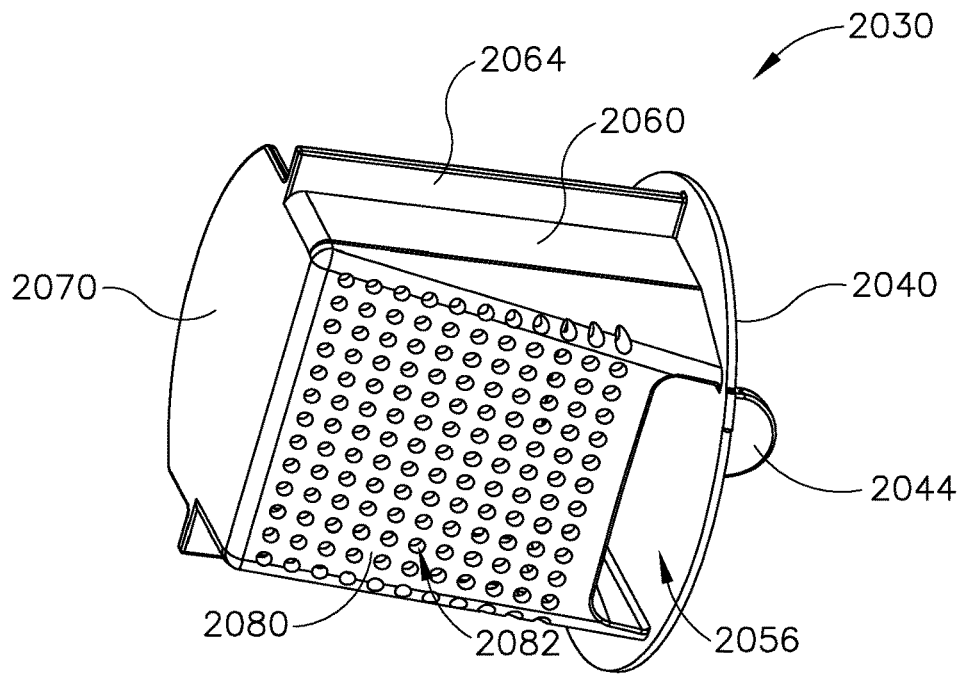
FIG. 85 depicts another perspective view of the tissue sample tray of FIG. 83.

As best seen in FIGS. 82-86, tissue sample tray (2030) of the present example comprises a distal wall (2040), a pair of sidewalls (2060), a proximal wall (2070), and an obliquely angled floor (2080). Walls (2040, 2060, 2070) and floor (2080) together define a tissue receiving compartment (2090). Distal wall (2040) defines an upper opening (2042) and a lower opening (2052). Distal wall (2040) further includes a distally projecting pull tab (2044). As best seen in FIG. 82, distal wall (2040) is configured to seal against annular shoulder (2011) of cover (2010) when tissue sample tray (2030) is inserted in cover (2010). Pull tab (2044) may be used to grasp tissue sample tray (2030) to facilitate removal of tissue sample tray (2030) from cover (2010).

Figure 79:
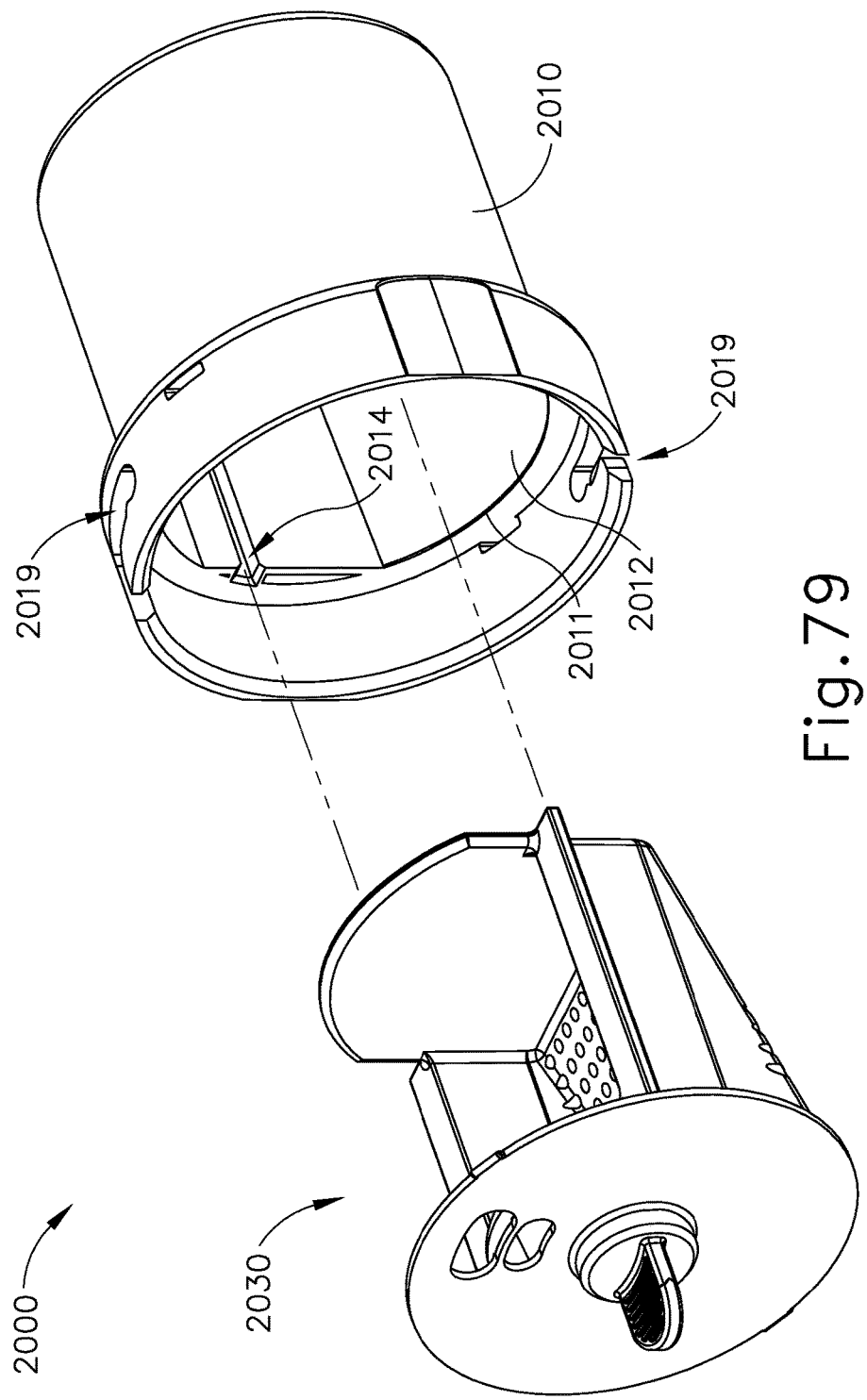
FIG. 79 depicts an exploded perspective view of the tissue sample holder assembly of FIG. 77.
Figure 80:
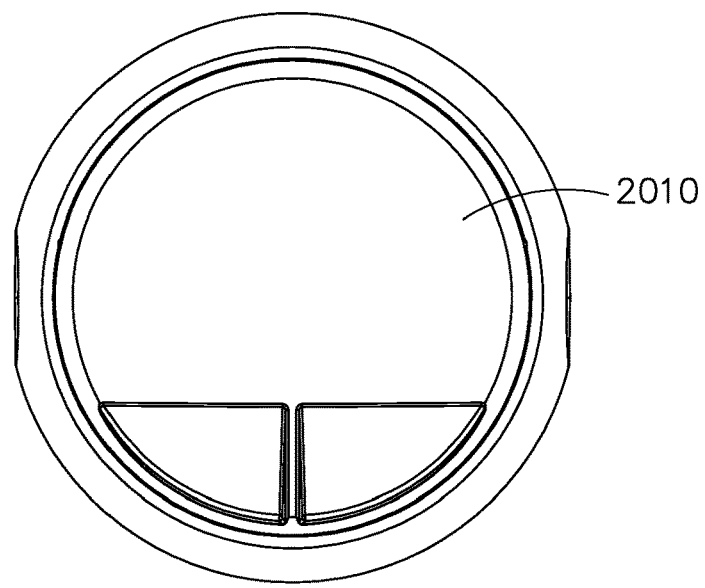
FIG. 80 depicts another end elevational view of the cover of FIG. 78.

Upper opening (2042) is in direct fluid communication with tissue receiving compartment (2090). Floor (2080) includes drainage openings (2082) that are also in fluid communication with tissue receiving compartment (2090) to provide drainage of fluids from tissue receiving compartment (2090). In some versions, sidewalls (2060) also include drainage openings. Drainage openings (2082) also provide pathways for communication of vacuum to tissue receiving compartment (2090) as will be described in greater detail below. Sidewalls (2060) also include corresponding outwardly extending flanges (2064). As shown in FIGS. 79 and 82, flanges (2064) are configured to fit in channel (2014) of cover (2010), such that flanges (2064) maintain support and positioning of tissue sample tray (2030) in cover (2010).

Figure 86:
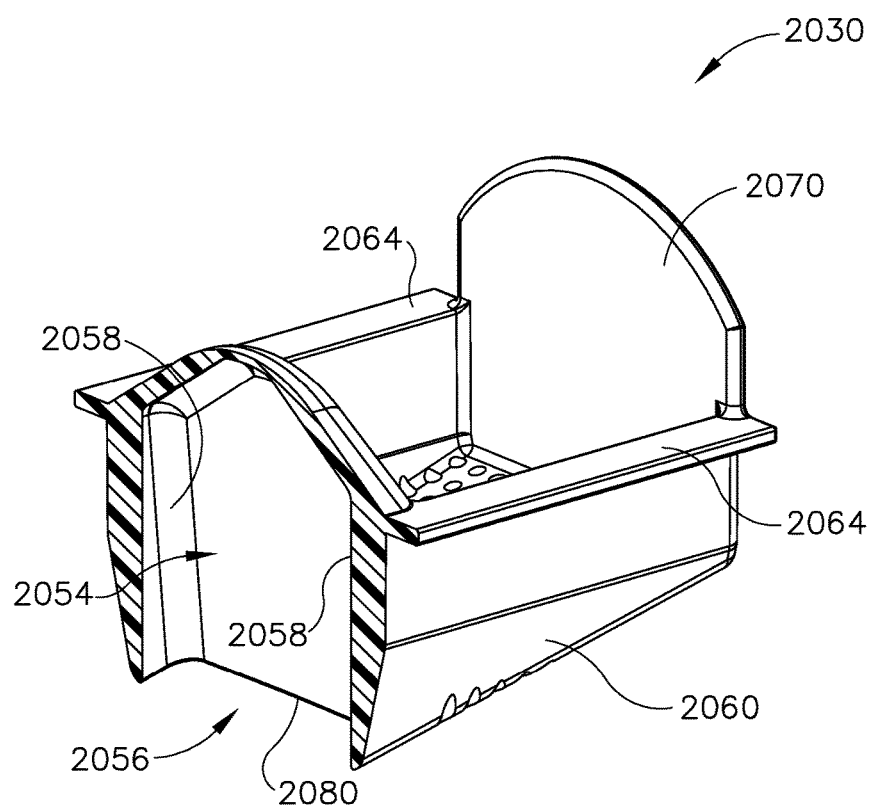
FIG. 86 depicts a cross-sectional perspective view of the tissue sample tray of FIG. 83, taken along line 86-86 of FIG. 84.
Figure 87:
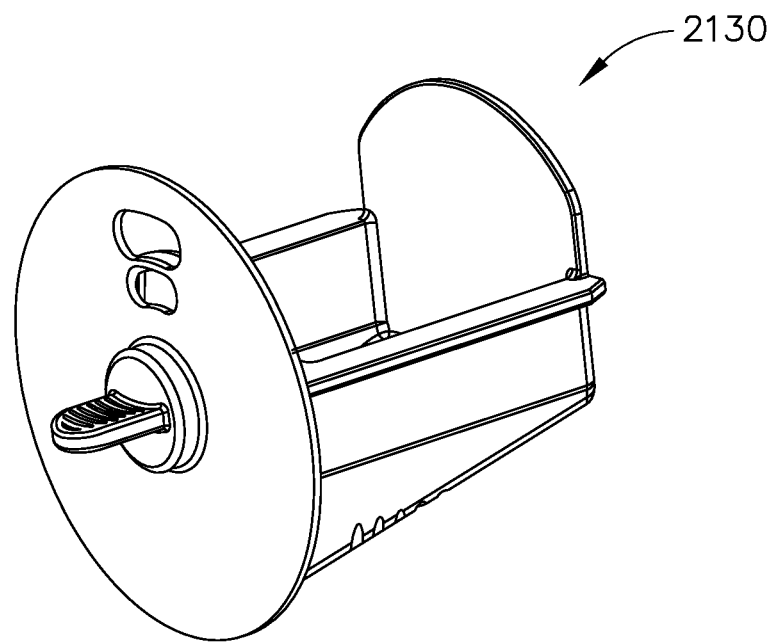
FIG. 87 depicts a perspective view of an exemplary alternative tissue sample tray that may be incorporated into the tissue sample holder assembly of FIG. 77.
Figure 88:
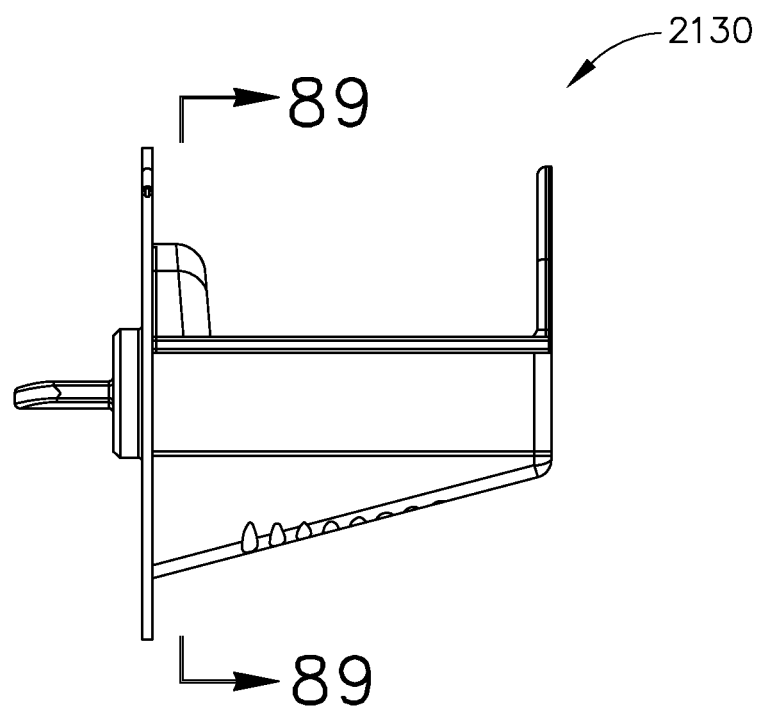
FIG. 88 depicts a side elevational view of the tissue sample tray of FIG. 87.
Figure 89:
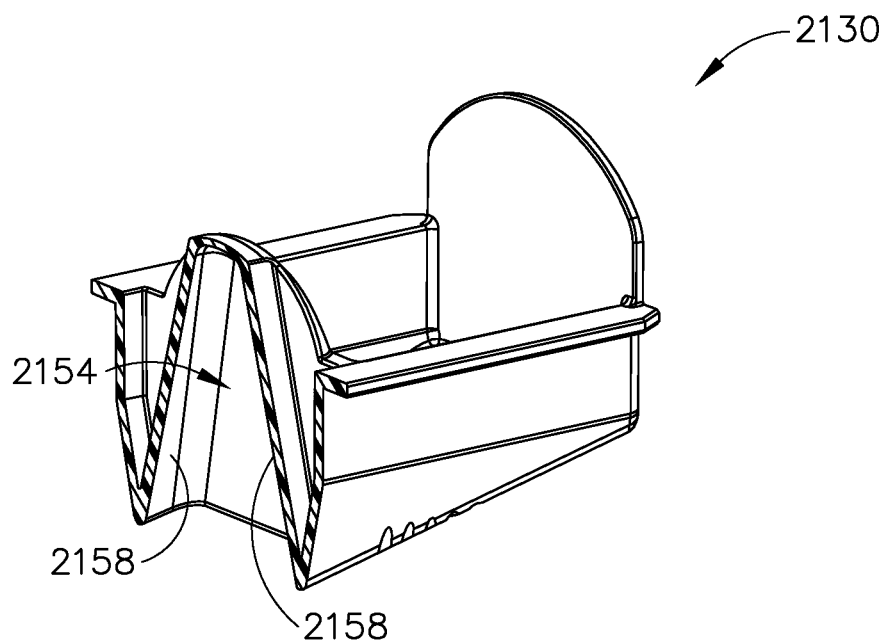
FIG. 89 depicts a cross-sectional perspective view of the tissue sample tray of FIG. 87, taken along line 89-89 of FIG. 88.

As best seen in FIG. 82, lower opening (2052) is in communication with a sump lumen (2054), which terminates in a sump opening (2056) that is located on the underside of tissue sample tray (2030). As can be seen in FIG. 82, a gap (2002) is defined between the underside of tissue sample tray (2030) and inner floor (2012) of cover (2010). Sump opening (2056) is positioned do draw fluids from this gap (2012). As best seen in FIG. 86, the lateral walls (2058) defining sump lumen (2054) are substantially vertically oriented in this example.

When tissue sample holder (2000) is coupled with probe (100), upper opening (2042) aligns with opening (174) of sealing member (170); while lower opening (2052) aligns with opening (176) of sealing member (170). Thus, when vacuum is applied via tube (20) and opening (176), this vacuum is communicated through lower opening (2052), sump lumen (2054), and sump opening (2056) to gap (2002). This vacuum is further communicated through drainage openings (2082) to tissue receiving compartment (2090); and further to openings (2042, 174) to reach lumen (151) of cutter (150). It should therefore be understood that vacuum from tube (20) may draw severed tissue samples proximally through lumen (151) to reach tissue receiving compartment (2090). It should also be understood that fluids drawn proximally through lumen (151) may be further drawn into tube (20) via openings (174, 2042), tissue receiving compartment (2090), drainage openings (2082), sump opening (2056), sump lumen (2054), and openings (2052, 176). Thus, when tissue sample holder (2030) is coupled with probe (100), biopsy device (10) may be operated to capture tissue samples in tissue receiving compartment (2090) and drain fluids. The angled configuration of floor (2012) may assist in guiding fluids toward sump opening (2056) during operation.

FIGS. 87-90 show an exemplary alternative tissue sample tray (2130) that may be readily incorporated into tissue sample holder assembly (200) in place of tissue sample tray (2030). Tissue sample tray (2130) of this example is substantially identical to tissue sample tray (2030) described above, except that the lateral walls (2158) defining sump lumen (2154) are obliquely oriented in this example. Tissue sample tray (2130) is otherwise identical to tissue sample tray (2030).

Figure 90:
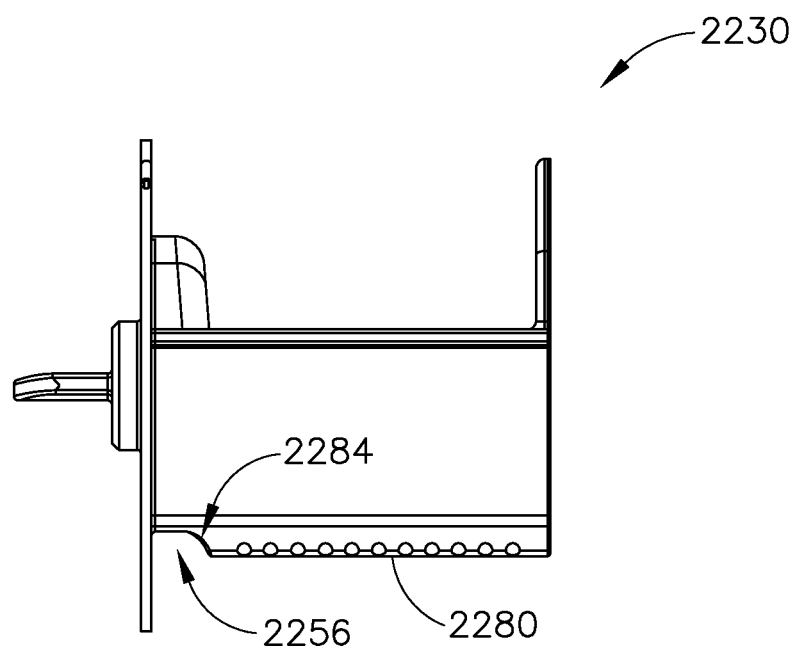
FIG. 90 depicts a side elevational view of another exemplary alternative tissue sample tray that may be incorporated into the tissue sample holder assembly of FIG. 77.
Figure 91:
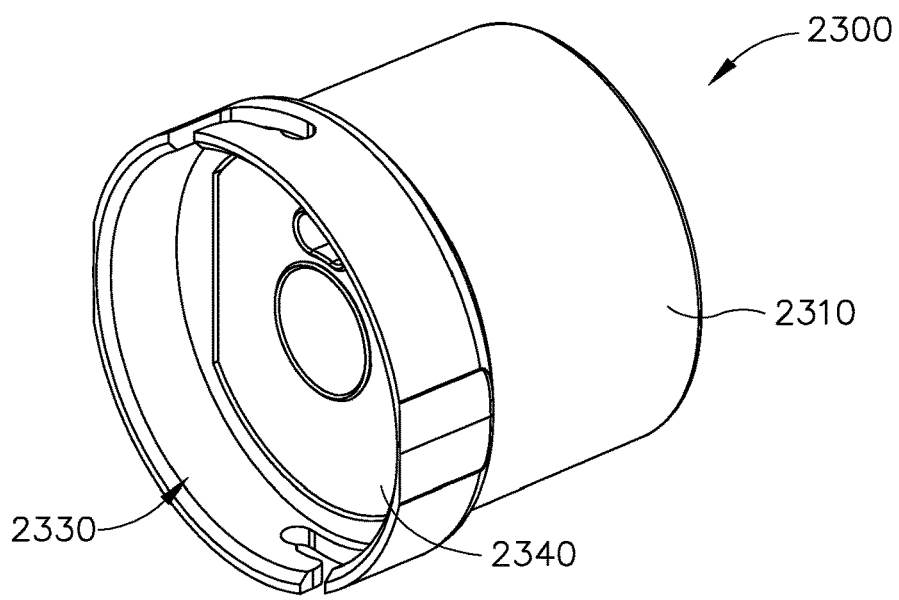
FIG. 91 depicts a perspective view of another exemplary alternative tissue sample holder assembly that may be incorporated into the probe of FIG. 4.
Figure 92:
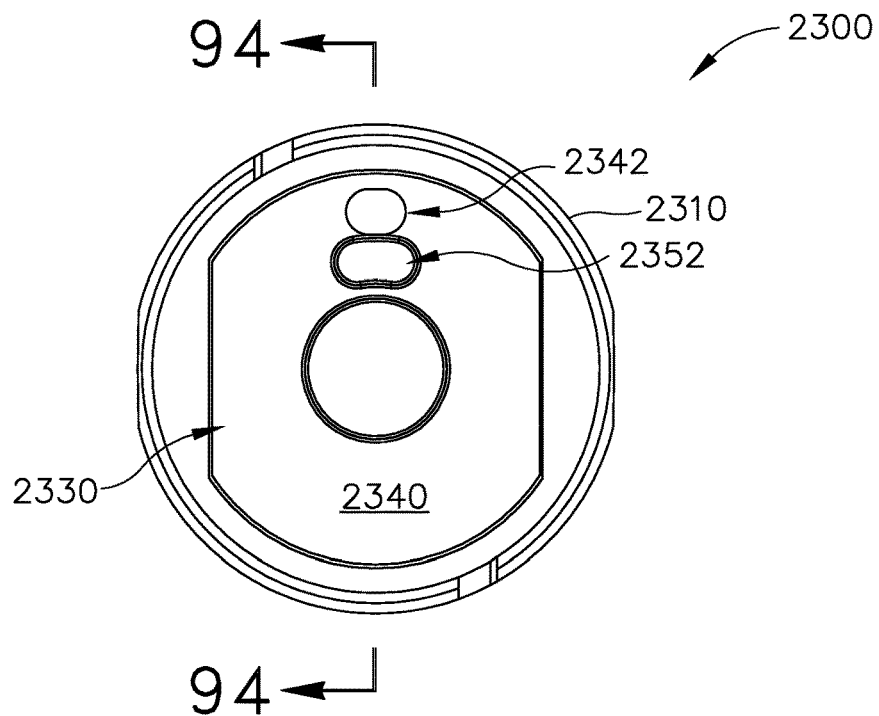
FIG. 92 depicts an end elevational view of the tissue sample holder assembly of FIG. 91.

FIG. 90 shows another exemplary alternative tissue sample tray (2230) that may be readily incorporated into tissue sample holder assembly (200) in place of tissue sample tray (2030). Tissue sample tray (2230) of this example is substantially identical to tissue sample tray (2030) described above, except that floor (2280) defines a recess (2284) adjacent to sump opening (2256). Tissue sample tray (2230) is otherwise identical to tissue sample tray (2030).

VI. Exemplary Alternative Tissue Sample Holder Assemblies with Push Eject

The examples described above provide removability of a tissue sample tray or basket from the distal end of the tissue sample holder, either using a handle or a pull tab to grasp the tissue sample tray or basket. In some instances, it may be desirable to provide removability of a tissue sample tray or basket from the proximal end of the tissue sample holder. This may minimize contact between the operator's hand and fluids that may be found at the distal end of the tissue sample tray or basket. Various examples of tissue sample holders that provide removability of a tissue sample tray or basket from the proximal end of the tissue sample holder will be described in greater detail below. Other examples will be apparent to those of ordinary skill in the art in view of the teachings herein. It should also be understood that the tissue sample trays described below include a distally presented recess that would accommodate grasping feature (184) of rotation member (180) of probe (100) when the tissue sample holder assembly is coupled with probe (100).

A. Exemplary Tissue Sample Holder Assembly with Proximal Tray Release Feature

Figure 93:
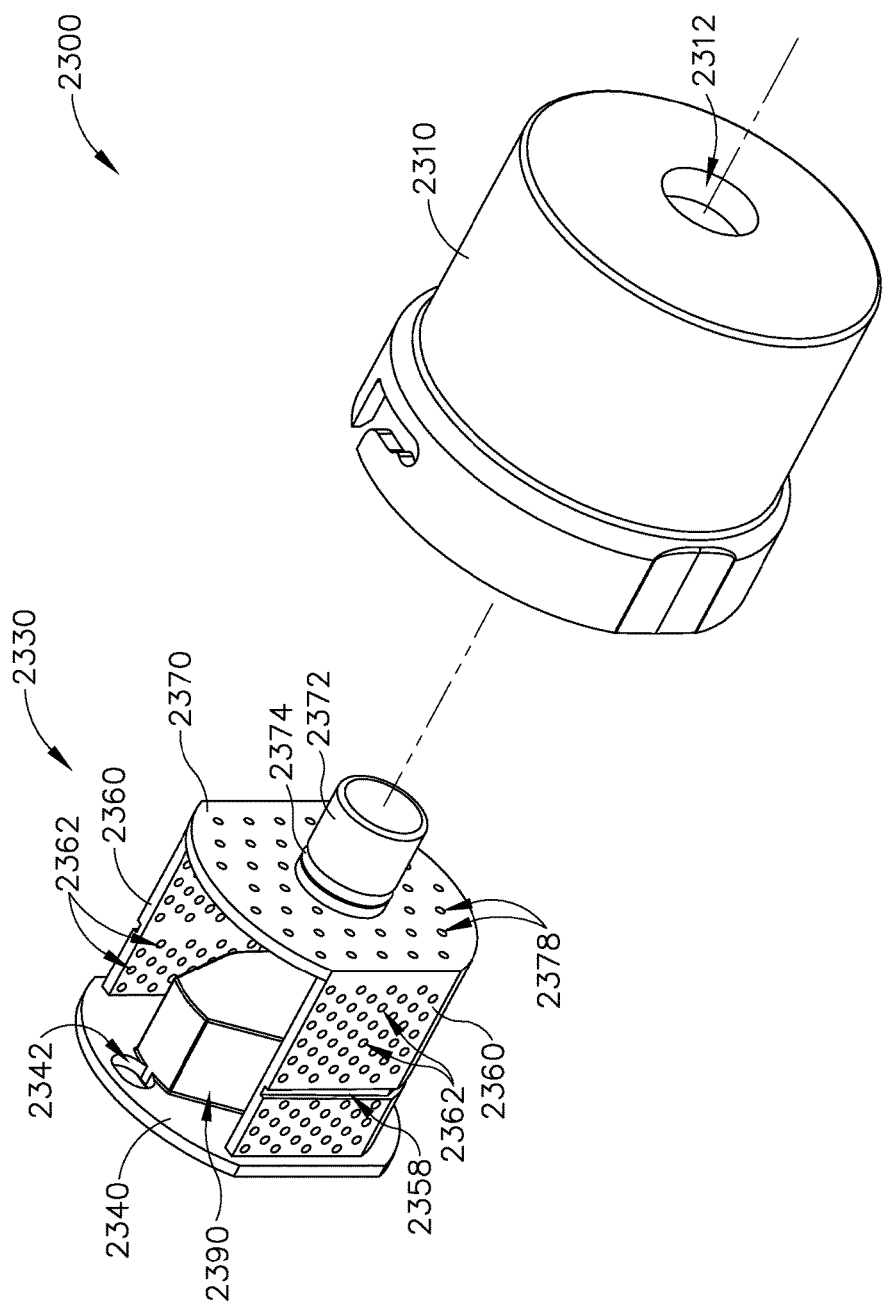
FIG. 93 depicts an exploded perspective view of the tissue sample holder assembly of FIG. 91.
Figure 94:
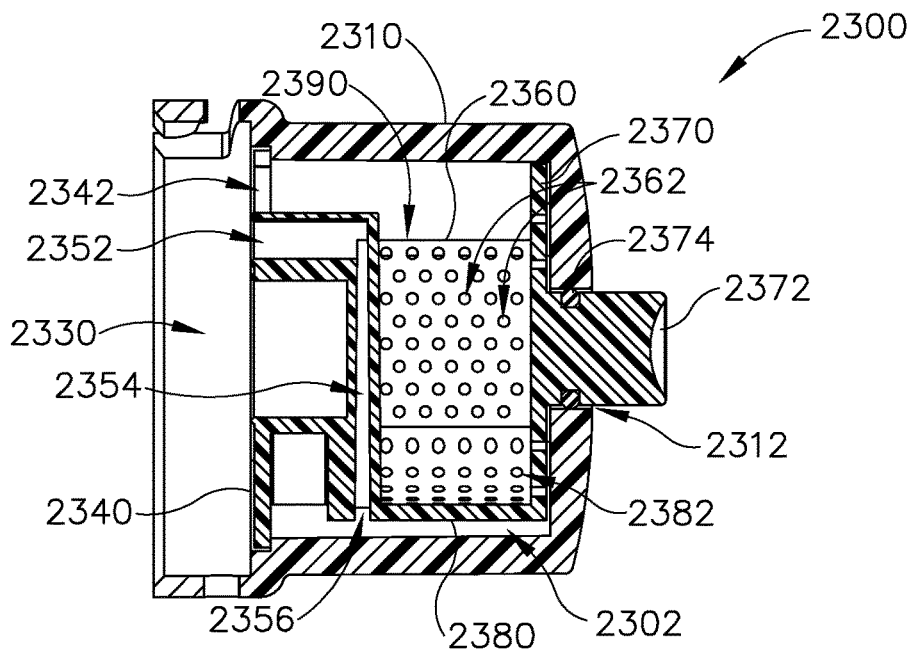
FIG. 94 depicts a cross-sectional side view of the tissue sample holder assembly of FIG. 91, taken along line 94-94 of FIG. 92.
Figure 95:
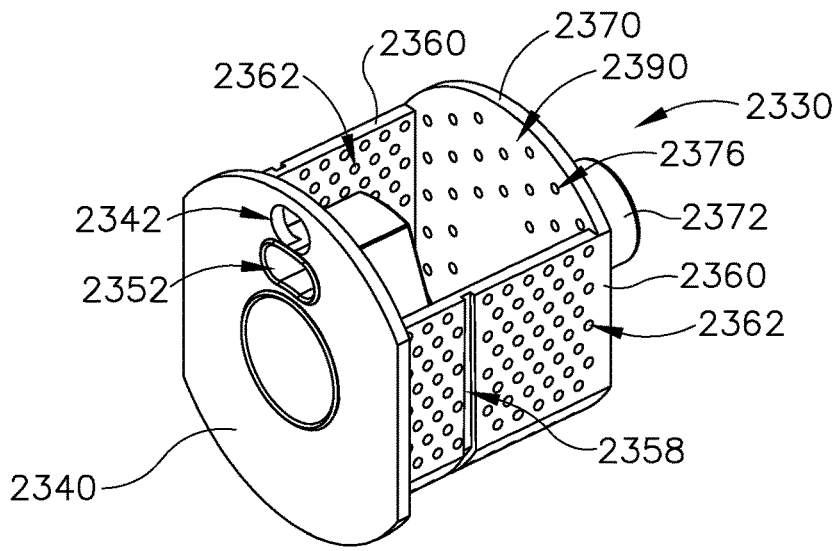
FIG. 95 depicts a perspective view of tissue sample tray of the tissue sample holder assembly of FIG. 91.
Figure 96:
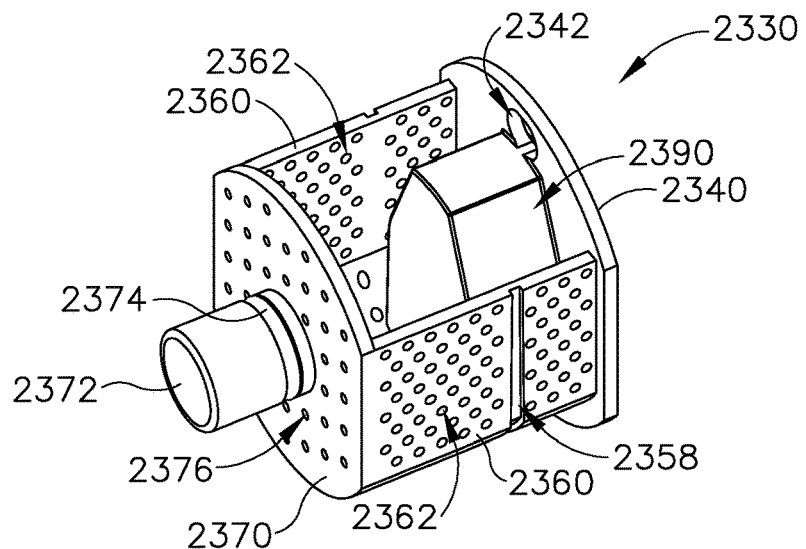
FIG. 96 depicts another perspective view of the tissue sample tray of FIG. 95.
Figure 97:
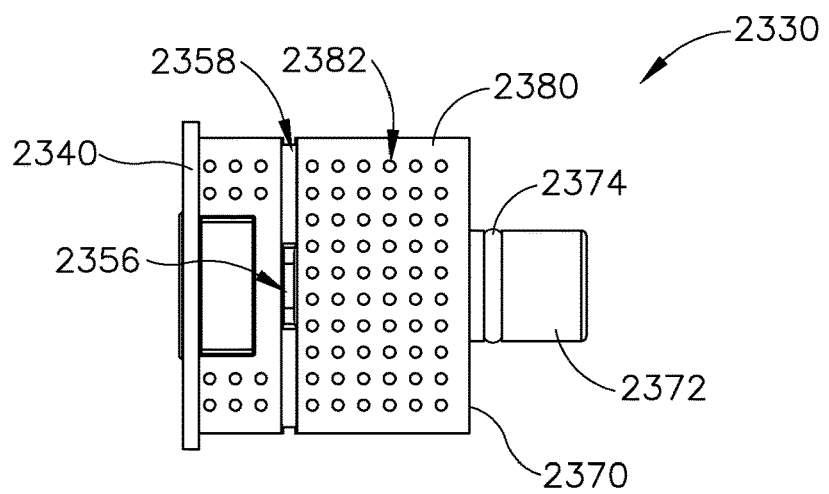
FIG. 97 depicts a bottom plan view of the tissue sample tray of FIG. 95.
Figure 98:
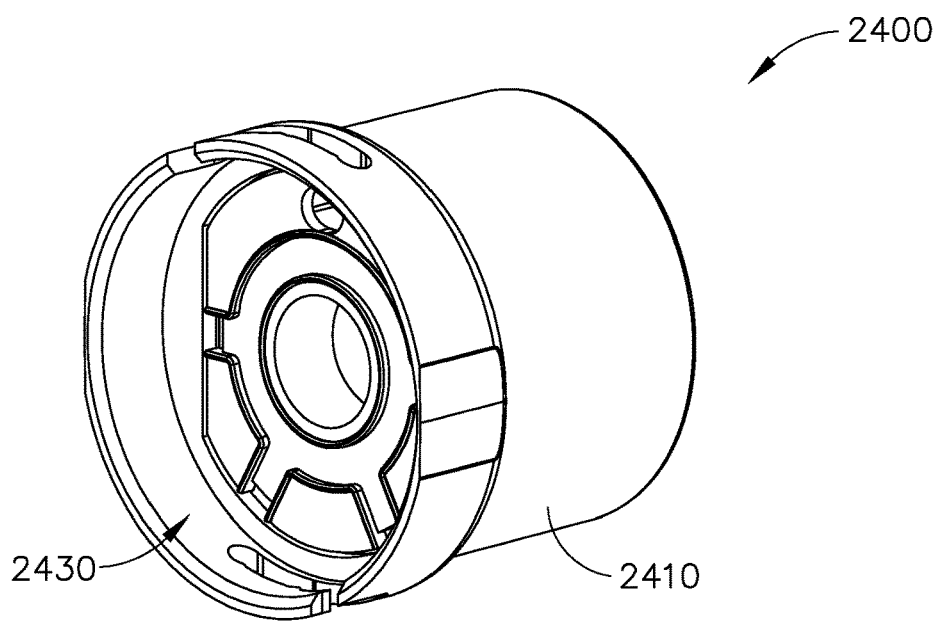
FIG. 98 depicts a perspective view of another exemplary alternative tissue sample holder assembly that may be incorporated into the probe of FIG. 4.
Figure 99:
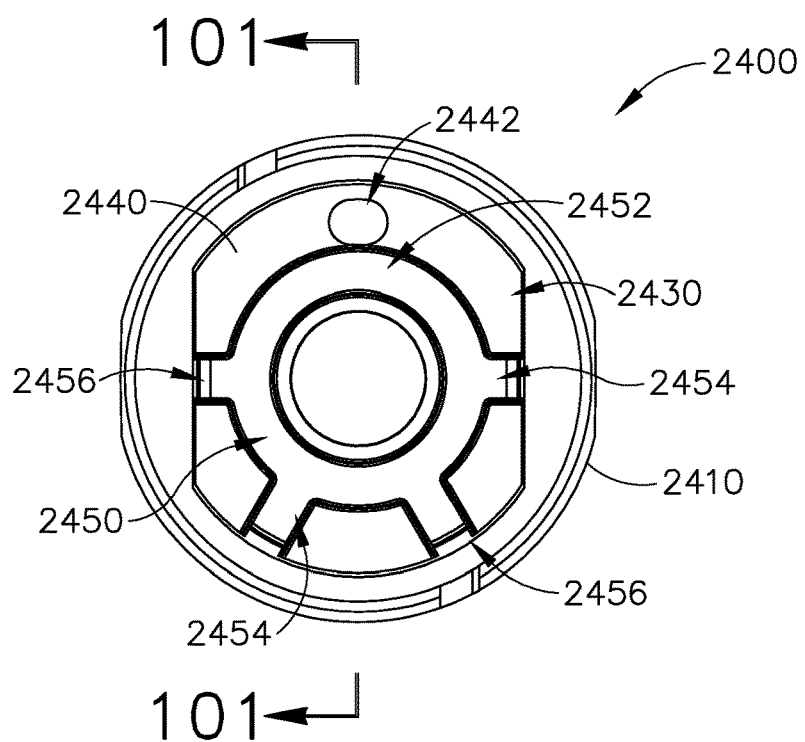
FIG. 99 depicts an end elevational view of the tissue sample holder assembly of FIG. 98.

FIGS. 91-97 show another exemplary tissue sample holder assembly (2300) that may be coupled with probe (100). Tissue sample holder assembly (2300) of this example comprises a cover (2310) and a tissue sample tray (2330), which is removably inserted in cover (2310). As best seen in FIG. 93, cover (2310) includes a proximal opening (2312). As best seen in FIGS. 95-97, tissue sample tray (2330) of the present example comprises a distal wall (2340), a pair of sidewalls (2360), a proximal wall (2370), and a floor (2380). Walls (2340, 2360, 2370) and floor (2380) together define a tissue receiving compartment (2390). Distal wall (2340) defines an upper opening (2342) and a lower opening (2352). Proximal wall (2370) includes a proximally oriented projection (2372). An o-ring (2374) is disposed about projection (2372). As best seen in FIGS. 93-94, projection (2372), is sized to fit through proximal opening (2312) of cover (2310) when tissue sample tray (2330) is inserted in cover (2310). O-ring (2374) is positioned and configured to provide a fluid seal within opening (2312) when projection (2372) is inserted in opening (2312). O-ring (2374) thus assists in maintaining vacuum within tissue sample holder assembly (2300) and preventing leakage of fluid from tissue sample holder assembly (2300). Projection (2372) protrudes proximally from cover (2310) such that an operator may readily grasp cover (2310) and press distally on projection (2372) to eject tissue sample tray (2330) from cover (2310). By way of example only, this may be done to retrieve tissue samples that have been collected in tissue receiving compartment (2390).

Upper opening (2342) is in direct fluid communication with tissue receiving compartment (2390). Walls (2360, 2370) and floor (2380) include corresponding drainage openings (2362, 2376, 2382) that are also in fluid communication with tissue receiving compartment (2390) to provide drainage of fluids from tissue receiving compartment (2390). Drainage openings (2362, 2376, 2382) also provide pathways for communication of vacuum to tissue receiving compartment (2390) as will be described in greater detail below. As best seen in FIG. 94, lower opening (2352) is in communication with a sump lumen (2354), which terminates in a sump opening (2356) that is located on the underside of tissue sample tray (2330). As can be seen in FIG. 94, a gap (2302) is defined between the underside of tissue sample tray (2030) and inner surface (2312) of cover (2310). Sump opening (2356) is positioned do draw fluids from this gap (2302). In the present example, walls (2360, 2370) and floor (2380) also include recesses (2358) that provide an additional path for fluid communication between sump opening (2356) and tissue receiving compartment (2390).

When tissue sample holder (2300) is coupled with probe (100), upper opening (2342) aligns with opening (174) of sealing member (170); while lower opening (2352) aligns with opening (176) of sealing member (170). Thus, when vacuum is applied via tube (20) and opening (176), this vacuum is communicated through lower opening (2352), sump lumen (2354), and sump opening (2356) to gap (2302). This vacuum is further communicated through drainage openings (2362, 2376, 2382) and recesses (2358) to tissue receiving compartment (2390); and further to openings (2342, 174) to reach lumen (151) of cutter (150). It should therefore be understood that vacuum from tube (20) may draw severed tissue samples proximally through lumen (151) to reach tissue receiving compartment (2390). It should also be understood that fluids drawn proximally through lumen (151) may be further drawn into tube (20) via openings (174, 2342), tissue receiving compartment (2390), drainage openings (2362, 2376, 2382), sump opening (2356), sump lumen (2354), and openings (2352, 176). Thus, when tissue sample holder (2330) is coupled with probe (100), biopsy device (10) may be operated to capture tissue samples in tissue receiving compartment (2390) and drain fluids.

Figure 100:
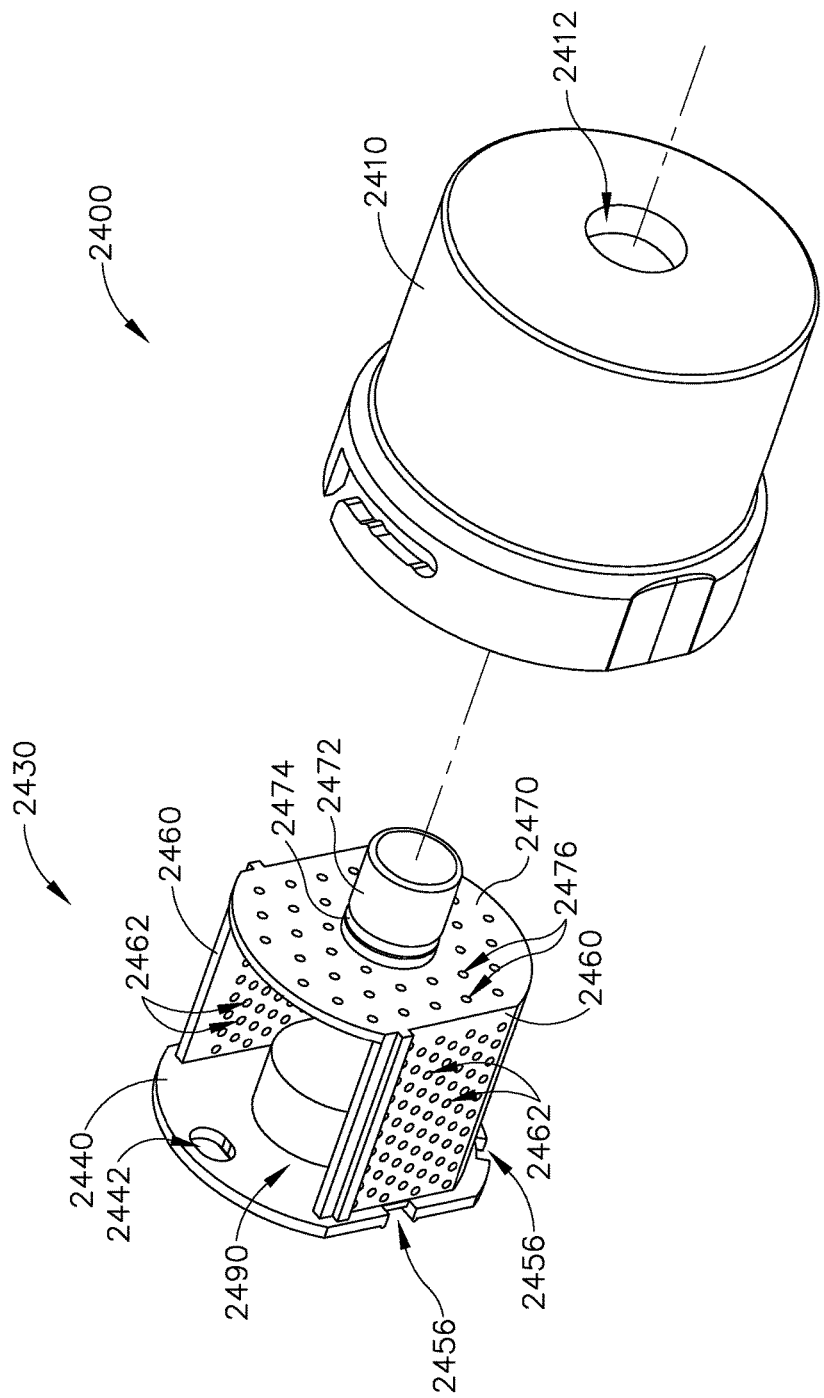
FIG. 100 depicts an exploded perspective view of the tissue sample holder assembly of FIG. 98.
Figure 101:
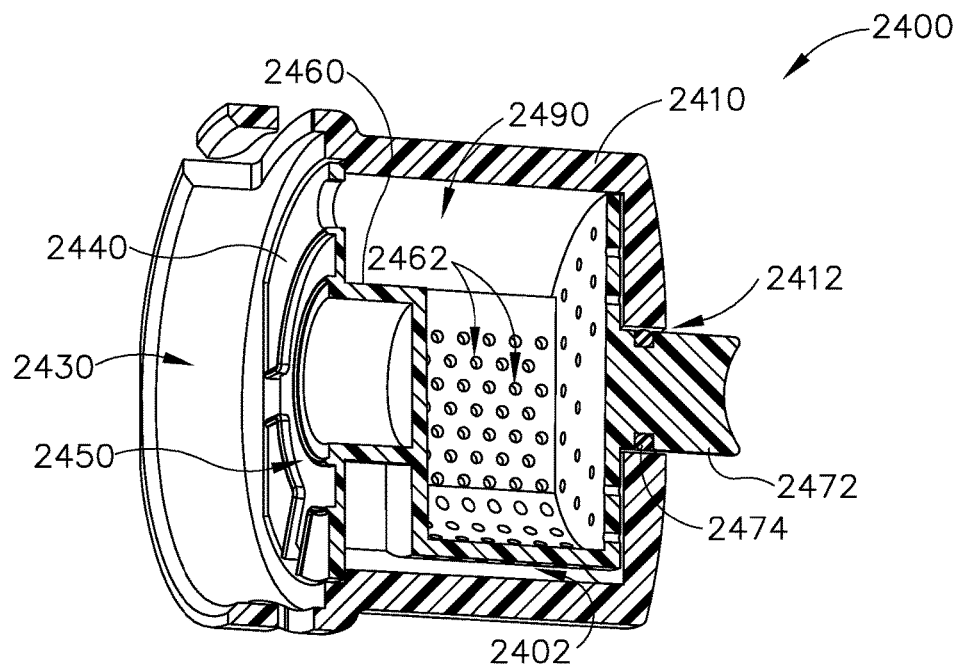
FIG. 101 depicts a cross-sectional perspective view of the tissue sample holder assembly of FIG. 98, taken along line 101-10 of FIG. 99.
Figure 102:
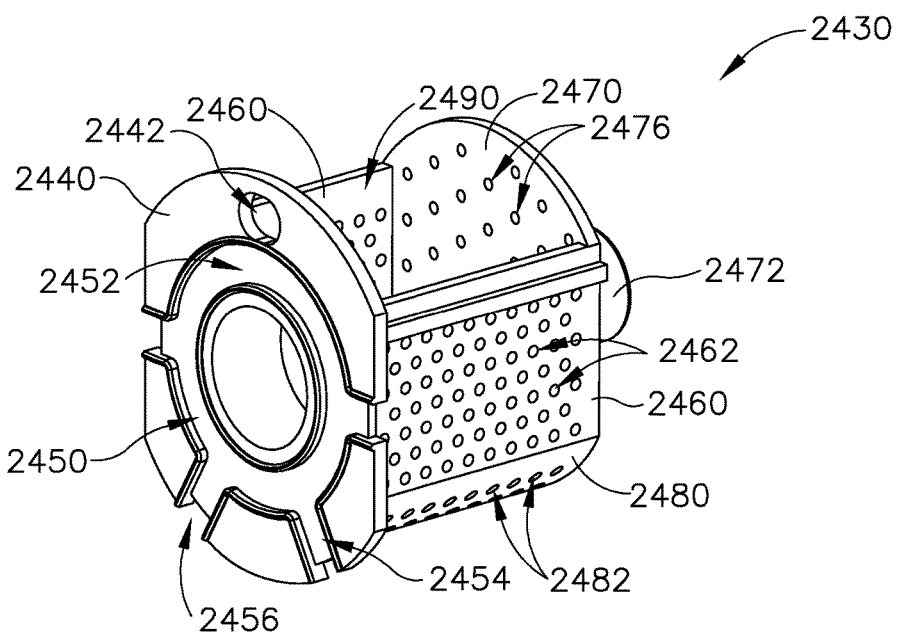
FIG. 102 depicts a perspective view of a tissue sample tray of the tissue sample holder assembly of FIG. 98.
Figure 103:
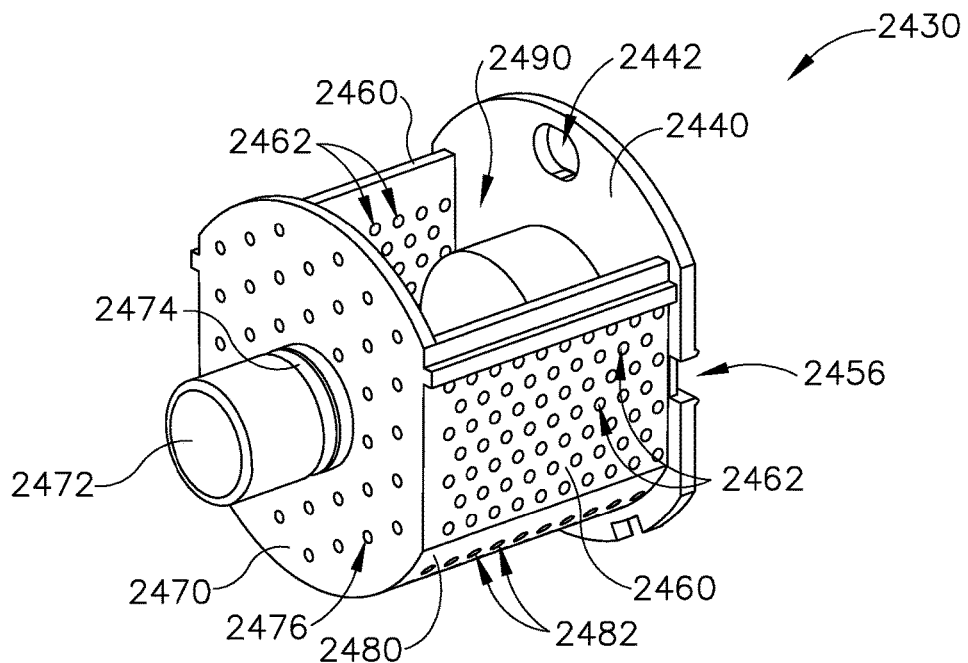
FIG. 103 depicts another perspective view of the tissue sample tray of FIG. 102.
Figure 104:
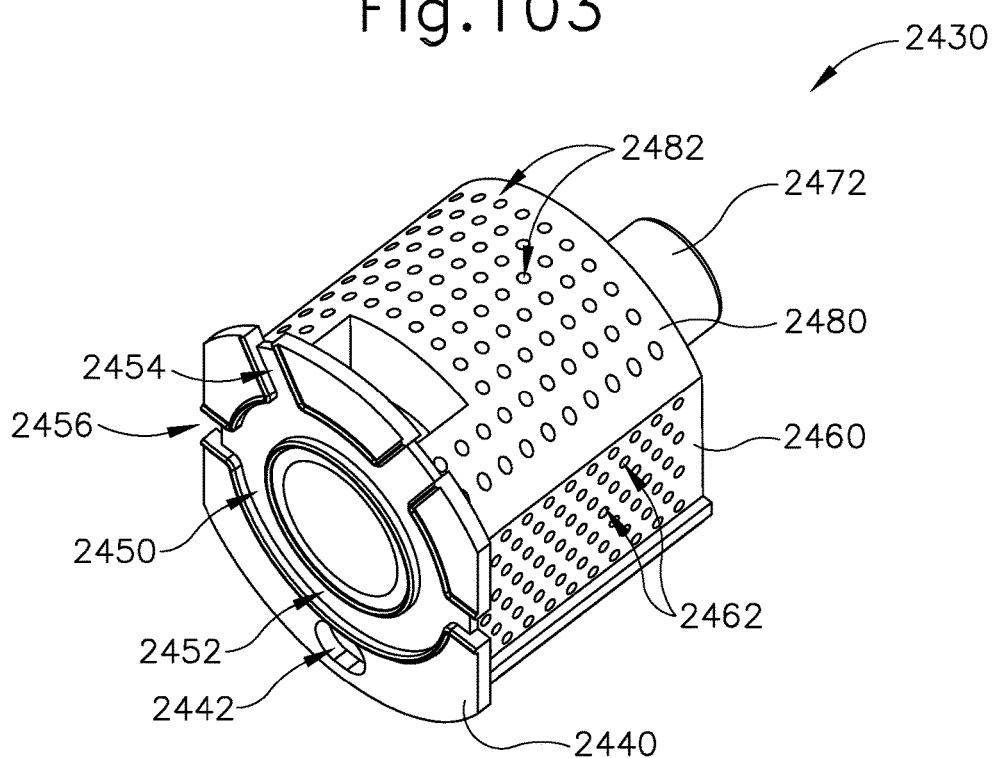
FIG. 104 depicts another perspective view of the tissue sample tray of FIG. 102.
Figure 105:
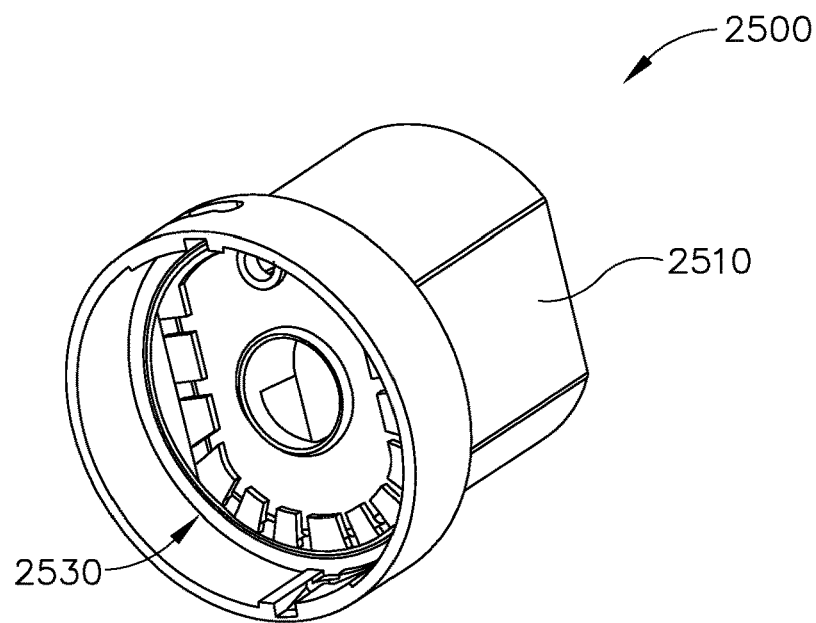
FIG. 105 depicts a perspective view of another exemplary alternative tissue sample holder assembly that may be incorporated into the probe of FIG. 4.

B. Exemplary Tissue Sample Holder Assembly with Proximal Tray Release Feature and Distal Trough FIGS. 98-104 show another exemplary tissue sample holder assembly (2400) that may be coupled with probe (100). Tissue sample holder assembly (2400) of this example comprises a cover (2410) and a tissue sample tray (2430), which is removably inserted in cover (2410). As best seen in FIG. 100, cover (2410) includes a proximal opening (2412). As best seen in FIGS. 102-104, tissue sample tray (2430) of the present example comprises a distal wall (2440), a pair of sidewalls (2460), a proximal wall (2470), and a floor (2480). Walls (2440, 2460, 2470) and floor (2480) together define a tissue receiving compartment (2490). Distal wall (2440) defines an upper opening (2442) and a lower trough (2450). Proximal wall (2470) includes a proximally oriented projection (2472). An o-ring (2474) is disposed about projection (2472). As best seen in FIGS. 100-101, projection (2472), is sized to fit through proximal opening (2412) of cover (2410) when tissue sample tray (2430) is inserted in cover (2410). O-ring (2474) is positioned and configured to provide a fluid seal within opening (2412) when projection (2472) is inserted in opening (2412). O-ring (2474) thus assists in maintaining vacuum within tissue sample holder assembly (2400) and preventing leakage of fluid from tissue sample holder assembly (2400). Projection (2472) protrudes proximally from cover (2410) such that an operator may readily grasp cover (2410) and press distally on projection (2472) to eject tissue sample tray (2430) from cover (2410). By way of example only, this may be done to retrieve tissue samples that have been collected in tissue receiving compartment (2490).

Upper opening (2442) is in direct fluid communication with tissue receiving compartment (2490). Walls (2460, 2470) and floor (2480) include corresponding drainage openings (2462, 2476, 2482) that are also in fluid communication with tissue receiving compartment (2490) to provide drainage of fluids from tissue receiving compartment (2490). Drainage openings (2462, 2476, 2482) also provide pathways for communication of vacuum to tissue receiving compartment (2490) as will be described in greater detail below. Lower trough (2450) forms a circular shape on the distal face of distal wall (2440), including an upper region (2452) that is just below upper opening (2442). Lower trough (2450) further includes four outwardly extending branches (2454), which terminate in radially inwardly extending notches (2456) that are formed in distal wall (2440). While four branches (2454) and notches (2456) are provided in the present example, it should be understood that any other suitable number of branches (2454) and notches (2456) may be provided. In the present example, notches (2456) are each sized to provide a path for fluid communication between trough (2450) and a gap (2402) defined between cover (2410) and tissue sample tray (2430). Notches (2456) thus provide functionality similar to that provided by sump openings in other examples described herein.

When tissue sample holder (2400) is coupled with probe (100), upper opening (2442) aligns with opening (174) of sealing member (170); while upper region (2452) of trough (2450) aligns with opening (176) of sealing member (170). Thus, when vacuum is applied via tube (20) and opening (176), this vacuum is communicated through trough (2450) and notches (2456) to gap (2402). This vacuum is further communicated through drainage openings (2462, 2476, 2482) to tissue receiving compartment (2490); and further to openings (2442, 174) to reach lumen (151) of cutter (150). It should therefore be understood that vacuum from tube (20) may draw severed tissue samples proximally through lumen (151) to reach tissue receiving compartment (2490). It should also be understood that fluids drawn proximally through lumen (151) may be further drawn into tube (20) via openings (174, 2442), tissue receiving compartment (2490), drainage openings (2462, 2476, 2482), notches (2456), trough (2450), and opening (176). Thus, when tissue sample holder (2430) is coupled with probe (100), biopsy device (10) may be operated to capture tissue samples in tissue receiving compartment (2490) and drain fluids.

Figure 106:
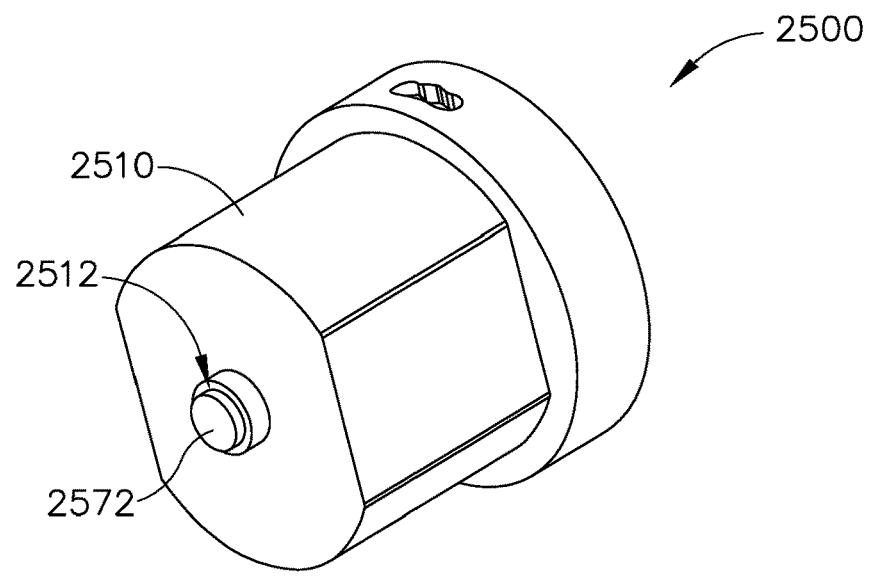
FIG. 106 depicts another perspective view of the tissue sample holder assembly of FIG. 105.
Figure 107:
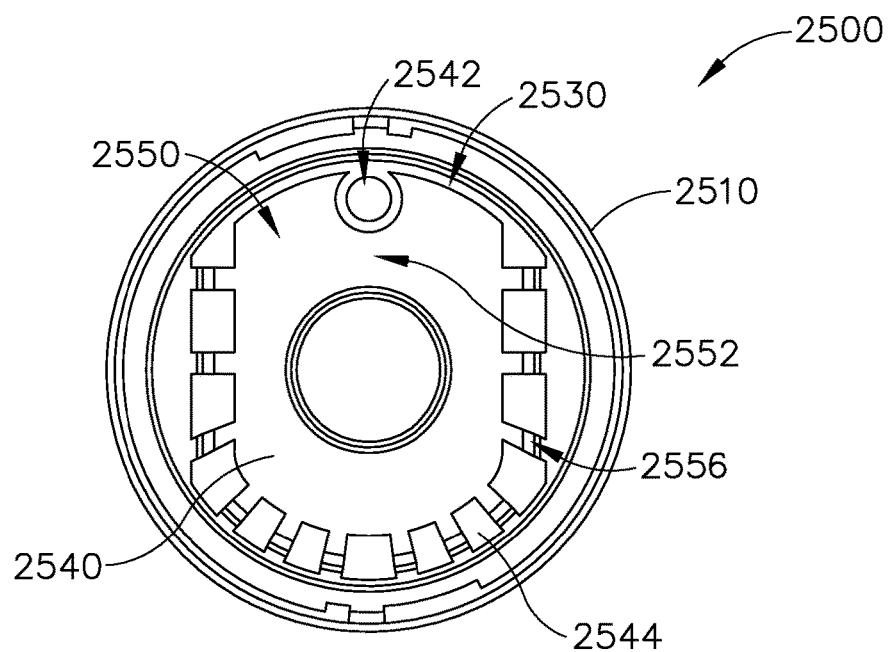
FIG. 107 depicts an end elevational view of the tissue sample holder assembly of FIG. 105.
Figure 108:
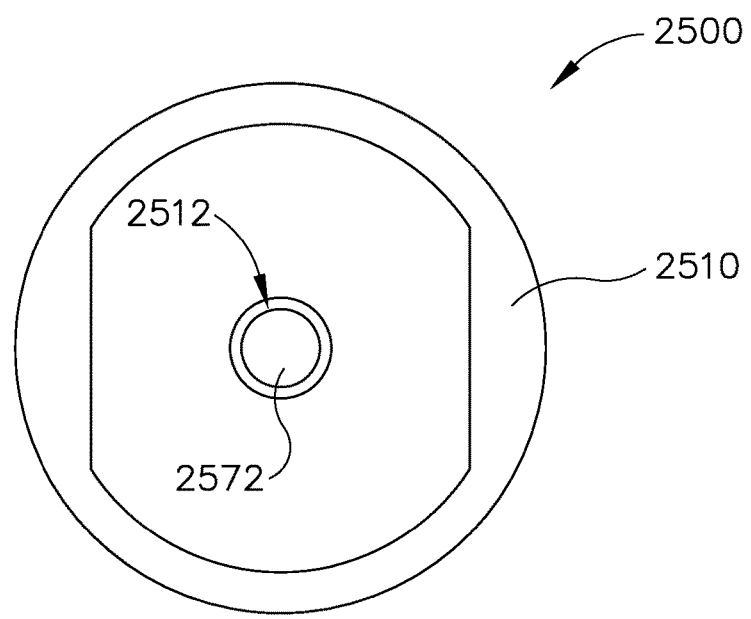
FIG. 108 depicts another end elevational view of the tissue sample holder assembly of FIG. 105.
Figure 109:
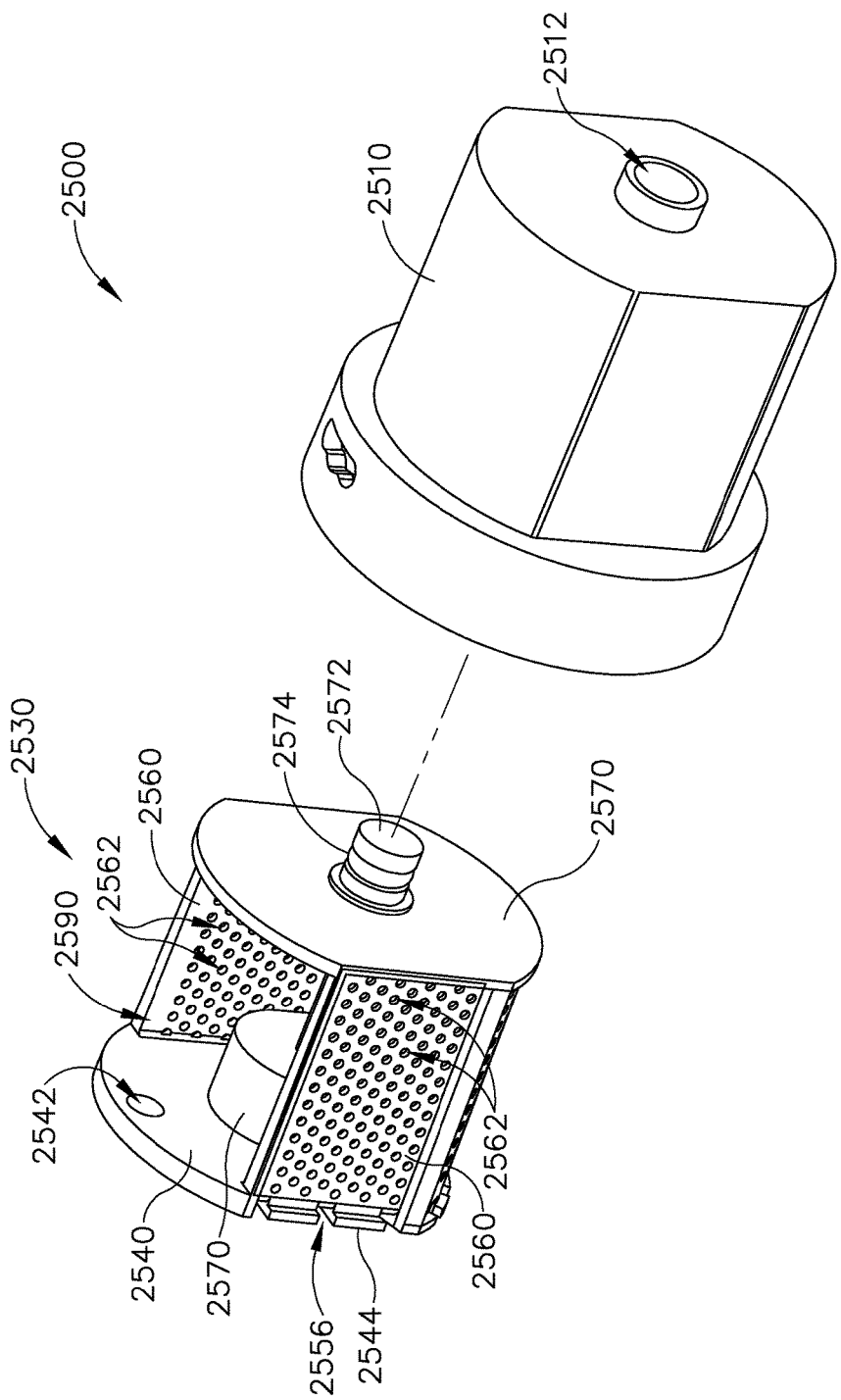
FIG. 109 depicts an exploded perspective view of the tissue sample holder assembly of FIG. 105.
Figure 110:
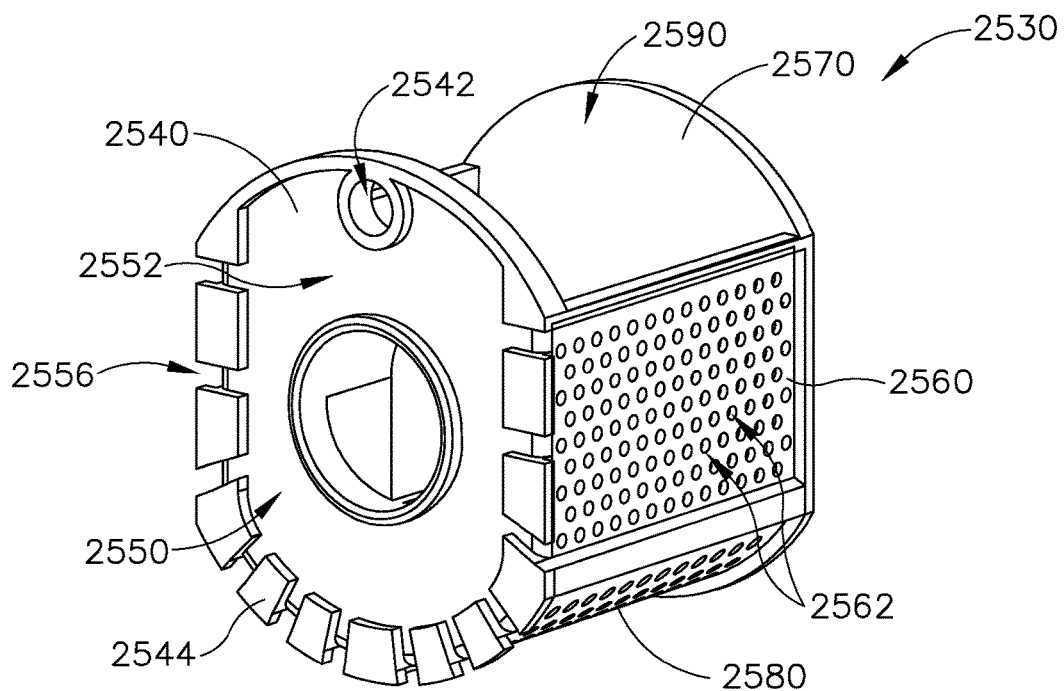
FIG. 110 depicts a perspective view of a tissue sample tray of the tissue sample holder assembly of FIG. 105.
Figure 111:
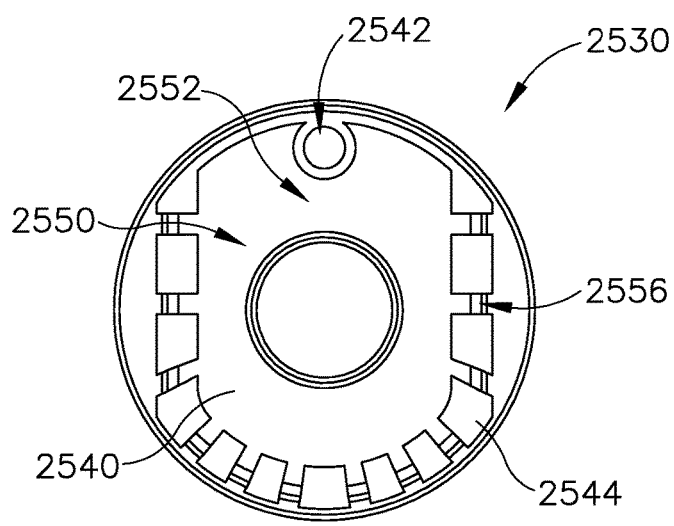
FIG. 111 depicts an end elevational view of the tissue sample tray of FIG. 110.
Figure 112:
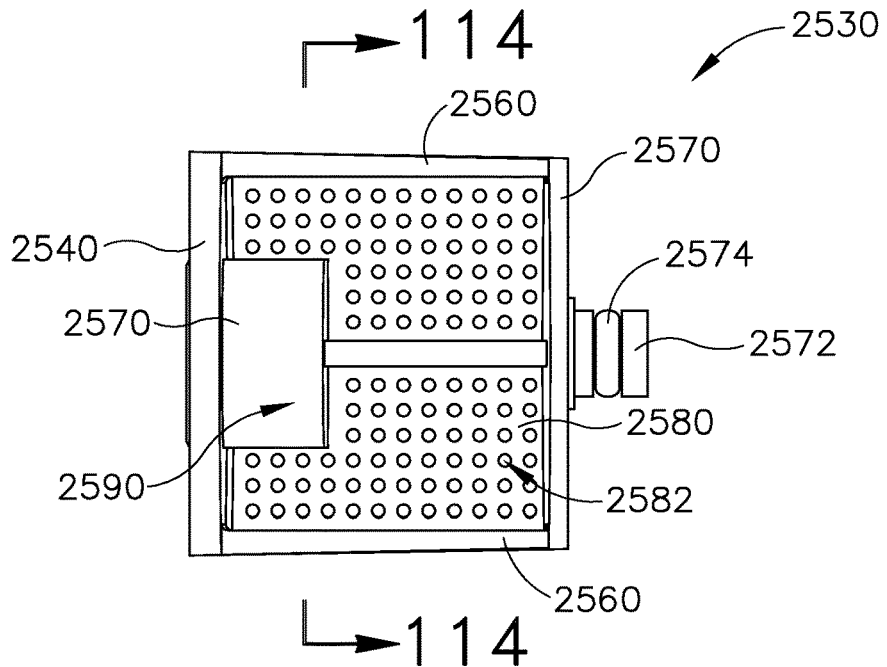
FIG. 112 depicts a top plan view of the tissue sample tray of FIG. 110.

C. Exemplary Tissue Sample Holder Assembly with Proximal Tray Release Feature and Array of Flanges FIGS. 105-114 show another exemplary tissue sample holder assembly (2500) that may be coupled with probe (100). Tissue sample holder assembly (2500) of this example comprises a cover (2510) and a tissue sample tray (2530), which is removably inserted in cover (2510). As best seen in FIG. 109, cover (2510) includes a proximal opening (2512). As best seen in FIGS. 110-113, tissue sample tray (2530) of the present example comprises a distal wall (2540), a pair of sidewalls (2560), a proximal wall (2570), and a floor (2580). Walls (2540, 2560, 2570) and floor (2580) together define a tissue receiving compartment (2590). Distal wall (2540) defines an upper opening (2542) and a trough (2550). Proximal wall (2570) includes a proximally oriented projection (2572). An o-ring (2574) is disposed about projection (2572). As best seen in FIGS. 106 and 109, projection (2572), is sized to fit through proximal opening (2512) of cover (2510) when tissue sample tray (2530) is inserted in cover (2510). O-ring (2574) is positioned and configured to provide a fluid seal within opening (2512) when projection (2572) is inserted in opening (2512). O-ring (2574) thus assists in maintaining vacuum within tissue sample holder assembly (2500) and preventing leakage of fluid from tissue sample holder assembly (2500). Projection (2572) protrudes proximally from cover (2510) such that an operator may readily grasp cover (2510) and press distally on projection (2572) to eject tissue sample tray (2530) from cover (2510). By way of example only, this may be done to retrieve tissue samples that have been collected in tissue receiving compartment (2590).

Upper opening (2542) is in direct fluid communication with tissue receiving compartment (2590). Walls (2560) and floor (2580) include corresponding drainage openings (2562, 2582) that are also in fluid communication with tissue receiving compartment (2590) to provide drainage of fluids from tissue receiving compartment (2590). Drainage openings (2562, 2582) also provide pathways for communication of vacuum to tissue receiving compartment (2590) as will be described in greater detail below. Trough (2550) extends across nearly the entire distal face of distal wall (2540), including a region (2552) that is just below upper opening (2542). Distal wall (2540) further includes a plurality of outwardly extending flanges (2544) that define notches (2556) therebetween. Notches (2556) are in fluid communication with trough (2550) and a gap (2502) that is defined between cover (2510) and tissue sample tray (2530).

Notches (2556) thus provide functionality similar to that provided by sump openings in other examples described herein.

Figure 113:
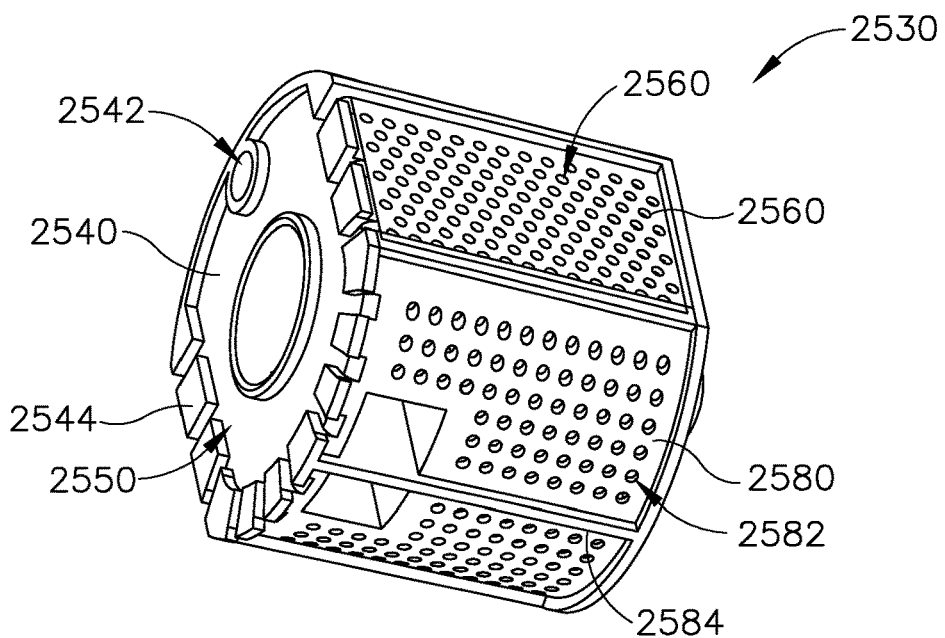
FIG. 113 depicts another perspective view of the tissue sample tray of FIG. 110.
Figure 114:
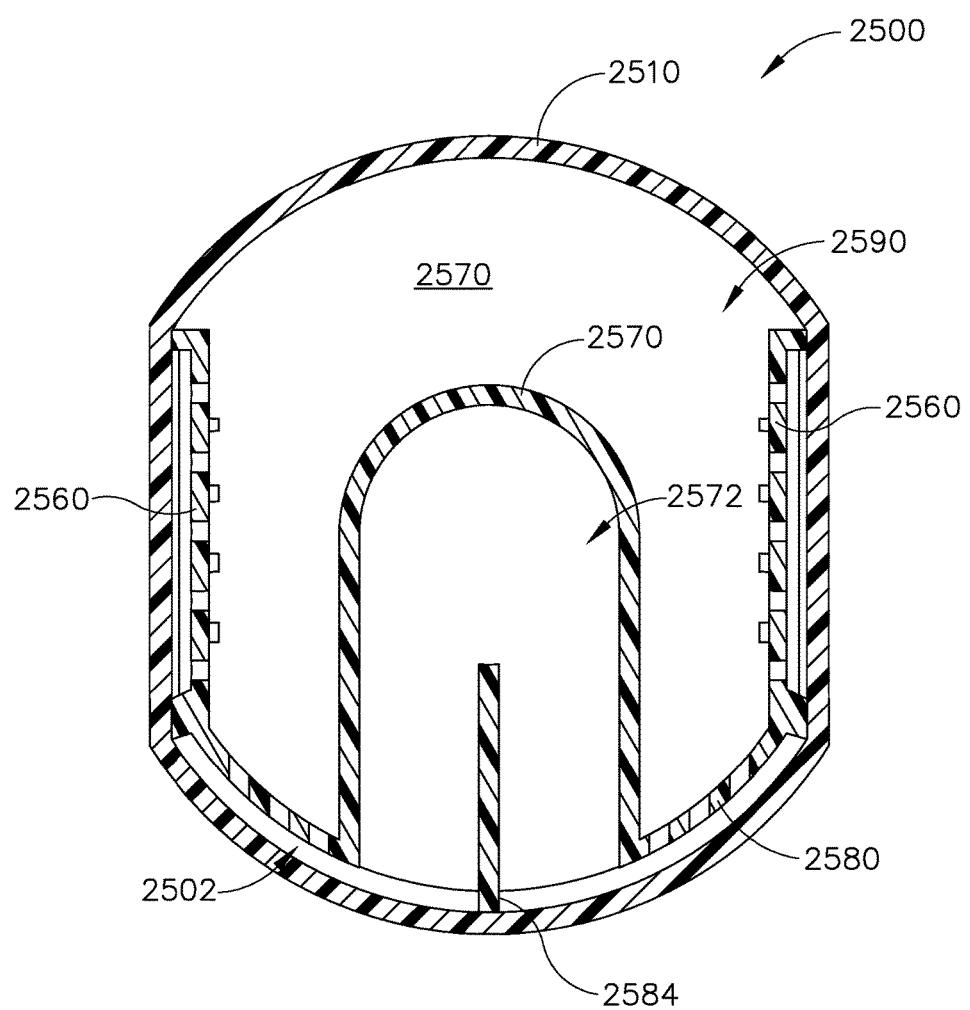
FIG. 114 depicts a cross-sectional end view of the tissue sample holder assembly of FIG. 105, taken along line 114-114 of FIG. 112.
Figure 115:
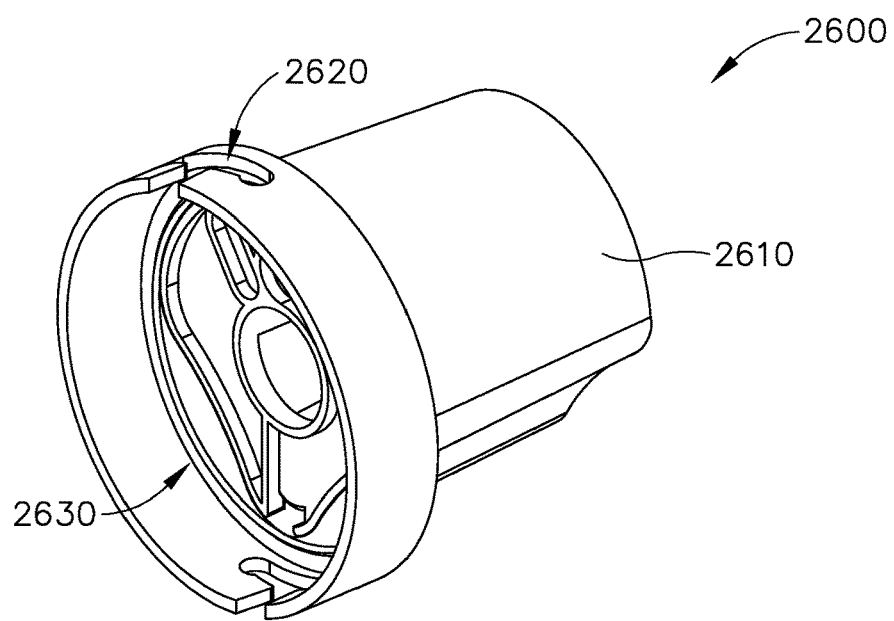
FIG. 115 depicts a perspective view of another exemplary alternative tissue sample holder assembly that may be incorporated into the probe of FIG. 4.

As best seen in FIGS. 113-114, floor (2580) of the present example further includes a longitudinally extending rib (2584). Rib (2584) is configured to engage cover (2510) to divide gap (2502) into two lateral sections at the bottom of tissue sample tray (2430). The distal region of tissue sample tray (2430) also includes a hollow hump (2570). As shown in FIG. 114, a distal portion of rib (2584) extends upwardly into hump (2570). Rib (2584) and hump (2570) nevertheless provide a fluid path (2572) from one lateral side of gap (2502) to the other lateral side of gap (2502).

When tissue sample holder (2500) is coupled with probe (100), upper opening (2542) aligns with opening (174) of sealing member (170); while region (2552) of trough (2550) aligns with opening (176) of sealing member (170). Thus, when vacuum is applied via tube (20) and opening (176), this vacuum is communicated through trough (2550) and notches (2556) to gap (2502). This vacuum is further communicated through drainage openings (2562, 2582) to tissue receiving compartment (2590); and further to openings (2542, 174) to reach lumen (151) of cutter (150). It should therefore be understood that vacuum from tube (20) may draw severed tissue samples proximally through lumen (151) to reach tissue receiving compartment (2590). It should also be understood that fluids drawn proximally through lumen (151) may be further drawn into tube (20) via openings (174, 2542), tissue receiving compartment (2590), drainage openings (2562, 2582), notches (2556), trough (2550), and opening (176). Thus, when tissue sample holder (2530) is coupled with probe (100), biopsy device (10) may be operated to capture tissue samples in tissue receiving compartment (2590) and drain fluids.

Figure 116:
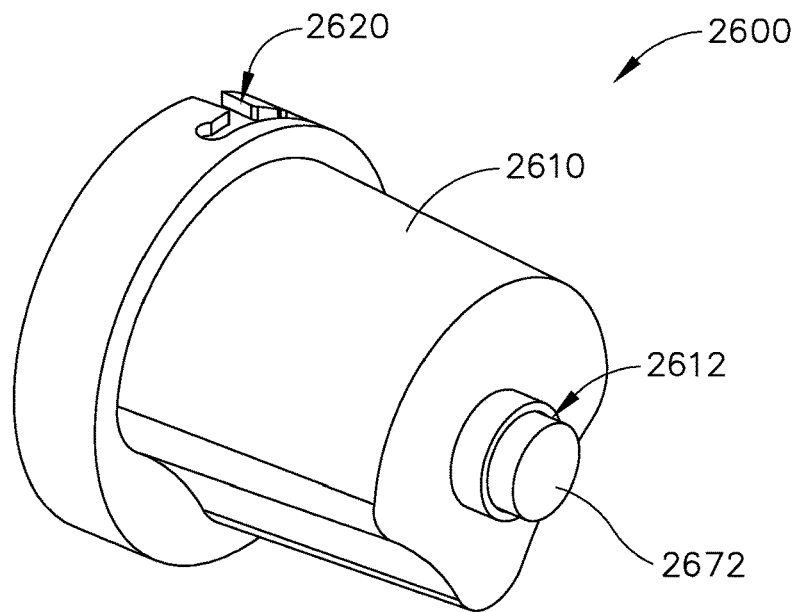
FIG. 116 depicts another perspective view of the tissue sample holder assembly of FIG. 115.
Figure 117:
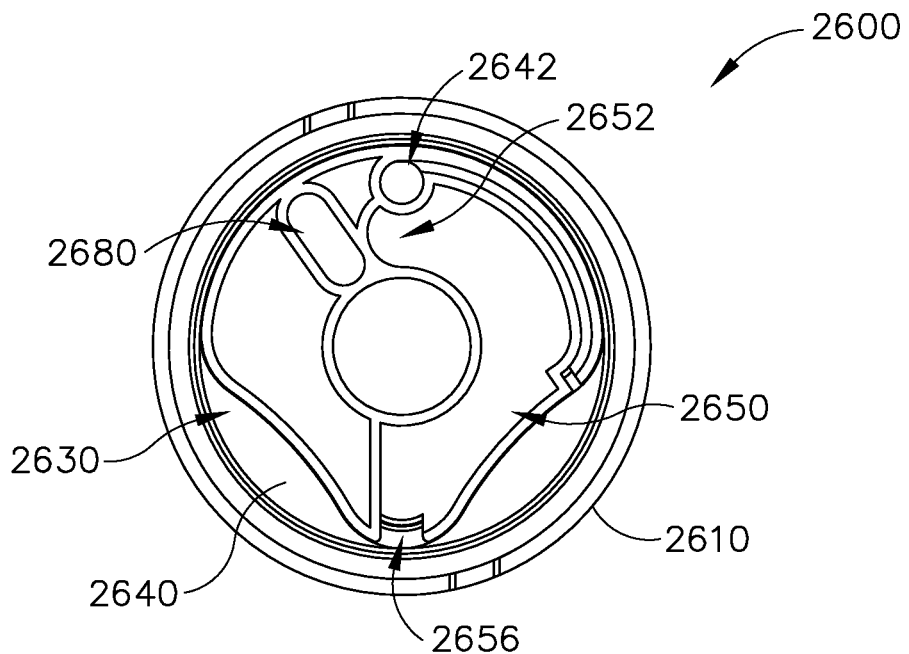
FIG. 117 depicts an end elevational view of the tissue sample holder assembly of FIG. 115.
Figure 118:
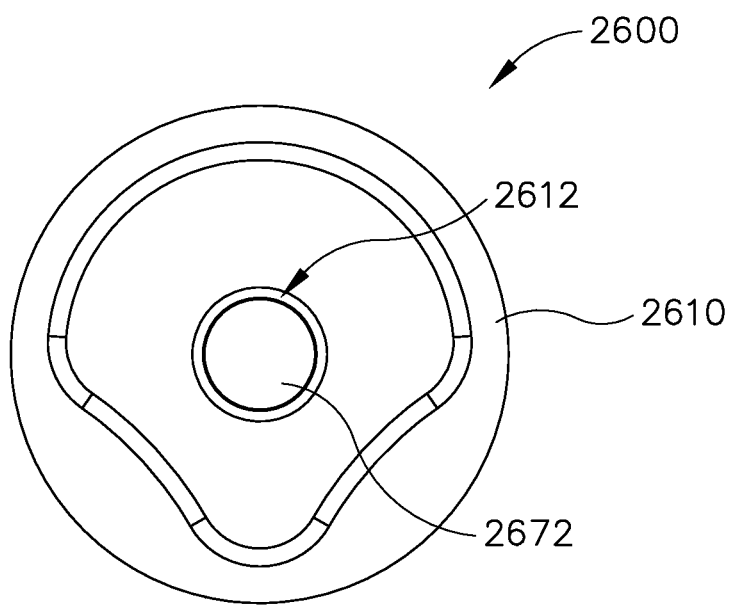
FIG. 118 depicts another end elevational view of the tissue sample holder assembly of FIG. 115.
Figure 119:
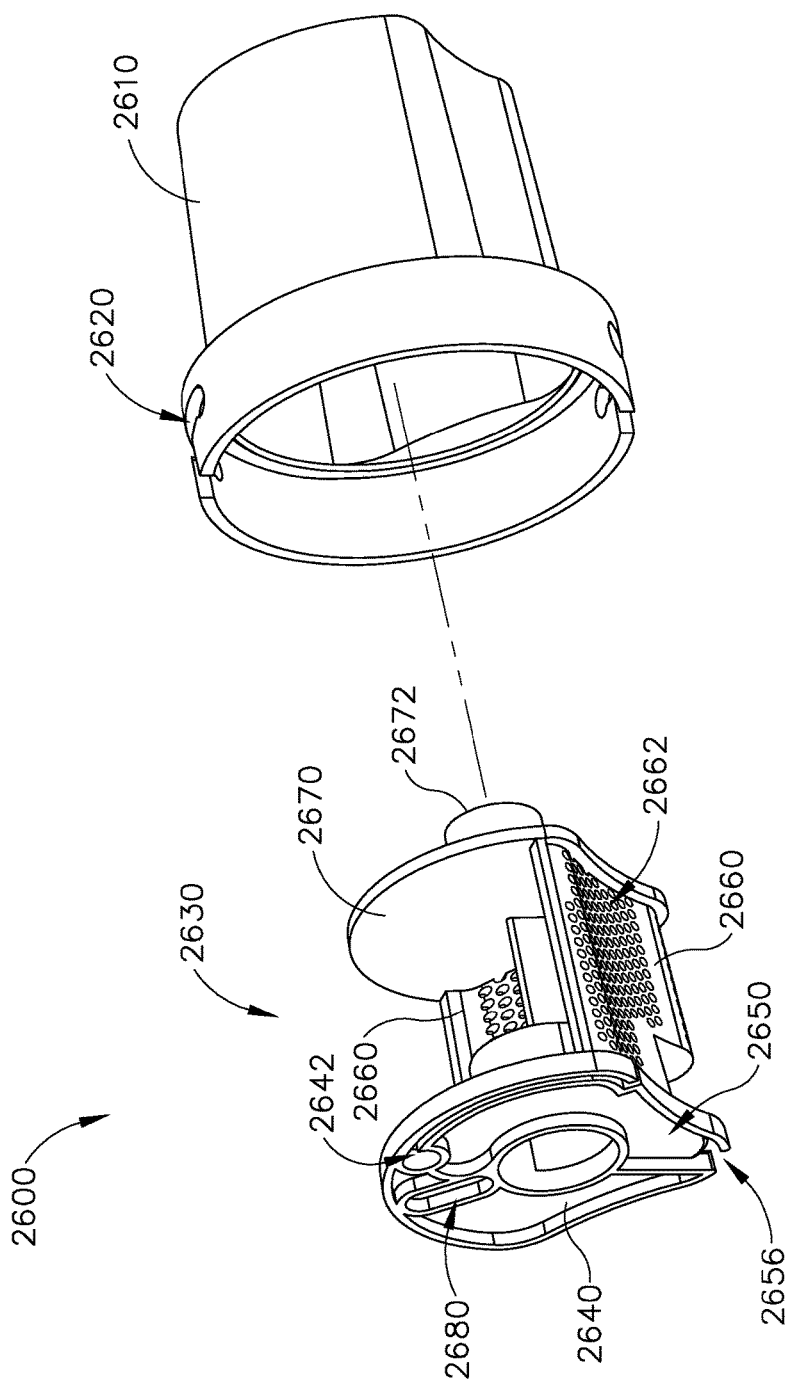
Figure 120:
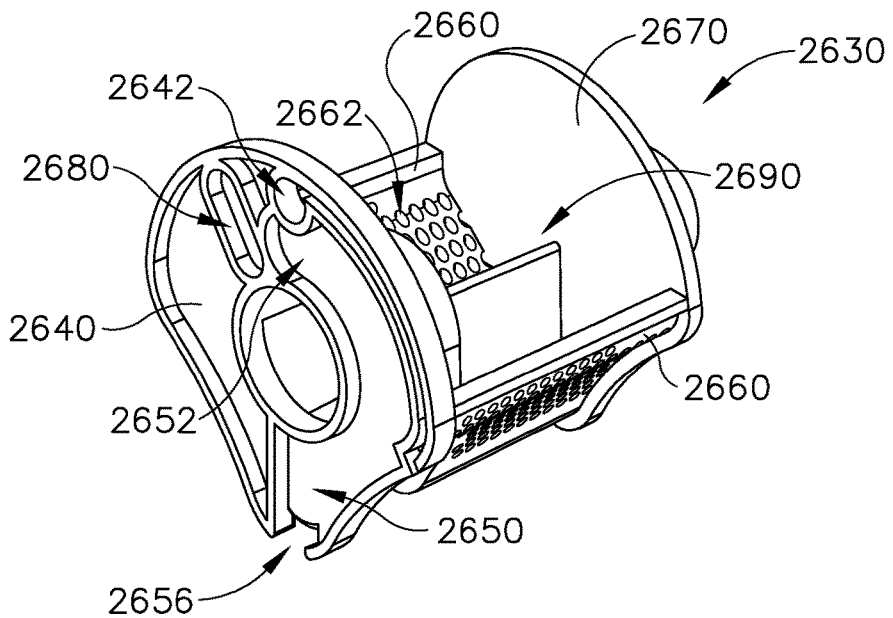
Figure 121:
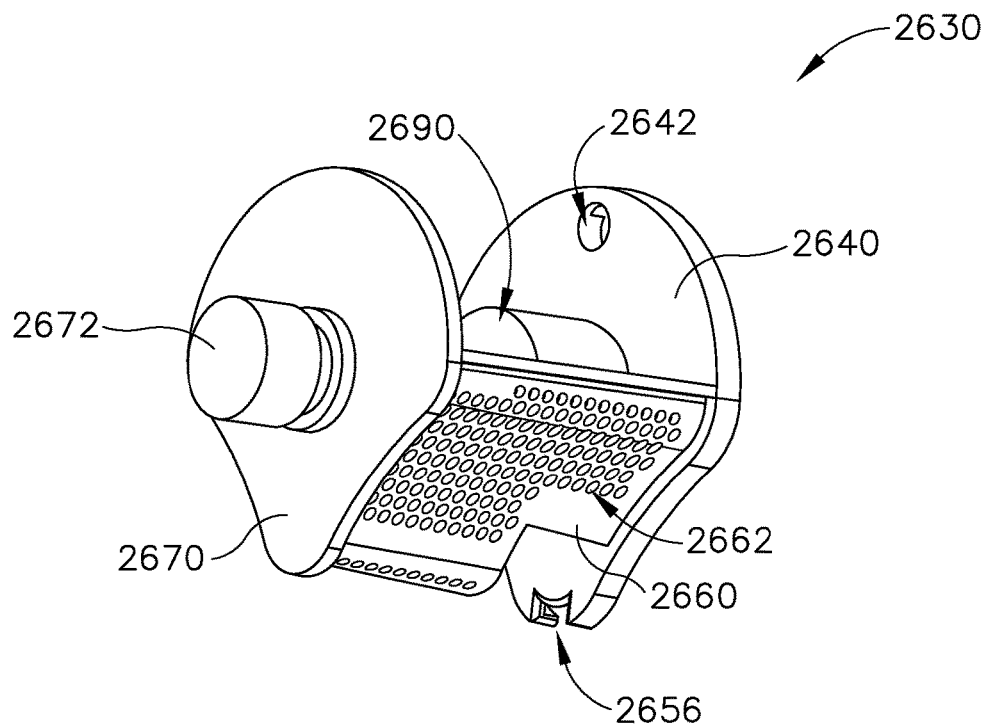
Figure 122:
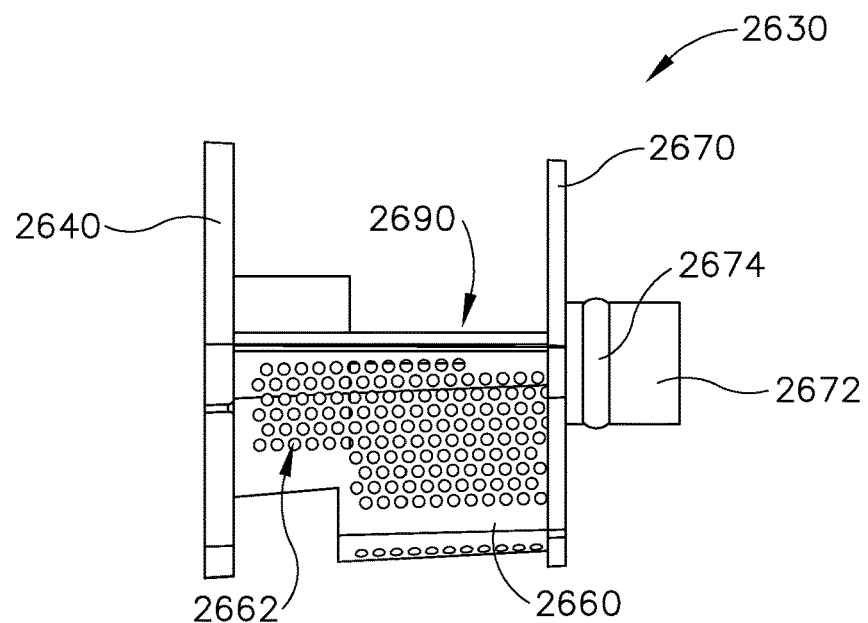
Figure 123:
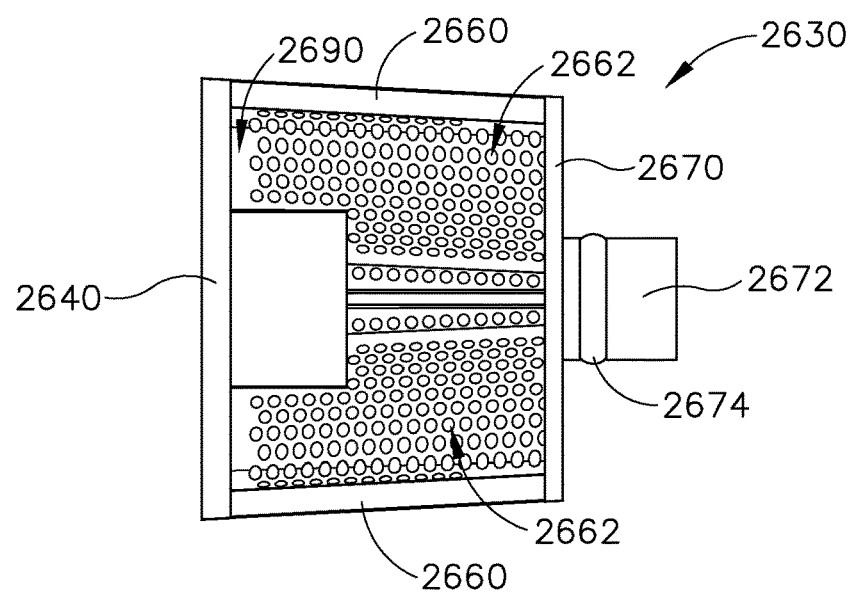
Figure 124:
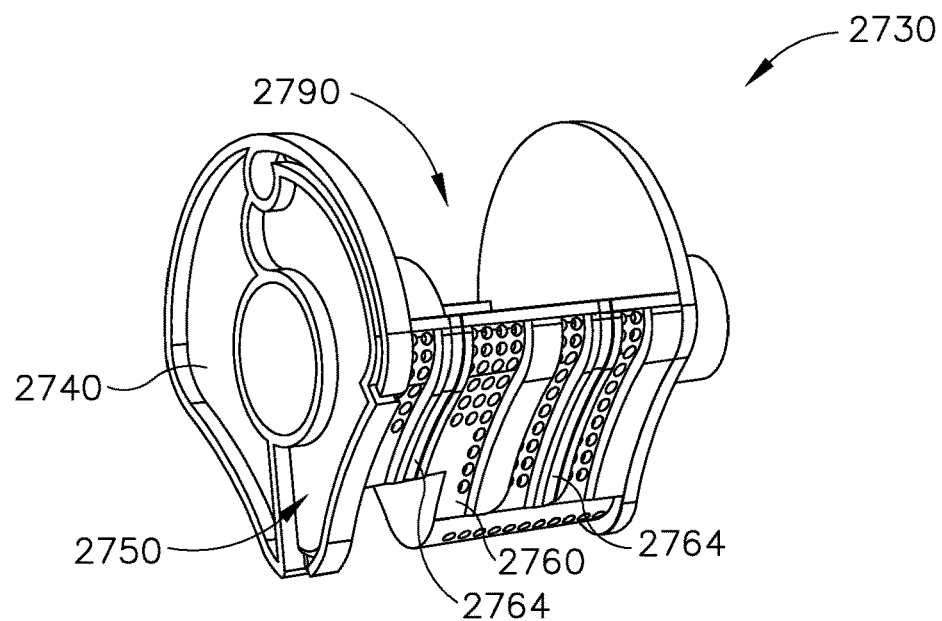
Figure 125:
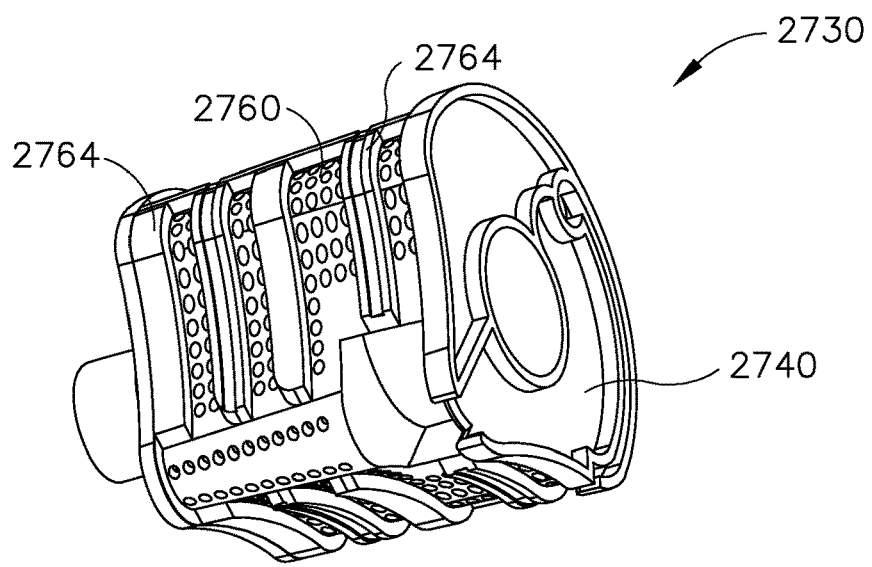
Figure 126:
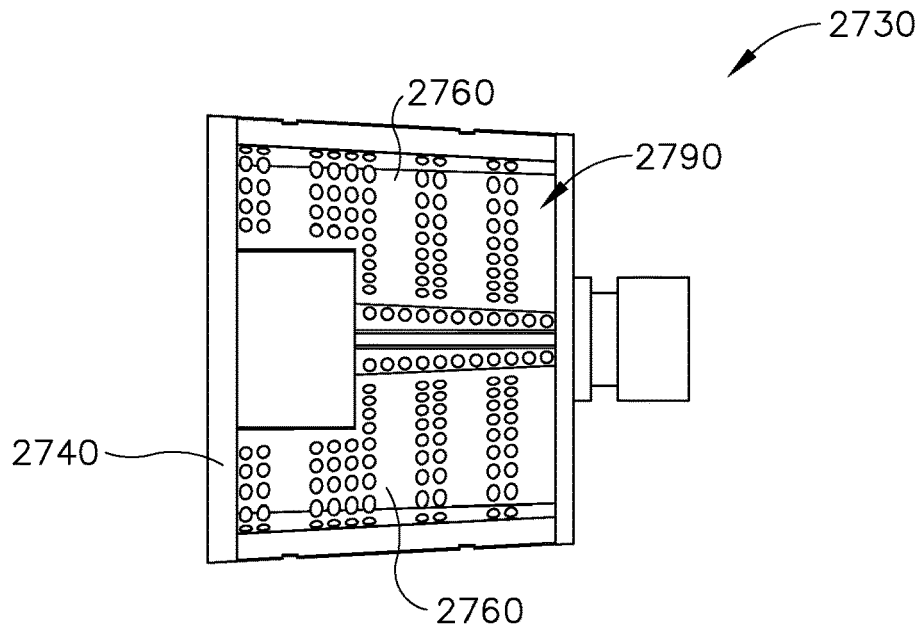
Figure 127:
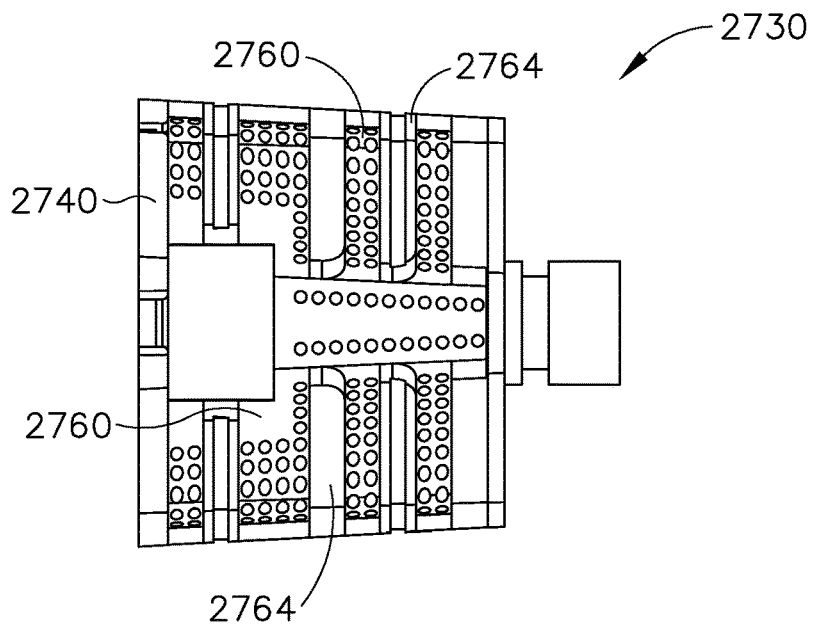

D. Exemplary Tissue Sample Holder Assembly with Proximal Tray Release Feature and Dual Troughs FIGS. 115-123 show another exemplary tissue sample holder assembly (2600) that may be coupled with probe (100). Tissue sample holder assembly (2600) of this example comprises a cover (2610) and a tissue sample tray (2630), which is removably inserted in cover (2610). As best seen in FIG. 116, cover (2610) includes a proximal opening (2612). Cover (2610) also comprises a proximal portion that has three lobes, similar to cover (1410), describe above. In addition, cover (2610) of this example comprises two-pronged bayonet slots (2620), similar to cover (1510) described above. As further described above, these two-pronged bayonet slots (2620) allow tissue sample holder assembly (2600) to be transitioned between a first angular orientation and a second angular orientation with respect to probe (100), with biopsy device (10) being operable when tissue sample holder assembly (2600) is in the first angular orientation; and also operable when tissue sample holder assembly (2600) is in the second angular orientation.

As best seen in FIGS. 120-123, tissue sample tray (2630) of the present example comprises a distal wall (2640), a pair of sidewalls (2660), and a proximal wall (2670). Walls (2640, 2660, 2670) together define a tissue receiving compartment (2690). Distal wall (2640) defines an upper opening (2642), a first trough (2650), and a second trough (2680), which is fluidly isolated from trough (2650). Proximal wall (2670) includes a proximally oriented projection (2672). An o-ring (2674) is disposed about projection (2672). As best seen in FIG. 116, projection (2672), is sized to fit through proximal opening (2612) of cover (2610) when tissue sample tray (2630) is inserted in cover (2610). O-ring (2674) is positioned and configured to provide a fluid seal within opening (2612) when projection (2672) is inserted in opening (2612). O-ring (2674) thus assists in maintaining vacuum within tissue sample holder assembly (2600) and preventing leakage of fluid from tissue sample holder assembly (2600). Projection (2672) protrudes proximally from cover (2610) such that an operator may readily grasp cover (2610) and press distally on projection (2672) to eject tissue sample tray (2630) from cover (2610). By way of example only, this may be done to retrieve tissue samples that have been collected in tissue receiving compartment (2690).

Upper opening (2642) is in direct fluid communication with tissue receiving compartment (2690). Walls (2660) include drainage openings (2662) that are also in fluid communication with tissue receiving compartment (2690) to provide drainage of fluids from tissue receiving compartment (2690). Drainage openings (2662) also provide pathways for communication of vacuum to tissue receiving compartment (2690) as will be described in greater detail below. Distal wall (2640) defines a notch (2656) at the bottom of trough (2650). Notch (2656) is configured to provide a pathway for fluid communication between trough (2650) and a gap (not shown) that is defined between cover (2610) and tissue sample tray (2630). Notch (2656) thus provides functionality similar to that provided by sump openings in other examples described herein.

As noted above, tissue sample holder assembly (2600) may be selectively rotated between first and second angular orientations relative to probe (100). When tissue sample holder assembly (2600) is disposed in the first angular orientation relative to probe (100), opening (2642) aligns with opening (174) of sealing member (170); while an upper region (2652) of trough (2650) aligns with opening (176) of sealing member (170).

This tissue sample holder assembly (2600) in the first angular orientation thus operates to draw severed tissue samples into tissue sample compartment (2690). Thus, when vacuum is applied via tube (20) and opening (176), this vacuum is communicated through trough (2650) and notch (2656) to the gap that is defined between cover (2610) and tissue sample tray (2630). This vacuum is further communicated through drainage openings (2662) to tissue receiving compartment (2690); and further to openings (2642, 174) to reach lumen (151) of cutter (150). It should therefore be understood that vacuum from tube (20) may draw severed tissue samples proximally through lumen (151) to reach tissue receiving compartment (2690). It should also be understood that fluids drawn proximally through lumen (151) may be further drawn into tube (20) via openings (174, 2642), tissue receiving compartment (2690), drainage openings (2662), notch (2656), trough (2650), and opening (176). Thus, when tissue sample holder (2630) is coupled with probe (100) at the first angular orientation, biopsy device (10) may be operated to capture tissue samples in tissue receiving compartment (2690) and drain fluids.

When tissue sample holder assembly (2600) is disposed in the second angular orientation, second trough (2680) is in fluid communication with both openings (174, 176) of sealing member (170); and opening (2642) and trough (2650) are both fluidly isolated from corresponding openings (174, 176). Trough (2680) thus effectively provides a short circuit coupling openings (174, 176) together; bypassing tissue sample compartment (2690) and other interior components/regions of tissue sample holder assembly (2600).

In some instances, it may be desirable to operate biopsy device (10) with tissue sample holder assembly (2600) in the second angular orientation in order to administer one or more fluids (e.g., medication(s) and/or other kinds of fluids) to a biopsy site. For instance, with needle (110) disposed in the patient's tissue, cutter (150) may be retracted to a proximal position to effectively open lateral aperture (114). A source of medical fluid (or other kind of fluid) may be coupled with either luer fitting (32, 42) in order to place tube (46) in fluid communication with the source of medical fluid (or other kind of fluid). As described above, tube (46) is in fluid communication with second lumen (192) via manifold (122). As also described above, second lumen (192) is in fluid communication with lateral aperture (114) via openings (194). Medical fluid (or other kind of fluid) may thereby be delivered to the tissue via lateral aperture (114). It should also be understood that vacuum may be applied through tube (20) to assist in drawing the medical fluid (or other kind of fluid) through tube (46). By providing a direct fluid path between openings (174, 176), trough (2680) allows this vacuum to bypass tissue receiving compartment (2690) and other interior components/regions of tissue sample holder assembly (2600).

It should be understood from the foregoing that a biopsy device (10) having a tissue sample holder assembly (2600) may be operated to alternate between the first and second angular orientations during a single biopsy procedure. For instance, biopsy device (10) may be operated with tissue sample holder assembly (2600) in the first angular orientation for a first portion of the procedure, where one or more tissue samples are collected in tissue receiving compartment (2690). The operator may then rotate outer cover (2610) (which will also rotate tissue sample tray (2630)) to place tissue sample holder assembly (2600) in the second angular orientation. In the second angular orientation, the operator may administer one or more fluids (e.g., medication(s) and/or other kinds of fluids) to the biopsy site. The operator may then transition tissue sample holder assembly (2600) back to the first angular orientation to collect one or more additional tissue samples. This alternation between the first and second angular orientations may be done as many times as desired.

E. Exemplary Tissue Sample Tray with Proximal Tray Release Feature and Drainage Ribs FIGS. 124-127 show an exemplary alternative tissue sample tray (2730) that may be incorporated into tissue sample holder assembly (2600) in lieu of tissue sample tray (2630). Tissue sample tray (2730) of this example is substantially identical to tissue sample tray (2630), except that distal wall (2740) of tissue sample tray (2730) of this example lacks second trough (2680). Alternatively, some other versions of tissue sample tray (2730) may include trough (2680). Also unlike tissue sample tray (2630), tissue sample tray (2730) of the present example includes a series of outwardly extending ribs (2764) on each sidewall (2760). Ribs (2764) terminate at the underside of tissue sample tray (2730). In some instances, ribs (2764) promote communication of vacuum from trough (2750) to tissue receiving compartment (2790). In addition or in the alternative, ribs (2764) may promote egress of fluids from tissue receiving compartment (2790). Aside from omitting second trough (2680) and including ribs (2764), tissue sample tray (2730) is identical to tissue sample tray (2630).

F. Exemplary Cover with Overmolded Button

Figure 128:
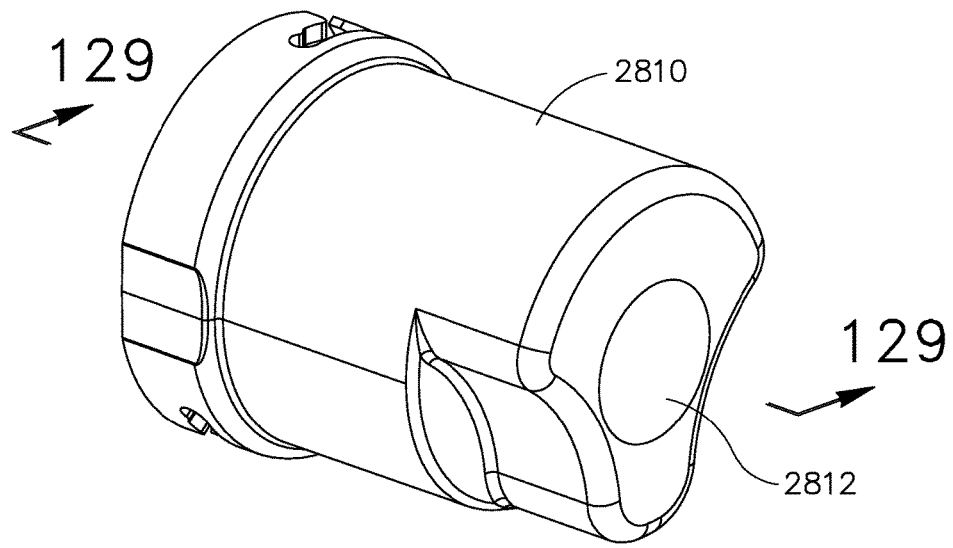
Figure 129:
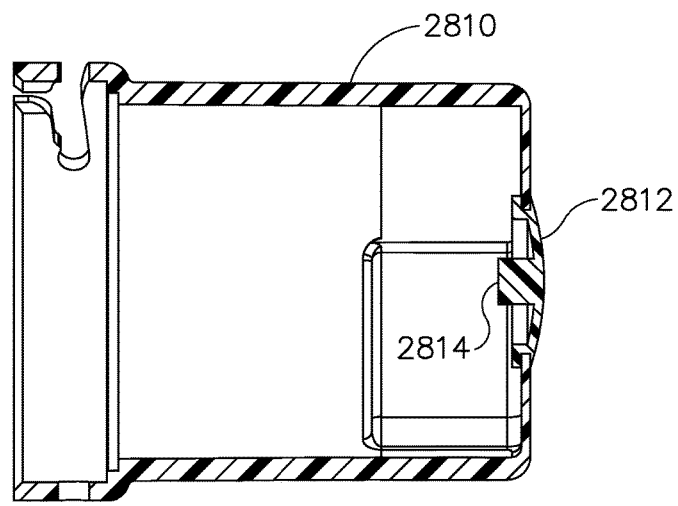

In various examples described above, a proximally extending projection of a tissue sample tray protrudes proximally from a cover of a tissue sample holder assembly, enabling the operator to press directly on the projection of the tissue sample tray in order to eject the tissue sample tray from the cover. FIGS. 128-129 show one merely illustrative example of a feature that may provide similar functionality while omitting the proximally protruding projection from the tissue sample tray. In particular, FIGS. 128-129 show an exemplary cover (2810) that may be readily incorporated into any of the various tissue sample holder assemblies described above. While cover (2810) of the present example has a three-lobed configuration at the proximal end of cover (2810), it should be understood that cover (2810) may instead have any other suitable shape.

Cover (2810) of the present example includes an integral pushbutton feature (2812) at the proximal end of cover (2810). Pushbutton feature (2812) is deformable. In some versions, pushbutton feature (2812) is formed of an elastomeric material. Pushbutton feature (2812) includes a distal projection (2814) that is configured to engage the proximal end of a tray or basket that is disposed within cover (2810). Thus, when an operator wishes eject a tray or basket from cover (2810), the operator may remove cover (2810) from probe (100) and then press distally on pushbutton feature (2812). This may cause pushbutton feature (2812) to deform distally, which may further cause projection (2814) to drive the tray or basket distally relative to cover (2810). Other suitable features and configurations will be apparent to those of ordinary skill in the art in view of the teachings herein.

VII. Exemplary Alternative Tissue Sample Holder Assemblies with Plurality of Removable Trays In some instances, it may be desirable to provide a tissue sample holder assembly that includes a plurality of removable trays, where each tray is sized and configured to hold a plurality of tissue samples. This may enable a rotation assembly in biopsy device (10) to rotate the tissue sample holder assembly, to distribute tissue samples in the various removable trays. Several examples of such tissue sample holder assemblies are disclosed in U.S. Pub. No. 2013/0053724, entitled "Biopsy Device Tissue Sample Holder with Bulk Chamber and Pathology Chamber," published Feb. 28, 2013, the disclosure of which is incorporated by reference herein. Several additional examples will be described in greater detail below; while still other examples will be apparent to those of ordinary skill in the art in view of the teachings herein.

A. Exemplary Tissue Sample Holder Assembly with Proximally Removable Trays

FIGS. 130-140 show another exemplary tissue sample holder assembly (2900) that may be coupled with probe (100). Tissue sample holder assembly (2900) of this example comprises a cover (2910), a body (2920), and a plurality of tissue sample trays (2940). Cover (2910) includes a pair of bayonet slots (2912) that are configured to receive bayonet pins (109), allowing tissue sample holder assembly (2900) to be removably coupled with probe (100). Cover (2910) also includes an open distal end (2914) and an open proximal end (2916). As will be described in greater detail below, cover (2910) is configured to contain body (2920) relative to probe (100), yet cover (2910) permits body (2920) to rotate within cover (2910).

As best seen in FIGS. 134 and 136, body (2920) includes a set of four passageways (2922) extending distally from the proximal end (2921) of body (2920). Passageways (2922) are configured to receive corresponding tissue sample trays (2940). As best seen in FIGS. 132 and 135, the distal end (2923) of body (2920) includes a set of inner openings (2924) and a set of outer openings (2926). Openings (2924, 2926) are provided in pairs, which are angularly spaced about distal end (2923). Each pair of openings (2924, 2926) is in fluid communication with a corresponding passageway (2922). Distal end (2923) also includes a trough (2980).

Trough (2980) is not in fluid communication with any openings (2924, 2926) or passageways (2922).

As best seen in FIGS. 130 and 132, body (2920) also includes a distally projecting stud (2930). Stud (2930) is configured to couple with grasping feature (184) of rotation member (180). Stud (2930) is a unitary feature of body (2920), such that rotation of stud (2930) will rotate body (2920) and tissue sample trays (2940) about the longitudinal axis of stud (2930). As noted above, rotation member (180) includes an integral gear (182), which meshes with gear (240) of holster (200) when probe (100) and holster (200) are coupled together. Gear (240) is driven by a motor in holster (200) to rotate rotation member (180) in predetermined angular increments each time cutter (150) is actuated to sever a tissue sample. By way of example only, gear (240) may be driven in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

As best seen in FIGS. 137-140, each tissue sample tray (2940) comprises a proximal wall (2942), a pair of sidewalls (2944), a distal wall (2946), and a floor (2948). Walls (2942, 2944, 2946) and floor (2948) together define a tissue receiving chamber (2990). Proximal wall (2942) is configured to provide a fluid tight seal against body (2920) when tissue sample tray (2940) is fully inserted in passageway (2922). A handle (2950) extends proximally from proximal wall (2942), facilitating proximal withdrawal of tissue sample tray (2940) from passageway (2922). Distal wall (2946) includes an upper arcuate opening (2952) and a lower V-shaped recess (2954). When tissue sample tray (2940) is inserted in passageway (2922), opening (2952) aligns with a corresponding opening (2926) of body (2920); while recess (2954) aligns with a corresponding opening (2924) of body (2920). Floor (2948) is shaped to provide a tapered transition from proximal wall (2942) to distal wall (2946), such that floor (2948) provides a transition into the V-shape of recess (2954). As best seen in FIG. 139, floor (2948) also tapers along another dimension such that floor (2948) fans outwardly as floor (2948) extends from proximal wall (2942) to distal wall (2946). Floor (2948) also includes a plurality of openings (2949) that are configured to provide communication of vacuum and fluids through openings (2949) while preventing the passage of tissue samples through openings (2949).

As noted above, body (2920) may be driven via stud (2930) to rotate to various angular orientations relative to probe (100). In some of those angular orientations, the inner opening (2924) of one pair of openings (2924, 2926) will be aligned with opening (176) of sealing member (170); while the outer opening (2926) of the same pair of openings (2924, 2926) will be aligned with opening (174) of sealing member (170). Thus, vacuum drawn via tube (20) will be communicated to the underside of the corresponding floor (2948) via openings (176, 2924). This vacuum will be further communicated through openings (2949) to the corresponding tissue receiving chamber (2990) above floor (2948); and then further to lumen (151) of cutter (150) via openings (2926, 174). This vacuum may assist in drawing severed tissue samples proximally through lumen (151). Such severed tissue samples may then be communicated further proximally through openings (2926, 174) and then reach tissue receiving chamber (2990). It should be understood that several tissue samples may be collected in each tissue receiving chamber (2990). It should also be understood that fluids drawn through lumen (151) of cutter (150) may pass through openings (2926, 174), tissue receiving chamber (2990), openings (2949), and openings (176, 2924) for drainage via tube (20). Furthermore, the fluid that is drawn through lumen (151) of cutter (150) will only pass through the particular passageway (2922) that is aligned with openings (174, 176) at that particular moment. In other words, tissue samples that are not within the "active" tissue receiving chamber (2990) associated with the passageway (2922) that is aligned with openings (174, 176) at that particular moment will not be saturated with fluid.

The motor that drives rotation member (180) to rotate body (2920) may be activated automatically after cutter (150) has been actuated a certain number of times, such that rotation member (180) indexes the next pair of openings (2924, 2926) to openings (174, 176) to deposit additional tissue samples in the next (empty) tissue receiving chamber (2990). Alternatively, the motor that drives rotation member (180) to rotate body (2920) may be selectively activated by the operator (e.g., by actuating a button or other user input feature, etc.), such that the operator decides when to index the next pair of openings (2924, 2926) to openings (174, 176). In some other versions, body (2920) is rotated manually, such that a motor is not activated to rotate body (2920). Various suitable ways in which body (2920) may be rotated will be apparent to those of ordinary skill in the art in view of the teachings herein.

In some instances, the operator may wish to administer one or more fluids (e.g., medication(s) and/or other kinds of fluids) to the biopsy site. In such instances, body (2920) may be rotated to align trough (2980) with openings (174, 176). As in other examples described herein, trough (2980) provides a short circuit coupling openings (174, 176) together, bypassing the interior of body (2920) and tissue sample trays (2940).

B. Exemplary Tissue Sample Holder Assembly with Distally Removable Trays

FIGS. 141-147 show yet another exemplary tissue sample holder assembly (3000) that may be coupled with probe (100). Tissue sample holder assembly (3000) of this example comprises a cover (3010), a body (3020), and a plurality of tissue sample trays (3040). Cover (3010) includes a pair of bayonet slots (3012) that are configured to receive bayonet pins (109), allowing tissue sample holder assembly (3000) to be removably coupled with probe (100). Cover (3010) also includes an open distal end (3014) and an open proximal end (3016). As will be described in greater detail below, cover (3010) is configured to contain body (3020) relative to probe (100), yet cover (3010) permits body (3020) to rotate within cover (3010).

As best seen in FIG. 143, body (3020) includes a set of four passageways (3022, 3024) extending proximally from the distal end (3021) of body (3020). Passageways (3022) are configured to receive corresponding tissue sample trays (3040). Passageway (3024) is configured to receive a removable plug (3050). As best seen in FIG. 142, the proximal end (3023) of body (3020) includes a single opening (3026) that is configured to permit selective insertion of plug (3050) through opening (3026) and into passageway (3024). As can be seen in FIG. 141, plug (3050) stops short of the full length of passageway (3024) when plug (3050) is fully inserted in passageway (3024), such that a recess (3028) remains in the distal end of passageway (3024) when plug (3050) is fully inserted in passageway (3024).

As best seen in FIGS. 141 and 143, body (3020) also includes a distally projecting stud (3030). Stud (3030) is configured to couple with grasping feature (184) of rotation member (180). Stud (3030) is a unitary feature of body (3020), such that rotation of stud (3030) will rotate body (3020) and tissue sample trays (3040) about the longitudinal axis of stud (3030). As noted above, rotation member (180) includes an integral gear (182), which meshes with gear (240) of holster (200) when probe (100) and holster (200) are coupled together. Gear (240) is driven by a motor in holster (200) to rotate rotation member (180) in predetermined angular increments each time cutter (150) is actuated to sever a tissue sample. By way of example only, gear (240) may be driven in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

As best seen in FIGS. 144-147, each tissue sample tray (3040) comprises a proximal wall (3042), a pair of sidewalls (3044), a distal wall (3046), and a floor (3048). Walls (3042, 3044, 3046) and floor (3048) together define a tissue receiving chamber (3090). Distal wall (3046) includes an upper opening (3052) and a lower opening (3054). When tissue sample tray (3040) is inserted in passageway (3022), distal wall (3046) and openings (3052, 3054) are exposed at distal end (3021) of body (3020). Floor (3048) tapers downwardly from proximal wall (3042) toward distal wall (3046); yet provides a channel (3056) leading to lower opening (3054). Floor (3048) also includes a plurality of openings (3049) that are configured to provide communication of vacuum and fluids through openings (3049) while preventing the passage of tissue samples through openings (3049).

As noted above, body (3020) may be driven via stud (3030) to rotate to various angular orientations relative to probe (100). In some of those angular orientations, the lower opening (3054) of one tissue sample tray (3040) will be aligned with opening (176) of sealing member (170); while the upper opening (3052) of the same tissue sample tray (3040) will be aligned with opening (174) of sealing member (170). Thus, vacuum drawn via tube (20) will be communicated to the underside of the corresponding floor (3048) via openings (176, 3024). This vacuum will be further communicated through openings (3049) to the corresponding tissue receiving chamber (3090) above floor (3048); and then further to lumen (151) of cutter (150) via openings (3052, 174). This vacuum may assist in drawing severed tissue samples proximally through lumen (151). Such severed tissue samples may then be communicated further proximally through openings (3052, 174) and then reach tissue receiving chamber (3090). It should be understood that several tissue samples may be collected in each tissue receiving chamber (3090). It should also be understood that fluids drawn through lumen (151) of cutter (150) may pass through openings (3052, 174), tissue receiving chamber (3090), openings (3049), and openings (176, 3054) for drainage via tube (20). Furthermore, the fluid that is drawn through lumen (151) of cutter (150) will only pass through the particular passageway (3022) that is aligned with openings (174, 176) at that particular moment. In other words, tissue samples that are not within the "active" tissue receiving chamber (3090) associated with the passageway (3022) that is aligned with openings (174, 176) at that particular moment will not be saturated with fluid.

The motor that drives rotation member (180) to rotate body (3020) may be activated automatically after cutter (150) has been actuated a certain number of times, such that rotation member (180) indexes the next pair of openings (3052, 3054) to openings (174, 176) to deposit additional tissue samples in the next (empty) tissue receiving chamber (3090). Alternatively, the motor that drives rotation member (180) to rotate body (3020) may be selectively activated by the operator (e.g., by actuating a button or other user input feature, etc.), such that the operator decides when to index the next pair of openings (3052, 3054) to openings (174, 176). In some other versions, body (3020) is rotated manually, such that a motor is not activated to rotate body (3020). Various suitable ways in which body (3020) may be rotated will be apparent to those of ordinary skill in the art in view of the teachings herein.

In some instances, the operator may wish to administer one or more fluids (e.g., medication(s) and/or other kinds of fluids) to the biopsy site. In such instances, body (3020) may be rotated to align passageway (3024) with openings (174, 176). At this stage, plug (3050) may be inserted in passageway (3024) such that openings (174, 176) are presented with sealed recess (3028). As in other examples described herein, recess (3028) provides a short circuit coupling openings (174, 176) together, bypassing tissue sample trays (3040).

In addition or in the alternative, the operator may wish to deploy a biopsy site marker to the biopsy site via needle (110). In such instances, body (3020) may be rotated to align passageway (3024) with openings (174, 176). At this stage, plug (3050) may be removed from passageway (3024), providing an open path to lumen (151) of cutter (150) via passageway (3024) and opening (174). Cutter (150) may be in a proximally retracted position at this stage, effectively opening lateral aperture (114). The shaft of a marker applier instrument may then be inserted through passageway (3024), opening (174), and lumen (151) of cutter (150) until the working end of the marker applier instrument reaches the open lateral aperture (114). The marker applier instrument may then be actuated to deploy the biopsy site marker at the biopsy site via the open lateral aperture (114). An exemplary marker applier instrument is disclosed in U.S. Pub. No. 2014/0039343, entitled "Biopsy System," published Feb. 6, 2014, the disclosure of which is incorporated by reference herein. Alternatively, any other suitable marker applier instrument may be used. Once the biopsy site has been suitably marked, the operator may replace plug (3050) in passageway (3024).

In some variations, the plug (3050) and passageway (3024) of tissue sample holder assembly (3000) is incorporated into tissue sample holder assembly (3000), such that trough (2980) is omitted; and passageways (2922) and tissue sample trays (2940) are reconfigured to accommodate plug (3050) and passageway (3024). Other suitable ways in which teachings herein may be combined among different examples will be apparent to those of ordinary skill in the art.

VIII. Exemplary Alternative Tissue Sample Holder Assembly with Plurality of Static Bulk Tissue Receiving Compartments FIGS. 148-152 show an exemplary assembly (3100) that may be incorporated into tissue sample holder assembly (3000) in place of body (3020) and tissue sample trays (3040). Assembly (3100) of this example comprises a body (3120) and a screen member (3140). Body (3120) of this example includes a set of seven passageways (3122, 3124) extending proximally from the distal end (3121) of body (3120). Passageways (3122) are defined by radially extending interior walls (3160, 3162) of body (3120). Passageway (3124) is defined by walls (3162). Each wall (3160, 3162) defines a corresponding channel (3164, 3166) that is configured to receive screen member (3140) as will be described in greater detail below. Passageway (3124) is configured to receive a removable plug just like plug (3050) described above. As best seen in FIGS. 149 and 151, the proximal end (3123) of body (3120) includes a single opening (3126) that is configured to permit selective insertion of the plug through opening (3126) and into passageway (3124). In the present example, an inserted plug will stop short of the full length of passageway (3124) when the plug is fully inserted in passageway (3124), such that a recess will remain in the distal end of passageway (3124) when the plug is fully inserted in passageway (3124).

As best seen in FIGS. 148 and 152, body (3120) also includes a distally projecting stud (3130). Stud (3130) is configured to couple with grasping feature (184) of rotation member (180). Stud (3130) is a unitary feature of body (3120), such that rotation of stud (3130) will rotate body (3120) and screen member (3140) about the longitudinal axis of stud (3130). As noted above, rotation member (180) includes an integral gear (182), which meshes with gear (240) of holster (200) when probe (100) and holster (200) are coupled together. Gear (240) is driven by a motor in holster (200) to rotate rotation member (180) in predetermined angular increments each time cutter (150) is actuated to sever a tissue sample. By way of example only, gear (240) may be driven in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

As best seen in FIG. 152, screen member (3140) comprises a sheet of material (e.g., metal, plastic, etc.) that is curved to form a "C" shape, such that edges (3142, 3144) of screen member (3140) define a longitudinally extending gap (3146). As noted above, screen member (3140) is inserted into body (3120) via channels (3164, 3166). Edges (3142, 3144) are positioned in channels (3166) of walls (3162), such that passageway (3124) is located in gap (3146). Screen member (3140) also includes a plurality of openings (3148) formed therethrough. Openings (3148) are configured to provide communication of vacuum and fluids through openings (3148) while preventing the passage of tissue samples through openings (3148).

As best seen in FIG. 150, screen member (3140) effectively divides each passageway (3122) into an inner chamber (3176) and an outer chamber (3174), such that each passageway (3122) has a respective pair of chambers (3176, 3174). As noted above, body (3120) may be driven via stud (3130) to rotate to various angular orientations relative to probe (100). In some of those angular orientations, the inner chamber (3176) of one passageway (3122) will be aligned with opening (176) of sealing member (170); while the outer chamber (3174) of the same passageway (3122) will be aligned with opening (174) of sealing member (170). Thus, vacuum drawn via tube (20) will be communicated to the underside of the portion of screen member (3140) in the corresponding passageway (3122) via opening (176) and chamber (3174). This vacuum will be further communicated through openings (3148) to the corresponding chamber (3174) above the same portion of screen member (3140); and then further to lumen (151) of cutter (150) via opening (174). This vacuum may assist in drawing severed tissue samples proximally through lumen (151). Such severed tissue samples may then be communicated further proximally through openings (174) and then reach chamber (3174). It should be understood that several tissue samples may be collected in each (3174). It should also be understood that fluids drawn through lumen (151) of cutter (150) may pass through openings (174), chamber (3174), openings (3148), chamber (3176), and opening (176) for drainage via tube (20). Furthermore, the fluid that is drawn through lumen (151) of cutter (150) will only pass through the particular passageway (3122) that is aligned with openings (174, 176) at that particular moment. In other words, tissue samples that are not within the "active" chamber (3174) associated with the passageway (3122) that is aligned with openings (174, 176) at that particular moment will not be saturated with fluid.

The motor that drives rotation member (180) to rotate body (3120) may be activated automatically after cutter (150) has been actuated a certain number of times, such that rotation member (180) indexes the next pair of chambers (3176, 3174) to openings (174, 176) to deposit additional tissue samples in the next (empty) tissue chamber (3174). Alternatively, the motor that drives rotation member (180) to rotate body (3120) may be selectively activated by the operator (e.g., by actuating a button or other user input feature, etc.), such that the operator decides when to index the next pair of chambers (3176, 3174) to openings (174, 176). In some other versions, body (3120) is rotated manually, such that a motor is not activated to rotate body (3120). Various suitable ways in which body (3120) may be rotated will be apparent to those of ordinary skill in the art in view of the teachings herein.

In some instances, the operator may wish to administer one or more fluids (e.g., medication(s) and/or other kinds of fluids) to the biopsy site. In such instances, body (3120) may be rotated to align passageway (3124) with openings (174, 176). At this stage, a plug may be inserted in passageway (3124) such that openings (174, 176) are presented with sealed recess. As in other examples described herein, the sealed recess provides a short circuit coupling openings (174, 176) together, bypassing chambers (3176, 3174).

In addition or in the alternative, the operator may wish to deploy a biopsy site marker to the biopsy site via needle (110). In such instances, body (3120) may be rotated to align passageway (3124) with openings (174, 176). At this stage, a plug may be removed from passageway (3124), providing an open path to lumen (151) of cutter (150) via passageway (3124) and opening (174). Cutter (150) may be in a proximally retracted position at this stage, effectively opening lateral aperture (114). The shaft of a marker applier instrument may then be inserted through passageway (3124), opening (174), and lumen (151) of cutter (150) until the working end of the marker applier instrument reaches the open lateral aperture (114). The marker applier instrument may then be actuated to deploy the biopsy site marker at the biopsy site via the open lateral aperture (114). An exemplary marker applier instrument is disclosed in U.S. Pub. No. 2014/0039343, entitled "Biopsy System," published Feb. 6, 2014, the disclosure of which is incorporated by reference herein. Alternatively, any other suitable marker applier instrument may be used. Once the biopsy site has been suitably marked, the operator may replace the plug in passageway (3124).

IX. Exemplary Alternative Tissue Sample Holder Assembly with Single Bulk Sample Tray and Plug FIGS. 163-171 show yet another exemplary tissue sample holder assembly (4900) that may be coupled with probe (100). Tissue sample holder assembly (4900) of this example comprises a cover (4910), a body (4920), a tissue sample tray (4940), and a plug (4980). Cover (4910) includes a pair of bayonet slots (4912) that are configured to receive bayonet pins (109), allowing tissue sample holder assembly (4900) to be removably coupled with probe (100).

Cover (4910) also includes an open distal end (4914) and an open proximal end (4916). As will be described in greater detail below, cover (4910) is configured to contain body (4920) relative to probe (100), yet cover (4910) permits body (4920) to rotate within cover (4910).

As best seen in FIG. 165, body (4920) includes a tray receiving passageway (4922) and a plug receiving passageway (4924), each passageway (4922, 4924) extending proximally from the distal end (3021) of body (3020). Passageway (4922) is configured to receive tissue sample trays (4940); while passageway (4924) is configured to receive removable plug (4980). As described above with respect to FIG. 141 and a similar plug (3050), plug (4980) of the present example stops short of the full length of passageway (4924) when plug (4980) is fully inserted in passageway (4924), such that a recess (4928) remains in the distal end of passageway (4924) when plug (4980) is fully inserted in passageway (4924). As shown in FIGS. 164 and 166-167, the distal wall (4932) of body (4920) includes an upper opening (4934) and a lower opening (4936). When tissue sample holder (4900) is coupled with probe (100) and body (4920) is indexed to a tissue sample receiving angular position relative to probe (100), upper opening (4934) aligns with opening (174) of sealing member (170); while lower opening (4936) aligns with opening (176) of sealing member (170). Thus, upper opening (4934) is in fluid communication with lumen (151) of cutter (150) when body (4920) is indexed to a tissue sample receiving angular position relative to probe (100); and lower opening (4936) is in fluid communication with tube (20) when body (4920) is indexed to a tissue sample receiving angular position relative to probe (100).

As best seen in FIGS. 166-167, body (4920) also includes a distally projecting stud (4930). Stud (4930) is configured to couple with grasping feature (184) of rotation member (180). Stud (4930) is a unitary feature of body (4920), such that rotation of stud (4930) will rotate body (4920) about the longitudinal axis of stud (4930). As noted above, rotation member (180) includes an integral gear (182), which meshes with gear (240) of holster (200) when probe (100) and holster (200) are coupled together. Gear (240) is driven by a motor in holster (200) to rotate rotation member (180) in predetermined angular increments each time cutter (150) is actuated to sever a tissue sample. By way of example only, gear (240) may be driven in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

As best seen in FIGS. 168-171, tissue sample tray (4940) comprises a distal wall (4942), a proximal wall (4944), a floor (4946), and a pair of sidewalls (4948) extending between walls (4942, 4944). Walls (4942, 4944, 4948), and floor (4946) cooperate to define a tissue receiving compartment (4950). A handle (4952) extends proximally from proximal wall (4944), facilitating proximal withdrawal of tissue sample tray (4940) from passageway (4922). As best seen in FIGS. 169 and 170-171, distal wall (4942) defines an upper opening (4962) and a lower recess (4964). Opening (4962) and recess (4964) are configured to align with corresponding openings (4934, 4936) of body (4920) and openings (174, 176) of sealing member (170) when tissue sample holder (4900) is coupled with probe (100). Thus, upper opening (4962) is in fluid communication with lumen (151) of cutter (150) when body (4920) is indexed to a tissue sample receiving angular position relative to probe (100); and lower recess (4964) is in fluid communication with tube (20) when body (4920) is indexed to a tissue sample receiving angular position relative to probe (100).

As best seen in FIGS. 168 and 170, upper opening (4962) is in direct fluid communication with tissue receiving compartment (4950). As best seen in FIGS. 169 and 171, lower recess (4964) is in fluid communication with a U-shaped sump lumen (4966). Sump lumen (4966) terminates in a pair of lower openings (4968) at the distal end of floor (4946). Openings (4968) are laterally offset from each other, due to the U-shaped configuration of sump lumen (4966). In the present example, a plurality of drainage apertures (4970, 4972) are formed through walls (4948) and floor (4946), respectively. Drainage apertures (4970, 4972) are configured and operable substantially identically to the various drainage apertures described above. It should be understood that, when vacuum from tube (20) is applied through openings (176, 4936) and recess (4964), such vacuum will be communicated via sump lumen (4966) and lower openings (4968) to the gap or space defined between the outer surface of floor (4946) and the inner surface of passageway (4922); and to the gap or space defined between the outer surfaces of sidewalls (4948) and the inner surface of passageway (4922). It should be understood further that fluid drained from tissue receiving compartment (4950) may be drawn out via openings (4968), sump lumen (4966), recess (4964), and opening (176).

It should be understood from the foregoing that, when tissue sample holder (4900) is coupled with probe (100), with body (4920) indexed to a tissue sample receiving angular position relative to probe (100), upper openings (4934, 4962) align with opening (174) of sealing member (170); while lower opening (4936) and recess (4964) align with opening (176) of sealing member (170). Thus, when vacuum is applied via tube (20) and opening (176), this vacuum is communicated through lower opening (4936), recess (4964), sump lumen (4966), and sump openings (4968) to a gap defined between floor (4946) and the inner surface of passageway (4922). This vacuum is further communicated through drainage openings (4970, 4972) to tissue receiving compartment (4950); and further to openings (4962, 4934, 174) to reach lumen (151) of cutter (150). It should therefore be understood that vacuum from tube (20) may draw severed tissue samples proximally through lumen (151) to reach tissue receiving compartment (4950). It should also be understood that fluids drawn proximally through lumen (151) may be further drawn into tube (20) via openings (174, 4934, 4962), tissue receiving compartment (4950), drainage openings (4970, 4972), sump openings (4968), sump lumen (4966), recess (4964) and openings (4936, 176). Thus, when tissue sample holder (4900) is coupled with probe (100), with body (4920) indexed to a tissue sample receiving angular position relative to probe (100), biopsy device (10) may be operated to capture tissue samples in tissue receiving compartment (4950) and drain fluids.

In some instances, the operator may wish to administer one or more fluids (e.g., medication(s) and/or other kinds of fluids) to the biopsy site. In such instances, the motor that drives rotation member (180) may be activated to rotate body (4920) to align passageway (4924) with openings (174, 176). At this stage, plug (4980) may be inserted in passageway (4924) such that openings (174, 176) are presented with sealed recess (4928). As in other examples described herein, recess (4928) provides a short circuit coupling openings (174, 176) together, bypassing tissue sample tray (4940).

In addition or in the alternative, the operator may wish to deploy a biopsy site marker to the biopsy site via needle (110). In such instances, body (4920) may be rotated to align passageway (4924) with openings (174, 176). At this stage, plug (4980) may be removed from passageway (4924), providing an open path to lumen (151) of cutter (150) via passageway (4924) and opening (174). Cutter (150) may be in a proximally retracted position at this stage, effectively opening lateral aperture (114). The shaft of a marker applier instrument may then be inserted through passageway (4924), opening (174), and lumen (151) of cutter (150) until the working end of the marker applier instrument reaches the open lateral aperture (114). The marker applier instrument may then be actuated to deploy the biopsy site marker at the biopsy site via the open lateral aperture (114). An exemplary marker applier instrument is disclosed in U.S. Pub. No. 2014/0039343, entitled "Biopsy System," published Feb. 6, 2014, the disclosure of which is incorporated by reference herein. Alternatively, any other suitable marker applier instrument may be used. Once the biopsy site has been suitably marked, the operator may replace plug (4980) in passageway (4924).

X. Exemplary Alternative Tissue Sample Holder Assembly with Proximally Removable Sample Trays and Plug FIGS. 172-182 show yet another exemplary tissue sample holder assembly (5900) that may be coupled with probe (100). Tissue sample holder assembly (5900) of this example comprises a cover (5910), a body (5920), a plurality of tissue sample trays (5940), and a plug (5980). Cover (5910) includes a pair of bayonet slots (5912) that are configured to receive bayonet pins (109), allowing tissue sample holder assembly (5900) to be removably coupled with probe (100). Cover (5910) also includes an open distal end (5914) and an open proximal end (5916). As will be described in greater detail below, cover (5910) is configured to contain body (5920) relative to probe (100), yet cover (5910) permits body (5920) to rotate within cover (5910).

As best seen in FIG. 176, body (5920) includes a plurality of tray receiving passageways (5922) and a plug receiving passageway (5924), each passageway (5922, 5924) extending proximally from the distal end (5921) of body (5920). Passageways (5922) are configured to receive tissue sample trays (5940); while passageway (5924) is configured to receive removable plug (5980). As described above with respect to FIG. 141 and a similar plug (3050), plug (5980) of the present example stops short of the full length of passageway (5924) when plug (5980) is fully inserted in passageway (5924), such that a recess (5928) remains in the distal end of passageway (5924) when plug (5980) is fully inserted in passageway (5924). As shown in FIGS. 172, 174, and 177, the distal wall (5932) of body (5920) includes a set of upper openings (5934) and a set of lower openings (5936) for each respective passageway (5922). When tissue sample holder (5900) is coupled with probe (100) and body (5920) is indexed to one of three tissue sample receiving angular positions relative to probe (100), a corresponding upper opening (5934) aligns with opening (174) of sealing member (170); while a corresponding lower opening (5936) aligns with opening (176) of sealing member (170). Thus, a given upper opening (5934) is in fluid communication with lumen (151) of cutter (150) when body (5920) is indexed to a given tissue sample receiving angular position relative to probe (100); and a given lower opening (5936) is in fluid communication with tube (20) when body (5920) is indexed to a given tissue sample receiving angular position relative to probe (100).

As best seen in FIGS. 172, 174 and 177, body (5920) also includes a distally projecting stud (5930). Stud (5930) is configured to couple with grasping feature (184) of rotation member (180). Stud (5930) is a unitary feature of body (5920), such that rotation of stud (5930) will rotate body (5920) about the longitudinal axis of stud (5930). As noted above, rotation member (180) includes an integral gear (182), which meshes with gear (240) of holster (200) when probe (100) and holster (200) are coupled together. Gear (240) is driven by a motor in holster (200) to rotate rotation member (180) in predetermined angular increments each time cutter (150) is actuated to sever a tissue sample. By way of example only, gear (240) may be driven in accordance with at least some of the teachings of U.S. Pub. No. 2014/0039343, entitled "Biopsy System," published Feb. 6, 2014, the disclosure of which is incorporated by reference herein; and/or in accordance with at least some of the teachings of any other references cited herein.

As best seen in FIGS. 176, 177, and 179-182, each tissue sample tray (5940) comprises a distal wall (5942), a proximal wall (5944), a floor (5946), and a pair of sidewalls (5948) extending between walls (5942, 5944). Walls (5942, 5944, 5948), and floor (5946) cooperate to define a tissue receiving compartment (5950). In particular, floor (5946) slopes downwardly as floor (5946) extends proximally from distal wall (5942). Correspondingly, side walls (5948) expand as side walls (5948) extend proximally from distal wall (5942) to accommodate the downwardly sloping floor (5946). A handle (5952) extends proximally from proximal wall (5944), facilitating proximal withdrawal of tissue sample tray (5940) from passageway (5922). As best seen in FIG. 180, distal wall (5942) defines an upper opening (5962) and a lower recess (5964). Opening (5962) and recess (5964) are configured to align with corresponding openings (5934, 5936) of body (5920) and openings (174, 176) of sealing member (170) when tissue sample holder (5900) is coupled with probe (100). Thus, a given upper opening (5962) is in fluid communication with lumen (151) of cutter (150) when body (5920) is indexed to a given tissue sample receiving angular position relative to probe (100); and a given lower recess (5964) is in fluid communication with tube (20) when body (5920) is indexed to a given tissue sample receiving angular position relative to probe (100).

As best seen in FIGS. 179 and 180, upper opening (5962) is in direct fluid communication with tissue receiving compartment (5950). As best seen in FIGS. 179, 180 and 182, lower recess (5964) is in fluid communication with a gap or space below floor (5946). In the present example, a plurality of drainage apertures (5970, 5972) are formed through walls (5948) and floor (5946), respectively. Drainage apertures (5970, 5972) are configured and operable substantially identically to the various drainage apertures described above. It should be understood that, when vacuum from tube (20) is applied through openings (176, 5936) and recess (5964), such vacuum will be communicated to the gap or space defined between the outer surface of floor (5946) and the inner surface of passageway (5922); and to the gap or space defined between the outer surfaces of sidewalls (5948) and the inner surface of passageway (5922). It should further be understood that fluid drained from tissue receiving compartment (5950) may be drawn out via openings (5968), recess (5964), and opening (176).

It should be understood from the foregoing that, when tissue sample holder (5900) is coupled with probe (100), with body (5920) indexed to a given tissue sample receiving angular position relative to probe (100), upper openings (5934, 5962) align with opening (174) of sealing member (170); while a given lower opening (5936) and recess (5964) align with opening (176) of sealing member (170). Thus, when vacuum is applied via tube (20) and opening (176), this vacuum is communicated through lower opening (5936), and recess (5964) to a gap defined between floor (5946) and the inner surface of passageway (5922). This vacuum is further communicated through drainage openings (5970, 5972) to tissue receiving compartment (5950); and further to openings (5962, 5934, 174) to reach lumen (151) of cutter (150). It should therefore be understood that vacuum from tube (20) may draw severed tissue samples proximally through lumen (151) to reach tissue receiving compartment (5950). It should also be understood that fluids drawn proximally through lumen (151) may be further drawn into tube (20) via openings (174, 5934, 5962), tissue receiving compartment (5950), drainage openings (5970, 5972), recess (5964) and openings (5936, 176). Thus, when tissue sample holder (5900) is coupled with probe (100), with body (5920) indexed to a given tissue sample receiving angular position relative to probe (100), biopsy device (10) may be operated to capture tissue samples in tissue receiving compartment (5950) and drain fluids.

In some instances, the operator may wish to administer one or more fluids (e.g., medication(s) and/or other kinds of fluids) to the biopsy site. In such instances, the motor that drives rotation member (180) may be activated to rotate body (5920) to align passageway (5924) with openings (174, 176). At this stage, plug (5980) may be inserted in passageway (5924) such that openings (174, 176) are presented with sealed recess (5928). As in other examples described herein, recess (5928) provides a short circuit coupling openings (174, 176) together, bypassing tissue sample trays (5940).

In addition or in the alternative, the operator may wish to deploy a biopsy site marker to the biopsy site via needle (110). In such instances, body (5920) may be rotated to align passageway (5924) with openings (174, 176). At this stage, plug (5980) may be removed from passageway (5924), providing an open path to lumen (151) of cutter (150) via passageway (5924) and opening (174). Cutter (150) may be in a proximally retracted position at this stage, effectively opening lateral aperture (114). The shaft of a marker applier instrument may then be inserted through passageway (5924), opening (174), and lumen (151) of cutter (150) until the working end of the marker applier instrument reaches the open lateral aperture (114). The marker applier instrument may then be actuated to deploy the biopsy site marker at the biopsy site via the open lateral aperture (114). An exemplary marker applier instrument is disclosed in U.S. Pub. No. 2014/0039343, entitled "Biopsy System," published Feb. 6, 2014, the disclosure of which is incorporated by reference herein. Alternatively, any other suitable marker applier instrument may be used. Once the biopsy site has been suitably marked, the operator may replace plug (5980) in passageway (5924).

XI. Exemplary Biopsy Device with Auxiliary Vacuum

In some instances, it may be desirable to provide auxiliary vacuum to a tissue sample holder assembly. Such auxiliary vacuum may be provided in addition to or in lieu of vacuum being applied via tube (20). FIG. 153 shows an exemplary configuration where probe (100) is fitted with an additional vacuum tube (3200) to provide auxiliary vacuum to tissue sample holder assembly (300). Vacuum tube (3200) of this example extends between tissue sample holder assembly (300) and a valve assembly (3202). Valve assembly (3202) is further coupled with luer fitting (22) of tube (20). Valve assembly (3202) also includes a fitting (3204) enabling valve assembly (3202) to be coupled with a vacuum source such as vacuum control module (250). In some versions, valve assembly (3202) allows vacuum to be applied to tissue sample holder assembly (300) simultaneously by both tubes (20, 3200). In addition or in the alternative, valve assembly (3202) may be operable to alternate between providing vacuum via just one tube (20, 3200) at a time. Various suitable forms that valve assembly (3202) may take will be apparent to those of ordinary skill in the art in view of the teachings herein. It should also be understood that the operator may wish to use tube (3200) in order to remove excess fluid from tissue sample holder assembly (300), based on the orientation of probe (100) and/or based on other factors. As yet another merely illustrative example, auxiliary vacuum may be provided in accordance with at least some of the teachings of U.S. Pat. No. 8,376,957, entitled "Biopsy Device with Auxiliary Vacuum Source," issued Feb. 19, 2013, the disclosure of which is incorporated by reference herein.

XII. Exemplary Process for Selecting Tissue Sample Holder Type

As noted above, biopsy system (2) may be configured to accept at least two different kinds of tissue sample holders, including at least one kind of tissue sample holder that includes trays with chambers configured to receive only one tissue sample per chamber and at least one kind of tissue sample holder that includes one or more trays that are configured to receive several tissue samples per chamber. For the sake of clarity, the first type of tissue sample holder will be referred to as a single sample chamber tissue sample holder; while the second type will be referred to as a bulk sample chamber tissue sample holder. Various examples of single sample chamber tissue sample holders are disclosed in U.S. Pub. No. 2014/0039343, entitled "Biopsy System," published Feb. 6, 2014, the disclosure of which is incorporated by reference herein; U.S. Pat. No. 8,702,623, entitled "Biopsy Device with Discrete Tissue Chambers," issued Apr. 22, 2014, the disclosure of which is incorporated by reference herein; and U.S. Pat. No. 7,938,786, entitled "Vacuum Timing Algorithm for Biopsy Device," issued May 10, 2011, the disclosure of which is incorporated by reference herein. Various examples of bulk sample chamber tissue sample holders are described above (with reference to FIGS. 9-152) and in U.S. Pub. No. 2013/0053724, entitled "Biopsy Device Tissue Sample Holder with Bulk Chamber and Pathology Chamber," published Feb. 28, 2013, the disclosure of which is incorporated by reference herein. Of course, various other kinds of single sample chamber tissue sample holders and bulk sample chamber tissue sample holders may be used with biopsy device (10).

FIG. 154 shows an exemplary process (4000) that may be carried out by biopsy system (2) to enable an operator to indicate which kind of tissue sample holder will be used. By way of example only, process (4000) may be carried out principally by vacuum control module (250), which may include a memory, processor, and/or any other suitable hardware that is needed to carry out process (4000). Various suitable kinds of hardware that may be incorporated into vacuum control module (250) in order to carry out process (4000) will be apparent to those of ordinary skill in the art in view of the teachings herein. FIGS. 155-162 show various kinds of graphical user interfaces (GUIs) that may be provided through biopsy system (2) during performance of process (4000). Again by way of example only, these GUIs may be provided through vacuum control module (250), which may include a regular screen, a touchscreen, and/or any other suitable hardware that is needed to provide GUIs. Various suitable kinds of hardware that may be incorporated into vacuum control module (250) in order to provide GUIs will be apparent to those of ordinary skill in the art in view of the teachings herein. It should also be understood that vacuum control module (250) may be configured and operable in accordance with at least some of the teachings of U.S. Pub. No. 2014/0039343, entitled "Biopsy System," published Feb. 6, 2014, the disclosure of which is incorporated by reference herein.

A shown in FIG. 154, process (4000) of the present example begins with step (4002), in which the operator is instructed to secure probe (100) to holster (200). By way of example only, biopsy system (2) may present the operator with GUI (4100) shown in FIG. 155 during step (4002). GUI (4100) of this example includes a graphical representation (4102) of probe (100) and a graphical representation (4104) of holster (200), along with a textual instruction (4106). Of course, GUI (4100) may have any other suitable appearance at this stage.

Once the operator couples probe (100) with holster (200), process (4000) proceeds to step (4004), where the operator is instructed to indicate the type of tissue sample holder that is secured (or will be secured) to probe (100). In some versions, biopsy system (2) includes sensing features that automatically detect coupling of probe (100) with holster (200), such that process (4000) automatically proceeds to step (4004) as soon as probe (100) is coupled with holster (200). In some other versions, the operator must provide some form of conformation via GUI (4100) to indicate that probe (100) has been coupled with holster (200) before process (4000) proceeds to step (4004). FIG. 156 shows an exemplary GUI (4200) that biopsy system (2) may present to the operator during step (4004). This GUI (4200) includes a graphical representation (4202) of a single sample chamber tissue sample holder and a graphical representation (4204) of a bulk sample chamber tissue sample holder, along with a textual instruction (4206). Of course, GUI (4200) may have any other suitable appearance at this stage.

The remainder of process (4000) proceeds based on which tissue sample holder type the operator selects during step (4004). In some versions where GUI (4200) is presented via a touchscreen, the operator selects the tissue sample holder type by tapping once, twice, or any other suitable number of times on the relevant graphical representation (4202, 4204). In the event that the operator selects the single sample chamber tissue sample holder (e.g., by tapping on graphical representation (4202), etc.), process (4000) proceeds to step (4006), where the operator is instructed to proceed to initialization. FIG. 157 shows an exemplary GUI (4300) that biopsy system (2) may present to the operator during step (4006). This GUI (4300) includes a graphical representation (4302) of a single sample chamber tissue sample holder and a graphical representation (4304) of a bulk sample chamber tissue sample holder, along with a textual instruction (4306) and input arrow (4308). Graphical representation (4302) is highlighted relative to graphical representation (4304), providing the operator with visual confirmation that the single sample chamber tissue sample holder type was selected. Of course, GUI (4300) may have any other suitable appearance at this stage.

Once the operator activates input arrow (4308) (e.g., by tapping directly on arrow (4308), etc.), biopsy system (2) provides initialization of the tissue sample holder, cutter (150), and a vacuum pump in vacuum control module (250). This initialization is shown as step (4008). By way of example only, such initialization may be performed in accordance with at least some of the teachings of U.S. Pub. No. 2014/0039343, entitled "Biopsy System," published Feb. 6, 2014, the disclosure of which is incorporated by reference herein. After completing the initialization, process (4000) reaches step (4010), which is a ready state. In the ready state, biopsy device (10) may be operated to obtain several tissue samples from a patient. FIG. 158 shows an exemplary GUI (4400) that biopsy system (2) may present to the operator during step (4010). GUI (4400) of this example comprises a first region (4410), a second region (4420), a third region (4430), and a standby input (4440). Of course, GUI (4400) may have any other suitable appearance at this stage.

First region (4410) includes a first input (4412), a second input (4414), and a graphical representation (4416) of needle (110) and cutter (150). First input (4412) enables the operator to selectively vary the effective length of lateral aperture (114). Second input (4414) enables the operator to vary other settings for cutter (150). Graphical representation (4416) provides visual feedback indicating the selected length setting for lateral aperture (114). It should be understood that first region (4410) may be constructed and operable in accordance with at least some of the teachings of U.S. Pub. No. 2014/0039343, entitled "Biopsy System," published Feb. 6, 2014, the disclosure of which is incorporated by reference herein.

Second region (4420) of GUI (4400) includes a first input (4422), a second input (4424), and a graphical representation (4426) of a single sample chamber tissue sample holder. First input (4422) enables the operator to identify which angular position the tissue sample holder should rotate to in order to present the most recently acquired tissue sample to the user for viewing right after the tissue sample is acquired. Second input (4424) enables the operator to rotate the tissue sample holder incrementally, one chamber at a time, relative to lumen (151) of cutter (150). Graphical representation (4426) may provide visual feedback to the operator, indicating the angular positioning of the tissue sample holder and/or the occupancy of tissue samples in the various tissue receiving chambers of the tissue sample holder. Second region (4420) may also be constructed and operable in accordance with at least some of the teachings of U.S. Pub. No. 2014/0039343, entitled "Biopsy System," published Feb. 6, 2014, the disclosure of which is incorporated by reference herein.

Third region (4430) of GUI (4400) includes a first input (4432), a second input (4434), and a graphical representation (4436) of the vacuum level provided by vacuum control module (250). First input (4432) enables the operator to select the vacuum level (e.g., by cycling through predetermined vacuum levels by tapping on input (4432), etc.). Graphical representation (4436) provides visual feedback to the operator to indicate the selected vacuum level. Second input (4434) enables the operator to initiate a clearing vacuum cycle. Third region (4430) may also be constructed and operable in accordance with at least some of the teachings of U.S. Pub. No. 2014/0039343, entitled "Biopsy System," published Feb. 6, 2014, the disclosure of which is incorporated by reference herein.

In the event that the operator activates standby input (4440), process (4000) proceeds to step (4012), where biopsy system (2) is placed in a standby mode. FIG. 159 shows an exemplary GUI (4500) that biopsy system (2) may present to the operator during step (4006). This GUI (4500) includes a graphical representation (4502) of a single sample chamber tissue sample holder and a graphical representation (4504) of a bulk sample chamber tissue sample holder, along with a textual instruction (4506) and input arrow (4508). Of course, GUI (4500) may have any other suitable appearance at this stage. At this stage, the operator may return back to step (4010) by activating input arrow (4508) (e.g., by tapping input arrow (4508) on a touchscreen, etc.). Alternatively, the operator may change the type of tissue sample holder that is coupled with probe (100) and correspondingly change the mode of operation of biopsy system (2) by activating graphical representation (4504) (e.g., by tapping graphical representation (4504) on a touchscreen, etc.). If the operator activates graphical representation (4504), process (4000) proceeds to step (4020), which is described in greater detail below.

As noted above, the progression of process (400) varies based on which tissue sample holder type the operator selects during step (4004). The discussion above focuses on an operator selecting the single sample chamber tissue sample holder type. In some instances, the operator may select the bulk sample chamber tissue sample holder type during step (4004) (e.g., by tapping on graphical representation (4204), etc.). When such a selection is made, process (4000) proceeds to step (4014), where the operator is instructed to proceed to initialization. FIG. 160 shows an exemplary GUI (4600) that biopsy system (2) may present to the operator during step (4014). This GUI (4600) includes a graphical representation (4602) of a single sample chamber tissue sample holder and a graphical representation (4604) of a bulk sample chamber tissue sample holder, along with a textual instruction (4606) and input arrow (4608). Graphical representation (4604) is highlighted relative to graphical representation (4604), providing the operator with visual confirmation that the bulk sample chamber tissue sample holder type was selected. Of course, GUI (4600) may have any other suitable appearance at this stage.

Once the operator activates input arrow (4608) (e.g., by tapping directly on arrow (4608), etc.), biopsy system (2) provides initialization of the cutter (150) and the vacuum pump in vacuum control module (250). This initialization is shown as step (4016). By way of example only, such initialization may be performed in accordance with at least some of the teachings of U.S. Pub. No. 2014/0039343, entitled "Biopsy System," published Feb. 6, 2014, the disclosure of which is incorporated by reference herein. After completing the initialization, process (4000) reaches step (4018), which is a ready state. In the ready state, biopsy device (10) may be operated to obtain several tissue samples from a patient. FIG. 161 shows an exemplary GUI (4700) that biopsy system (2) may present to the operator during step (4018). GUI (4700) of this example comprises a first region (4710), a second region (4720), a third region (4730), and a standby input (4740). Of course, GUI (4700) may have any other suitable appearance at this stage.

First region (4710) includes a first input (4712), a second input (4714), and a graphical representation (4716) of needle (110) and cutter (150). First input (4712) enables the operator to selectively vary the effective length of lateral aperture (114). Second input (4714) enables the operator to vary other settings for cutter (150). Graphical representation (4716) provides visual feedback indicating the selected length setting for lateral aperture (114). It should be understood that first region (4710) may be constructed and operable in accordance with at least some of the teachings of U.S. Pub. No. 2014/0039343, entitled "Biopsy System," published Feb. 6, 2014, the disclosure of which is incorporated by reference herein.

Second region (4720) of GUI (4700) includes a first input (4722), a second input (4724), and a graphical representation (4726) of a bulk sample chamber tissue sample holder. First input (4722) enables the operator to select a mode of operation to indicate that medical fluid (or other kind of fluid) will be applied through needle (110) as described above. In versions of bulk chamber tissue sample holder that includes a "short circuit" trough such as those described above, biopsy device (100) may actuate the tissue sample holder to position the "short circuit" trough over openings (174, 176) of sealing member (170) as described above, in response to the operator activating first input (4722). Second input (4724) enables the operator to reset biopsy system when the operator applies a biopsy site marker through needle (110) as described above. Graphical representation (4726) may provide visual feedback to the operator, indicating the occupancy of tissue samples in the one or more bulk chambers of the tissue sample holder.

Third region (4730) of GUI (4700) includes a first input (4732), a second input (4734), and a graphical representation (4736) of the vacuum level provided by vacuum control module (250). First input (4732) enables the operator to select the vacuum level (e.g., by cycling through predetermined vacuum levels by tapping on input (4732), etc.). Graphical representation (4736) provides visual feedback to the operator to indicate the selected vacuum level. Second input (4734) enables the operator to initiate a clearing vacuum cycle. Third region (4730) may also be constructed and operable in accordance with at least some of the teachings of U.S. Pub. No. 2014/0039343, entitled "Biopsy System," published Feb. 6, 2014, the disclosure of which is incorporated by reference herein.

In the event that the operator activates standby input (4740), process (4000) proceeds to step (4020), where biopsy system (2) is placed in a standby mode. FIG. 162 shows an exemplary GUI (4800) that biopsy system (2) may present to the operator during step (4020). This GUI (4800) includes a graphical representation (4804) of a bulk sample chamber tissue sample holder, along with a textual instruction (4806) and input arrow (4808). Of course, GUI (4800) may have any other suitable appearance at this stage. At this stage, the operator may return back to step (4018) by activating input arrow (4808) (e.g., by tapping input arrow (4808) on a touchscreen, etc.). In the present example, step (4020) is unlike step (4012), and GUI (4800) is unlike GUI (4500), in that biopsy system (2) does not let the operator use GUI (4800) to change the type of tissue sample holder that is coupled with probe (100) and correspondingly change the mode of operation of biopsy system (2) during step (4020). If the operator wishes to change to a single chamber tissue sample holder and corresponding mode of operation, the operator must decouple probe (100) from holster (200), which will start process (4000) back at step (4002) and GUI (4100). In some other versions, biopsy system (2) allows the operator use GUI (4800) to change the type of tissue sample holder that is coupled with probe (100) and correspondingly change the mode of operation of biopsy system (2) during step (4020).

In the present example, if the operator decouples probe (100) from holster (200) at any time during process (4000), process (4000) returns back to step (4002). Of course, process (4000) and all of the GUIs described above are merely illustrative. Any other suitable processes and/or GUIs may be used in addition to or in lieu of those described above.

XIII. Miscellaneous

In the various examples described above, the tissue sample holder is coupled directly with probe (100). In some other versions, the tissue sample holder is not coupled directly with probe (100). By way of example only, the tissue sample holder may be coupled with one or more tubes (e.g., flexible tubes) and/or other conduits that are further coupled with openings (174, 176) (or equivalents to openings (174, 176), etc.), such that the tissue sample holder is remotely spaced from probe (100) via one or more tubes. In some such versions, the suction drawn through the one or more tubes and/or other conduits is sufficient to draw tissue into opened lateral aperture (114); and to draw severed tissue samples proximally through the length of lumen (151) of cutter (150) and a flexible tube that couples the tissue sample holder with lumen (151), even when the flexible tube is bent. Various suitable ways in which a tissue sample holder may be remotely coupled with probe (100) via one or more flexible tubes and/or other conduits will be apparent to those of ordinary skill in the art in view of the teachings herein. It should also be understood that any of the tissue sample holders described herein may be remotely coupled with probe (100) via one or more flexible tubes and/or other conduits.

Some examples tissue sample holders described herein have just one single tissue receiving chamber. While such a chamber is configured to receive and hold a plurality of tissue samples at once, there is just one single chamber in those examples. Some other examples of tissue sample holders described herein have four tissue receiving chambers. Some other examples of tissue sample holders described herein have three tissue receiving chambers. Some other examples of tissue sample holders described herein have six tissue receiving chambers. It should be understood that any suitable number of tissue receiving chambers may be provided by a tissue sample holder. The numbers of tissue receiving chambers described herein should not be viewed as limiting.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, the biopsy device comprising:
   (a) a probe body;
   (b) a needle portion extending distally from the probe body, wherein the needle portion includes a transverse tissue receiving aperture;
   (c) a hollow cutter, wherein the cutter is translatable relative to the needle portion to sever a tissue sample from tissue protruding through the aperture, wherein the hollow cutter defines a cutter lumen; and
   (d) a tissue sample holder, wherein the tissue sample holder includes:
      (i) a body, wherein the body defines a plurality of discrete tray chambers extending axially through at least a portion of the body, and
      (ii) a plurality of discrete tissue sample trays, wherein each tissue sample tray of the plurality of tissue sample trays is removably engaged with a single tray chamber of the body independently relative to all other tissue sample trays, wherein each tray of the plurality of trays includes a pair of side walls, a proximal wall, a distal wall, and a floor, wherein the distal wall includes a sample opening, wherein the pair of side walls, the proximal wall, the distal wall, and the floor of each tissue sample tray define a bulk sample chamber, wherein the bulk sample chamber is configured to receive a plurality of tissue samples,
   wherein the body is rotatable between a plurality of discrete bulk sample collection positions, wherein the number of bulk sample collection positions corresponds to the specific number of tissue sample trays of the plurality of tissue sample trays, wherein the body is manually rotatable between each bulk sample collection position to collect a plurality of tissue samples within each tissue sample tray before moving the body to the next bulk sample collection position to collect a plurality of tissue samples in another tissue sample tray,
   wherein the bulk sample chamber of each tissue sample tray of the plurality of tissue sample trays is in communication with a vacuum recess defined by the floor through a plurality of openings disposed within the floor.

2. The biopsy device of claim 1, wherein the floor of each tissue sample tray defines a v-shaped cross-sectional profile, wherein the v-shaped cross-sectional profile defines a tapered portion, wherein the tapered portion increases in size as the floor extends from the proximal wall to the distal wall of each tissue sample tray.

3. The biopsy device of claim 2, wherein the tapered portion includes a plurality of openings.

4. The biopsy device of claim 1, wherein the body of the tissue sample holder further includes a trough, wherein the tough is disposed between a selected pair of tray chambers.

5. The biopsy device of claim 4, wherein the trough is disposed on a distal wall of the body of the tissue sample holder.

6. The biopsy device of claim 4, wherein the trough is configured to act as a fluid short circuit.

7. The biopsy device of claim 4, wherein the trough is configured to redirect fluid flow relative to a longitudinal axis of the body to prevent entry of fluid into an interior portion of the body.

8. The biopsy device of claim 1, wherein the body of the tissue sample holder further includes a stud extending distally from a distal wall of the body.

9. The biopsy device of claim 8, wherein the stud is configured to engage at least a portion of the probe body to drive rotation of the body.

10. The biopsy device of claim 9, wherein the body of the tissue sample holder is rotatable using a motor.

11. A biopsy device, comprising:
(a) a probe body;
(b) a needle portion extending distally from the probe body, wherein the needle portion includes a transverse tissue receiving aperture;
(c) a hollow cutter, wherein the cutter is translatable relative to the needle portion through a cutting sequence to sever a tissue sample from tissue protruding through the aperture, wherein the hollow cutter defines a cutter lumen; and
(d) a tissue sample holder, wherein the tissue sample holder includes:
(i) a rotatable body, wherein the body includes an outer cylindrical wall and an inner divider, wherein the outer cylindrical wall and the inner divider define a plurality of discrete body chambers within an interior of the body, and
(ii) a plurality of discrete tissue sample trays, wherein the tissue sample trays are removably engaged with a respective body chamber of the body, wherein each tray of the plurality of trays includes a pair of side walls, a proximal wall, a distal wall, and a floor, wherein each tissue sample tray defines a basket-style sample chamber, wherein the basket-style sample chamber of each tissue sample tray is configured to receive a plurality of tissue samples,
wherein the body is movable in a predetermined sequence to sequentially align a selected tissue sample tray of the plurality of sample trays with the cutter, wherein the body is configured to move in response to a movement of the cutter through a plurality of discrete cutting sequences,
wherein the basket-style sample chamber of each tissue sample tray of the plurality of tissue sample trays is in communication with a vacuum recess defined by the floor through a plurality of openings disposed within the floor.

12. The biopsy device of claim 11, wherein the distal wall of each tissue sample tray includes a vacuum opening and a sample opening.

13. The biopsy device of claim 12, wherein the vacuum opening is in communication with a tapered recess defined by the floor.

14. The biopsy device of claim 12, wherein the body of the tissue sample holder includes a distal wall defining a sample opening, wherein the sample opening includes an arcuate shape.

15. A biopsy device, comprising:
(a) a probe body;
(b) a needle portion extending distally from the probe body, wherein the needle portion includes a transverse tissue receiving aperture;
(c) a hollow cutter, wherein the cutter is translatable relative to the needle portion to sever a tissue sample from tissue protruding through the aperture, wherein the hollow cutter defines a cutter lumen; and
(d) a tissue sample holder, wherein the tissue sample holder includes:
(i) a body, wherein the body includes a plurality of discrete chambers, and
(ii) a plurality of tissue sample trays, wherein each tissue sample tray of the plurality of tissue sample trays is insertable into a corresponding chamber of the body, wherein each tissue sample tray of the plurality of tissue sample trays includes a sample opening, wherein each tissue sample tray defines a single discrete tissue sample chamber, wherein each tissue sample chamber of each tissue sample tray is configured to receive at least two tissue samples,
wherein the body is rotatable relative to the probe body to position each tissue sample tray in a tissue receiving position, wherein the body is configured to sequentially rotate between each tissue sample tray after receipt of two or more tissue samples within a single tissue sample tray,
wherein the tissue sample chamber of each tissue sample tray of the plurality of tissue sample trays is in communication with a vacuum recess defined by a floor through a plurality of openings disposed within the floor.

* * * * *